US010556959B2

(12) United States Patent
Chen et al.

(10) Patent No.: US 10,556,959 B2
(45) Date of Patent: Feb. 11, 2020

(54) ANTI-CD39 ANTIBODIES AND USES THEREOF

(71) Applicant: Xencor, Inc., Monrovia, CA (US)

(72) Inventors: Guoqing Chen, Burlingame, CA (US); Gregory M. Hayes, Burlingame, CA (US); Jan-Willem Theunissen, Burlingame, CA (US); Edward Thein H. Van Der Horst, Burlingame, CA (US); Leonard G. Presta, Burlingame, CA (US)

(73) Assignee: Xencor, Inc., Monrovia, CA (US)

( * ) Notice: Subject to any disclaimer, the term of this patent is extended or adjusted under 35 U.S.C. 154(b) by 11 days.

(21) Appl. No.: 15/525,007

(22) PCT Filed: Nov. 6, 2015

(86) PCT No.: PCT/US2015/059455
§ 371 (c)(1),
(2) Date: May 5, 2017

(87) PCT Pub. No.: WO2016/073845
PCT Pub. Date: May 12, 2016

(65) Prior Publication Data
US 2017/0335007 A1    Nov. 23, 2017

Related U.S. Application Data

(60) Provisional application No. 62/153,926, filed on Apr. 28, 2015, provisional application No. 62/077,085, filed on Nov. 7, 2014.

(51) Int. Cl.
| | | |
|---|---|---|
| *C07K 16/28* | (2006.01) | |
| *A61K 47/68* | (2017.01) | |
| *C07K 16/30* | (2006.01) | |
| *A61K 39/00* | (2006.01) | |
| *G01N 33/574* | (2006.01) | |

(52) U.S. Cl.
CPC ...... *C07K 16/2896* (2013.01); *A61K 47/6803* (2017.08); *A61K 47/6811* (2017.08); *A61K 47/6851* (2017.08); *C07K 16/30* (2013.01); *C07K 16/3061* (2013.01); *G01N 33/57492* (2013.01); *A61K 2039/505* (2013.01); *C07K 2317/24* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/626* (2013.01); *C07K 2317/76* (2013.01); *C07K 2317/92* (2013.01); *G01N 2333/70596* (2013.01)

(58) Field of Classification Search
CPC ............... C07K 16/14; C07K 16/2896; C07K 2317/565; A61K 47/6871; A61K 47/6849
See application file for complete search history.

(56) References Cited

U.S. PATENT DOCUMENTS

| | | |
|---|---|---|
| 2006/0286104 A1 | 12/2006 | Hanke et al. |
| 2010/0303828 A1 | 12/2010 | Levy et al. |
| 2013/0224228 A1 | 8/2013 | Jackson et al. |
| 2013/0273062 A1 | 10/2013 | Bensussan et al. |

FOREIGN PATENT DOCUMENTS

| | | | |
|---|---|---|---|
| WO | WO 2004/035732 | 4/2004 | |
| WO | WO-2008079849 A2 * | 7/2008 | ........... A61K 31/337 |
| WO | WO 2012/072268 | 6/2012 | |
| WO | WO-2012085132 A1 * | 6/2012 | ......... C07K 16/2896 |
| WO | WO 2012/118547 | 9/2012 | |

* cited by examiner

*Primary Examiner* — Karen A. Canella
(74) *Attorney, Agent, or Firm* — Robin M. Silva; Kun Ma; Morgan, Lewis & Bockius, LLP

(57) ABSTRACT

The present disclosure relates generally to anti-CD39 antibodies, including antibody-drug conjugates comprising the antibodies, and methods of their use.

5 Claims, 21 Drawing Sheets
Specification includes a Sequence Listing.

Figure 1A: anti-CD39 R21 Antibodies VH Sequences

```
            1              10           22         26----32      40         50--a-----60----65
Kabat       1              10           22         26----35      40         50--a-----60----65
AbM         1              10           22         26----35      40         50--a-----58    65
Chothia     1              10           22         26----32      40            a-55         65
Contact     1              10           22         30----35      40      47---a-----58      65
IMGT        1              10           23         27----38   41            56--a-----65    74
5-13A       QVQLQQSGPELVKPGASVRISCKAS GYTFTG-YYVH WVKQRPGQGLEWIG WIYPGNVNTKYNEKFKA
9-8B        QIQLVQSGPELKKPGETVKISCKAS GYTFTH-YGMN WVKQAPGKGLKWMG WINTYTGELTYADDFKG 5-71A       DVQLVESGGGLVQPGGSRKLSCAAS GFTFSS-FGMH WVRQAPEKGLELVA YISSGSTIRYYSDTVKG
5-165C      EVQLVESGGDLVKPGGSLKLSCAAF GFTFSR-YGMS WVRQTPDKRLEWVA TITSGGIYTYYPDSVKG
consensus                               GFTFSx-xGMx(10)              xIxSGxxxxYYxDxVKG(11)

70         80    abc    90         95--100-----102           110
Kabat       70         80    abc    90         95--100-----102           110
AbM         70         80    abc    90         96--100-----101           110
Chothia     70         80    abc    90      93--100-----101              110
Contact     75                  89          105---------------117
IMGT
5-13A       KATLTADKSSSTGYMQLSRLTSEDSAVYFCAR SPYYGTTYYYTMDY WGQGTSVTVSS(2)
9-8B        RFAFSLETSASTAYLQINNLKNEDTATYFCAR RAYYRYDYV--MDY WGQGTSVTVSS(3)

5-71A       RFTISRDNPKNTLFLQMTSLRSEDTAMYYCAR FLYEGFRYG--MDY WGQGTSVTVSS(4)
5-165C      RFTISRDNAKNTLYLQMSSLKSEETAMYYCAR HGQFGDYYG---MDY WGQGTSVTVSS(5)
consensus                                    xxxxGxxYG--MDY(12)
```

Figure 1B: anti-CD39 R21 Antibodies VL Sequences

```
Kabat       1          10         20         24-27abcdef----34         40          50-----56
AbM         1          10         20         24---30abcdef--34         40          50-----56
Chothia     1          10         20            26-30abcde-32          40          50---
Contact     1          10         20            30abcdef----36         40     46-----55
IMGT        1                        23         27-------38  41                    56-65 69

5-13A       EIVLTQSPAFMAASPGEKVTITC  SVSLIISS----RNLH  WYQQKSETSPKPWIY  GTSNLAS
9-8B        DIVMTQSQKFMSTSVGDRVSVTC  KASHNVG-----TNVA  WYQQKPGQSPKALIY  SASYRYS 5-71A       DVLMTQTPLSLPVSLGDQASISC  RSSQSIVHSNG-NTYLE  WYLQKPGQSPKLLIY  KVSNRFS
5-165C      DVVMTQTPLSLPVSLGDQASISC  RSSQSLLHSNG-NTYLH  WYLQKPGQSPKLLIY  KVSNRFS
consensus                            RSSQSxxHSNG-NTYLx(13)             KVSNRFS(14)

Kabat       60         70         80         89------97
AbM         60         70         80         89------97
Chothia     60         70         80            91----96
Contact     60         70         80         89------96
IMGT     70       89                          105-----117

5-13A       GVPVRFSGSGSGTSYSLTISSMEAEDAATYYC  QQWSDYPLT  FGSGTKLEIK(6)
9-8B        GVPGRFTGSGSGTDFTLTISNVQSEDLAEYFC  HQYNNYPYT  FGGGTKLEIK(7)

5-71A       GVPDRFSGSGSGTDFTLKISRVEAEDLGIYYC  FQGSHVPNT  FGGGTKLEIK(8)
5-165C      GVPDRFSGSGSGTDFTLKISRVEAEDLGVYFC  SQSTHVPYT  FGGGTKLEIK(9)
consensus                                     xQxxHVPxT(15)
```

Figure 2A: Antibody R21-5-13A VH
Humanized sequence based on IMGT IGHV1-2*02 acceptor framework (method 1)
QVQLVQSGAEVKKPGASVKVSCKAS GYTFTGYYMH WVRQAPGQGLEWMG WINPNSGGTNYAQKFQG RVTSTRDTSISTAYMELSRLRSDDTVYYYCAR (188)
Joining region    IMGT J00256|IGHJ4*01|YFDYWGQGTLVTVSS (189)

```
seq        b b b     p     b b b    b b   i  b b   b i  i       b b       b     b b  b b b b b   b b b  b      b i b i b b
           1         10        20             30         40          50         60         70         80     abc   90
5-13A      QVQLQQSGPELVKPGASVRISCKAS GYTFTGYYVH WVKQRPGQGLEWIG WINPNSGGTNYNEKFKA KATLTADKSSTGYMQLSRLITSEDSAVYFCAR
                *          **          *             *   *****   *  **  **    *  *     *       *  *      *

1-2*2      QVQLVQSGAEVKKPGASVKVSCKAS GYTFTGYYMH WVRQAPGQGLEWMG WINPGNVNTKYAQKFQG RVTMTRDTSISTAYMELSRLRSDDTVYYYCAR (188)
huVH1a     QVQLVQSGAEVKKPGASVKVSCKAS GYTFTGYYVH WVRQAPGQGLEWIG WIYPGNVNTKYNEKFKA RVTMTRDTSISTAYMELSRLRSDDTVYYYCAR
huVH1b     QVQLVQSGAEVKKPGASVKISCKAS GYTFTGYYVH WVRQAPGQGLEWIG WIYPGNVNTKYNEKFKA RATLTRDTSISTGYMELSRLRSDDTVYYYCAR
huVH1c     QVQLVQSGAEVKKPGASVKISCKAS GYTFTGYYVH WVRQAPGQGLEWIG WIYPGNVNTKYNEKFKA RATLTADTSISTGYMELSRLRSDDTVYYYCAR
huVH1d     QVQLVQSGAEVKKPGASVKISCKAS GYTFTGYYVH WVRQAPGQGLEWIG WIYPGNVNTKYNEKFKA RATLTADKSISTGYMELSRLRSDDTVYYYCAR
                                                                Q Q Q
                                                                S S
```

```
AbM                                              50 a                 60
huVH1e     QVQLVQSGAEVKKPGASVKVSCKAS GYTFTGYYVH WVRQAPGQGLEWIG WIYPGNVNTKYAQKFQG RVTMTRDTSISTAYMELSRLRSDDTVYYYCAR
huVH1f     QVQLVQSGAEVKKPGASVKISCKAS GYTFTGYYVH WVRQAPGQGLEWIG WIYPGNVNTKYAQKFQG RATLTRDTSISTGYMELSRLRSDDTVYYYCAR
huVH1g     QVQLVQSGAEVKKPGASVKISCKAS GYTFTGYYVH WVRQAPGQGLEWIG WIYPGNVNTKYAQKFQG RATLTADTSISTGYMELSRLRSDDTVYYYCAR
huVH1h     QVQLVQSGAEVKKPGASVKISCKAS GYTFTGYYVH WVRQAPGQGLEWIG WIYPGNVNTKYAQKFQG RATLTADKSISTGYMELSRLRSDDTVYYYCAR
                                                                Q Q
                                                                S S                                                  F
```

```
seq        100       110       120
               b   i b b b
5-13A      SPYYGTTYYYTMDY WGQGTSVTVSS (2)
                         *
huVH1a     SPYYGTTYYYTMDY WGQGTLVTVSS (24)
huVH1b     SPYYGTTYYYTMDY WGQGTLVTVSS (25)
huVH1c     SPYYGTTYYYTMDY WGQGTLVTVSS (26)
huVH1d     SPYYGTTYYYTMDY WGQGTLVTVSS (27)

AbM        100abcdef     110
huVH1e     SPYYGTTYYYTMDY WGQGTLVTVSS (28)
huVH1f     SPYYGTTYYYTMDY WGQGTLVTVSS (29)
huVH1g     SPYYGTTYYYTMDY WGQGTLVTVSS (30)
huVH1h     SPYYGTTYYYTMDY WGQGTLVTVSS (31)
```

Figure 2B: Antibody R21-5-13A VH
Humanized sequence based on IMGT IGHV3-48 acceptor framework (method 2)
EVQLVESGGGLVQPGGSLRLSCAAS GFTFSSYSMN WVRQAPGKGLEWVS YISSSSSTIYYADSVKG RFTISRDNAKNSLYLQMNSLRAEDTAVYYCAR (190)
Joining region    IMGT J00256|IGHJ4*01|YFDYWGQGTLVTVSS (189)

```
seq            b b b          p  b b b b             b  bi i    b b     b i ibb b             b  b  b b      bibibb
               *             *        *           *       **    *      *     ********    ** *** ******    * **    *
5-13A     QVQLQQSGPELVKPGASVRISCKAS GYTFTGYYVH WVKQRPGQGLEWIG KATLTADKSSTGYMQLSRLTSEDSAVYFCAR
                    10           20           30          40           50          60          70          80          90

3-48      EVQLVESGGGLVQPGGSLRLSCAAS GFTFSSYSMN WVRQAPGKGLEWVS YISSSSSTIYYADSVKG RFTISRDNAKNSLYLQMNSLRAEDTAVYYCAR (190)
huVH3a    EVQLVESGGGLVQPGGSLRLSCAAS GYTFTGYYVH WVRQAPGKGLEWIG WIYPGNVNTKYNEKFKA RFTISRDNAKNSLYLQMNSLRAEDTAVYYCAR
huVH3b    EVQLVESGGGLVQPGGSVRISCAAS GYTFTGYYVH WVRQAPGKGLEWIG WIYPGNVNTKYNEKFKA RATLSRDNAKNSGYMQLNSLRAEDTAVYYCAR
huVH3c    EVQLVESGGGLVQPGGSVRISCAAS GYTFTGYYVH WVRQAPGKGLEWIG WIYPGNVNTKYNEKFKA RATLSADNAKNSGYMQLNSLRAEDTAVYYCAR
huVH3d    EVQLVESGGGLVQPGGSVRISCAAS GYTFTGYYVH WVRQAPGKGLEWIG WIYPGNVNTKYNEKFKA RATLSADKAKNSGYMQLNSLRAEDTAVYYCAR
                                                                            Q Q                                  F
                                                                            S S

AbM                                                    b                        a              abc
huVH3e    EVQLVESGGGLVQPGGSVRISCAAS GYTFTGYYVH WVRQAPGKGLEWIG WIYPGNVNTKYADSVKG RFTISRDNAKNSLYLQMNSLRAEDTAVYYCAR
huVH3f    EVQLVESGGGLVQPGGSVRISCAAS GYTFTGYYVH WVRQAPGKGLEWIG WIYPGNVNTKYADSVKG RATLSRDNAKNSGYMQLNSLRAEDTAVYYCAR
huVH3g    EVQLVESGGGLVQPGGSVRISCAAS GYTFTGYYVH WVRQAPGKGLEWIG WIYPGNVNTKYADSVKG RATLSADNAKNSGYMQLNSLRAEDTAVYYCAR
huVH3h    EVQLVESGGGLVQPGGSVRISCAAS GYTFTGYYVH WVRQAPGKGLEWIG WIYPGNVNTKYADSVKG RATLSADKAKNSGYMQLNSLRAEDTAVYYCAR
                                                                           Q Q                                   F
                                                                           S S seq       100abcdef      110         120
               b          i   b b b
               *                    *
5-13A     SPYYGTTYYYTMDY WGQGTSVTVSS (2)

huVH3a    SPYYGTTYYYTMDY WGQGTLVTVSS (32)
huVH3b    SPYYGTTYYYTMDY WGQGTLVTVSS (33)
huVH3c    SPYYGTTYYYTMDY WGQGTLVTVSS (34)
huVH3d    SPYYGTTYYYTMDY WGQGTLVTVSS (35)

AbM       100abcdef      110
huVH3e    SPYYGTTYYYTMDY WGQGTLVTVSS (36)
huVH3f    SPYYGTTYYYTMDY WGQGTLVTVSS (37)
huVH3g    SPYYGTTYYYTMDY WGQGTLVTVSS (38)
huVH3h    SPYYGTTYYYTMDY WGQGTLVTVSS (39)
```

Figure 2C
(1) CDR sequences noted in bold. CDR definitions are from website www.bioinf.org.uk/abs/ and are either a combination of Kabat&AbM (seq) or solely AbM (AbM).
(2) Human germline and joining sequences from IMGT® the international ImMunoGeneTics® information system www.imgt.org (founder and director: Marie-Paule Lefranc, Montpellier, France).
(3) Residue numbering shown as sequential (seq) or according to Chothia from website www.bioinf.org.uk/abs/ (AbM).
(4) "b" notes buried sidechain; "p" notes partially buried sidechain; "i" notes sidechain at interface between VH and VL domains.
(5) Sequence differences between each humanized sequence and murine sequence noted by asterisk (*).
(6) Humanized framework mutations from human sequence to parental mouse sequence are noted in sequence in bold. Potential additional mutations in frameworks are noted below sequence; those in bold would be altered first, followed by the others if needed.
(7) Potential changes in CDR sequences noted below each CDR sequence. These may prevent asparagine (N) deamidation.

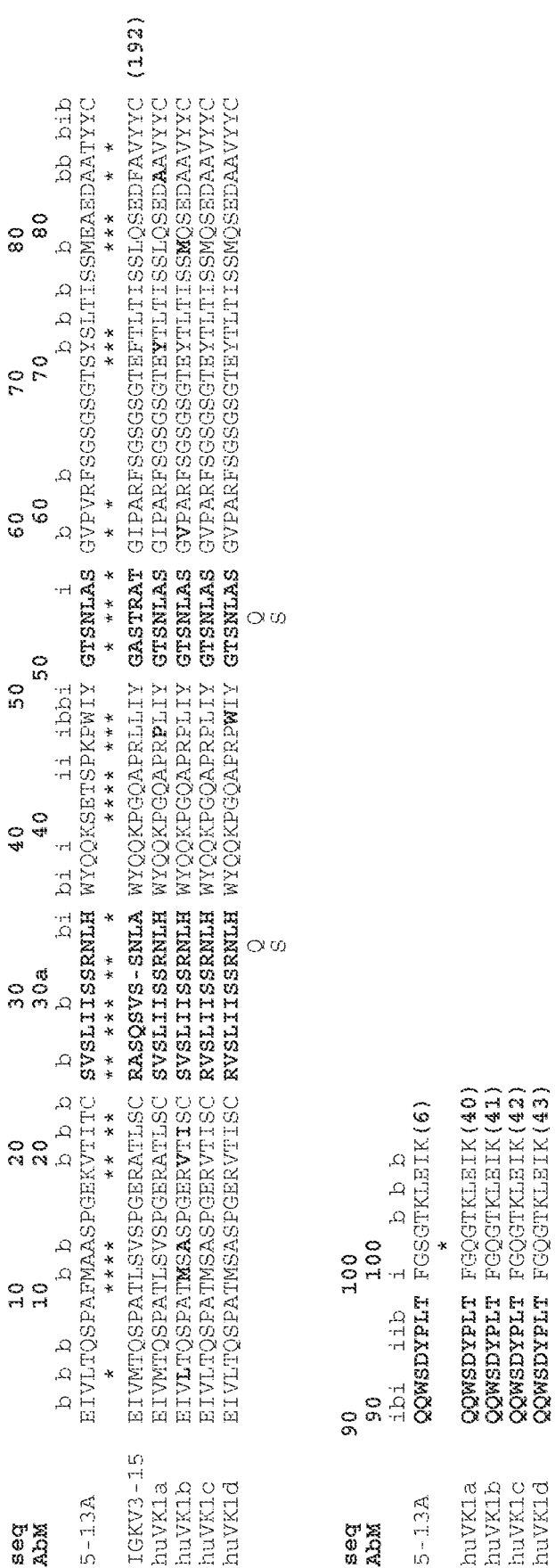
Figure 3A: Antibody R21-5-13A VL

Figure 3B: Antibody R21-5-13A VL

Humanized sequence based on IMGT IGKV1-39 acceptor framework (method 2)
DIQMTQSPSSLSASVGDRVTITC RASQSISSYLN WYQQKPGKAPKLLIY AASSLQS GVPSRFSGSGSGTDFTLTISSLQPEDFATYYC QQSYSTP (194)
Joining region IMGT J00242|IGKJ2*01|YTFGQGTKLEIK (193)

```
                             10         20         30        40         50          60         70         80
seq                          10         20         30a       40         50          60         70         80
AbM                    b b b b b    b b b b b    b bi b   bi i  ii ibbi i         b b       b b b    b b b  bb bib
5-13A             EIVLTQSPAFMAASPGEKVTITC SVSLIISSRNLH WYQQKSETSPKPWIY GTSNLAS GVPVRFSGSGSGTDFTLTISSMEAEDAATYYC
                       * **            ****   *     *         ****    * *                *                   ***

IGKV1-39          DIQMTQSPSSLSASVGDRVTITC RASQSISS-YLN WYQQKPGKAPKLLIY AASSLQS GVPSRFSGSGSGTDFTLTISSLQPEDFATYYC (195)
huVK2a            DIQMTQSPSSLSASVGDRVTITC SVSLIISSRNLH WYQQKPGKAPKPLIY GTSNLAS GVPSRFSGSGSGTDYTLTISSLQPEDAATYYC
huVK2b            DIQLTQSPSSMSASVGDRVTITC SVSLIISSRNLH WYQQKPGKAPKPLIY GTSNLAS GVPSRFSGSGSGTDYTLTISSMQPEDAATYYC
huVK2b            DIQLTQSPSSMSASVGDRVTITC RVSLIISSRNLH WYQQKPGKAPKPLIY GTSNLAS GVPSRFSGSGSGTDYTLTISSMQPEDAATYYC
huVK2d            DIQLTQSPSSMSASVGDRVTITC RVSLIISSRNLH WYQQKPGKAPKPWIY GTSNLAS GVPSRFSGSGSGTDYTLTISSMQPEDAATYYC
                                                                    Q                Q
                                                                    S                S 90        100
seq                     90        100
AbM                 ibi iib i    b b b
5-13A             QQWSDYPLT FGSGTKLEIK(6)
                      * huVK2a             QQWSDYPLT FGQGTKLEIK(44)
huVK2b             QQWSDYPLT FGQGTKLEIK(45)
huVK2c             QQWSDYPLT FGQGTKLEIK(46)
huVK2d             QQWSDYPLT FGQGTKLEIK(47)
```

Figure 3C
(1) CDR sequences noted in bold. CDR definitions are from website www.bioinf.org.uk/abs/ and are either a combination of Kabat&AbM (seq) or solely AbM (AbM).
(2) Human germline and joining sequences from IMGT® the international ImMunoGeneTics® information system www.imgt.org (founder and director: Marie-Paule Lefranc, Montpellier, France).
(3) Residue numbering shown as sequential (seq) or according to Chothia from website www.bioinf.org.uk/abs/ (AbM).
(4) "b" notes buried sidechain; "i" notes sidechain at interface between VH and VL domains.
(5) Sequence differences between each humanized sequence and murine sequence noted by asterisk (*).
(6) Humanized framework mutations from human sequence to parental mouse sequence are noted in sequence in bold. Potential additional mutations in frameworks are noted below sequence; those in bold would be altered first, followed by the others if needed.
(7) Potential changes in CDR sequences noted below each CDR sequence. These may prevent asparagine (N) deamidation.

Figure 4A: Antibody R21-5-165C VH

Humanized sequence based on IMGT IGHV3-21 acceptor framework (method 1)
EVQLVESGGGLVKPGGSLRLSCAAS GFTFSSYSMN WVRQAPGKGLEWVS SISSSSSYIYYADSVKG RFTISRDNAKNSLYLQMNSLRAEDTAVYYCAR (196)
Joining region IMGT J00256|IGHJ4*01|YFDYWGQGTLVTVSS (189)

```
seq             10                  20                  30           40                  50                   60                  70                  80              90
         b b b  b          p  b b b b                b b         b b  b i i             i ibb  b b             b  b i                 b b b                b  b b b   bibibb
5-165C   EVQLVESGGGLVKPGGSLRLSCAAF GFTFSSYSMN WVRQTPDKRLEWVA TITSGGIYTTYYPDSVKG RFTISRDNAKNTLYLQMSSLKSEETAMYYCAR
                              *                         *   *         * ***  * *            *         * *** *  *   *

3-21     EVQLVESGGGLVKPGGSLRLSCAAS GFTFSSYSYSMN WVRQAPGKGLEWVS SISSSSSYIYYYADSVKG RFTISRDNAKNSLYLQMNSLRAEDTAVYYCAR
huVH1a   EVQLVESGGGLVKPGGSLRLSCAAS GFTFSRYGMS   WVRQAPGKGLEWVS TITSGGIYTTYYPDSVKG RFTISRDNAKNSLYLQMNSLRAEDTAVYYCAR
huVH1b   EVQLVESGGGLVKPGGSLRLSCAAS GFTFSRYGMS   WVRQAPGKGLEWVS TITSGGIYTTYYPDSVKG RFTISRDNAKNSLYLQMNSLRAEDTAVYYCAR
                                          F

AbM             10                  20                  30           40                  50   a               60                  70                  80   abc        90
huVH1c   EVQLVESGGGLVKPGGSLRLSCAAS GFTFSRYGMS   WVRQAPGKGLEWVA TITSGGIYTTYYADSVKG RFTISRDNAKNSLYLQMNSLRAEDTAVYYCAR
huVH1d   EVQLVESGGGLVKPGGSLRLSCAAS GFTFSRYGMS   WVRQAPGKGLEWVA TITSGGIYTTYYADSVKG RFTISRDNAKNSLYLQMNSLRAEDTAVYYCAR
                                          F seq      100            110            120
                    b   i   b b b
5-165C   HGQFGDYYGMDY WGQGTSVTVSS(5)
                         * huVH1a   HGQFGDYYGMDY WGQGTLVTVSS(48)
huVH1b   HGQFGDYYGMDY WGQGTLVTVSS(49)

AbM      100abcd        110
huVH1c   HGQFGDYYGMDY WGQGTLVTVSS(50)
huVH1d   HGQFGDYYGMDY WGQGTLVTVSS(51)
```

Figure 4B: Antibody R21-5-165C VH

```
Humanized sequence based on IMGT IGHV3-48 acceptor framework (method 2)
EVQLVESGGGLVQPGGSLRLSCAASGFTFSSYSMNWVRQAPGKGLEWVSYISSSSTIYYADSVKGRFTISRDNAKNSLYLQMNSLRAEDTAVYYCAR (197)
Joining region IMGT J00256|IGHJ4*01|YFDYWGQGTLVTVSS (189)

seq              10          20          30          40          50          60          70          80          90
          b b b  p       p b b b        b b      b   bi i  ibb b b         i   bb b b       b b  b     b b  b     bibibb
5-165C   EVQLVESGGGLVQPGGSLKLSCAAFGFTFSSYSMNWVRQTPDKRLEWVSTITSGGIYTYYPDSVKGRFTISRDNAKNTLYLQMSSLKSEETAMYYCAR
             *                    *         *      *      *  * *****     *               *  * ***   *

3-48     EVQLVESGGGLVQPGGSLRLSCAASGFTFSSYSMNWVRQAPGKGLEWVSYISSSSTIYYADSVKGRFTISRDNAKNSLYLQMNSLRAEDTAVYYCAR (197)
huVH3a   EVQLVESGGGLVQPGGSLRLSCAASGFTFSRYGMSWVRQAPGKGLEWVSTITSGGIYTYYPDSVKGRFTISRDNAKNSLYLQMNSLRAEDTAVYYCAR
                                         F
huVH3b   EVQLVESGGGLVQPGGSLRLSCAASGFTFSRYGMSWVRQAPGKGLEWVATITSGGIYTYYPDSVKGRFTISRDNAKNSLYLQMNSLRAEDTAVYYCAR
                                         F

AbM              10          20          30          40          50 a        60          70          80 abc       90
huVH3c   EVQLVESGGGLVQPGGSLRLSCAASGFTFSRYGMSWVRQAPGKGLEWVSTITSGGIYTYYPDSVKGRFTISRDNAKNSLYLQMNSLRAEDTAVYYCAR
huVH3d   EVQLVESGGGLVQPGGSLRLSCAASGFTFSRYGMSWVRQAPGKGLEWVATITSGGIYTYYPDSVKGRFTISRDNAKNSLYLQMNSLRAEDTAVYYCAR seq            100          110         120
           b       b    i    b b b
5-165C   HGQFGDYYGMDYWGQGTSVTVSS (5)
                              *

100abcd             110
huVH3a   HGQFGDYYGMDYWGQGTLVTVSS (52)
huVH3b   HGQFGDYYGMDYWGQGTLVTVSS (53)

AbM      100abcd             110
huVH3c   HGQFGDYYGMDYWGQGTLVTVSS (54)
huVH3d   HGQFGDYYGMDYWGQGTLVTVSS (55)
```

Figure 4C
(1) CDR sequences noted in bold. CDR definitions are from website www.bioinf.org.uk/abs/ and are either a combination of Kabat&AbM (seq) or solely AbM (AbM).
(2) Human germline and joining sequences from IMGT® the international ImMunoGeneTics® information system www.imgt.org (founder and director: Marie-Paule Lefranc, Montpellier, France).
(3) Residue numbering shown as sequential (seq) or according to Chothia from website www.bioinf.org.uk/abs/ (AbM).
(4) "b" notes buried sidechain; "p" notes partially buried sidechain; "i" notes sidechain at interface between VH and VL domains.
(5) Sequence differences between each humanized sequence and murine sequence noted by asterisk (*).
(6) Humanized framework mutations from human sequence to parental mouse sequence are noted in sequence in bold. Potential additional mutations in frameworks are noted below sequence; those in bold would be altered first, followed by the others if needed.

Figure 5A: Antibody R21-5-165C VL

Humanized sequence based on IMGT IGKV2D-29 acceptor framework (method 1)
DIVMTQTPLSLSVTPGQPASISC KSSQSLLHSDGKTYLY WYLQKPGQPPQLLIY EVSNRFS GVPDRFSGSGSGTDFTLKISRVEAEDVGVYYC MQSIQLP (198)
Joining region IMGT J00242|IGKJ2*01|YTFGQGTKLEIK (193)

```
                10         20         30           40         50         60         70         80         90
seq             10         20         30abcde      40         50         60         70         80         90
AbM     b b  b    b  b b b   b b b    bi bi i ibbi      ii ibbi     i   b bi b b b    b  bb bib
5-165C  DVVMTQTPLSLPVSLGDQASISC RSSQSLLHSNGNTYLH WYLQKPGQSPKLLIY KVSNRFS GVPDRFSGSGSGTDFTLKISRVEAEDLGVYFC
          *  **  *  *  ***               *                    *                                       *
IGKV2D-29 DIVMTQTPLSLSVTPGQPASISC KSSQSLLHSDGKTYLY WYLQKPGQPPQLLIY EVSNRFS GVPDRFSGSGSGTDFTLKISRVEAEDVGVYYC (199)
huVK1a  DIVMTQTPLSLSVTPGQPASISC KSSQSLLHSNGNTYLH WYLQKPGQPPQLLIY EVSNRFS GVPDRFSGSGSGTDFTLKISRVEAEDVGVYYC
huVK1b  DIVMTQTPLSLSVTPGQPASISC RSSQSLLHSNGNTYLH WYLQKPGQPPQLLIY KVSNRFS GVPDRFSGSGSGTDFTLKISRVEADLGVYYC
                                   Q Q                         Q                                      F
                                   S S                         S
                                   G 90         100        110
seq      90         100        110
AbM      ibi  iiib  i   b b b
5-165C   SQSTHVPYT FGGGTKLEIK (9)
            *
huVK1a   SQSTHVPYT FGQGTKLEIK (56)
huVK1b   SQSTHVPYT FGQGTKLEIK (57)
```

Figure 5B: Antibody R21-5-165C VL
Humanized sequence based on IMGT IGKV1-39 acceptor framework (method 2)
DIQMTQSPSSLSASVGDRVTITC RASQSISSYLN WYQQKPGKAPKLLIY AASSLQS GVPSRFSGSGSGTDFTLTISSLQPEDFATYC QQSYSTP (200)
Joining region IMGT J00242|IGKJ2*01|YTFGQGTKLEIK (193)

```
                  10         20          30               40         50           60           70         80         90
seq               10         20          30abcde          40         50           60           70         80         90
AbM           b b b        b b b       b b  bi bi i  ii ibbi       bi bi i ii ibbi                i  b  b     b  b b b b  b bib
5-165C        DVVMTQTPLSLPVSLGDQASISC RSSQSLLHSNGNTYLH WYLQKPGQSPKLLIY KVSNRFS GVPDRFSGSGSGTDFTLKISRVEAEDLGVYFC (201)
                **                  ********           *         **        *    *          *****          ***

IGKV1-39      DIQMTQSPSSLSASVGDRVTITC RASQSI-----SSYLN WYQQKPGKAPKLLIY AASSLQS GVPSRFSGSGSGTDFTLTISSLQPEDFATYYC
huVK2a        DIQMTQSPSSLSASVGDRVTITC RSSQSLLHSNGNTYLH WYQQKPGKAPKLLIY KVSNRFS GVPSRFSGSGSGTDFTLTISSLQPEDFATYYC
huVK2b        DVQMTQSPSSLSVSVGDRATITC RSSQSLLHSNGNTYLH WYQQKPGKAPKLLIY KVSNRFS GVPSRFSGSGSGTDFTLTISSVQPEDFGTYYC
huVK2c        DVQMTQSPSSLSVSVGDRATITC RSSQSLLHSNGNTYLH WYQQKPGKAPKLLIY KVSNRFS GVPSRFSGSGSGTDFTLTISSVQPEDLGTYYC
                                          Q Q                Q                                              F
                                          S S                S
                                                             G 90         100        110
seq           90         100        110
AbM        ibi iib  i     b  b b
5-165C     SQSTHVPYT FGGGTKLEIK(9)
              * huVK2a     SQSTHVPYT FGQGTKLEIK(58)
huVK2b     SQSTHVPYT FGQGTKLEIK(59)
huVK2c     SQSTHVPYT FGQGTKLEIK(60)
```

Figure 5C
(1) CDR sequences noted in bold. CDR definitions are from website www.bioinf.org.uk/abs/ and are either a combination of Kabat&AbM (seq) or solely AbM (AbM).
(2) Human germline and joining sequences from IMGT® the international ImMunoGeneTics® information system www.imgt.org (founder and director: Marie-Paule Lefranc, Montpellier, France).
(3) Residue numbering shown as sequential (seq) or according to Chothia from website www.bioinf.org.uk/abs/ (AbM).
(4) "b" notes buried sidechain; "i" notes sidechain at interface between VH and VL domains.
(5) Sequence differences between each humanized sequence and murine sequence noted by asterisk (*).
(6) Humanized framework mutations from human sequence to parental mouse sequence are noted in sequence in bold. Potential additional mutations in frameworks are noted below sequence; those in bold would be altered first, followed by the others if needed.
(7) Potential changes in CDR sequences noted below each CDR sequence. These may prevent asparagine (N) deamidation or Asp-Gly (DG) isoaspartate formation.

Figure 6A: Antibody R21-9-8B VH

Humanized sequence based on IMGT IGHV7-4-1*02 acceptor framework (method 1)
QVQLVQSGSELKKPGASVKVSCKAS GYTFTSYAMN WVRQAPGQGLEWMG WINTNTGNPTYAQGFTG RFVFSLDTSVSTAYLQISSLKAEDTAVYYCAR (202)
Joining region    IMGT J00256|IGHJ4*01|YFDYWGQGTLVTVSS (189)

```
seq            b b b   b      p b b b  b bii     i ibb b  b       b b b b b b b bibibb
               10            20           30             40          50           60          70          80          90
9-8B       QIQLVQSGPELKKPGETVKISCKAS GYTFTSYAMN WVKQAPGKGLKWMG WINTNTGNPTYAQGFTG RFAFSLETSASTAYLQINNLKNEDTATYFCAR
                         *         **    **                *                                  *         **   * *     **
7-4-1      QVQLVQSGSELKKPGASVKVSCKAS GYTFTSYAMN WVRQAPGQGLEWMG WINTNTGNPTYAQGFTG RFVFSLDTSVSTAYLQISSLKAEDTAVYYCAR (202)
huVH7a     QVQLVQSGSELKKPGASVKVSCKAS GYTFTFHYGMN WVRQAPGQGLEWMG WINTYTGELTYADDFKG RFVFSLDTSVSTAYLQISSLKAEDTAVYYCAR
huVH7b     QVQLVQSGSELKKPGASVKISCKAS  GYTFTFHYGMN WVRQAPGQGLEWMG WINTYTGELTYADDFKG RFVFSLDTSVSTAYLQISSLKAEDTAVYYCAR
huVH7c     QIQLVQSGSELKKPGASVKISCKAS  GYTFTFHYGMN WVRQAPGQGLEWMG WINTYTGELTYADDFKG RFVFSLDTSVSTAYLQISSLKAEDTAVYYCAR AbM                                                         b b  i b                a                      abc
               10            20           30             40          50           60          70          80
huVH7d     QVQLVQSGSELKKPGASVKVSCKAS GYTFTFHYGMN WVRQAPGQGLEWMG WINTYTGELTYAQGFTG RFVFSLDTSVSTAYLQISSLKAEDTAVYYCAR
huVH7e     QVQLVQSGSELKKPGASVKISCKAS  GYTFTFHYGMN WVRQAPGQGLEWMG WINTYTGELTYAQGFTG RFVFSLDTSVSTAYLQISSLKAEDTAVYYCAR
huVH7f     QIQLVQSGSELKKPGASVKISCKAS  GYTFTFHYGMN WVRQAPGQGLEWMG WINTYTGELTYAQGFTG RFVFSLDTSVSTAYLQISSLKAEDTAVYYCAR
                                                                        Q                                  T
                                                                        S                                  F seq            b b    i b b b
              100           110          120
9-8B       RAYYRYDYVMDY WGQGTSVTVSS (3)
                 *
huVH7a     RAYYRYDYVMDY WGQGTLVTVSS (61)
huVH7b     RAYYRYDYVMDY WGQGTLVTVSS (62)
huVH7c     RAYYRYDYVMDY WGQGTLVTVSS (63)

AbM            100abcd        110
huVH7d     RAYYRYDYVMDY WGQGTLVTVSS (64)
huVH7e     RAYYRYDYVMDY WGQGTLVTVSS (65)
huVH7f     RAYYRYDYVMDY WGQGTLVTVSS (66)
```

Figure 6B: Antibody R21-9-8B VH
Humanized sequence based on IMGT IGHV1-18*01 acceptor framework (method 1)
QVQLVQSGAEVKKPGASVKVSCKAS GYTFTSYGIS WVRQAPGQGLEWMG WISAYNGNTNYAQKLQG RVTMTTDTSTSTAYMELRSLRSDDTAVYYCAR (203)
Joining region      IMGT J00256|IGHJ4*01|YFDYWGQGTLVTVSS (189)

```
seq              10             20              30              40              50              60              70              80              90
             b b  b         p   b b b b              b b         b i i   i ibb b              b i  ibb b                          i b          b b  b              b b  b   b       bibibb
9-8B    QIQLVQSGPELKPGETVKISCKAS  GYTFTSYGIS  WVKQAPGKGLKWMG  WISAYNGNTNYAQKLQG  RFAFSLETSASTAYLQINNLKNEDTATYFCAR (203)
         *                           *                  *              *                 ******           ******* *
1-18    QVQLVQSGAEVKKPGASVKVSCKAS GYTFTHYGMN  WVRQAPGQGLEWMG  WINTYTGELTTYADDFKG RVTMTTDTSTSTAYMELRSLRSDDTAVYYCAR
huVH1a  QVQLVQSGAEVKKPGASVKVSCKAS GYTFTHYGMN  WVRQAPGQGLEWMG  WINTYTGELTTYADDFKG RVTMTTDTSTSTAYMELRSLRSDDTAVYYCAR
huVH1b  QVQLVQSGAEVKKPGASVKVSCKAS GYTFTHYGMN  WVRQAPGQGLEWMG  WINTYTGELTTYADDFKG RVTMFLDTSTSTAYMELRSLRSDDTAVYYCAR
huVH1c  QVQLVQSGAEVKKPGASVKISCKAS GYTFTHYGMN  WVRQAPGQGLEWMG  WINTYTGELTTYADDFKG RFTFTLDTSTAYLEIRSLRSDDTAVYYCAR
huVH1d  QIQLVQSGAEVKKPGASVKISCKAS GYTFTHYGMN  WVRQAPGQGLEWMG  WINTYTGELTTYADDFKG RFTFTLDTSTSTAYLEIRSLRSDDTAVYYCAR
                                                                                 Q                    T F
                                                                                 S AbM              10             20              30              40              50 a            60              70              80 abc          90
huVH1e  QVQLVQSGAEVKKPGASVKVSCKAS GYTFTHYGMN  WVRQAPGQGLEWMG  WINTYTGELTTYAQKLQG RVTMTTDTSTSTAYMELRSLRSDDTAVYYCAR
huVH1f  QVQLVQSGAEVKKPGASVKVSCKAS GYTFTHYGMN  WVRQAPGQGLEWMG  WINTYTGELTTYAQKLQG RVTMLDTSTSTAYMELRSLRSDDTAVYYCAR
huVH1g  QVQLVQSGAEVKKPGASVKISCKAS GYTFTHYGMN  WVRQAPGQGLEWMG  WINTYTGELTTYAQKLQG RFTFTLDTSTAYLEIRSLRSDDTAVYYCAR
huVH1h  QIQLVQSGAEVKKPGASVKISCKAS GYTFTHYGMN  WVRQAPGQGLEWMG  WINTYTGELTTYAQKLQG RFTFTLDTSTSTAYLEIRSLRSDDTAVYYCAR
                                                                                 Q                    T F
                                                                                 S seq           100      110          120
                       b    i    b b b
9-8B    RAYYRYDYVMDY WGQGTSVTVSS (3)
                              *
huVH1a  RAYYRYDYVMDY WGQGTLVTVSS (67)
huVH1b  RAYYRYDYVMDY WGQGTLVTVSS (68)
huVH1c  RAYYRYDYVMDY WGQGTLVTVSS (69)
huVH1d  RAYYRYDYVMDY WGQGTLVTVSS (70)

AbM     100abcd      110
huVH1e  RAYYRYDYVMDY WGQGTLVTVSS (71)
huVH1f  RAYYRYDYVMDY WGQGTLVTVSS (72)
huVH1g  RAYYRYDYVMDY WGQGTLVTVSS (73)
huVH1h  RAYYRYDYVMDY WGQGTLVTVSS (74)
```

Figure 6C: Antibody R21-9-8B VH

Humanized sequence based on IMGT IGHV3-48 acceptor framework (method 2)
EVQLVESGGGLVQPGGSLRLSCAAS GFTFSSYSMN WVRQAPGKGLEWVS YISSSSSTIYYADSVKG RFTISRDNAKNSLYLQMNSLRAEDTAVYYCAR (204)
Joining region   IMGT J00256|IGHJ4*01|YFDYWGQGTLVTVSS (189)

```
seq          b b b         p b b b b         b b            b  b i b b   b b               i b b     b b b   b b b  b    bibibb
              10           20           30           40           50           60           70           80           90
9-8B    QIQLVQSGPELKKPGETVKISCKAS GYTFTHYGMN WVKQAPGKGLKWMG WINTYTGELTYADDFKG RFAFSLETSASTAYLQINNLKNEDTATYFCAR (204)
         **  **     * *********  *  ****  * *  **  *  *    *  *  *********  **  ********   *   *   ** *   *
3-48    EVQLVESGGGLVQPGGSLRLSCAAS GFTFSSYSMN WVRQAPGKGLEWVS YISSSSSTIYYADSVKG RFTISRDNAKNSLYLQMNSLRAEDTAVYYCAR
huVH3a  EVQLVESGGGLVQPGGSLRLSCAAS GYTFTHYGMN WVRQAPGKGLEWVS WINTYTGELTYADDFKG RFTISRDNAKNSLYLQMNSLRAEDTAVYYCAR
huVH3b  EVQLVESGGGLVQPGGSLRISCAAS GYTFTHYGMN WVRQAPGKGLEWMG WINTYTGELTYADDFKG RFTFSLDNAKNSAVLQINSLRAEDTAVYYCAR
huVH3c  EIQLVESGGGLVQPGGSLRISCAAS GYTFTHYGMN WVRQAPGKGLEWMG WINTYTGELTYADDFKG RFTFSLDTAKNSAVLQINSLRAEDTAVYYCAR
                                                              Q                                T F
                                                              S AbM          b b         b b i b b b       b b            b b         a          b b b       abc          b bibibb
              10           20           30           40           50           60           70           80           90
huVH3d  EVQLVESGGGLVQPGGSLRLSCAAS GYTFTHYGMN WVRQAPGKGLEWVS WINTYTGELTYADSVKG RFTISRDNAKNSLYLQMNSLRAEDTAVYYCAR
huVH3e  EVQLVESGGGLVQPGGSLRISCAAS GYTFTHYGMN WVRQAPGKGLEWMG WINTYTGELTYADSVKG RFTFSLDNAKNSAVLQINSLRAEDTAVYYCAR
huVH3f  EIQLVESGGGLVQPGGSLRISCAAS GYTFTHYGMN WVRQAPGKGLEWMG WINTYTGELTYADSVKG RFTFSLDTAKNSAVLQINSLRAEDTAVYYCAR
                                                              Q                F                T F
                                                              S seq         100          110        120
                          b   i  b b b
9-8B    RAYYRYDYVMDY WGQGTSVTVSS (3)
             *
huVH3a  RAYYRYDYVMDY WGQGTLVTVSS (75)
huVH3b  RAYYRYDYVMDY WGQGTLVTVSS (76)
huVH3c  RAYYRYDYVMDY WGQGTLVTVSS (77)

AbM        100abcd          110
huVH3d  RAYYRYDYVMDY WGQGTLVTVSS (78)
huVH3e  RAYYRYDYVMDY WGQGTLVTVSS (79)
huVH3f  RAYYRYDYVMDY WGQGTLVTVSS (80)
```

Figure 6D
(1) CDR sequences noted in bold. CDR definitions are from website www.bioinf.org.uk/abs/ and are either a combination of Kabat&AbM (seq) or solely AbM (AbM).
(2) Human germline and joining sequences from IMGT® the international ImMunoGeneTics® information system www.imgt.org (founder and director: Marie-Paule Lefranc, Montpellier, France).
(3) Residue numbering shown as sequential (seq) or according to Chothia from website www.bioinf.org.uk/abs/ (AbM).
(4) "b" notes buried sidechain; "p" notes partially buried sidechain; "i" notes sidechain at interface between VH and VL domains.
(5) Sequence differences between human and murine germlines noted by asterisk. (*).
(6) Potential changes in CDR sequences noted below each CDR sequence. These may prevent asparagine (N) deamidation.

Figure 7A: Antibody R21-9-8B VL

Humanized sequence based on IMGT IGKV1-16 acceptor framework (method 1)
DIQMTQSPSSLSASVGDRVTITC RASQGISNYLA WFQQKPGKAPKSLIY AASSLQS GVPSRFSGSGSGTDFTLTISSLQPEDFATYYCQQYNSYP (205)
Joining region IMGT J00242|IGKJ2*01|YTFGQGTKLEIK (193)

```
                  10         20         30         40         50         60         70         80
                  10         20         30         40         50         60         70         80
seq             b b b       b b b       b  b  bi bi i   ii ibbi     b  b        b  b        b b  b       bb bib
AbM
9-8B            DIVMTQSQKFMSTSVGDRVTITC KASHNVGTNVA WFQQKPGQSPKALIY SASYRYS GVPGRFTGSGSGTDFTLTISNVQSEDLAEYFC (206)
                ****     *           ***           **     *                *                **  **   *  *

IGKV1-16        DIQMTQSPSSLSASVGDRVTITC RASQGISNYLA WFQQKPGKAPKSLIY AASSLQS GVPSRFSGSGSGTDFTLTISSLQPEDFATYYC
huVK1a          DIQMTQSPSSLSASVGDRVTITC KASHNVGTNVA WFQQKPGKAPKSLIY AASSLQS GVPSRFSGSGSGTDFTLTISSLQPEDFATYYC
huVK1b          DIQMTQSPSSLSASVGDRVTITC KASHNVGTNVA WFQQKPGKAPKALIY SASYRYS GVPSRFSGSGSGTDFTLTISSLQPEDFATYYC
huVK1c          DIQMTQSPSSMSASVGDRVTVTC KASHNVGTNVA WYQQKPGKAPKALIY SASYRYS GVPSRFSGSGSGTDFTLTISSVQPEDFATYYC
                                                                                                  L   F 90        100
                  90        100
seq             ibi iib i   b b b
AbM
9-8B            HQYNNYPYT FGGGTKLEIK (7)
                           * huVK1a          HQYNNYPYT FGQGTKLEIK (81)
huVK1b          HQYNNYPYT FGQGTKLEIK (82)
huVK1c          HQYNNYPYT FGQGTKLEIK (83)
                QQ
                SS
```

Figure 7B: Antibody R21-9-8B VL

Potential humanized sequence based on IMGT IGKV1-39 acceptor framework (method 2)
DIQMTQSPSSLSASVGDRVTITC RASQSISSYLN WYQQKPGKAPKLLIY AASSLQS GVPSRFSGSGSGTDFTLTISSLQPEDFATYYC QQSYSTP (207)
Joining region  IMGT J00242|IGKJ2*01|YTFGQGTKLEIK (193)

```
              10         20         30         40         50         60         70         80
              10         20         30         40         50         60         70         80
seq           b b    b b   b b b    b b b b   bi bb i   iii ibbi    i       b  b       b b b  b   bb bib
AbM
9-8B          DIVMTQSQKFMSTSVGDRVSVTC KASHNVGTNVA WYQQKPGQSPKALIY SASYRYS GVPGRFTGSGSGTDFTLTISNVQSEDLAEYFC
              *   ****  *    **          **              **            *      *  *  *   ** *  *   * *

IGKV1-39      DIQMTQSPSSLSASVGDRVTITC RASQSISSYLN WYQQKPGKAPKLLIY AASSLQS GVPSRFSGSGSGTDFTLTISSLQPEDFATYYC (208)
huVK2a        DIQMTQSPSSLSASVGDRVTITC KASHNVGTNVA WYQQKPGKAPKLLIY AASSLQS GVPSRFSGSGSGTDFTLTISSLQPEDFATYYC
huVK2b        DIQMTQSPSSLSASVGDRVTITC RASHNVGTNVA WYQQKPGKAPKALIY SASYRYS GVPSRFSGSGSGTDFTLTISSLQPEDFATYYC
huVK2c        DIQMTQSPSSMSASVGDRVTVTC RASHNVGTNVA WYQQKPGKAPKALIY SASYRYS GVPSRFSGSGSGTDFTLTISSVQPEDFATYYC
                         Q                                                                L
                         S                                                                F 90        100
              90        100
seq           ibi iib i  b b b
AbM
9-8B          HQYNNYPYT FGGGTKLEIK (7)
              * huVK2a        HQYNNYPYT FGQGTKLEIK (84)
huVK2b        HQYNNYPYT FGQGTKLEIK (85)
huVK2c        HQYNNYPYT FGQGTKLEIK (86)
              QQ
              SS
```

Figure 7C
(1) CDR sequences noted in bold. CDR definitions are from website www.bioinf.org.uk/abs/ and are either a combination of Kabat&AbM (seq) or solely AbM (AbM).
(2) Human germline and joining sequences from IMGT® the international ImMunoGeneTics® information system www.imgt.org (founder and director: Marie-Paule Lefranc, Montpellier, France).
(3) Residue numbering shown as sequential (seq) or according to Chothia from website www.bioinf.org.uk/abs/ (AbM).
(4) "b" notes buried sidechain; "i" notes sidechain at interface between VH and VL domains.
(5) Sequence differences between each humanized sequence and murine sequence noted by asterisk (*).
(6) Humanized framework mutations from human sequence to parental mouse sequence are noted in sequence in bold. Potential additional mutations in frameworks are noted below sequence; those in bold would be altered first, followed by the others if needed.
(7) Potential changes in CDR sequences noted below each CDR sequence. These may prevent asparagine (N) deamidation.

SEQUENCE LISTING

<160> NUMBER OF SEQ ID NOS: 208

<210> SEQ ID NO 1
<211> LENGTH: 510
<212> TYPE: PRT
<213> ORGANISM: Homo sapiens
<220> FEATURE:
<223> OTHER INFORMATION: human CD39 sequence

<400> SEQUENCE: 1

```
Met Glu Asp Thr Lys Glu Ser Asn Val Lys Thr Phe Cys Ser Lys Asn
1               5                   10                  15

Ile Leu Ala Ile Leu Gly Phe Ser Ser Ile Ala Val Ile Ala Leu
            20                  25                  30

Leu Ala Val Gly Leu Thr Gln Asn Lys Ala Leu Pro Glu Asn Val Lys
        35                  40                  45

Tyr Gly Ile Val Leu Asp Ala Gly Ser Ser His Thr Ser Leu Tyr Ile
    50                  55                  60

Tyr Lys Trp Pro Ala Glu Lys Glu Asn Asp Thr Gly Val Val His Gln
65                  70                  75                  80

Val Glu Glu Cys Arg Val Lys Gly Pro Gly Ile Ser Lys Phe Val Gln
                85                  90                  95

Lys Val Asn Glu Ile Gly Ile Tyr Leu Thr Asp Cys Met Glu Arg Ala
                100                 105                 110

Arg Glu Val Ile Pro Arg Ser Gln His Gln Glu Thr Pro Val Tyr Leu
            115                 120                 125

Gly Ala Thr Ala Gly Met Arg Leu Leu Arg Met Glu Ser Glu Glu Leu
130                 135                 140

Ala Asp Arg Val Leu Asp Val Val Glu Arg Ser Leu Ser Asn Tyr Pro
145                 150                 155                 160

Phe Asp Phe Gln Gly Ala Arg Ile Ile Thr Gly Gln Glu Glu Gly Ala
                165                 170                 175

Tyr Gly Trp Ile Thr Ile Asn Tyr Leu Leu Gly Lys Phe Ser Gln Lys
                180                 185                 190

Thr Arg Trp Phe Ser Ile Val Pro Tyr Glu Thr Asn Asn Gln Glu Thr
            195                 200                 205

Phe Gly Ala Leu Asp Leu Gly Gly Ala Ser Thr Gln Val Thr Phe Val
210                 215                 220

Pro Gln Asn Gln Thr Ile Glu Ser Pro Asp Asn Ala Leu Gln Phe Arg
225                 230                 235                 240

Leu Tyr Gly Lys Asp Tyr Asn Val Tyr Thr His Ser Phe Leu Cys Tyr
                245                 250                 255

Gly Lys Asp Gln Ala Leu Trp Gln Lys Leu Ala Lys Asp Ile Gln Val
                260                 265                 270

Ala Ser Asn Glu Ile Leu Arg Asp Pro Cys Phe His Pro Gly Tyr Lys
            275                 280                 285

Lys Val Val Asn Val Ser Asp Leu Tyr Lys Thr Pro Cys Thr Lys Arg
290                 295                 300

Phe Glu Met Thr Leu Pro Phe Gln Gln Phe Glu Ile Gln Gly Ile Gly
305                 310                 315                 320

Asn Tyr Gln Gln Cys His Gln Ser Ile Leu Glu Leu Phe Asn Thr Ser
                325                 330                 335

Tyr Cys Pro Tyr Ser Gln Cys Ala Phe Asn Gly Ile Phe Leu Pro Pro
            340                 345                 350

Leu Gln Gly Asp Phe Gly Ala Phe Ser Ala Phe Tyr Phe Val Met Lys
        355                 360                 365

Phe Leu Asn Leu Thr Ser Glu Lys Val Ser Glu Lys Val Thr Glu
    370                 375                 380

Met Met Lys Lys Phe Cys Ala Gln Pro Trp Glu Glu Ile Lys Thr Ser
385                 390                 395                 400

Tyr Ala Gly Val Lys Glu Lys Tyr Leu Ser Glu Tyr Cys Phe Ser Gly
                405                 410                 415
```

```
Thr Tyr Ile Leu Ser Leu Leu Leu Gln Gly Tyr His Phe Thr Ala Asp
                420                 425                 430

Ser Trp Glu His Ile His Phe Ile Gly Lys Ile Gln Gly Ser Asp Ala
                435                 440                 445

Gly Trp Thr Leu Gly Tyr Met Leu Asn Leu Thr Asn Met Ile Pro Ala
    450                 455                 460

Glu Gln Pro Leu Ser Thr Pro Leu Ser His Ser Thr Tyr Val Phe Leu
465                 470                 475                 480

Met Val Leu Phe Ser Leu Val Leu Phe Thr Val Ala Ile Ile Gly Leu
                485                 490                 495

Leu Ile Phe His Lys Pro Ser Tyr Phe Trp Lys Asp Met Val
                500                 505                 510

<210> SEQ ID NO 2
<211> LENGTH: 123
<212> TYPE: PRT
<213> ORGANISM: Artificial Sequence
<220> FEATURE:
<223> OTHER INFORMATION: anti-CD39 R21 Antibody clone 5-13A VH Sequence

<400> SEQUENCE: 2

Gln Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr Gly Tyr
            20                  25                  30

Tyr Val His Trp Val Lys Gln Arg Pro Gly Gln Gly Leu Glu Trp Ile
        35                  40                  45

Gly Trp Ile Tyr Pro Gly Asn Val Asn Thr Lys Tyr Asn Glu Lys Phe
    50                  55                  60

Lys Ala Lys Ala Thr Leu Thr Ala Asp Lys Ser Ser Thr Gly Tyr
65                  70                  75                  80

Met Gln Leu Ser Arg Leu Thr Ser Glu Asp Ser Ala Val Tyr Phe Cys
                85                  90                  95

Ala Arg Ser Pro Tyr Tyr Gly Thr Thr Tyr Tyr Tyr Thr Met Asp Tyr
            100                 105                 110

Trp Gly Gln Gly Thr Ser Val Thr Val Ser Ser
        115                 120

<210> SEQ ID NO 3
<211> LENGTH: 121
<212> TYPE: PRT
<213> ORGANISM: Artificial Sequence
<220> FEATURE:
<223> OTHER INFORMATION: anti-CD39 R21 Antibody clone 9-8B VH Sequence

<400> SEQUENCE: 3

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr His Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Leu Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
```

```
                85                  90                  95
Ala Arg Arg Ala Tyr Tyr Arg Tyr Asp Tyr Val Met Asp Tyr Trp Gly
            100                 105                 110

Gln Gly Thr Ser Val Thr Val Ser Ser
        115                 120

<210> SEQ ID NO 4
<211> LENGTH: 121
<212> TYPE: PRT
<213> ORGANISM: Artificial Sequence
<220> FEATURE:
<223> OTHER INFORMATION: anti-CD39 R21 Antibody clone 5-71A VH Sequence

<400> SEQUENCE: 4

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Leu Val
        35                  40                  45

Ala Tyr Ile Ser Ser Gly Ser Thr Ile Arg Tyr Tyr Ser Asp Thr Val
50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Phe Leu Tyr Glu Gly Phe Arg Tyr Gly Met Asp Tyr Trp Gly
            100                 105                 110

Gln Gly Thr Ser Val Thr Val Ser Ser
        115                 120

<210> SEQ ID NO 5
<211> LENGTH: 121
<212> TYPE: PRT
<213> ORGANISM: Artificial Sequence
<220> FEATURE:
<223> OTHER INFORMATION: anti-CD39 R21 Antibody clone 5-165C VH Sequence

<400> SEQUENCE: 5

Glu Val Gln Leu Val Glu Ser Gly Gly Asp Leu Val Lys Pro Gly Gly
1               5                   10                  15

Ser Leu Lys Leu Ser Cys Ala Ala Phe Gly Phe Thr Phe Ser Arg Tyr
            20                  25                  30

Gly Met Ser Trp Val Arg Gln Thr Pro Asp Lys Arg Leu Glu Trp Val
        35                  40                  45

Ala Thr Ile Thr Ser Gly Gly Ile Tyr Thr Tyr Tyr Pro Asp Ser Val
50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Glu Thr Ala Met Tyr Tyr Cys
                85                  90                  95

Ala Arg His Gly Gln Phe Gly Asp Tyr Tyr Gly Met Asp Tyr Trp Gly
            100                 105                 110

Gln Gly Thr Ser Val Thr Val Ser Ser
        115                 120

<210> SEQ ID NO 6
<211> LENGTH: 108
```

```
<212> TYPE: PRT
<213> ORGANISM: Artificial Sequence
<220> FEATURE:
<223> OTHER INFORMATION: anti-CD39 R21 Antibody clone 5-13A VL Sequence

<400> SEQUENCE: 6

Glu Ile Val Leu Thr Gln Ser Pro Ala Phe Met Ala Ala Ser Pro Gly
1               5                   10                  15

Glu Lys Val Thr Ile Thr Cys Ser Val Ser Leu Ile Ile Ser Ser Arg
            20                  25                  30

Asn Leu His Trp Tyr Gln Gln Lys Ser Glu Thr Ser Pro Lys Pro Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Asp Tyr Pro
                85                  90                  95

Leu Thr Phe Gly Ser Gly Thr Lys Leu Glu Ile Lys
            100                 105

<210> SEQ ID NO 7
<211> LENGTH: 107
<212> TYPE: PRT
<213> ORGANISM: Artificial Sequence
<220> FEATURE:
<223> OTHER INFORMATION: anti-CD39 R21 Antibody clone 9-8B VL Sequence

<400> SEQUENCE: 7

Asp Ile Val Met Thr Gln Ser Gln Lys Phe Met Ser Thr Ser Val Gly
1               5                   10                  15

Asp Arg Val Ser Val Thr Cys Lys Ala Ser His Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Gly Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys His Gln Tyr Asn Asn Tyr Pro Tyr
                85                  90                  95

Thr Phe Gly Gly Gly Thr Lys Leu Glu Ile Lys
            100                 105

<210> SEQ ID NO 8
<211> LENGTH: 112
<212> TYPE: PRT
<213> ORGANISM: Artificial Sequence
<220> FEATURE:
<223> OTHER INFORMATION: anti-CD39 R21 Antibody clone 5-71A VL Sequence

<400> SEQUENCE: 8

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
```

```
                    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Ile Tyr Tyr Cys Phe Gln Gly
                     85                  90                  95

Ser His Val Pro Asn Thr Phe Gly Gly Gly Thr Lys Leu Glu Ile Lys
                100                 105                 110

<210> SEQ ID NO 9
<211> LENGTH: 112
<212> TYPE: PRT
<213> ORGANISM: Artificial Sequence
<220> FEATURE:
<223> OTHER INFORMATION: anti-CD39 R21 Antibody clone 5-165C VL Sequence

<400> SEQUENCE: 9

Asp Val Val Met Thr Gln Thr Pro Leu Ser Leu Pro Val Ser Leu Gly
  1               5                  10                  15

Asp Gln Ala Ser Ile Ser Cys Arg Ser Gln Ser Leu Leu His Ser
                 20                  25                  30

Asn Gly Asn Thr Tyr Leu His Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                     85                  90                  95

Thr His Val Pro Tyr Thr Phe Gly Gly Gly Thr Lys Leu Glu Ile Lys
                100                 105                 110

<210> SEQ ID NO 10
<211> LENGTH: 10
<212> TYPE: PRT
<213> ORGANISM: Artificial Sequence
<220> FEATURE:
<223> OTHER INFORMATION: consensus sequence of VH CDR1
<220> FEATURE:
<221> NAME/KEY: VARIANT
<222> LOCATION: 6
<223> OTHER INFORMATION: Xaa = Gly, His, Ser or Arg
<220> FEATURE:
<221> NAME/KEY: VARIANT
<222> LOCATION: 7
<223> OTHER INFORMATION: Xaa = Tyr or Phe
<220> FEATURE:
<221> NAME/KEY: VARIANT
<222> LOCATION: 10
<223> OTHER INFORMATION: Xaa = His, Asn or Ser

<400> SEQUENCE: 10

Gly Phe Thr Phe Ser Xaa Xaa Gly Met Xaa
  1               5                  10

<210> SEQ ID NO 11
<211> LENGTH: 17
<212> TYPE: PRT
<213> ORGANISM: Artificial Sequence
<220> FEATURE:
<223> OTHER INFORMATION: consensus sequence of VH CDR2
<220> FEATURE:
<221> NAME/KEY: VARIANT
<222> LOCATION: 1
<223> OTHER INFORMATION: Xaa = Trp, Tyr or Thr
<220> FEATURE:
```

```
<221> NAME/KEY: VARIANT
<222> LOCATION: 3
<223> OTHER INFORMATION: Xaa = Tyr, Asn, Ser or Thr
<220> FEATURE:
<221> NAME/KEY: VARIANT
<222> LOCATION: 6
<223> OTHER INFORMATION: Xaa = Asn, Thr, Ser or Gly
<220> FEATURE:
<221> NAME/KEY: VARIANT
<222> LOCATION: 7
<223> OTHER INFORMATION: Xaa = Val, Gly, Thr or Ile
<220> FEATURE:
<221> NAME/KEY: VARIANT
<222> LOCATION: 8
<223> OTHER INFORMATION: Xaa = Asn, Glu, Ile or Tyr
<220> FEATURE:
<221> NAME/KEY: VARIANT
<222> LOCATION: 9
<223> OTHER INFORMATION: Xaa = Thr, Leu or Arg
<220> FEATURE:
<221> NAME/KEY: VARIANT
<222> LOCATION: 12
<223> OTHER INFORMATION: Xaa = Asn, Ala, Ser or Pro
<220> FEATURE:
<221> NAME/KEY: VARIANT
<222> LOCATION: 14
<223> OTHER INFORMATION: Xaa = Phe or Val

<400> SEQUENCE: 11

Xaa Ile Xaa Ser Gly Xaa Xaa Xaa Xaa Tyr Tyr Xaa Asp Xaa Val Lys
1               5                   10                  15

Gly

<210> SEQ ID NO 12
<211> LENGTH: 12
<212> TYPE: PRT
<213> ORGANISM: Artificial Sequence
<220> FEATURE:
<223> OTHER INFORMATION: consensus sequence of VH CDR3
<220> FEATURE:
<221> NAME/KEY: VARIANT
<222> LOCATION: 1
<223> OTHER INFORMATION: Xaa = Ser, Arg, Phe or His
<220> FEATURE:
<221> NAME/KEY: VARIANT
<222> LOCATION: 2
<223> OTHER INFORMATION: Xaa = Pro, Ala, Leu or Gly
<220> FEATURE:
<221> NAME/KEY: VARIANT
<222> LOCATION: 3
<223> OTHER INFORMATION: Xaa = Tyr or Gln
<220> FEATURE:
<221> NAME/KEY: VARIANT
<222> LOCATION: 4
<223> OTHER INFORMATION: Xaa = Tyr or Phe
<220> FEATURE:
<221> NAME/KEY: VARIANT
<222> LOCATION: 6
<223> OTHER INFORMATION: Xaa = Thr, Tyr, Phe or Asp
<220> FEATURE:
<221> NAME/KEY: VARIANT
<222> LOCATION: 7
<223> OTHER INFORMATION: Xaa = Thr, Asp, Arg or Tyr

<400> SEQUENCE: 12

Xaa Xaa Xaa Xaa Gly Xaa Xaa Tyr Gly Met Asp Tyr
1               5                   10

<210> SEQ ID NO 13
<211> LENGTH: 16
<212> TYPE: PRT
<213> ORGANISM: Artificial Sequence
<220> FEATURE:
<223> OTHER INFORMATION: consensus sequence of VL CDR1
```

```
<220> FEATURE:
<221> NAME/KEY: VARIANT
<222> LOCATION: 6
<223> OTHER INFORMATION: Xaa = Ile, Val or Leu
<220> FEATURE:
<221> NAME/KEY: VARIANT
<222> LOCATION: 7
<223> OTHER INFORMATION: Xaa = Ser, Gly, Val or Leu
<220> FEATURE:
<221> NAME/KEY: VARIANT
<222> LOCATION: 16
<223> OTHER INFORMATION: Xaa = His, Ala or Glu

<400> SEQUENCE: 13

Arg Ser Ser Gln Ser Xaa Xaa His Ser Asn Gly Asn Thr Tyr Leu Xaa
1               5                   10                  15

<210> SEQ ID NO 14
<211> LENGTH: 7
<212> TYPE: PRT
<213> ORGANISM: Artificial Sequence
<220> FEATURE:
<223> OTHER INFORMATION: consensus sequence of VL CDR2

<400> SEQUENCE: 14

Lys Val Ser Asn Arg Phe Ser
1               5

<210> SEQ ID NO 15
<211> LENGTH: 9
<212> TYPE: PRT
<213> ORGANISM: Artificial Sequence
<220> FEATURE:
<223> OTHER INFORMATION: consensus sequence of VL CDR3
<220> FEATURE:
<221> NAME/KEY: VARIANT
<222> LOCATION: 1
<223> OTHER INFORMATION: Xaa = Gln, His, Phe or Ser
<220> FEATURE:
<221> NAME/KEY: VARIANT
<222> LOCATION: 3
<223> OTHER INFORMATION: Xaa = Trp, Tyr,Gly or Ser
<220> FEATURE:
<221> NAME/KEY: VARIANT
<222> LOCATION: 4
<223> OTHER INFORMATION: Xaa = Ser, Asn or Thr
<220> FEATURE:
<221> NAME/KEY: VARIANT
<222> LOCATION: 8
<223> OTHER INFORMATION: Xaa = Leu, Tyr or Asn

<400> SEQUENCE: 15

Xaa Gln Xaa Xaa His Val Pro Xaa Thr
1               5

<210> SEQ ID NO 16
<211> LENGTH: 142
<212> TYPE: PRT
<213> ORGANISM: Artificial Sequence
<220> FEATURE:
<223> OTHER INFORMATION: Antibody R21-5-13A VH Sequence with Leader
      Sequence

<400> SEQUENCE: 16

Met Gly Trp Ser Arg Ile Phe Leu Phe Leu Leu Ser Ile Ile Ala Gly
1               5                   10                  15

Val His Cys Gln Val Gln Leu Gln Gln Ser Gly Pro Glu Leu Val Lys
            20                  25                  30

Pro Gly Ala Ser Val Arg Ile Ser Cys Lys Ala Ser Gly Tyr Thr Phe
        35                  40                  45
```

```
Thr Gly Tyr Tyr Val His Trp Val Lys Gln Arg Pro Gly Gln Gly Leu
         50                  55                  60

Glu Trp Ile Gly Trp Ile Tyr Pro Gly Asn Val Asn Thr Lys Tyr Asn
 65                  70                  75                  80

Glu Lys Phe Lys Ala Lys Ala Thr Leu Thr Ala Asp Lys Ser Ser Ser
                 85                  90                  95

Thr Gly Tyr Met Gln Leu Ser Arg Leu Thr Ser Glu Asp Ser Ala Val
                100                 105                 110

Tyr Phe Cys Ala Arg Ser Pro Tyr Tyr Gly Thr Thr Tyr Tyr Tyr Thr
            115                 120                 125

Met Asp Tyr Trp Gly Gln Gly Thr Ser Val Thr Val Ser Ser
        130                 135                 140

<210> SEQ ID NO 17
<211> LENGTH: 130
<212> TYPE: PRT
<213> ORGANISM: Artificial Sequence
<220> FEATURE:
<223> OTHER INFORMATION: Antibody R21-5-13A VL Sequence with Leader
      Sequence

<400> SEQUENCE: 17

Met Asp Phe His Val Gln Ile Phe Ser Phe Met Leu Ile Ser Val Thr
 1               5                  10                  15

Val Ile Leu Ser Ser Gly Glu Ile Val Leu Thr Gln Ser Pro Ala Phe
                 20                  25                  30

Met Ala Ala Ser Pro Gly Glu Lys Val Thr Ile Thr Cys Ser Val Ser
             35                  40                  45

Leu Ile Ile Ser Ser Arg Asn Leu His Trp Tyr Gln Gln Lys Ser Glu
 50                  55                  60

Thr Ser Pro Lys Pro Trp Ile Tyr Gly Thr Ser Asn Leu Ala Ser Gly
 65                  70                  75                  80

Val Pro Val Arg Phe Ser Gly Ser Gly Ser Gly Thr Ser Tyr Ser Leu
                 85                  90                  95

Thr Ile Ser Ser Met Glu Ala Glu Asp Ala Ala Thr Tyr Tyr Cys Gln
                100                 105                 110

Gln Trp Ser Asp Tyr Pro Leu Thr Phe Gly Ser Gly Thr Lys Leu Glu
            115                 120                 125

Ile Lys
    130

<210> SEQ ID NO 18
<211> LENGTH: 140
<212> TYPE: PRT
<213> ORGANISM: Artificial Sequence
<220> FEATURE:
<223> OTHER INFORMATION: Antibody R21-5-71A VH Sequence with Leader
      Sequence

<400> SEQUENCE: 18

Met Asp Ser Arg Leu Asn Leu Val Phe Leu Val Leu Ile Leu Lys Gly
 1               5                  10                  15

Val Gln Cys Asp Val Gln Leu Val Glu Ser Gly Gly Gly Leu Val Gln
                 20                  25                  30

Pro Gly Gly Ser Arg Lys Leu Ser Cys Ala Ala Ser Gly Phe Thr Phe
             35                  40                  45

Ser Ser Phe Gly Met His Trp Val Arg Gln Ala Pro Glu Lys Gly Leu
 50                  55                  60
```

```
Glu Leu Val Ala Tyr Ile Ser Ser Gly Ser Thr Ile Arg Tyr Tyr Ser
 65                  70                  75                  80

Asp Thr Val Lys Gly Arg Phe Thr Ile Ser Arg Asp Asn Pro Lys Asn
                 85                  90                  95

Thr Leu Phe Leu Gln Met Thr Ser Leu Arg Ser Glu Asp Thr Ala Met
            100                 105                 110

Tyr Tyr Cys Ala Arg Phe Leu Tyr Glu Gly Phe Arg Tyr Gly Met Asp
        115                 120                 125

Tyr Trp Gly Gln Gly Thr Ser Val Thr Val Ser Ser
130                 135                 140

<210> SEQ ID NO 19
<211> LENGTH: 131
<212> TYPE: PRT
<213> ORGANISM: Artificial Sequence
<220> FEATURE:
<223> OTHER INFORMATION: Antibody R21-5-71A VL Sequence with Leader
      Sequence

<400> SEQUENCE: 19

Met Lys Leu Pro Val Arg Leu Leu Val Leu Met Phe Trp Ile Pro Ala
  1               5                  10                  15

Ser Ser Ser Asp Val Leu Met Thr Gln Thr Pro Leu Ser Leu Pro Val
                 20                  25                  30

Ser Leu Gly Asp Gln Ala Ser Ile Ser Cys Arg Ser Ser Gln Ser Ile
            35                  40                  45

Val His Ser Asn Gly Asn Thr Tyr Leu Glu Trp Tyr Leu Gln Lys Pro
 50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Ile Tyr Tyr Cys
            100                 105                 110

Phe Gln Gly Ser His Val Pro Asn Thr Phe Gly Gly Gly Thr Lys Leu
        115                 120                 125

Glu Ile Lys
    130

<210> SEQ ID NO 20
<211> LENGTH: 140
<212> TYPE: PRT
<213> ORGANISM: Artificial Sequence
<220> FEATURE:
<223> OTHER INFORMATION: Antibody R21-5-165C VH Sequence with Leader
      Sequence

<400> SEQUENCE: 20

Met His Phe Gly Leu Ser Leu Ile Phe Leu Ala Leu Ile Leu Lys Gly
  1               5                  10                  15

Val Gln Cys Glu Val Gln Leu Val Glu Ser Gly Gly Asp Leu Val Lys
                 20                  25                  30

Pro Gly Gly Ser Leu Lys Leu Ser Cys Ala Ala Phe Gly Phe Thr Phe
            35                  40                  45

Ser Arg Tyr Gly Met Ser Trp Val Arg Gln Thr Pro Asp Lys Arg Leu
        50                  55                  60

Glu Trp Val Ala Thr Ile Thr Ser Gly Gly Ile Tyr Thr Tyr Tyr Pro
 65                  70                  75                  80
```

```
Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Glu Thr Ala Met
            100                 105                 110

Tyr Tyr Cys Ala Arg His Gly Gln Phe Gly Asp Tyr Tyr Gly Met Asp
        115                 120                 125

Tyr Trp Gly Gln Gly Thr Ser Val Thr Val Ser Ser
    130                 135                 140

<210> SEQ ID NO 21
<211> LENGTH: 131
<212> TYPE: PRT
<213> ORGANISM: Artificial Sequence
<220> FEATURE:
<223> OTHER INFORMATION: Antibody R21-5-165C VL Sequence with Leader
      Sequence

<400> SEQUENCE: 21

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Gln Ser Leu
        35                  40                  45

Leu His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Tyr Thr Phe Gly Gly Gly Thr Lys Leu
        115                 120                 125

Glu Ile Lys
    130

<210> SEQ ID NO 22
<211> LENGTH: 140
<212> TYPE: PRT
<213> ORGANISM: Artificial Sequence
<220> FEATURE:
<223> OTHER INFORMATION: Antibody R21-9-8B VH Sequence with Leader
      Sequence

<400> SEQUENCE: 22

Met Ala Trp Val Trp Thr Leu Leu Phe Leu Met Ala Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr His Tyr Gly Met Asn Trp Val Lys Gln Ala Pro Gly Lys Gly Leu
    50                  55                  60

Lys Trp Met Gly Trp Ile Asn Thr Tyr Thr Gly Glu Leu Thr Tyr Ala
65                  70                  75                  80

Asp Asp Phe Lys Gly Arg Phe Ala Phe Ser Leu Glu Thr Ser Ala Ser
                85                  90                  95
```

```
Thr Ala Tyr Leu Gln Ile Asn Asn Leu Lys Asn Glu Asp Thr Ala Thr
            100                 105                 110

Tyr Phe Cys Ala Arg Arg Ala Tyr Arg Tyr Asp Tyr Val Met Asp
            115                 120                 125

Tyr Trp Gly Gln Gly Thr Ser Val Thr Val Ser Ser
            130                 135             140

<210> SEQ ID NO 23
<211> LENGTH: 131
<212> TYPE: PRT
<213> ORGANISM: Artificial Sequence
<220> FEATURE:
<223> OTHER INFORMATION: Antibody R21-9-8B VL Sequence with Leader
      Sequence

<400> SEQUENCE: 23

Met Gly Ile Lys Met Glu Ser Gln Thr Gln Val Phe Val Tyr Met Leu
1               5                   10                  15

Leu Trp Leu Ser Gly Val Asp Gly Asp Ile Val Met Thr Gln Ser Gln
            20                  25                  30

Lys Phe Met Ser Thr Ser Val Gly Asp Arg Val Ser Val Thr Cys Lys
            35                  40                  45

Ala Ser His Asn Val Gly Thr Asn Val Ala Trp Tyr Gln Gln Lys Pro
    50                  55                  60

Gly Gln Ser Pro Lys Ala Leu Ile Tyr Ser Ala Ser Tyr Arg Tyr Ser
65                  70                  75                  80

Gly Val Pro Gly Arg Phe Thr Gly Ser Gly Ser Gly Thr Asp Phe Thr
                85                  90                  95

Leu Thr Ile Ser Asn Val Gln Ser Glu Asp Leu Ala Glu Tyr Phe Cys
            100                 105                 110

His Gln Tyr Asn Asn Tyr Pro Tyr Thr Phe Gly Gly Gly Thr Lys Leu
            115                 120                 125

Glu Ile Lys
    130

<210> SEQ ID NO 24
<211> LENGTH: 123
<212> TYPE: PRT
<213> ORGANISM: Artificial Sequence
<220> FEATURE:
<223> OTHER INFORMATION: humanized anti-CD39 antibody clone R21-5-13A VH
      region (Fig.2A)

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Val His Trp Val Arg Gln Ala Pro Gly Gln Gly Leu Glu Trp Met
            35                  40                  45

Gly Trp Ile Tyr Pro Gly Asn Val Asn Thr Lys Tyr Asn Glu Lys Phe
    50                  55                  60

Lys Ala Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Tyr Tyr Gly Thr Tyr Tyr Tyr Thr Met Asp Tyr
            100                 105                 110
```

```
Trp Gly Gln Gly Thr Leu Val Thr Val Ser Ser
        115                 120

<210> SEQ ID NO 25
<211> LENGTH: 123
<212> TYPE: PRT
<213> ORGANISM: Artificial Sequence
<220> FEATURE:
<223> OTHER INFORMATION: humanized anti-CD39 antibody clone R21-5-13A VH
      region (Fig.2A)

<400> SEQUENCE: 25

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Gly Tyr
            20                  25                  30

Tyr Val His Trp Val Arg Gln Ala Pro Gly Gln Gly Leu Glu Trp Ile
        35                  40                  45

Gly Trp Ile Tyr Pro Gly Asn Val Asn Thr Lys Tyr Asn Glu Lys Phe
    50                  55                  60

Lys Ala Arg Ala Thr Leu Thr Arg Asp Thr Ser Ile Ser Thr Gly Tyr
65                  70                  75                  80

Met Glu Leu Ser Arg Leu Arg Ser Asp Asp Thr Ala Val Tyr Tyr Cys
                85                  90                  95

Ala Arg Ser Pro Tyr Tyr Gly Thr Thr Tyr Tyr Tyr Thr Met Asp Tyr
            100                 105                 110

Trp Gly Gln Gly Thr Leu Val Thr Val Ser Ser
        115                 120

<210> SEQ ID NO 26
<211> LENGTH: 123
<212> TYPE: PRT
<213> ORGANISM: Artificial Sequence
<220> FEATURE:
<223> OTHER INFORMATION: humanized anti-CD39 antibody clone R21-5-13A VH
      region (Fig.2A)

<400> SEQUENCE: 26

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Gly Tyr
            20                  25                  30

Tyr Val His Trp Val Arg Gln Ala Pro Gly Gln Gly Leu Glu Trp Ile
        35                  40                  45

Gly Trp Ile Tyr Pro Gly Asn Val Asn Thr Lys Tyr Asn Glu Lys Phe
    50                  55                  60

Lys Ala Arg Ala Thr Leu Thr Ala Asp Thr Ser Ile Ser Thr Gly Tyr
65                  70                  75                  80

Met Glu Leu Ser Arg Leu Arg Ser Asp Asp Thr Ala Val Tyr Tyr Cys
                85                  90                  95

Ala Arg Ser Pro Tyr Tyr Gly Thr Thr Tyr Tyr Tyr Thr Met Asp Tyr
            100                 105                 110

Trp Gly Gln Gly Thr Leu Val Thr Val Ser Ser
        115                 120

<210> SEQ ID NO 27
<211> LENGTH: 123
<212> TYPE: PRT
<213> ORGANISM: Artificial Sequence
```

```
<220> FEATURE:
<223> OTHER INFORMATION: humanized anti-CD39 antibody clone R21-5-13A VH
      region (Fig.2A)

<400> SEQUENCE: 27

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Gly Tyr
            20                  25                  30

Tyr Val His Trp Val Arg Gln Ala Pro Gly Gln Gly Leu Glu Trp Ile
        35                  40                  45

Gly Trp Ile Tyr Pro Gly Asn Val Asn Thr Lys Tyr Asn Glu Lys Phe
    50                  55                  60

Lys Ala Arg Ala Thr Leu Thr Ala Asp Lys Ser Ile Ser Thr Gly Tyr
65                  70                  75                  80

Met Glu Leu Ser Arg Leu Arg Ser Asp Asp Thr Ala Val Tyr Tyr Cys
                85                  90                  95

Ala Arg Ser Pro Tyr Tyr Gly Thr Thr Tyr Tyr Tyr Met Asp Tyr
            100                 105                 110

Trp Gly Gln Gly Thr Leu Val Thr Val Ser Ser
        115                 120

<210> SEQ ID NO 28
<211> LENGTH: 123
<212> TYPE: PRT
<213> ORGANISM: Artificial Sequence
<220> FEATURE:
<223> OTHER INFORMATION: humanized anti-CD39 antibody clone R21-5-13A VH
      region (Fig.2A)

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Val His Trp Val Arg Gln Ala Pro Gly Gln Gly Leu Glu Trp Met
        35                  40                  45

Gly Trp Ile Tyr Pro Gly Asn Val Asn Thr Lys Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Tyr Tyr Gly Thr Thr Tyr Tyr Tyr Thr Met Asp Tyr
            100                 105                 110

Trp Gly Gln Gly Thr Leu Val Thr Val Ser Ser
        115                 120

<210> SEQ ID NO 29
<211> LENGTH: 123
<212> TYPE: PRT
<213> ORGANISM: Artificial Sequence
<220> FEATURE:
<223> OTHER INFORMATION: humanized anti-CD39 antibody clone R21-5-13A VH
      region (Fig.2A)

<400> SEQUENCE: 29

Gln Val Gln Leu Val Gln Ser Gly Ala Glu Val Lys Lys Pro Gly Ala
1               5                   10                  15
```

```
Ser Val Lys Ile Ser Cys Lys Ala Ser Gly Tyr Thr Phe Thr Gly Tyr
            20                  25                  30

Tyr Val His Trp Val Arg Gln Ala Pro Gly Gln Gly Leu Glu Trp Ile
        35                  40                  45

Gly Trp Ile Tyr Pro Gly Asn Val Asn Thr Lys Tyr Ala Gln Lys Phe
    50                  55                  60

Gln Gly Arg Ala Thr Leu Thr Arg Asp Thr Ser Ile Ser Thr Gly Tyr
65                  70                  75                  80

Met Glu Leu Ser Arg Leu Arg Ser Asp Asp Thr Ala Val Tyr Tyr Cys
                85                  90                  95

Ala Arg Ser Pro Tyr Tyr Gly Thr Thr Tyr Tyr Tyr Thr Met Asp Tyr
            100                 105                 110

Trp Gly Gln Gly Thr Leu Val Thr Val Ser Ser
            115                 120

<210> SEQ ID NO 30
<211> LENGTH: 123
<212> TYPE: PRT
<213> ORGANISM: Artificial Sequence
<220> FEATURE:
<223> OTHER INFORMATION: humanized anti-CD39 antibody clone R21-5-13A VH
      region (Fig.2A)

<400> SEQUENCE: 30

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Gly Tyr
            20                  25                  30

Tyr Val His Trp Val Arg Gln Ala Pro Gly Gln Gly Leu Glu Trp Ile
        35                  40                  45

Gly Trp Ile Tyr Pro Gly Asn Val Asn Thr Lys Tyr Ala Gln Lys Phe
    50                  55                  60

Gln Gly Arg Ala Thr Leu Thr Ala Asp Thr Ser Ile Ser Thr Gly Tyr
65                  70                  75                  80

Met Glu Leu Ser Arg Leu Arg Ser Asp Asp Thr Ala Val Tyr Tyr Cys
                85                  90                  95

Ala Arg Ser Pro Tyr Tyr Gly Thr Thr Tyr Tyr Tyr Thr Met Asp Tyr
            100                 105                 110

Trp Gly Gln Gly Thr Leu Val Thr Val Ser Ser
            115                 120

<210> SEQ ID NO 31
<211> LENGTH: 123
<212> TYPE: PRT
<213> ORGANISM: Artificial Sequence
<220> FEATURE:
<223> OTHER INFORMATION: humanized anti-CD39 antibody clone R21-5-13A VH
      region (Fig.2A)

<400> SEQUENCE: 31

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Gly Tyr
            20                  25                  30

Tyr Val His Trp Val Arg Gln Ala Pro Gly Gln Gly Leu Glu Trp Ile
        35                  40                  45

Gly Trp Ile Tyr Pro Gly Asn Val Asn Thr Lys Tyr Ala Gln Lys Phe
    50                  55                  60
```

```
Gln Gly Arg Ala Thr Leu Thr Ala Asp Lys Ser Ile Ser Thr Gly Tyr
 65                  70                  75                  80

Met Glu Leu Ser Arg Leu Arg Ser Asp Asp Thr Ala Val Tyr Tyr Cys
                 85                  90                  95

Ala Arg Ser Pro Tyr Tyr Gly Thr Thr Tyr Tyr Tyr Thr Met Asp Tyr
            100                 105                 110

Trp Gly Gln Gly Thr Leu Val Thr Val Ser Ser
        115                 120

<210> SEQ ID NO 32
<211> LENGTH: 123
<212> TYPE: PRT
<213> ORGANISM: Artificial Sequence
<220> FEATURE:
<223> OTHER INFORMATION: humanized anti-CD39 antibody clone R21-5-13A VH
      region (Fig.2B)

<400> SEQUENCE: 32

Glu Val Gln Leu Val Glu Ser Gly Gly Gly Leu Val Gln Pro Gly Gly
  1               5                  10                  15

Ser Leu Arg Leu Ser Cys Ala Ala Ser Gly Tyr Thr Phe Thr Gly Tyr
                 20                  25                  30

Tyr Val His Trp Val Arg Gln Ala Pro Gly Lys Gly Leu Glu Trp Val
             35                  40                  45

Ser Trp Ile Tyr Pro Gly Asn Val Asn Thr Lys Tyr Asn Glu Lys Phe
 50                  55                  60

Lys Ala Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Pro Tyr Tyr Gly Thr Thr Tyr Tyr Tyr Thr Met Asp Tyr
            100                 105                 110

Trp Gly Gln Gly Thr Leu Val Thr Val Ser Ser
        115                 120

<210> SEQ ID NO 33
<211> LENGTH: 123
<212> TYPE: PRT
<213> ORGANISM: Artificial Sequence
<220> FEATURE:
<223> OTHER INFORMATION: humanized anti-CD39 antibody clone R21-5-13A VH
      region (Fig.2B)

<400> SEQUENCE: 33

Glu Val Gln Leu Val Glu Ser Gly Gly Gly Leu Val Gln Pro Gly Gly
  1               5                  10                  15

Ser Val Arg Ile Ser Cys Ala Ala Ser Gly Tyr Thr Phe Thr Gly Tyr
                 20                  25                  30

Tyr Val His Trp Val Arg Gln Ala Pro Gly Lys Gly Leu Glu Trp Ile
             35                  40                  45

Gly Trp Ile Tyr Pro Gly Asn Val Asn Thr Lys Tyr Asn Glu Lys Phe
 50                  55                  60

Lys Ala Arg Ala Thr Leu Ser Arg Asp Asn Ala Lys Asn Ser Gly Tyr
 65                  70                  75                  80

Met Gln Leu Asn Ser Leu Arg Ala Glu Asp Thr Ala Val Tyr Tyr Cys
                 85                  90                  95

Ala Arg Ser Pro Tyr Tyr Gly Thr Thr Tyr Tyr Tyr Thr Met Asp Tyr
            100                 105                 110
```

Trp Gly Gln Gly Thr Leu Val Thr Val Ser Ser
        115                 120

<210> SEQ ID NO 34
<211> LENGTH: 123
<212> TYPE: PRT
<213> ORGANISM: Artificial Sequence
<220> FEATURE:
<223> OTHER INFORMATION: humanized anti-CD39 antibody clone R21-5-13A VH
      region (Fig.2B)

<400> SEQUENCE: 34

Glu Val Gln Leu Val Glu Ser Gly Gly Gly Leu Val Gln Pro Gly Gly
1               5                   10                  15

Ser Val Arg Ile Ser Cys Ala Ala Ser Gly Tyr Thr Phe Thr Gly Tyr
            20                  25                  30

Tyr Val His Trp Val Arg Gln Ala Pro Gly Lys Gly Leu Glu Trp Ile
        35                  40                  45

Gly Trp Ile Tyr Pro Gly Asn Val Asn Thr Lys Tyr Asn Glu Lys Phe
    50                  55                  60

Lys Ala Arg Ala Thr Leu Ser Ala Asp Asn Ala Lys Asn Ser Gly Tyr
65                  70                  75                  80

Met Gln Leu Asn Ser Leu Arg Ala Glu Asp Thr Ala Val Tyr Tyr Cys
                85                  90                  95

Ala Arg Ser Pro Tyr Tyr Gly Thr Thr Tyr Tyr Tyr Met Asp Tyr
            100                 105                 110

Trp Gly Gln Gly Thr Leu Val Thr Val Ser Ser
        115                 120

<210> SEQ ID NO 35
<211> LENGTH: 123
<212> TYPE: PRT
<213> ORGANISM: Artificial Sequence
<220> FEATURE:
<223> OTHER INFORMATION: humanized anti-CD39 antibody clone R21-5-13A VH
      region (Fig.2B)

<400> SEQUENCE: 35

Glu Val Gln Leu Val Glu Ser Gly Gly Gly Leu Val Gln Pro Gly Gly
1               5                   10                  15

Ser Val Arg Ile Ser Cys Ala Ala Ser Gly Tyr Thr Phe Thr Gly Tyr
            20                  25                  30

Tyr Val His Trp Val Arg Gln Ala Pro Gly Lys Gly Leu Glu Trp Ile
        35                  40                  45

Gly Trp Ile Tyr Pro Gly Asn Val Asn Thr Lys Tyr Asn Glu Lys Phe
    50                  55                  60

Lys Ala Arg Ala Thr Leu Ser Asp Lys Ala Lys Asn Ser Gly Tyr
65                  70                  75                  80

Met Gln Leu Asn Ser Leu Arg Ala Glu Asp Thr Ala Val Tyr Tyr Cys
                85                  90                  95

Ala Arg Ser Pro Tyr Tyr Gly Thr Thr Tyr Tyr Tyr Met Asp Tyr
            100                 105                 110

Trp Gly Gln Gly Thr Leu Val Thr Val Ser Ser
        115                 120

<210> SEQ ID NO 36
<211> LENGTH: 123
<212> TYPE: PRT
<213> ORGANISM: Artificial Sequence
<220> FEATURE:

```
<223> OTHER INFORMATION: humanized anti-CD39 antibody clone R21-5-13A VH
      region (Fig.2B)

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Gly Tyr
            20                  25                  30

Tyr Val His Trp Val Arg Gln Ala Pro Gly Lys Gly Leu Glu Trp Val
        35                  40                  45

Ser Trp Ile Tyr Pro Gly Asn Val Asn Thr Lys Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Pro Tyr Tyr Gly Thr Thr Tyr Tyr Tyr Thr Met Asp Tyr
            100                 105                 110

Trp Gly Gln Gly Thr Leu Val Thr Val Ser Ser
        115                 120

<210> SEQ ID NO 37
<211> LENGTH: 123
<212> TYPE: PRT
<213> ORGANISM: Artificial Sequence
<220> FEATURE:
<223> OTHER INFORMATION: humanized anti-CD39 antibody clone R21-5-13A VH
      region (Fig.2B)

<400> SEQUENCE: 37

Glu Val Gln Leu Val Glu Ser Gly Gly Gly Leu Val Gln Pro Gly Gly
1               5                   10                  15

Ser Val Arg Ile Ser Cys Ala Ala Ser Gly Tyr Thr Phe Thr Gly Tyr
            20                  25                  30

Tyr Val His Trp Val Arg Gln Ala Pro Gly Lys Gly Leu Glu Trp Ile
        35                  40                  45

Gly Trp Ile Tyr Pro Gly Asn Val Asn Thr Lys Tyr Ala Asp Ser Val
    50                  55                  60

Lys Gly Arg Ala Thr Leu Ser Arg Asp Asn Ala Lys Asn Ser Gly Tyr
65                  70                  75                  80

Met Gln Leu Asn Ser Leu Arg Ala Glu Asp Thr Ala Val Tyr Tyr Cys
                85                  90                  95

Ala Arg Ser Pro Tyr Tyr Gly Thr Thr Tyr Tyr Tyr Thr Met Asp Tyr
            100                 105                 110

Trp Gly Gln Gly Thr Leu Val Thr Val Ser Ser
        115                 120

<210> SEQ ID NO 38
<211> LENGTH: 123
<212> TYPE: PRT
<213> ORGANISM: Artificial Sequence
<220> FEATURE:
<223> OTHER INFORMATION: humanized anti-CD39 antibody clone R21-5-13A VH
      region (Fig.2B)

<400> SEQUENCE: 38

Glu Val Gln Leu Val Glu Ser Gly Gly Gly Leu Val Gln Pro Gly Gly
1               5                   10                  15

Ser Val Arg Ile Ser Cys Ala Ala Ser Gly Tyr Thr Phe Thr Gly Tyr
```

```
                    20                  25                  30
Tyr Val His Trp Val Arg Gln Ala Pro Gly Lys Gly Leu Glu Trp Ile
        35                  40                  45
Gly Trp Ile Tyr Pro Gly Asn Val Asn Thr Lys Tyr Ala Asp Ser Val
    50                  55                  60
Lys Gly Arg Ala Thr Leu Ser Ala Asp Asn Ala Lys Asn Ser Gly Tyr
65                  70                  75                  80
Met Gln Leu Asn Ser Leu Arg Ala Glu Asp Thr Ala Val Tyr Tyr Cys
                85                  90                  95
Ala Arg Ser Pro Tyr Tyr Gly Thr Thr Tyr Tyr Tyr Thr Met Asp Tyr
            100                 105                 110
Trp Gly Gln Gly Thr Leu Val Thr Val Ser Ser
        115                 120
```

<210> SEQ ID NO 39
<211> LENGTH: 123
<212> TYPE: PRT
<213> ORGANISM: Artificial Sequence
<220> FEATURE:
<223> OTHER INFORMATION: humanized anti-CD39 antibody clone R21-5-13A VH
      region (Fig.2B)

<400> SEQUENCE: 39

```
Glu Val Gln Leu Val Glu Ser Gly Gly Gly Leu Val Gln Pro Gly Gly
1               5                   10                  15
Ser Val Arg Ile Ser Cys Ala Ala Ser Gly Tyr Thr Phe Thr Gly Tyr
            20                  25                  30
Tyr Val His Trp Val Arg Gln Ala Pro Gly Lys Gly Leu Glu Trp Ile
        35                  40                  45
Gly Trp Ile Tyr Pro Gly Asn Val Asn Thr Lys Tyr Ala Asp Ser Val
    50                  55                  60
Lys Gly Arg Ala Thr Leu Ser Ala Asp Lys Ala Lys Asn Ser Gly Tyr
65                  70                  75                  80
Met Gln Leu Asn Ser Leu Arg Ala Glu Asp Thr Ala Val Tyr Tyr Cys
                85                  90                  95
Ala Arg Ser Pro Tyr Tyr Gly Thr Thr Tyr Tyr Tyr Thr Met Asp Tyr
            100                 105                 110
Trp Gly Gln Gly Thr Leu Val Thr Val Ser Ser
        115                 120
```

<210> SEQ ID NO 40
<211> LENGTH: 108
<212> TYPE: PRT
<213> ORGANISM: Artificial Sequence
<220> FEATURE:
<223> OTHER INFORMATION: humanized anti-CD39 antibody clone R21-5-13A VL
      region (Fig.3A)

<400> SEQUENCE: 40

```
Glu Ile Val Met Thr Gln Ser Pro Ala Thr Leu Ser Val Ser Pro Gly
1               5                   10                  15
Glu Arg Ala Thr Leu Ser Cys Ser Val Ser Leu Ile Ile Ser Ser Arg
            20                  25                  30
Asn Leu His Trp Tyr Gln Gln Lys Pro Gly Gln Ala Pro Arg Pro Leu
        35                  40                  45
Ile Tyr Gly Thr Ser Asn Leu Ala Ser Gly Ile Pro Ala Arg Phe Ser
    50                  55                  60
Gly Ser Gly Ser Gly Thr Glu Tyr Thr Leu Thr Ile Ser Ser Leu Gln
```

```
65                  70                  75                  80
Ser Glu Asp Ala Ala Val Tyr Tyr Cys Gln Gln Trp Ser Asp Tyr Pro
                85                  90                  95

Leu Thr Phe Gly Gln Gly Thr Lys Leu Glu Ile Lys
                100                 105

<210> SEQ ID NO 41
<211> LENGTH: 108
<212> TYPE: PRT
<213> ORGANISM: Artificial Sequence
<220> FEATURE:
<223> OTHER INFORMATION: humanized anti-CD39 antibody clone R21-5-13A VL
      region (Fig.3A)

<400> SEQUENCE: 41

Glu Ile Val Leu Thr Gln Ser Pro Ala Thr Met Ser Ala Ser Pro Gly
1               5                   10                  15

Glu Arg Val Thr Ile Ser Cys Ser Val Ser Leu Ile Ile Ser Ser Arg
                20                  25                  30

Asn Leu His Trp Tyr Gln Gln Lys Pro Gly Gln Ala Pro Arg Pro Leu
            35                  40                  45

Ile Tyr Gly Thr Ser Asn Leu Ala Ser Gly Val Pro Ala Arg Phe Ser
        50                  55                  60

Gly Ser Gly Ser Gly Thr Glu Tyr Thr Leu Thr Ile Ser Ser Met Gln
65                  70                  75                  80

Ser Glu Asp Ala Ala Val Tyr Tyr Cys Gln Gln Trp Ser Asp Tyr Pro
                85                  90                  95

Leu Thr Phe Gly Gln Gly Thr Lys Leu Glu Ile Lys
                100                 105

<210> SEQ ID NO 42
<211> LENGTH: 108
<212> TYPE: PRT
<213> ORGANISM: Artificial Sequence
<220> FEATURE:
<223> OTHER INFORMATION: humanized anti-CD39 antibody clone R21-5-13A VL
      region (Fig.3A)

<400> SEQUENCE: 42

Glu Ile Val Leu Thr Gln Ser Pro Ala Thr Met Ser Ala Ser Pro Gly
1               5                   10                  15

Glu Arg Val Thr Ile Ser Cys Arg Val Ser Leu Ile Ile Ser Ser Arg
                20                  25                  30

Asn Leu His Trp Tyr Gln Gln Lys Pro Gly Gln Ala Pro Arg Pro Leu
            35                  40                  45

Ile Tyr Gly Thr Ser Asn Leu Ala Ser Gly Val Pro Ala Arg Phe Ser
        50                  55                  60

Gly Ser Gly Ser Gly Thr Glu Tyr Thr Leu Thr Ile Ser Ser Met Gln
65                  70                  75                  80

Ser Glu Asp Ala Ala Val Tyr Tyr Cys Gln Gln Trp Ser Asp Tyr Pro
                85                  90                  95

Leu Thr Phe Gly Gln Gly Thr Lys Leu Glu Ile Lys
                100                 105

<210> SEQ ID NO 43
<211> LENGTH: 108
<212> TYPE: PRT
<213> ORGANISM: Artificial Sequence
<220> FEATURE:
<223> OTHER INFORMATION: humanized anti-CD39 antibody clone R21-5-13A VL
``` region (Fig.3A)

<400> SEQUENCE: 43

Glu Ile Val Leu Thr Gln Ser Pro Ala Thr Met Ser Ala Ser Pro Gly
1               5                   10                  15

Glu Arg Val Thr Ile Ser Cys Arg Val Ser Leu Ile Ile Ser Ser Arg
            20                  25                  30

Asn Leu His Trp Tyr Gln Gln Lys Pro Gly Gln Ala Pro Arg Pro Trp
        35                  40                  45

Ile Tyr Gly Thr Ser Asn Leu Ala Ser Gly Val Pro Ala Arg Phe Ser
    50                  55                  60

Gly Ser Gly Ser Gly Thr Glu Tyr Thr Leu Thr Ile Ser Ser Met Gln
65                  70                  75                  80

Ser Glu Asp Ala Ala Val Tyr Tyr Cys Gln Gln Trp Ser Asp Tyr Pro
                85                  90                  95

Leu Thr Phe Gly Gln Gly Thr Lys Leu Glu Ile Lys
            100                 105

<210> SEQ ID NO 44
<211> LENGTH: 108
<212> TYPE: PRT
<213> ORGANISM: Artificial Sequence
<220> FEATURE:
<223> OTHER INFORMATION: humanized anti-CD39 antibody clone R21-5-13A VL
      region (Fig.3A)

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Ser Val Ser Leu Ile Ile Ser Ser Arg
            20                  25                  30

Asn Leu His Trp Tyr Gln Gln Lys Pro Gly Lys Ala Pro Lys Pro Leu
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Ala Ala Thr Tyr Tyr Cys Gln Gln Trp Ser Asp Tyr Pro
                85                  90                  95

Leu Thr Phe Gly Gln Gly Thr Lys Leu Glu Ile Lys
            100                 105

<210> SEQ ID NO 45
<211> LENGTH: 108
<212> TYPE: PRT
<213> ORGANISM: Artificial Sequence
<220> FEATURE:
<223> OTHER INFORMATION: humanized anti-CD39 antibody clone R21-5-13A VL
      region (Fig.3A)

<400> SEQUENCE: 45

Asp Ile Gln Leu Thr Gln Ser Pro Ser Ser Met Ser Ala Ser Val Gly
1               5                   10                  15

Asp Arg Val Thr Ile Thr Cys Ser Val Ser Leu Ile Ile Ser Ser Arg
            20                  25                  30

Asn Leu His Trp Tyr Gln Gln Lys Pro Gly Lys Ala Pro Lys Pro Leu
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Met Gln
65                  70                  75                  80

Pro Glu Asp Ala Ala Thr Tyr Tyr Cys Gln Gln Trp Ser Asp Tyr Pro
                85                  90                  95

Leu Thr Phe Gly Gln Gly Thr Lys Leu Glu Ile Lys
            100                 105

<210> SEQ ID NO 46
<211> LENGTH: 108
<212> TYPE: PRT
<213> ORGANISM: Artificial Sequence
<220> FEATURE:
<223> OTHER INFORMATION: humanized anti-CD39 antibody clone R21-5-13A VL
      region (Fig.3A)

<400> SEQUENCE: 46

Asp Ile Gln Leu Thr Gln Ser Pro Ser Ser Met Ser Ala Ser Val Gly
1               5                   10                  15

Asp Arg Val Thr Ile Thr Cys Arg Val Ser Leu Ile Ile Ser Ser Arg
            20                  25                  30

Asn Leu His Trp Tyr Gln Gln Lys Pro Gly Lys Ala Pro Lys Pro Leu
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Met Gln
65                  70                  75                  80

Pro Glu Asp Ala Ala Thr Tyr Tyr Cys Gln Gln Trp Ser Asp Tyr Pro
                85                  90                  95

Leu Thr Phe Gly Gln Gly Thr Lys Leu Glu Ile Lys
            100                 105

<210> SEQ ID NO 47
<211> LENGTH: 108
<212> TYPE: PRT
<213> ORGANISM: Artificial Sequence
<220> FEATURE:
<223> OTHER INFORMATION: humanized anti-CD39 antibody clone R21-5-13A VL
      region (Fig.3A)

<400> SEQUENCE: 47

Asp Ile Gln Leu Thr Gln Ser Pro Ser Ser Met Ser Ala Ser Val Gly
1               5                   10                  15

Asp Arg Val Thr Ile Thr Cys Arg Val Ser Leu Ile Ile Ser Ser Arg
            20                  25                  30

Asn Leu His Trp Tyr Gln Gln Lys Pro Gly Lys Ala Pro Lys Pro Trp
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Met Gln
65                  70                  75                  80

Pro Glu Asp Ala Ala Thr Tyr Tyr Cys Gln Gln Trp Ser Asp Tyr Pro
                85                  90                  95

Leu Thr Phe Gly Gln Gly Thr Lys Leu Glu Ile Lys
            100                 105

<210> SEQ ID NO 48
<211> LENGTH: 121
<212> TYPE: PRT
<213> ORGANISM: Artificial Sequence

```
<220> FEATURE:
<223> OTHER INFORMATION: humanized anti-CD39 antibody clone R21-5-165C
      VH region (Fig.4A)

<400> SEQUENCE: 48

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Thr Ile Thr Ser Gly Gly Ile Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Gly Gln Phe Gly Asp Tyr Tyr Gly Met Asp Tyr Trp Gly
            100                 105                 110

Gln Gly Thr Leu Val Thr Val Ser Ser
        115                 120

<210> SEQ ID NO 49
<211> LENGTH: 121
<212> TYPE: PRT
<213> ORGANISM: Artificial Sequence
<220> FEATURE:
<223> OTHER INFORMATION: humanized anti-CD39 antibody clone R21-5-165C
      VH region (Fig.4A)

<400> SEQUENCE: 49

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ala Thr Ile Thr Ser Gly Gly Ile Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Gly Gln Phe Gly Asp Tyr Tyr Gly Met Asp Tyr Trp Gly
            100                 105                 110

Gln Gly Thr Leu Val Thr Val Ser Ser
        115                 120

<210> SEQ ID NO 50
<211> LENGTH: 121
<212> TYPE: PRT
<213> ORGANISM: Artificial Sequence
<220> FEATURE:
<223> OTHER INFORMATION: humanized anti-CD39 antibody clone R21-5-165C
      VH region (Fig.4A)

<400> SEQUENCE: 50

Glu Val Gln Leu Val Glu Ser Gly Gly Gly Leu Val Lys Pro Gly Gly
1               5                   10                  15
```

-continued

```
Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Thr Ile Thr Ser Gly Gly Ile Tyr Thr Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg His Gly Gln Phe Gly Asp Tyr Tyr Gly Met Asp Tyr Trp Gly
            100                 105                 110

Gln Gly Thr Leu Val Thr Val Ser Ser
            115                 120
```

<210> SEQ ID NO 51
<211> LENGTH: 121
<212> TYPE: PRT
<213> ORGANISM: Artificial Sequence
<220> FEATURE:
<223> OTHER INFORMATION: humanized anti-CD39 antibody clone R21-5-165C
      VH region (Fig.4A)

<400> SEQUENCE: 51

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ala Thr Ile Thr Ser Gly Gly Ile Tyr Thr Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg His Gly Gln Phe Gly Asp Tyr Tyr Gly Met Asp Tyr Trp Gly
            100                 105                 110

Gln Gly Thr Leu Val Thr Val Ser Ser
            115                 120
```

<210> SEQ ID NO 52
<211> LENGTH: 121
<212> TYPE: PRT
<213> ORGANISM: Artificial Sequence
<220> FEATURE:
<223> OTHER INFORMATION: humanized anti-CD39 antibody clone R21-5-165C
      VH region (Fig.4B)

<400> SEQUENCE: 52

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Thr Ile Thr Ser Gly Gly Ile Tyr Thr Tyr Tyr Pro Asp Ser Val
 50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg His Gly Gln Phe Gly Asp Tyr Tyr Gly Met Asp Tyr Trp Gly
            100                 105                 110

Gln Gly Thr Leu Val Thr Val Ser Ser
            115                 120
```

<210> SEQ ID NO 53
<211> LENGTH: 121
<212> TYPE: PRT
<213> ORGANISM: Artificial Sequence
<220> FEATURE:
<223> OTHER INFORMATION: humanized anti-CD39 antibody clone R21-5-165C
      VH region (Fig.4B)

<400> SEQUENCE: 53

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
                 20                  25                  30

Gly Met Ser Trp Val Arg Gln Ala Pro Gly Lys Gly Leu Glu Trp Val
             35                  40                  45

Ala Thr Ile Thr Ser Gly Gly Ile Tyr Thr Tyr Tyr Pro Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg His Gly Gln Phe Gly Asp Tyr Tyr Gly Met Asp Tyr Trp Gly
            100                 105                 110

Gln Gly Thr Leu Val Thr Val Ser Ser
            115                 120
```

<210> SEQ ID NO 54
<211> LENGTH: 121
<212> TYPE: PRT
<213> ORGANISM: Artificial Sequence
<220> FEATURE:
<223> OTHER INFORMATION: humanized anti-CD39 antibody clone R21-5-165C
      VH region (Fig.4B)

<400> SEQUENCE: 54

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
                 20                  25                  30

Gly Met Ser Trp Val Arg Gln Ala Pro Gly Lys Gly Leu Glu Trp Val
             35                  40                  45

Ser Thr Ile Thr Ser Gly Gly Ile Tyr Thr Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg His Gly Gln Phe Gly Asp Tyr Tyr Gly Met Asp Tyr Trp Gly
            100                 105                 110
```

```
Gln Gly Thr Leu Val Thr Val Ser Ser
        115                 120
```

<210> SEQ ID NO 55
<211> LENGTH: 121
<212> TYPE: PRT
<213> ORGANISM: Artificial Sequence
<220> FEATURE:
<223> OTHER INFORMATION: humanized anti-CD39 antibody clone R21-5-165C
      VH region (Fig.4B)

<400> SEQUENCE: 55

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ala Thr Ile Thr Ser Gly Gly Ile Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Gly Gln Phe Gly Asp Tyr Tyr Gly Met Asp Tyr Trp Gly
            100                 105                 110

Gln Gly Thr Leu Val Thr Val Ser Ser
        115                 120
```

<210> SEQ ID NO 56
<211> LENGTH: 112
<212> TYPE: PRT
<213> ORGANISM: Artificial Sequence
<220> FEATURE:
<223> OTHER INFORMATION: humanized anti-CD39 antibody clone R21-5-165C
      VL region (Fig.5A)

<400> SEQUENCE: 56

```
Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Leu His Ser
            20                  25                  30

Asn Gly Asn Thr Tyr Leu His Trp Tyr Leu Gln Lys Pro Gly Gln Pro
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gln Gly Thr Lys Leu Glu Ile Lys
            100                 105                 110
```

<210> SEQ ID NO 57
<211> LENGTH: 112
<212> TYPE: PRT
<213> ORGANISM: Artificial Sequence
<220> FEATURE:
<223> OTHER INFORMATION: humanized anti-CD39 antibody clone R21-5-165C
      VL region (Fig.5A)

-continued

```
<400> SEQUENCE: 57

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Leu His Ser
            20                  25                  30

Asn Gly Asn Thr Tyr Leu His Trp Tyr Leu Gln Lys Pro Gly Gln Pro
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Ser Gln Ser
                85                  90                  95

Thr His Val Pro Tyr Thr Phe Gly Gln Gly Thr Lys Leu Glu Ile Lys
            100                 105                 110

<210> SEQ ID NO 58
<211> LENGTH: 112
<212> TYPE: PRT
<213> ORGANISM: Artificial Sequence
<220> FEATURE:
<223> OTHER INFORMATION: humanized anti-CD39 antibody clone R21-5-165C
      VL region (Fig.5B)

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Ser
                85                  90                  95

Thr His Val Pro Tyr Thr Phe Gly Gln Gly Thr Lys Leu Glu Ile Lys
            100                 105                 110

<210> SEQ ID NO 59
<211> LENGTH: 112
<212> TYPE: PRT
<213> ORGANISM: Artificial Sequence
<220> FEATURE:
<223> OTHER INFORMATION: humanized anti-CD39 antibody clone R21-5-165C
      VL region (Fig.5B)

<400> SEQUENCE: 59

Asp Val Gln Met Thr Gln Ser Pro Ser Ser Leu Ser Val Ser Val Gly
1               5                   10                  15

Asp Arg Ala Thr Ile Thr Cys Arg Ser Ser Gln Ser Leu Leu His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
```

```
                65                  70                  75                  80
Ser Ser Val Gln Pro Glu Asp Phe Gly Thr Tyr Tyr Cys Ser Gln Ser
                    85                  90                  95

Thr His Val Pro Tyr Thr Phe Gly Gln Gly Thr Lys Leu Glu Ile Lys
                100                 105                 110

<210> SEQ ID NO 60
<211> LENGTH: 112
<212> TYPE: PRT
<213> ORGANISM: Artificial Sequence
<220> FEATURE:
<223> OTHER INFORMATION: humanized anti-CD39 antibody clone R21-5-165C
      VL region (Fig.5B)

<400> SEQUENCE: 60

Asp Val Gln Met Thr Gln Ser Pro Ser Ser Leu Ser Val Ser Val Gly
1               5                   10                  15

Asp Arg Ala Thr Ile Thr Cys Arg Ser Gln Ser Leu Leu His Ser
                20                  25                  30

Asn Gly Asn Thr Tyr Leu His Trp Tyr Gln Gln Lys Pro Gly Lys Ala
                35                  40                  45

Pro Lys Leu Leu Ile Tyr Lys Val Ser Asn Arg Phe Ser Gly Val Pro
        50                  55                  60

Ser Arg Phe Ser Gly Ser Gly Ser Gly Thr Asp Phe Thr Leu Thr Ile
65                  70                  75                  80

Ser Ser Val Gln Pro Glu Asp Leu Gly Thr Tyr Tyr Cys Ser Gln Ser
                    85                  90                  95

Thr His Val Pro Tyr Thr Phe Gly Gln Gly Thr Lys Leu Glu Ile Lys
                100                 105                 110

<210> SEQ ID NO 61
<211> LENGTH: 121
<212> TYPE: PRT
<213> ORGANISM: Artificial Sequence
<220> FEATURE:
<223> OTHER INFORMATION: humanized anti-CD39 antibody clone R21-9-8B VH
      region (Fig.6A)

<400> SEQUENCE: 61

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr His Tyr
                20                  25                  30

Gly Met Asn Trp Val Arg Gln Ala Pro Gly Gln Gly Leu Glu Trp Met
                35                  40                  45

Gly Trp Ile Asn Thr Tyr Thr Gly Glu Leu Thr Tyr Ala Asp Asp Phe
        50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                    85                  90                  95

Ala Arg Arg Ala Tyr Tyr Arg Tyr Asp Tyr Val Met Asp Tyr Trp Gly
                100                 105                 110

Gln Gly Thr Leu Val Thr Val Ser Ser
        115                 120

<210> SEQ ID NO 62
<211> LENGTH: 121
<212> TYPE: PRT
```

<213> ORGANISM: Artificial Sequence
<220> FEATURE:
<223> OTHER INFORMATION: humanized anti-CD39 antibody clone R21-9-8B VH
      region (Fig.6A)

<400> SEQUENCE: 62

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr His Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Leu Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Arg Ala Tyr Tyr Arg Tyr Asp Tyr Val Met Asp Tyr Trp Gly
            100                 105                 110

Gln Gly Thr Leu Val Thr Val Ser Ser
        115                 120

<210> SEQ ID NO 63
<211> LENGTH: 121
<212> TYPE: PRT
<213> ORGANISM: Artificial Sequence
<220> FEATURE:
<223> OTHER INFORMATION: humanized anti-CD39 antibody clone R21-9-8B VH
      region (Fig.6A)

<400> SEQUENCE: 63

Gln Ile Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr His Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Leu Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Arg Ala Tyr Tyr Arg Tyr Asp Tyr Val Met Asp Tyr Trp Gly
            100                 105                 110

Gln Gly Thr Leu Val Thr Val Ser Ser
        115                 120

<210> SEQ ID NO 64
<211> LENGTH: 121
<212> TYPE: PRT
<213> ORGANISM: Artificial Sequence
<220> FEATURE:
<223> OTHER INFORMATION: humanized anti-CD39 antibody clone R21-9-8B VH
      region (Fig.6A)

<400> SEQUENCE: 64

Gln Val Gln Leu Val Gln Ser Gly Ser Glu Leu Lys Lys Pro Gly Ala
1               5                   10                  15

-continued

Ser Val Lys Val Ser Cys Lys Ala Ser Gly Tyr Thr Phe Thr His Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Leu Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Arg Ala Tyr Tyr Arg Tyr Asp Tyr Val Met Asp Tyr Trp Gly
            100                 105                 110

Gln Gly Thr Leu Val Thr Val Ser Ser
        115                 120

<210> SEQ ID NO 65
<211> LENGTH: 121
<212> TYPE: PRT
<213> ORGANISM: Artificial Sequence
<220> FEATURE:
<223> OTHER INFORMATION: humanized anti-CD39 antibody clone R21-9-8B VH
      region (Fig.6A)

<400> SEQUENCE: 65

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr His Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Leu Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Arg Ala Tyr Tyr Arg Tyr Asp Tyr Val Met Asp Tyr Trp Gly
            100                 105                 110

Gln Gly Thr Leu Val Thr Val Ser Ser
        115                 120

<210> SEQ ID NO 66
<211> LENGTH: 121
<212> TYPE: PRT
<213> ORGANISM: Artificial Sequence
<220> FEATURE:
<223> OTHER INFORMATION: humanized anti-CD39 antibody clone R21-9-8B VH
      region (Fig.6A)

<400> SEQUENCE: 66

Gln Ile Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr His Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Leu Thr Tyr Ala Gln Gly Phe
    50                  55                  60

```
Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
             85                  90                  95

Ala Arg Arg Ala Tyr Tyr Arg Tyr Asp Tyr Val Met Asp Tyr Trp Gly
            100                 105                 110

Gln Gly Thr Leu Val Thr Val Ser Ser
        115                 120

<210> SEQ ID NO 67
<211> LENGTH: 121
<212> TYPE: PRT
<213> ORGANISM: Artificial Sequence
<220> FEATURE:
<223> OTHER INFORMATION: humanized anti-CD39 antibody clone R21-9-8B VH
      region (Fig.6B)

<400> SEQUENCE: 67

Gln Val Gln Leu Val Gln Ser Gly Ala Glu Val Lys Lys Pro Gly Ala
1               5                  10                   15

Ser Val Lys Val Ser Cys Lys Ala Ser Gly Tyr Thr Phe Thr His Tyr
            20                  25                  30

Gly Met Asn Trp Val Arg Gln Ala Pro Gly Gln Gly Leu Glu Trp Met
         35                  40                  45

Gly Trp Ile Asn Thr Tyr Thr Gly Glu Leu Thr Tyr Ala Asp Asp Phe
 50                  55                  60

Lys Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
             85                  90                  95

Ala Arg Arg Ala Tyr Tyr Arg Tyr Asp Tyr Val Met Asp Tyr Trp Gly
            100                 105                 110

Gln Gly Thr Leu Val Thr Val Ser Ser
        115                 120

<210> SEQ ID NO 68
<211> LENGTH: 121
<212> TYPE: PRT
<213> ORGANISM: Artificial Sequence
<220> FEATURE:
<223> OTHER INFORMATION: humanized anti-CD39 antibody clone R21-9-8B VH
      region (Fig.6B)

<400> SEQUENCE: 68

Gln Val Gln Leu Val Gln Ser Gly Ala Glu Val Lys Lys Pro Gly Ala
1               5                  10                   15

Ser Val Lys Val Ser Cys Lys Ala Ser Gly Tyr Thr Phe Thr His Tyr
            20                  25                  30

Gly Met Asn Trp Val Arg Gln Ala Pro Gly Gln Gly Leu Glu Trp Met
         35                  40                  45

Gly Trp Ile Asn Thr Tyr Thr Gly Glu Leu Thr Tyr Ala Asp Asp Phe
 50                  55                  60

Lys Gly Arg Val Thr Met Thr Leu Asp Thr Ser Thr Ser Thr Ala Tyr
 65                  70                  75                  80

Met Glu Leu Arg Ser Leu Arg Ser Asp Asp Thr Ala Val Tyr Tyr Cys
             85                  90                  95

Ala Arg Arg Ala Tyr Tyr Arg Tyr Asp Tyr Val Met Asp Tyr Trp Gly
            100                 105                 110
```

Gln Gly Thr Leu Val Thr Val Ser Ser
        115                 120

<210> SEQ ID NO 69
<211> LENGTH: 121
<212> TYPE: PRT
<213> ORGANISM: Artificial Sequence
<220> FEATURE:
<223> OTHER INFORMATION: humanized anti-CD39 antibody clone R21-9-8B VH
      region (Fig.6B)

<400> SEQUENCE: 69

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr His Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Leu Thr Tyr Ala Asp Asp Phe
    50                  55                  60

Lys Gly Arg Phe Thr Phe Thr Leu Asp Thr Ser Thr Ser Thr Ala Tyr
65                  70                  75                  80

Leu Glu Ile Arg Ser Leu Arg Ser Asp Asp Thr Ala Val Tyr Tyr Cys
                85                  90                  95

Ala Arg Arg Ala Tyr Tyr Arg Tyr Asp Tyr Val Met Asp Tyr Trp Gly
            100                 105                 110

Gln Gly Thr Leu Val Thr Val Ser Ser
        115                 120

<210> SEQ ID NO 70
<211> LENGTH: 121
<212> TYPE: PRT
<213> ORGANISM: Artificial Sequence
<220> FEATURE:
<223> OTHER INFORMATION: humanized anti-CD39 antibody clone R21-9-8B VH
      region (Fig.6B)

<400> SEQUENCE: 70

Gln Ile Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr His Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Leu Thr Tyr Ala Asp Asp Phe
    50                  55                  60

Lys Gly Arg Phe Thr Phe Thr Leu Asp Thr Ser Thr Ser Thr Ala Tyr
65                  70                  75                  80

Leu Glu Ile Arg Ser Leu Arg Ser Asp Asp Thr Ala Val Tyr Tyr Cys
                85                  90                  95

Ala Arg Arg Ala Tyr Tyr Arg Tyr Asp Tyr Val Met Asp Tyr Trp Gly
            100                 105                 110

Gln Gly Thr Leu Val Thr Val Ser Ser
        115                 120

<210> SEQ ID NO 71
<211> LENGTH: 121
<212> TYPE: PRT
<213> ORGANISM: Artificial Sequence

```
<220> FEATURE:
<223> OTHER INFORMATION: humanized anti-CD39 antibody clone R21-9-8B VH
      region (Fig.6B)

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr His Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Leu Thr Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Ala Tyr Tyr Arg Tyr Asp Tyr Val Met Asp Tyr Trp Gly
                100                 105                 110

Gln Gly Thr Leu Val Thr Val Ser Ser
            115                 120

<210> SEQ ID NO 72
<211> LENGTH: 121
<212> TYPE: PRT
<213> ORGANISM: Artificial Sequence
<220> FEATURE:
<223> OTHER INFORMATION: humanized anti-CD39 antibody clone R21-9-8B VH
      region (Fig.6B)

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr His Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Leu Thr Tyr Ala Gln Lys Leu
        50                  55                  60

Gln Gly Arg Val Thr Met Thr Leu Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Ala Tyr Tyr Arg Tyr Asp Tyr Val Met Asp Tyr Trp Gly
                100                 105                 110

Gln Gly Thr Leu Val Thr Val Ser Ser
            115                 120

<210> SEQ ID NO 73
<211> LENGTH: 121
<212> TYPE: PRT
<213> ORGANISM: Artificial Sequence
<220> FEATURE:
<223> OTHER INFORMATION: humanized anti-CD39 antibody clone R21-9-8B VH
      region (Fig.6B)

<400> SEQUENCE: 73

Gln Val Gln Leu Val Gln Ser Gly Ala Glu Val Lys Lys Pro Gly Ala
1               5                   10                  15
```

```
Ser Val Lys Ile Ser Cys Lys Ala Ser Gly Tyr Thr Phe Thr His Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Leu Thr Tyr Ala Gln Lys Leu
 50                  55                  60

Gln Gly Arg Phe Thr Phe Thr Leu Asp Thr Ser Thr Ser Thr Ala Tyr
 65                  70                  75                  80

Leu Glu Ile Arg Ser Leu Arg Ser Asp Asp Thr Ala Val Tyr Tyr Cys
                85                  90                  95

Ala Arg Arg Ala Tyr Tyr Arg Tyr Asp Tyr Val Met Asp Tyr Trp Gly
            100                 105                 110

Gln Gly Thr Leu Val Thr Val Ser Ser
            115                 120

<210> SEQ ID NO 74
<211> LENGTH: 121
<212> TYPE: PRT
<213> ORGANISM: Artificial Sequence
<220> FEATURE:
<223> OTHER INFORMATION: humanized anti-CD39 antibody clone R21-9-8B VH
      region (Fig.6B)

<400> SEQUENCE: 74

Gln Ile Gln Leu Val Gln Ser Gly Ala Glu Val Lys Lys Pro Gly Ala
 1               5                  10                  15

Ser Val Lys Ile Ser Cys Lys Ala Ser Gly Tyr Thr Phe Thr His Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Leu Thr Tyr Ala Gln Lys Leu
 50                  55                  60

Gln Gly Arg Phe Thr Phe Thr Leu Asp Thr Ser Thr Ser Thr Ala Tyr
 65                  70                  75                  80

Leu Glu Ile Arg Ser Leu Arg Ser Asp Asp Thr Ala Val Tyr Tyr Cys
                85                  90                  95

Ala Arg Arg Ala Tyr Tyr Arg Tyr Asp Tyr Val Met Asp Tyr Trp Gly
            100                 105                 110

Gln Gly Thr Leu Val Thr Val Ser Ser
            115                 120

<210> SEQ ID NO 75
<211> LENGTH: 121
<212> TYPE: PRT
<213> ORGANISM: Artificial Sequence
<220> FEATURE:
<223> OTHER INFORMATION: humanized anti-CD39 antibody clone R21-9-8B VH
      region (Fig.6C)

<400> SEQUENCE: 75

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Thr His Tyr
            20                  25                  30

Gly Met Asn Trp Val Arg Gln Ala Pro Gly Lys Gly Leu Glu Trp Val
        35                  40                  45

Ser Trp Ile Asn Thr Tyr Thr Gly Glu Leu Thr Tyr Ala Asp Asp Phe
 50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Arg Ala Tyr Tyr Arg Tyr Asp Tyr Val Met Asp Tyr Trp Gly
            100                 105                 110

Gln Gly Thr Leu Val Thr Val Ser Ser
            115                 120

<210> SEQ ID NO 76
<211> LENGTH: 121
<212> TYPE: PRT
<213> ORGANISM: Artificial Sequence
<220> FEATURE:
<223> OTHER INFORMATION: humanized anti-CD39 antibody clone R21-9-8B VH
      region (Fig.6C)

<400> SEQUENCE: 76

Glu Val Gln Leu Val Glu Ser Gly Gly Gly Leu Val Gln Pro Gly Gly
1                5                  10                  15

Ser Leu Arg Ile Ser Cys Ala Ala Ser Gly Tyr Thr Phe Thr His Tyr
                20                  25                  30

Gly Met Asn Trp Val Arg Gln Ala Pro Gly Lys Gly Leu Glu Trp Met
            35                  40                  45

Gly Trp Ile Asn Thr Tyr Thr Gly Glu Leu Thr Tyr Ala Asp Asp Phe
    50                  55                  60

Lys Gly Arg Phe Thr Phe Ser Leu Asp Asn Ala Lys Asn Ser Ala Tyr
 65                  70                  75                  80

Leu Gln Ile Asn Ser Leu Arg Ala Glu Asp Thr Ala Val Tyr Tyr Cys
                 85                  90                  95

Ala Arg Arg Ala Tyr Tyr Arg Tyr Asp Tyr Val Met Asp Tyr Trp Gly
            100                 105                 110

Gln Gly Thr Leu Val Thr Val Ser Ser
            115                 120

<210> SEQ ID NO 77
<211> LENGTH: 121
<212> TYPE: PRT
<213> ORGANISM: Artificial Sequence
<220> FEATURE:
<223> OTHER INFORMATION: humanized anti-CD39 antibody clone R21-9-8B VH
      region (Fig.6C)

<400> SEQUENCE: 77

Glu Ile Gln Leu Val Glu Ser Gly Gly Gly Leu Val Gln Pro Gly Gly
1                5                  10                  15

Ser Leu Arg Ile Ser Cys Ala Ala Ser Gly Tyr Thr Phe Thr His Tyr
                20                  25                  30

Gly Met Asn Trp Val Arg Gln Ala Pro Gly Lys Gly Leu Glu Trp Met
            35                  40                  45

Gly Trp Ile Asn Thr Tyr Thr Gly Glu Leu Thr Tyr Ala Asp Asp Phe
    50                  55                  60

Lys Gly Arg Phe Thr Phe Ser Leu Asp Thr Ala Lys Asn Ser Ala Tyr
 65                  70                  75                  80

Leu Gln Ile Asn Ser Leu Arg Ala Glu Asp Thr Ala Val Tyr Tyr Cys
                 85                  90                  95

Ala Arg Arg Ala Tyr Tyr Arg Tyr Asp Tyr Val Met Asp Tyr Trp Gly
            100                 105                 110
```

```
Gln Gly Thr Leu Val Thr Val Ser Ser
        115                 120

<210> SEQ ID NO 78
<211> LENGTH: 121
<212> TYPE: PRT
<213> ORGANISM: Artificial Sequence
<220> FEATURE:
<223> OTHER INFORMATION: humanized anti-CD39 antibody clone R21-9-8B VH
      region (Fig.6C)

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr His Tyr
            20                  25                  30

Gly Met Asn Trp Val Arg Gln Ala Pro Gly Lys Gly Leu Glu Trp Val
        35                  40                  45

Ser Trp Ile Asn Thr Tyr Thr Gly Glu Leu Thr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Tyr Tyr Arg Tyr Asp Tyr Val Met Asp Tyr Trp Gly
            100                 105                 110

Gln Gly Thr Leu Val Thr Val Ser Ser
        115                 120

<210> SEQ ID NO 79
<211> LENGTH: 121
<212> TYPE: PRT
<213> ORGANISM: Artificial Sequence
<220> FEATURE:
<223> OTHER INFORMATION: humanized anti-CD39 antibody clone R21-9-8B VH
      region (Fig.6C)

<400> SEQUENCE: 79

Glu Val Gln Leu Val Glu Ser Gly Gly Gly Leu Val Gln Pro Gly Gly
1               5                   10                  15

Ser Leu Arg Ile Ser Cys Ala Ala Ser Gly Tyr Thr Phe Thr His Tyr
            20                  25                  30

Gly Met Asn Trp Val Arg Gln Ala Pro Gly Lys Gly Leu Glu Trp Met
        35                  40                  45

Gly Trp Ile Asn Thr Tyr Thr Gly Glu Leu Thr Tyr Ala Asp Ser Val
    50                  55                  60

Lys Gly Arg Phe Thr Phe Ser Leu Asp Asn Ala Lys Asn Ser Ala Tyr
65                  70                  75                  80

Leu Gln Ile Asn Ser Leu Arg Ala Glu Asp Thr Ala Val Tyr Tyr Cys
                85                  90                  95

Ala Arg Arg Ala Tyr Tyr Arg Tyr Asp Tyr Val Met Asp Tyr Trp Gly
            100                 105                 110

Gln Gly Thr Leu Val Thr Val Ser Ser
        115                 120

<210> SEQ ID NO 80
<211> LENGTH: 121
<212> TYPE: PRT
<213> ORGANISM: Artificial Sequence
<220> FEATURE:
```

<223> OTHER INFORMATION: humanized anti-CD39 antibody clone R21-9-8B VH
      region (Fig.6C)

<400> SEQUENCE: 80

Glu Ile Gln Leu Val Glu Ser Gly Gly Gly Leu Val Gln Pro Gly Gly
1               5                   10                  15

Ser Leu Arg Ile Ser Cys Ala Ala Ser Gly Tyr Thr Phe Thr His Tyr
            20                  25                  30

Gly Met Asn Trp Val Arg Gln Ala Pro Gly Lys Gly Leu Glu Trp Met
        35                  40                  45

Gly Trp Ile Asn Thr Tyr Thr Gly Glu Leu Tyr Ala Asp Ser Val
    50                  55                  60

Lys Gly Arg Phe Thr Phe Ser Leu Asp Thr Ala Lys Asn Ser Ala Tyr
65                  70                  75                  80

Leu Gln Ile Asn Ser Leu Arg Ala Glu Asp Thr Ala Val Tyr Tyr Cys
                85                  90                  95

Ala Arg Arg Ala Tyr Tyr Arg Tyr Asp Tyr Val Met Asp Tyr Trp Gly
            100                 105                 110

Gln Gly Thr Leu Val Thr Val Ser Ser
        115                 120

<210> SEQ ID NO 81
<211> LENGTH: 107
<212> TYPE: PRT
<213> ORGANISM: Artificial Sequence
<220> FEATURE:
<223> OTHER INFORMATION: humanized anti-CD39 antibody clone R21-9-8B VL
      region (Fig.7A)

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Lys Ala Ser His Asn Val Gly Thr Asn
            20                  25                  30

Val Ala Trp Phe Gln Gln Lys Pro Gly Lys Ala Pro Lys Ser Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Asn Asn Tyr Pro Tyr
                85                  90                  95

Thr Phe Gly Gln Gly Thr Lys Leu Glu Ile Lys
            100                 105

<210> SEQ ID NO 82
<211> LENGTH: 107
<212> TYPE: PRT
<213> ORGANISM: Artificial Sequence
<220> FEATURE:
<223> OTHER INFORMATION: humanized anti-CD39 antibody clone R21-9-8B VL
      region (Fig.7A)

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser His Asn Val Gly Thr Asn
            20                  25                  30

Val Ala Trp Tyr Gln Gln Lys Pro Gly Lys Ala Pro Lys Ala Leu Ile

```
                35                  40                  45
Tyr Ser Ala Ser Tyr Arg Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Asn Asn Tyr Pro Tyr
                85                  90                  95

Thr Phe Gly Gln Gly Thr Lys Leu Glu Ile Lys
            100                 105

<210> SEQ ID NO 83
<211> LENGTH: 107
<212> TYPE: PRT
<213> ORGANISM: Artificial Sequence
<220> FEATURE:
<223> OTHER INFORMATION: humanized anti-CD39 antibody clone R21-9-8B VL
      region (Fig.7A)

<400> SEQUENCE: 83

Asp Ile Gln Met Thr Gln Ser Pro Ser Ser Met Ser Ala Ser Val Gly
1               5                   10                  15

Asp Arg Val Thr Val Thr Cys Arg Ala Ser His Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Val Gln Pro
65                  70                  75                  80

Glu Asp Phe Ala Thr Tyr Tyr Cys His Gln Tyr Asn Asn Tyr Pro Tyr
                85                  90                  95

Thr Phe Gly Gln Gly Thr Lys Leu Glu Ile Lys
            100                 105

<210> SEQ ID NO 84
<211> LENGTH: 107
<212> TYPE: PRT
<213> ORGANISM: Artificial Sequence
<220> FEATURE:
<223> OTHER INFORMATION: humanized anti-CD39 antibody clone R21-9-8B VL
      region (Fig.7A)

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Lys Ala Ser His Asn Val Gly Thr Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Asn Asn Tyr Pro Tyr
                85                  90                  95

Thr Phe Gly Gln Gly Thr Lys Leu Glu Ile Lys
            100                 105
```

```
<210> SEQ ID NO 85
<211> LENGTH: 107
<212> TYPE: PRT
<213> ORGANISM: Artificial Sequence
<220> FEATURE:
<223> OTHER INFORMATION: humanized anti-CD39 antibody clone R21-9-8B VL
      region (Fig.7A)

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser His Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Asn Asn Tyr Pro Tyr
                85                  90                  95

Thr Phe Gly Gln Gly Thr Lys Leu Glu Ile Lys
            100                 105

<210> SEQ ID NO 86
<211> LENGTH: 107
<212> TYPE: PRT
<213> ORGANISM: Artificial Sequence
<220> FEATURE:
<223> OTHER INFORMATION: humanized anti-CD39 antibody clone R21-9-8B VL
      region (Fig.7A)

<400> SEQUENCE: 86

Asp Ile Gln Met Thr Gln Ser Pro Ser Ser Met Ser Ala Ser Val Gly
1               5                   10                  15

Asp Arg Val Thr Val Thr Cys Arg Ala Ser His Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
50                  55                  60

Ser Gly Ser Gly Thr Asp Phe Thr Leu Thr Ile Ser Ser Val Gln Pro
65                  70                  75                  80

Glu Asp Phe Ala Thr Tyr Tyr Cys His Gln Tyr Asn Asn Tyr Pro Tyr
                85                  90                  95

Thr Phe Gly Gln Gly Thr Lys Leu Glu Ile Lys
            100                 105

<210> SEQ ID NO 87
<211> LENGTH: 8
<212> TYPE: PRT
<213> ORGANISM: Artificial Sequence
<220> FEATURE:
<223> OTHER INFORMATION: Antibody R21-5-13A VH CDR1 - IMGT

<400> SEQUENCE: 87

Gly Tyr Thr Phe Thr Gly Tyr Tyr
1               5

<210> SEQ ID NO 88
<211> LENGTH: 5
```

```
<212> TYPE: PRT
<213> ORGANISM: Artificial Sequence
<220> FEATURE:
<223> OTHER INFORMATION: Antibody R21-5-13A VH CDR1 - Kabat

<400> SEQUENCE: 88

Gly Tyr Tyr Val His
1               5

<210> SEQ ID NO 89
<211> LENGTH: 7
<212> TYPE: PRT
<213> ORGANISM: Artificial Sequence
<220> FEATURE:
<223> OTHER INFORMATION: Antibody R21-5-13A VH CDR1 - Chothia

<400> SEQUENCE: 89

Gly Tyr Thr Phe Thr Gly Tyr
1               5

<210> SEQ ID NO 90
<211> LENGTH: 6
<212> TYPE: PRT
<213> ORGANISM: Artificial Sequence
<220> FEATURE:
<223> OTHER INFORMATION: Antibody R21-5-13A VH CDR1 - Contact

<400> SEQUENCE: 90

Thr Gly Tyr Tyr Val His
1               5

<210> SEQ ID NO 91
<211> LENGTH: 8
<212> TYPE: PRT
<213> ORGANISM: Artificial Sequence
<220> FEATURE:
<223> OTHER INFORMATION: Antibody R21-5-13A VH CDR2 - IMGT

<400> SEQUENCE: 91

Ile Tyr Pro Gly Asn Val Asn Thr
1               5

<210> SEQ ID NO 92
<211> LENGTH: 17
<212> TYPE: PRT
<213> ORGANISM: Artificial Sequence
<220> FEATURE:
<223> OTHER INFORMATION: Antibody R21-5-13A VH CDR2 - Kabat

<400> SEQUENCE: 92

Trp Ile Tyr Pro Gly Asn Val Asn Thr Lys Tyr Asn Glu Lys Phe Lys
1               5                   10                  15

Ala

<210> SEQ ID NO 93
<211> LENGTH: 4
<212> TYPE: PRT
<213> ORGANISM: Artificial Sequence
<220> FEATURE:
<223> OTHER INFORMATION: Antibody R21-5-13A VH CDR2 - Chothia

<400> SEQUENCE: 93

Pro Gly Asn Val
1

<210> SEQ ID NO 94
```

<211> LENGTH: 13
<212> TYPE: PRT
<213> ORGANISM: Artificial Sequence
<220> FEATURE:
<223> OTHER INFORMATION: Antibody R21-5-13A VH CDR2 - Contact

<400> SEQUENCE: 94

Trp Ile Gly Trp Ile Tyr Pro Gly Asn Val Asn Thr Lys
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Antibody R21-5-13A VH CDR2 - AbM

<400> SEQUENCE: 95

Trp Ile Tyr Pro Gly Asn Val Asn Thr Lys
1               5                   10

<210> SEQ ID NO 96
<211> LENGTH: 16
<212> TYPE: PRT
<213> ORGANISM: Artificial Sequence
<220> FEATURE:
<223> OTHER INFORMATION: Antibody R21-5-13A VH CDR3 - IMGT

<400> SEQUENCE: 96

Ala Arg Ser Pro Tyr Tyr Gly Thr Thr Tyr Tyr Tyr Thr Met Asp Tyr
1               5                   10                  15

<210> SEQ ID NO 97
<211> LENGTH: 14
<212> TYPE: PRT
<213> ORGANISM: Artificial Sequence
<220> FEATURE:
<223> OTHER INFORMATION: Antibody R21-5-13A VH CDR3 - Kabat

<400> SEQUENCE: 97

Ser Pro Tyr Tyr Gly Thr Thr Tyr Tyr Tyr Thr Met Asp Tyr
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Antibody R21-5-13A VH CDR3 - Chothia

<400> SEQUENCE: 98

Pro Tyr Tyr Gly Thr Thr Tyr Tyr Tyr Thr Met Asp
1               5                   10

<210> SEQ ID NO 99
<211> LENGTH: 15
<212> TYPE: PRT
<213> ORGANISM: Artificial Sequence
<220> FEATURE:
<223> OTHER INFORMATION: Antibody R21-5-13A VH CDR3 - Contact

<400> SEQUENCE: 99

Ala Arg Ser Pro Tyr Tyr Gly Thr Thr Tyr Tyr Tyr Thr Met Asp
1               5                   10                  15

<210> SEQ ID NO 100
<211> LENGTH: 7

<212> TYPE: PRT
<213> ORGANISM: Artificial Sequence
<220> FEATURE:
<223> OTHER INFORMATION: Antibody R21-5-13A VL CDR1 - IMGT

<400> SEQUENCE: 100

Leu Ile Ile Ser Ser Arg Asn
1               5

<210> SEQ ID NO 101
<211> LENGTH: 12
<212> TYPE: PRT
<213> ORGANISM: Artificial Sequence
<220> FEATURE:
<223> OTHER INFORMATION: Antibody R21-5-13A VL CDR1 - Kabat

<400> SEQUENCE: 101

Ser Val Ser Leu Ile Ile Ser Ser Arg Asn Leu His
1               5                   10

<210> SEQ ID NO 102
<211> LENGTH: 8
<212> TYPE: PRT
<213> ORGANISM: Artificial Sequence
<220> FEATURE:
<223> OTHER INFORMATION: Antibody R21-5-13A VL CDR1 - Chothia

<400> SEQUENCE: 102

Ser Leu Ile Ile Ser Ser Arg Asn
1               5

<210> SEQ ID NO 103
<211> LENGTH: 8
<212> TYPE: PRT
<213> ORGANISM: Artificial Sequence
<220> FEATURE:
<223> OTHER INFORMATION: Antibody R21-5-13A VL CDR1 - Contact

<400> SEQUENCE: 103

Ser Ser Arg Asn Leu His Trp Tyr
1               5

<210> SEQ ID NO 104
<211> LENGTH: 7
<212> TYPE: PRT
<213> ORGANISM: Artificial Sequence
<220> FEATURE:
<223> OTHER INFORMATION: Antibody R21-5-13A VL CDR2 - Kabat

<400> SEQUENCE: 104

Gly Thr Ser Asn Leu Ala Ser
1               5

<210> SEQ ID NO 105
<211> LENGTH: 10
<212> TYPE: PRT
<213> ORGANISM: Artificial Sequence
<220> FEATURE:
<223> OTHER INFORMATION: Antibody R21-5-13A VL CDR2 - Contact

<400> SEQUENCE: 105

Pro Trp Ile Tyr Gly Thr Ser Asn Leu Ala
1               5                   10

<210> SEQ ID NO 106
<211> LENGTH: 9
<212> TYPE: PRT

```
<213> ORGANISM: Artificial Sequence
<220> FEATURE:
<223> OTHER INFORMATION: Antibody R21-5-13A VL CDR3 - IMGT

<400> SEQUENCE: 106

Gln Gln Trp Ser Asp Tyr Pro Leu Thr
1               5

<210> SEQ ID NO 107
<211> LENGTH: 6
<212> TYPE: PRT
<213> ORGANISM: Artificial Sequence
<220> FEATURE:
<223> OTHER INFORMATION: Antibody R21-5-13A VL CDR3 - Chothia

<400> SEQUENCE: 107

Trp Ser Asp Tyr Pro Leu
1               5

<210> SEQ ID NO 108
<211> LENGTH: 8
<212> TYPE: PRT
<213> ORGANISM: Artificial Sequence
<220> FEATURE:
<223> OTHER INFORMATION: Antibody R21-5-13A VL CDR3 - Contact

<400> SEQUENCE: 108

Gln Gln Trp Ser Asp Tyr Pro Leu
1               5

<210> SEQ ID NO 109
<211> LENGTH: 8
<212> TYPE: PRT
<213> ORGANISM: Artificial Sequence
<220> FEATURE:
<223> OTHER INFORMATION: Antibody R21-5-71A VH CDR1 - IMGT

<400> SEQUENCE: 109

Gly Phe Thr Phe Ser Ser Phe Gly
1               5

<210> SEQ ID NO 110
<211> LENGTH: 5
<212> TYPE: PRT
<213> ORGANISM: Artificial Sequence
<220> FEATURE:
<223> OTHER INFORMATION: Antibody R21-5-71A VH CDR1 - Kabat

<400> SEQUENCE: 110

Ser Phe Gly Met His
1               5

<210> SEQ ID NO 111
<211> LENGTH: 7
<212> TYPE: PRT
<213> ORGANISM: Artificial Sequence
<220> FEATURE:
<223> OTHER INFORMATION: Antibody R21-5-71A VH CDR1 - Chothia

<400> SEQUENCE: 111

Gly Phe Thr Phe Ser Ser Phe
1               5

<210> SEQ ID NO 112
<211> LENGTH: 6
<212> TYPE: PRT
<213> ORGANISM: Artificial Sequence
```

```
<220> FEATURE:
<223> OTHER INFORMATION: Antibody R21-5-71A VH CDR1 - Contact

<400> SEQUENCE: 112

Ser Ser Phe Gly Met His
1               5

<210> SEQ ID NO 113
<211> LENGTH: 10
<212> TYPE: PRT
<213> ORGANISM: Artificial Sequence
<220> FEATURE:
<223> OTHER INFORMATION: Antibody R21-5-71A VH CDR1 - AbM

<400> SEQUENCE: 113

Gly Phe Thr Phe Ser Ser Phe Gly Met His
1               5                   10

<210> SEQ ID NO 114
<211> LENGTH: 8
<212> TYPE: PRT
<213> ORGANISM: Artificial Sequence
<220> FEATURE:
<223> OTHER INFORMATION: Antibody R21-5-71A VH CDR2 - IMGT

<400> SEQUENCE: 114

Ile Ser Ser Gly Ser Thr Ile Arg
1               5

<210> SEQ ID NO 115
<211> LENGTH: 17
<212> TYPE: PRT
<213> ORGANISM: Artificial Sequence
<220> FEATURE:
<223> OTHER INFORMATION: Antibody R21-5-71A VH CDR2 - Kabat

<400> SEQUENCE: 115

Tyr Ile Ser Ser Gly Ser Thr Ile Arg Tyr Tyr Ser Asp Thr Val Lys
1               5                   10                  15

Gly

<210> SEQ ID NO 116
<211> LENGTH: 4
<212> TYPE: PRT
<213> ORGANISM: Artificial Sequence
<220> FEATURE:
<223> OTHER INFORMATION: Antibody R21-5-71A VH CDR2 - Chothia

<400> SEQUENCE: 116

Ser Gly Ser Thr
1

<210> SEQ ID NO 117
<211> LENGTH: 13
<212> TYPE: PRT
<213> ORGANISM: Artificial Sequence
<220> FEATURE:
<223> OTHER INFORMATION: Antibody R21-5-71A VH CDR2 - Contact

<400> SEQUENCE: 117

Leu Val Ala Tyr Ile Ser Ser Gly Ser Thr Ile Arg Tyr
1               5                   10

<210> SEQ ID NO 118
<211> LENGTH: 10
<212> TYPE: PRT
```

<213> ORGANISM: Artificial Sequence
<220> FEATURE:
<223> OTHER INFORMATION: Antibody R21-5-71A VH CDR2 - AbM

<400> SEQUENCE: 118

Tyr Ile Ser Ser Gly Ser Thr Ile Arg Tyr
1               5                   10

<210> SEQ ID NO 119
<211> LENGTH: 14
<212> TYPE: PRT
<213> ORGANISM: Artificial Sequence
<220> FEATURE:
<223> OTHER INFORMATION: Antibody R21-5-71A VH CDR3 - IMGT

<400> SEQUENCE: 119

Ala Arg Phe Leu Tyr Glu Gly Phe Arg Tyr Gly Met Asp Tyr
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Antibody R21-5-71A VH CDR3 - Kabat

<400> SEQUENCE: 120

Phe Leu Tyr Glu Gly Phe Arg Tyr Gly Met Asp Tyr
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Antibody R21-5-71A VH CDR3 - Chothia

<400> SEQUENCE: 121

Leu Tyr Glu Gly Phe Arg Tyr Gly Met Asp
1               5                   10

<210> SEQ ID NO 122
<211> LENGTH: 13
<212> TYPE: PRT
<213> ORGANISM: Artificial Sequence
<220> FEATURE:
<223> OTHER INFORMATION: Antibody R21-5-71A VH CDR3 - Contact

<400> SEQUENCE: 122

Ala Arg Phe Leu Tyr Glu Gly Phe Arg Tyr Gly Met Asp
1               5                   10

<210> SEQ ID NO 123
<211> LENGTH: 11
<212> TYPE: PRT
<213> ORGANISM: Artificial Sequence
<220> FEATURE:
<223> OTHER INFORMATION: Antibody R21-5-71A VL CDR1 - IMGT

<400> SEQUENCE: 123

Gln Ser Ile Val His Ser Asn Gly Asn Thr Tyr
1               5                   10

<210> SEQ ID NO 124
<211> LENGTH: 16
<212> TYPE: PRT
<213> ORGANISM: Artificial Sequence

```
<220> FEATURE:
<223> OTHER INFORMATION: Antibody R21-5-71A VL CDR1 - Kabat

<400> SEQUENCE: 124

Arg Ser Ser Gln Ser Ile Val His Ser Asn Gly Asn Thr Tyr Leu Glu
1               5                   10                  15

<210> SEQ ID NO 125
<211> LENGTH: 12
<212> TYPE: PRT
<213> ORGANISM: Artificial Sequence
<220> FEATURE:
<223> OTHER INFORMATION: Antibody R21-5-71A VL CDR1 - Chothia

<400> SEQUENCE: 125

Ser Gln Ser Ile Val His Ser Asn Gly Asn Thr Tyr
1               5                   10

<210> SEQ ID NO 126
<211> LENGTH: 12
<212> TYPE: PRT
<213> ORGANISM: Artificial Sequence
<220> FEATURE:
<223> OTHER INFORMATION: Antibody R21-5-71A VL CDR1 - Contact

<400> SEQUENCE: 126

Val His Ser Asn Gly Asn Thr Tyr Leu Glu Trp Tyr
1               5                   10

<210> SEQ ID NO 127
<211> LENGTH: 3
<212> TYPE: PRT
<213> ORGANISM: Artificial Sequence
<220> FEATURE:
<223> OTHER INFORMATION: Antibody R21-5-71A VL CDR2 - IMGT

<400> SEQUENCE: 127

Lys Val Ser
1

<210> SEQ ID NO 128
<211> LENGTH: 7
<212> TYPE: PRT
<213> ORGANISM: Artificial Sequence
<220> FEATURE:
<223> OTHER INFORMATION: Antibody R21-5-71A VL CDR2 - Kabat

<400> SEQUENCE: 128

Lys Val Ser Asn Arg Phe Ser
1               5

<210> SEQ ID NO 129
<211> LENGTH: 10
<212> TYPE: PRT
<213> ORGANISM: Artificial Sequence
<220> FEATURE:
<223> OTHER INFORMATION: Antibody R21-5-71A VL CDR2 - Contact

<400> SEQUENCE: 129

Leu Leu Ile Tyr Lys Val Ser Asn Arg Phe
1               5                   10

<210> SEQ ID NO 130
<211> LENGTH: 9
<212> TYPE: PRT
<213> ORGANISM: Artificial Sequence
<220> FEATURE:
```

<223> OTHER INFORMATION: Antibody R21-5-71A VL CDR3 - IMGT

<400> SEQUENCE: 130

Phe Gln Gly Ser His Val Pro Asn Thr
1               5

<210> SEQ ID NO 131
<211> LENGTH: 6
<212> TYPE: PRT
<213> ORGANISM: Artificial Sequence
<220> FEATURE:
<223> OTHER INFORMATION: Antibody R21-5-71A VL CDR3 - Chothia

<400> SEQUENCE: 131

Gly Ser His Val Pro Asn
1               5

<210> SEQ ID NO 132
<211> LENGTH: 8
<212> TYPE: PRT
<213> ORGANISM: Artificial Sequence
<220> FEATURE:
<223> OTHER INFORMATION: Antibody R21-5-71A VL CDR3 - Contact

<400> SEQUENCE: 132

Phe Gln Gly Ser His Val Pro Asn
1               5

<210> SEQ ID NO 133
<211> LENGTH: 8
<212> TYPE: PRT
<213> ORGANISM: Artificial Sequence
<220> FEATURE:
<223> OTHER INFORMATION: Antibody R21-5-165C VH CDR1 - IMGT

<400> SEQUENCE: 133

Gly Phe Thr Phe Ser Arg Tyr Gly
1               5

<210> SEQ ID NO 134
<211> LENGTH: 5
<212> TYPE: PRT
<213> ORGANISM: Artificial Sequence
<220> FEATURE:
<223> OTHER INFORMATION: Antibody R21-5-165C VH CDR1 - Kabat

<400> SEQUENCE: 134

Arg Tyr Gly Met Ser
1               5

<210> SEQ ID NO 135
<211> LENGTH: 7
<212> TYPE: PRT
<213> ORGANISM: Artificial Sequence
<220> FEATURE:
<223> OTHER INFORMATION: Antibody R21-5-165C VH CDR1 - Chothia

<400> SEQUENCE: 135

Gly Phe Thr Phe Ser Arg Tyr
1               5

<210> SEQ ID NO 136
<211> LENGTH: 6
<212> TYPE: PRT
<213> ORGANISM: Artificial Sequence
<220> FEATURE:
<223> OTHER INFORMATION: Antibody R21-5-165C VH CDR1 - Contact

```
<400> SEQUENCE: 136

Ser Arg Tyr Gly Met Ser
1               5

<210> SEQ ID NO 137
<211> LENGTH: 10
<212> TYPE: PRT
<213> ORGANISM: Artificial Sequence
<220> FEATURE:
<223> OTHER INFORMATION: Antibody R21-5-165C VH CDR1 - AbM

<400> SEQUENCE: 137

Gly Phe Thr Phe Ser Arg Tyr Gly Met Ser
1               5                   10

<210> SEQ ID NO 138
<211> LENGTH: 8
<212> TYPE: PRT
<213> ORGANISM: Artificial Sequence
<220> FEATURE:
<223> OTHER INFORMATION: Antibody R21-5-165C VH CDR2 - IMGT

<400> SEQUENCE: 138

Ile Thr Ser Gly Gly Ile Tyr Thr
1               5

<210> SEQ ID NO 139
<211> LENGTH: 17
<212> TYPE: PRT
<213> ORGANISM: Artificial Sequence
<220> FEATURE:
<223> OTHER INFORMATION: Antibody R21-5-165C VH CDR2 - Kabat

<400> SEQUENCE: 139

Thr Ile Thr Ser Gly Gly Ile Tyr Thr Tyr Tyr Pro Asp Ser Val Lys
1               5                   10                  15
Gly

<210> SEQ ID NO 140
<211> LENGTH: 4
<212> TYPE: PRT
<213> ORGANISM: Artificial Sequence
<220> FEATURE:
<223> OTHER INFORMATION: Antibody R21-5-165C VH CDR2 - Chothia

<400> SEQUENCE: 140

Ser Gly Gly Ile
1

<210> SEQ ID NO 141
<211> LENGTH: 13
<212> TYPE: PRT
<213> ORGANISM: Artificial Sequence
<220> FEATURE:
<223> OTHER INFORMATION: Antibody R21-5-165C VH CDR2 - Contact

<400> SEQUENCE: 141

Trp Val Ala Thr Ile Thr Ser Gly Gly Ile Tyr Thr Tyr
1               5                   10

<210> SEQ ID NO 142
<211> LENGTH: 10
<212> TYPE: PRT
<213> ORGANISM: Artificial Sequence
<220> FEATURE:
```

<223> OTHER INFORMATION: Antibody R21-5-165C VH CDR2 - AbM

<400> SEQUENCE: 142

Thr Ile Thr Ser Gly Gly Ile Tyr Thr Tyr
1               5                   10

<210> SEQ ID NO 143
<211> LENGTH: 14
<212> TYPE: PRT
<213> ORGANISM: Artificial Sequence
<220> FEATURE:
<223> OTHER INFORMATION: Antibody R21-5-165C VH CDR3 - IMGT

<400> SEQUENCE: 143

Ala Arg His Gly Gln Phe Gly Asp Tyr Tyr Gly Met Asp Tyr
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Antibody R21-5-165C VH CDR3 - Kabat

<400> SEQUENCE: 144

His Gly Gln Phe Gly Asp Tyr Tyr Gly Met Asp Tyr
1               5                   10

<210> SEQ ID NO 145
<211> LENGTH: 10
<212> TYPE: PRT
<213> ORGANISM: Artificial Sequence
<220> FEATURE:
<223> OTHER INFORMATION: Antibody R21-5-165C VH CDR3 - Chothia

<400> SEQUENCE: 145

Gly Gln Phe Gly Asp Tyr Tyr Gly Met Asp
1               5                   10

<210> SEQ ID NO 146
<211> LENGTH: 13
<212> TYPE: PRT
<213> ORGANISM: Artificial Sequence
<220> FEATURE:
<223> OTHER INFORMATION: Antibody R21-5-165C VH CDR3 - Contact

<400> SEQUENCE: 146

Ala Arg His Gly Gln Phe Gly Asp Tyr Tyr Gly Met Asp
1               5                   10

<210> SEQ ID NO 147
<211> LENGTH: 11
<212> TYPE: PRT
<213> ORGANISM: Artificial Sequence
<220> FEATURE:
<223> OTHER INFORMATION: Antibody R21-5-165C VL CDR1 - IMGT

<400> SEQUENCE: 147

Gln Ser Leu Leu His Ser Asn Gly Asn Thr Tyr
1               5                   10

<210> SEQ ID NO 148
<211> LENGTH: 16
<212> TYPE: PRT
<213> ORGANISM: Artificial Sequence
<220> FEATURE:
<223> OTHER INFORMATION: Antibody R21-5-165C VL CDR1 - Kabat

```
<400> SEQUENCE: 148

Arg Ser Ser Gln Ser Leu Leu His Ser Asn Gly Asn Thr Tyr Leu His
1               5                   10                  15

<210> SEQ ID NO 149
<211> LENGTH: 12
<212> TYPE: PRT
<213> ORGANISM: Artificial Sequence
<220> FEATURE:
<223> OTHER INFORMATION: Antibody R21-5-165C VL CDR1 - Chothia

<400> SEQUENCE: 149

Ser Gln Ser Leu Leu His Ser Asn Gly Asn Thr Tyr
1               5                   10

<210> SEQ ID NO 150
<211> LENGTH: 12
<212> TYPE: PRT
<213> ORGANISM: Artificial Sequence
<220> FEATURE:
<223> OTHER INFORMATION: Antibody R21-5-165C VL CDR1 - Contact

<400> SEQUENCE: 150

Leu His Ser Asn Gly Asn Thr Tyr Leu His Trp Tyr
1               5                   10

<210> SEQ ID NO 151
<211> LENGTH: 9
<212> TYPE: PRT
<213> ORGANISM: Artificial Sequence
<220> FEATURE:
<223> OTHER INFORMATION: Antibody R21-5-165C VL CDR3 - IMGT

<400> SEQUENCE: 151

Ser Gln Ser Thr His Val Pro Tyr Thr
1               5

<210> SEQ ID NO 152
<211> LENGTH: 6
<212> TYPE: PRT
<213> ORGANISM: Artificial Sequence
<220> FEATURE:
<223> OTHER INFORMATION: Antibody R21-5-165C VL CDR3 - Chothia

<400> SEQUENCE: 152

Ser Thr His Val Pro Tyr
1               5

<210> SEQ ID NO 153
<211> LENGTH: 8
<212> TYPE: PRT
<213> ORGANISM: Artificial Sequence
<220> FEATURE:
<223> OTHER INFORMATION: Antibody R21-5-165C VL CDR3 - Contact

<400> SEQUENCE: 153

Ser Gln Ser Thr His Val Pro Tyr
1               5

<210> SEQ ID NO 154
<211> LENGTH: 8
<212> TYPE: PRT
<213> ORGANISM: Artificial Sequence
<220> FEATURE:
<223> OTHER INFORMATION: Antibody R21-9-8B VH CDR1 - IMGT
```

<400> SEQUENCE: 154

Gly Tyr Thr Phe Thr His Tyr Gly
1               5

<210> SEQ ID NO 155
<211> LENGTH: 5
<212> TYPE: PRT
<213> ORGANISM: Artificial Sequence
<220> FEATURE:
<223> OTHER INFORMATION: Antibody R21-9-8B VH CDR1 - Kabat

<400> SEQUENCE: 155

His Tyr Gly Met Asn
1               5

<210> SEQ ID NO 156
<211> LENGTH: 7
<212> TYPE: PRT
<213> ORGANISM: Artificial Sequence
<220> FEATURE:
<223> OTHER INFORMATION: Antibody R21-9-8B VH CDR1 - Chothia

<400> SEQUENCE: 156

Gly Tyr Thr Phe Thr His Tyr
1               5

<210> SEQ ID NO 157
<211> LENGTH: 6
<212> TYPE: PRT
<213> ORGANISM: Artificial Sequence
<220> FEATURE:
<223> OTHER INFORMATION: Antibody R21-9-8B VH CDR1 - Contact

<400> SEQUENCE: 157

Thr His Tyr Gly Met Asn
1               5

<210> SEQ ID NO 158
<211> LENGTH: 10
<212> TYPE: PRT
<213> ORGANISM: Artificial Sequence
<220> FEATURE:
<223> OTHER INFORMATION: Antibody R21-9-8B VH CDR1 - AbM

<400> SEQUENCE: 158

Gly Tyr Thr Phe Thr His Tyr Gly Met Asn
1               5                   10

<210> SEQ ID NO 159
<211> LENGTH: 8
<212> TYPE: PRT
<213> ORGANISM: Artificial Sequence
<220> FEATURE:
<223> OTHER INFORMATION: Antibody R21-9-8B VH CDR2 - IMGT

<400> SEQUENCE: 159

Ile Asn Thr Tyr Thr Gly Glu Leu
1               5

<210> SEQ ID NO 160
<211> LENGTH: 17
<212> TYPE: PRT
<213> ORGANISM: Artificial Sequence
<220> FEATURE:
<223> OTHER INFORMATION: Antibody R21-9-8B VH CDR2 - Kabat

<400> SEQUENCE: 160

Trp Ile Asn Thr Tyr Thr Gly Glu Leu Thr Tyr Ala Asp Asp Phe Lys
1               5                   10                  15

Gly

<210> SEQ ID NO 161
<211> LENGTH: 4
<212> TYPE: PRT
<213> ORGANISM: Artificial Sequence
<220> FEATURE:
<223> OTHER INFORMATION: Antibody R21-9-8B VH CDR2 - Chothia

<400> SEQUENCE: 161

Thr Tyr Thr Gly
1

<210> SEQ ID NO 162
<211> LENGTH: 13
<212> TYPE: PRT
<213> ORGANISM: Artificial Sequence
<220> FEATURE:
<223> OTHER INFORMATION: Antibody R21-9-8B VH CDR2 - Contact

<400> SEQUENCE: 162

Trp Met Gly Trp Ile Asn Thr Tyr Thr Gly Glu Leu Thr
1               5                   10

<210> SEQ ID NO 163
<211> LENGTH: 10
<212> TYPE: PRT
<213> ORGANISM: Artificial Sequence
<220> FEATURE:
<223> OTHER INFORMATION: Antibody R21-9-8B VH CDR2 - AbM

<400> SEQUENCE: 163

Trp Ile Asn Thr Tyr Thr Gly Glu Leu Thr
1               5                   10

<210> SEQ ID NO 164
<211> LENGTH: 14
<212> TYPE: PRT
<213> ORGANISM: Artificial Sequence
<220> FEATURE:
<223> OTHER INFORMATION: Antibody R21-9-8B VH CDR3 - IMGT

<400> SEQUENCE: 164

Ala Arg Arg Ala Tyr Tyr Arg Tyr Asp Tyr Val Met Asp Tyr
1               5                   10

<210> SEQ ID NO 165
<211> LENGTH: 12
<212> TYPE: PRT
<213> ORGANISM: Artificial Sequence
<220> FEATURE:
<223> OTHER INFORMATION: Antibody R21-9-8B VH CDR3 - Kabat

<400> SEQUENCE: 165

Arg Ala Tyr Tyr Arg Tyr Asp Tyr Val Met Asp Tyr
1               5                   10

<210> SEQ ID NO 166
<211> LENGTH: 10
<212> TYPE: PRT
<213> ORGANISM: Artificial Sequence
<220> FEATURE:
<223> OTHER INFORMATION: Antibody R21-9-8B VH CDR3 - Chothia

<400> SEQUENCE: 166

Ala Tyr Tyr Arg Tyr Asp Tyr Val Met Asp
1               5                   10

<210> SEQ ID NO 167
<211> LENGTH: 13
<212> TYPE: PRT
<213> ORGANISM: Artificial Sequence
<220> FEATURE:
<223> OTHER INFORMATION: Antibody R21-9-8B VH CDR3 - Contact

<400> SEQUENCE: 167

Ala Arg Arg Ala Tyr Tyr Arg Tyr Asp Tyr Val Met Asp
1               5                   10

<210> SEQ ID NO 168
<211> LENGTH: 6
<212> TYPE: PRT
<213> ORGANISM: Artificial Sequence
<220> FEATURE:
<223> OTHER INFORMATION: Antibody R21-9-8B VL CDR1 - IMGT

<400> SEQUENCE: 168

His Asn Val Gly Thr Asn
1               5

<210> SEQ ID NO 169
<211> LENGTH: 11
<212> TYPE: PRT
<213> ORGANISM: Artificial Sequence
<220> FEATURE:
<223> OTHER INFORMATION: Antibody R21-9-8B VL CDR1 - Kabat

<400> SEQUENCE: 169

Lys Ala Ser His Asn Val Gly Thr Asn Val Ala
1               5                   10

<210> SEQ ID NO 170
<211> LENGTH: 7
<212> TYPE: PRT
<213> ORGANISM: Artificial Sequence
<220> FEATURE:
<223> OTHER INFORMATION: Antibody R21-9-8B VL CDR1 - Chothia

<400> SEQUENCE: 170

Ser His Asn Val Gly Thr Asn
1               5

<210> SEQ ID NO 171
<211> LENGTH: 7
<212> TYPE: PRT
<213> ORGANISM: Artificial Sequence
<220> FEATURE:
<223> OTHER INFORMATION: Antibody R21-9-8B VL CDR1 - Contact

<400> SEQUENCE: 171

Gly Thr Asn Val Ala Trp Tyr
1               5

<210> SEQ ID NO 172
<211> LENGTH: 3
<212> TYPE: PRT
<213> ORGANISM: Artificial Sequence
<220> FEATURE:
<223> OTHER INFORMATION: Antibody R21-9-8B VL CDR2 - IMGT

<400> SEQUENCE: 172

Ser Ala Ser
1

<210> SEQ ID NO 173
<211> LENGTH: 7
<212> TYPE: PRT
<213> ORGANISM: Artificial Sequence
<220> FEATURE:
<223> OTHER INFORMATION: Antibody R21-9-8B VL CDR2 - Kabat

<400> SEQUENCE: 173

Ser Ala Ser Tyr Arg Tyr Ser
1               5

<210> SEQ ID NO 174
<211> LENGTH: 10
<212> TYPE: PRT
<213> ORGANISM: Artificial Sequence
<220> FEATURE:
<223> OTHER INFORMATION: Antibody R21-9-8B VL CDR2 - Contact

<400> SEQUENCE: 174

Ala Leu Ile Tyr Ser Ala Ser Tyr Arg Tyr
1               5                   10

<210> SEQ ID NO 175
<211> LENGTH: 9
<212> TYPE: PRT
<213> ORGANISM: Artificial Sequence
<220> FEATURE:
<223> OTHER INFORMATION: Antibody R21-9-8B VL CDR3 - IMGT

<400> SEQUENCE: 175

His Gln Tyr Asn Asn Tyr Pro Tyr Thr
1               5

<210> SEQ ID NO 176
<211> LENGTH: 6
<212> TYPE: PRT
<213> ORGANISM: Artificial Sequence
<220> FEATURE:
<223> OTHER INFORMATION: Antibody R21-9-8B VL CDR3 - Chothia

<400> SEQUENCE: 176

Tyr Asn Asn Tyr Pro Tyr
1               5

<210> SEQ ID NO 177
<211> LENGTH: 8
<212> TYPE: PRT
<213> ORGANISM: Artificial Sequence
<220> FEATURE:
<223> OTHER INFORMATION: Antibody R21-9-8B VL CDR3 - Contact

<400> SEQUENCE: 177

His Gln Tyr Asn Asn Tyr Pro Tyr
1               5

<210> SEQ ID NO 178
<211> LENGTH: 330
<212> TYPE: PRT
<213> ORGANISM: Artificial Sequence
<220> FEATURE:
<223> OTHER INFORMATION: exemplary human heavy chain constant region

<400> SEQUENCE: 178

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 179
<211> LENGTH: 107
<212> TYPE: PRT
<213> ORGANISM: Artificial Sequence
<220> FEATURE:
<223> OTHER INFORMATION: exemplary human light chain constant region

<400> SEQUENCE: 179

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30
```

```
Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

```
<210> SEQ ID NO 180
<211> LENGTH: 427
<212> TYPE: DNA
<213> ORGANISM: Artificial Sequence
<220> FEATURE:
<223> OTHER INFORMATION: clone 5-13A heavy chain variable region

<400> SEQUENCE: 180
datgggatgg agccggatct ttctcttcct cctgtcaata attgcaggtg tccattgcca      60
ggtccagctg cagcagtctg gacctgagct ggtgaagcct ggggcttcag tgaggatatc     120
ctgcaaggct tctggctaca ccttcacagg ctactatgta cactgggtga agcagaggcc     180
tggacaggga cttgagtgga ttggatggat ttatcctgga aatgtaaata ctaagtacaa     240
tgagaagttc aaggccaagg ccacactgac tgcagacaaa tcctccagca caggctacat     300
gcagctcagc agactgacct ctgaggactc tgcggtctat ttctgtgcaa gatcccctta     360
ctacggtact acctattact atactatgga ctactggggt caaggaacct cagtcaccgt     420
ctcctca                                                               427
```

```
<210> SEQ ID NO 181
<211> LENGTH: 390
<212> TYPE: DNA
<213> ORGANISM: Artificial Sequence
<220> FEATURE:
<223> OTHER INFORMATION: clone 5-13A light chain variable region

<400> SEQUENCE: 181 atggatttc atgtgcagat tttcagcttc atgctaatca gtgtcacagt catattgtcc       60
agtggagaaa ttgtgctcac ccagtctcca gcattcatgg ctgcatctcc aggggagaag    120
gtcaccatca cctgcagtgt cagtttaatt ataagttcca ggaacttgca ctggtaccag    180
cagaagtcag aaacctcccc caaaccctgg atttatggca catccaacct ggcttctgga    240
gtccctgttc gcttcagtgg cagtggatct gggacctctt attctctcac aatcagcagc    300
atggaggctg aagatgctgc cacttattac tgtcaacagt ggagtgatta cccacttacg    360
ttcggctcgg ggacaaagtt ggaaataaaa                                     390
```

```
<210> SEQ ID NO 182
<211> LENGTH: 420
<212> TYPE: DNA
<213> ORGANISM: Artificial Sequence
<220> FEATURE:
<223> OTHER INFORMATION: clone 5-71A heavy chain variable region

<400> SEQUENCE: 182
atggactcca ggctcaattt agttttcctt gtccttattt taaaaggtgt ccagtgtgat      60
gtgcagctgg tggagtcggg gggaggctta gtgcagcctg gagggtcccg gaaactctcc    120
```

| | |
|---|---:|
| tgtgcagcct ctggattcac tttcagtagc tttggaatgc actgggttcg tcaggctcca | 180 |
| gagaagggc tggagttggt cgcatacatt agtagtggca gtactatcag atactattca | 240 |
| gacacagtga agggccgatt caccatctcc agagacaatc caagaacac cctgttcctg | 300 |
| caaatgacca gtctaaggtc tgaggacacg gccatgtatt actgtgcaag atttctctat | 360 |
| gaaggtttcc gctatggtat ggactactgg ggtcaaggaa cctcagtcac cgtctcctca | 420 |

<210> SEQ ID NO 183
<211> LENGTH: 393
<212> TYPE: DNA
<213> ORGANISM: Artificial Sequence
<220> FEATURE:
<223> OTHER INFORMATION: clone 5-71A light chain variable region

<400> SEQUENCE: 183

| | |
|---|---:|
| atgaagttgc ctgttaggct gttggtgctg atgttctgga ttcctgcttc cagcagtgat | 60 |
| gttttgatga cccagactcc actctccctg cctgtcagtc ttggagatca agcctccatc | 120 |
| tcttgcagat ctagtcagag cattgtacat agtaatggaa acacctattt gaatggtac | 180 |
| ctgcagaaac caggccagtc tccaaagctc ctgatctaca agtttccaa ccgattttct | 240 |
| ggggtcccag acaggttcag tggcagtgga tcagggacag atttcacact caagatcagc | 300 |
| agagtggagg ctgaggatct gggaatttat tactgctttc aaggttcaca tgttccgaac | 360 |
| acgttcggag gggggaccaa gctggaaata aaa | 393 |

<210> SEQ ID NO 184
<211> LENGTH: 420
<212> TYPE: DNA
<213> ORGANISM: Artificial Sequence
<220> FEATURE:
<223> OTHER INFORMATION: clone 5-165C heavy chain variable region

<400> SEQUENCE: 184

| | |
|---|---:|
| atgcacttcg ggctcagctt gattttcctt gccctcattt taaaaggtgt ccagtgtgag | 60 |
| gtgcagctgg tggagtcggg gggagactta gtgaagcctg agggtccct gaaactctcc | 120 |
| tgtgcagcct ttggattcac tttcagtagg tatggcatgt cttgggttcg ccagactcca | 180 |
| gacaagaggc tggagtgggt cgcaaccatt actagtggtg gtatttacac ctactatcca | 240 |
| gacagtgtga agggccgatt caccatttcc agagacaatg ccaagaacac cctgtacctg | 300 |
| caaatgagca gtctgaagtc cgaggagaca gccatgtatt actgtgcaag acatggccag | 360 |
| tttggggatt actatggtat ggactattgg ggtcaaggaa cctcagtcac cgtctcctca | 420 |

<210> SEQ ID NO 185
<211> LENGTH: 393
<212> TYPE: DNA
<213> ORGANISM: Artificial Sequence
<220> FEATURE:
<223> OTHER INFORMATION: clone 5-165C light chain variable region

<400> SEQUENCE: 185

| | |
|---|---:|
| atgaagttgc ctgttaggct gttggtgctg atgttctgga ttcctgcttc cagcagtgat | 60 |
| gttgtgatga cccaaactcc actctccctg cctgtcagtc ttggagatca agcctccatc | 120 |
| tcttgcagat ctagtcagag ccttttacac agtaatggaa acacctattt acattggtac | 180 |
| ctgcagaagc caggccagtc tccaaagctc ctgatctaca agtttccaa ccgattttct | 240 |
| ggggtcccag acaggttcag tggcagtgga tcagggacag atttcacact caagatcagc | 300 |
| agagtggagg ctgaggatct gggagtttat ttctgctctc aaagtacaca tgttccgtac | 360 |

```
acgttcggag gggggaccaa gctggaaata aaa                               393
```

```
<210> SEQ ID NO 186
<211> LENGTH: 420
<212> TYPE: DNA
<213> ORGANISM: Artificial Sequence
<220> FEATURE:
<223> OTHER INFORMATION: clone 9-8B heavy chain variable region

<400> SEQUENCE: 186
atggcttggg tgtggacctt gctattcctg atggcagctg cccaaagtgc caagcacag    60 atccagttgg tgcagtctgg acctgagctg aagaagcctg agagacagt caagatctcc   120 tgcaaggctt ctggatatac cttcacacac tatggaatga actgggtgaa gcaggctcca  180
ggaaagggtt taaagtggat gggctggata acacctaca ctggagagtt aacatatgct   240
gatgacttca agggacggtt tgccttctct ttggagacct ctgccagcac tgcctatttg   300
cagatcaaca acctcaaaaa tgaggacacg gctacatatt tctgtgcaag aagagcctac   360
tataggtacg actatgtaat ggactactgg ggtcaaggaa cctcagtcac cgtctcctca   420
```

```
<210> SEQ ID NO 187
<211> LENGTH: 393
<212> TYPE: DNA
<213> ORGANISM: Artificial Sequence
<220> FEATURE:
<223> OTHER INFORMATION: clone 9-8B light chain variable region

<400> SEQUENCE: 187
atgggcatca agatggagtc acagactcag gtctttgtat acatgttgct gtggttgtct   60
ggtgttgatg agacattgt gatgacccag tctcaaaaat tcatgtccac atcagtagga   120
gacagggtca gcgtcacctg caaggccagt cacaatgtgg gtactaatgt agcctggtat   180
caacagaaac cagggcaatc tcctaaagca ctgatttact cggcatccta ccggtacagt   240
ggagtccctg gtcgcttcac aggcagtgga tctgggacag atttcactct caccatcagc   300
aatgtgcagt ctgaagactt ggcagagtat ttctgtcacc aatataacaa ctatccgtac   360
acgttcggag gggggaccaa gctggaaata aaa                                393
```

```
<210> SEQ ID NO 188
<211> LENGTH: 98
<212> TYPE: PRT
<213> ORGANISM: Artificial Sequence
<220> FEATURE:
<223> OTHER INFORMATION: human germline sequence IGHV1-2*02 (Fig. 2A)

<400> SEQUENCE: 188

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Ser Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95
```

Ala Arg

<210> SEQ ID NO 189
<211> LENGTH: 15
<212> TYPE: PRT
<213> ORGANISM: Artificial Sequence
<220> FEATURE:
<223> OTHER INFORMATION: joining region IGHJ4*01 (Fig. 2A)

<400> SEQUENCE: 189

Tyr Phe Asp Tyr Trp Gly Gln Gly Thr Leu Val Thr Val Ser Ser
1               5                   10                  15

<210> SEQ ID NO 190
<211> LENGTH: 98
<212> TYPE: PRT
<213> ORGANISM: Artificial Sequence
<220> FEATURE:
<223> OTHER INFORMATION: human germline sequence IGHV3-48 (Fig. 2B)

<400> SEQUENCE: 190

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 191
<211> LENGTH: 95
<212> TYPE: PRT
<213> ORGANISM: Artificial Sequence
<220> FEATURE:
<223> OTHER INFORMATION: human germline sequence IGHV3-15 (Fig. 3A)

<400> SEQUENCE: 191

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95

<210> SEQ ID NO 192
<211> LENGTH: 88
<212> TYPE: PRT
<213> ORGANISM: Artificial Sequence
<220> FEATURE:

<223> OTHER INFORMATION: partial sequence of human germline IGHV3-15
(Fig. 3A)

<400> SEQUENCE: 192

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys
                85

<210> SEQ ID NO 193
<211> LENGTH: 12
<212> TYPE: PRT
<213> ORGANISM: Artificial Sequence
<220> FEATURE:
<223> OTHER INFORMATION: joining region IGKJ2*01 (Fig. 3A)

<400> SEQUENCE: 193

Tyr Thr Phe Gly Gln Gly Thr Lys Leu Glu Ile Lys
1               5                   10

<210> SEQ ID NO 194
<211> LENGTH: 95
<212> TYPE: PRT
<213> ORGANISM: Artificial Sequence
<220> FEATURE:
<223> OTHER INFORMATION: human germline sequence IGKV1-39 (Fig. 3B)

<400> SEQUENCE: 194

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 195
<211> LENGTH: 88
<212> TYPE: PRT
<213> ORGANISM: Artificial Sequence
<220> FEATURE:
<223> OTHER INFORMATION: partial human germline sequence IGKV1-39 (Fig. 3B)

<400> SEQUENCE: 195

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr

```
                    20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys
                85

<210> SEQ ID NO 196
<211> LENGTH: 98
<212> TYPE: PRT
<213> ORGANISM: Artificial Sequence
<220> FEATURE:
<223> OTHER INFORMATION: human germline sequence IGHV3-21 (Fig. 4A)

<400> SEQUENCE: 196

Glu Val Gln Leu Val Glu Ser Gly Gly Gly Leu Val Lys Pro Gly Gly
 1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 197
<211> LENGTH: 98
<212> TYPE: PRT
<213> ORGANISM: Artificial Sequence
<220> FEATURE:
<223> OTHER INFORMATION: human germline sequence IGHV3-48 (Fig. 4B)

<400> SEQUENCE: 197

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Tyr Ile Ser Ser Ser Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 198
<211> LENGTH: 100
<212> TYPE: PRT
<213> ORGANISM: Artificial Sequence
```

```
<220> FEATURE:
<223> OTHER INFORMATION: human germline sequence IGKV2D-29 (Fig. 5A)

<400> SEQUENCE: 198

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro
            100

<210> SEQ ID NO 199
<211> LENGTH: 93
<212> TYPE: PRT
<213> ORGANISM: Artificial Sequence
<220> FEATURE:
<223> OTHER INFORMATION: partial human germline sequence IGKV2D-29 (Fig.
      5A)

<400> SEQUENCE: 199

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys
                85                  90

<210> SEQ ID NO 200
<211> LENGTH: 95
<212> TYPE: PRT
<213> ORGANISM: Artificial Sequence
<220> FEATURE:
<223> OTHER INFORMATION: human germline sequence IGKV1-39 (Fig. 5B)

<400> SEQUENCE: 200

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ser Tyr Ser Thr Pro
            85                  90                  95

<210> SEQ ID NO 201
<211> LENGTH: 88
<212> TYPE: PRT
<213> ORGANISM: Artificial Sequence
<220> FEATURE:
<223> OTHER INFORMATION: partial human germline sequence IGKV1-39 (Fig.
      5B)

<400> SEQUENCE: 201

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys
            85

<210> SEQ ID NO 202
<211> LENGTH: 98
<212> TYPE: PRT
<213> ORGANISM: Artificial Sequence
<220> FEATURE:
<223> OTHER INFORMATION: human germline sequence IGHV7-4-1*02 (Fig. 6A)

<400> SEQUENCE: 202

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg

<210> SEQ ID NO 203
<211> LENGTH: 98
<212> TYPE: PRT
<213> ORGANISM: Artificial Sequence
<220> FEATURE:
<223> OTHER INFORMATION: human germline sequence IGHV1-18*01 (Fig. 6B)

<400> SEQUENCE: 203

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

```
Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg

<210> SEQ ID NO 204
<211> LENGTH: 98
<212> TYPE: PRT
<213> ORGANISM: Artificial Sequence
<220> FEATURE:
<223> OTHER INFORMATION: human germline sequence IGHV3-48 (Fig. 6C)

<400> SEQUENCE: 204

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Tyr Ile Ser Ser Ser Ser Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 205
<211> LENGTH: 95
<212> TYPE: PRT
<213> ORGANISM: Artificial Sequence
<220> FEATURE:
<223> OTHER INFORMATION: human germline sequence IGKV1-16 (Fig. 7A)

<400> SEQUENCE: 205

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro
                 85                  90                  95

<210> SEQ ID NO 206
<211> LENGTH: 88
<212> TYPE: PRT
<213> ORGANISM: Artificial Sequence
<220> FEATURE:
<223> OTHER INFORMATION: partial human germline sequence IGKV1-16 (Fig.
```

7A)

<400> SEQUENCE: 206

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys
                85

<210> SEQ ID NO 207
<211> LENGTH: 95
<212> TYPE: PRT
<213> ORGANISM: Artificial Sequence
<220> FEATURE:
<223> OTHER INFORMATION: human germline sequence IGKV1-39 (Fig. 7B)

<400> SEQUENCE: 207

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 208
<211> LENGTH: 88
<212> TYPE: PRT
<213> ORGANISM: Artificial Sequence
<220> FEATURE:
<223> OTHER INFORMATION: partial human germline sequence IGKV1-39 (Fig. 7B)

<400> SEQUENCE: 208

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys
                85

ANTI-CD39 ANTIBODIES AND USES THEREOF

CROSS-REFERENCE TO RELATED APPLICATIONS

This application is a 371 U.S. National Phase application of PCT International Application No. PCT/US2015/059455, filed Nov. 6, 2015 which claims the benefit of priority of U.S. Provisional Application No. 62/153,926, filed Apr. 28, 2015, and U.S. Provisional Application No. 62/077,085, filed Nov. 7, 2014, the entire contents of which are each incorporated herein by reference.

FIELD

The present disclosure relates generally to anti-CD39 antibodies, including antibody-drug conjugates comprising the antibodies, and methods of their use.

BACKGROUND

Ectonucleoside triphosphate diphosphohydrolase 1 (EN-TPD1; also known as CD39), works in concert with 5'-nucleotidase (also known as ecto-5'-nucleotidase or CD73), to modulate the duration, magnitude and chemical nature of purinergic signals by hydrolyzing extracellular adenosine triphosphate (ATP) and adenosine diphosphate (ADP) into adenosine monophosphate (AMP) (by CD39) and AMP to adenosine (by CD73). Immune cell-expressed P1 receptors (G protein-coupled receptors) and P2 receptors a are activated by adenosine and ATP, respectively and mediate the immunomodulatory effect of purines. ATP-driven effects are proinflammatory, while adenosine promotes anti-inflammatory effects in immune cells. Both CD39 and CD73 are highly expressed on regulatory T cells (Tregs), which are a CD4+ subpopulation that help maintain immune system homeostasis. Expression of both CD39 and CD73 is upregulated on Tregs upon activation. The ATP-metabolizing activity appears to be critical for the immunosuppressive activity of Tregs. The inhibitory control by Treg-derived adenosine is mediated by the engagement of A2A P1 receptors on effector T cells, resulting in reduction of proinflammatory cytokines and chemokines Increased adenosine levels mediated by CD39 and CD73 generate an immunosuppressive environment which promotes the development and progression of cancer. CD39 and CD73 participates in the evasion of tumors by the immune system by inhibiting the activation, clonal expansion and homing of tumor-specific helper T (Th) cells and cytotoxic T cells (CTL), by impairing the cytolytic effector T cells.

Myeloid-derived suppressor cells (MDSCs) also promote tumor growth by a CD39-mediated mechanism. For example, CD39 expression is elevated on MDSCs isolated from cancer patients and these cells display inhibitory effects against anti-tumor T cells, as compared with MDSCs from healthy donors.

In addition, Tregs from CD39 knockout mice are constitutively activated, proliferate excessively, and have lost their suppressive function. Melanoma growth, as well as lung metastases, was also markedly decreased in knockout mice as compared to wild-type mice, with severe defects in angiogenesis also observed.

There is a need understand the role of CD39 in diseases, including cancers, and the development of therapies directed against CD39.

SUMMARY

The present disclosure, provides antibodies that bind to CD39, including a CD39 polypeptide, a CD39 polypeptide fragment or a CD39 epitope, collectively referred to herein as anti-CD39 antibodies. Also provided herein are antibodies that are conjugated to drugs as antibody-drug conjugates (ADCs), including ADCs of the formula A-L-CTX, wherein A is an antibody, L is a linker, and CTX is cytotoxin. In some embodiments the anti-CD39 antibodies are humanized antibodies that bind to CD39, including a CD39 polypeptide, a CD39 polypeptide fragment or a CD39 epitope. In certain embodiments, the anti-CD39 antibody comprises a VH region, VL region, VH CDR1, VH CDR2, VH CDR3, VL CDR1, VL CDR2, and/or VL CDR3 of a monoclonal antibody as described herein, or a humanized variant thereof. In certain embodiments, the anti-CD39 antibody can further comprise a VH FR1, VH FR2, VH FR3, VH FR4, VL FR1, VL FR2, VL FR3, and/or VL FR4 of a human germline immunoglobulin amino acid sequence or a variant thereof.

In certain embodiments, the antibody comprises less than six CDRs. In some embodiments, the antibody comprises or consists of one, two, three, four, or five CDRs selected from the group consisting of VH CDR1, VH CDR2, VH CDR3, VL CDR1, VL CDR2, and/or VL CDR3. In specific embodiments, the antibody comprises or consists of one, two, three, four, or five CDRs selected from the group consisting of VH CDR1, VH CDR2, VH CDR3, VL CDR1, VL CDR2, and/or VL CDR3 of a monoclonal antibody described herein, or a humanized variant thereof. In specific embodiments, the antibody further comprises a VH FR1, VH FR2, VH FR3, VH FR4, VL FR1, VL FR2, VL FR3, and/or VL FR4 of a human germline immunoglobulin amino acid sequence or a variant thereof.

In specific embodiments, the antibody is a humanized antibody, a monoclonal antibody, a recombinant antibody, an antigen binding fragment or any combination thereof. In particular embodiments, the antibody is a humanized monoclonal antibody, or antigen binding fragment thereof, that binds to CD39 (e.g., a cell surface-expressed or soluble CD39), including a CD39 polypeptide, a CD39 fragment, or a CD39 epitope.

The present disclosure also provides antibodies (i) that competitively block (e.g., in a dose-dependent manner) an anti-CD39 antibody provided herein from binding to CD39 (e.g., a cell surface-expressed or soluble CD39), including a CD39 polypeptide, a CD39 fragment, or a CD39 epitope and/or (ii) that bind to a CD39 epitope that is bound by an anti-CD39 antibody provided herein. In other embodiments, the antibody competitively blocks (e.g., in a dose-dependent manner) a monoclonal antibody as described herein or a humanized variant thereof from binding to CD39 (e.g., a cell surface-expressed or soluble CD39), including a CD39 polypeptide, a CD39 fragment, or a CD39 epitope.

In certain embodiments, the anti-CD39 antibodies provided herein are conjugated or recombinantly fused to a diagnostic agent, detectable agent or therapeutic agent. In some aspects, the therapeutic agent is a chemotherapeutic agent (e.g., a cystotoxic agent such as cytotoxin). In some aspects, the detectable agent is a radioisotope, an enzyme, a fluorescent compound, a bioluminescent compound or a chemiluminescent compound. In certain embodiments, the anti-CD39 antibodies provided herein are conjugated to drugs as antibody-drug conjugates (ADCs). In some aspects, the antibody-drug conjugate (ADC) is of the formula A-L-CTX, wherein A is an antibody, L is a linker, and CTX is a cytotoxin.

In certain embodiments, provided are compositions comprising an anti-CD39 antibody described herein. In some embodiments, the compositions comprise an antibody-drug conjugate wherein the antibody is an anti-CD39 antibody. Also provided herein are pharmaceutical compositions comprising an anti-CD39 antibody provided herein.

The present disclosure also provides isolated nucleic acid molecules encoding a VH chain, VL chain, VH region, VL region, VH CDR1, VH CDR2, VH CDR3, VL CDR1, VL CDR2, and/or VL CDR3 of anti-CD39 antibodies that bind to CD39 (e.g., a cell surface-expressed or soluble CD39), including a CD39 polypeptide, a CD39 polypeptide fragment, or a CD39 epitope. In certain embodiments, the nucleic acid molecule encodes a VH region, VL region, VH CDR1, VH CDR2, VH CDR3, VL CDR1, VL CDR2, and/or VL CDR3 of a monoclonal antibody as described herein, or a humanized variant thereof. In certain embodiments, the nucleic acid molecule further encodes a VH FR1, VH FR2, VH FR3, VH FR4, VL FR1, VL FR2, VL FR3, and/or VL FR4 of a human germline immunoglobulin amino acid sequence or a variant thereof. Also provided herein are vectors and host cells comprising the nucleic acid molecules encoding an anti-CD39 antibody, as well as methods of producing an anti-CD39 antibody by culturing the host cells provided herein under conditions that promote the production of the anti-CD39 antibody.

The present disclosure also provides methods of treating, preventing or alleviating one or more symptoms of a disease, disorder or condition comprising administering a therapeutically effective amount of an anti-CD39 antibody provided herein to a subject, thereby treating, preventing or alleviating one or more symptoms of the disease. In one embodiment, the disease, disorder or condition is caused by or otherwise associated with CD39. In certain embodiments, the disease is a cancer, such as a leukemia, a lymphoma or a sarcoma. In one embodiment, the cancer is a sarcoma. In another embodiment, the cancer is a chronic lymphocytic leukemia (CLL). In other embodiments, the cancer is multiple myeloma (MM), T and or B cell lymphoma, GI organ interstitialoma, pancreatic cancer, colorectal (CRC) cancer or soft tissue tumor. Additional methods provided include using an anti-CD39 antibody provided herein, for example, as an unconjugated antibody or conjugated antibody (ADC), with anti-tumor activity to mediate anti-tumor effects. In certain embodiments, the anti-CD39 antibodies provided herein have immunomodulatory effects. In certain embodiments, the anti-CD39 antibodies provided herein directly kill CD39-bearing tumor cells (e.g., via antibody-dependent cellular cytotoxicity (ADCC) and/or complement-dependent cytotoxicity (CDC). In certain embodiments, antibody drug conjugates (ADCs) comprising anti-CD39 antibodies provided herein directly kill CD39-bearing tumor cells (e.g., by binding to tumor cells expressing CD39 and allowing internalization of the cytotoxic drug).

The present disclosure, provides methods of inhibiting the growth of cells having cell surface expression of CD39 comprising contacting the cells with an effective amount of an antibody provided herein. In one embodiment, the cell is a regulatory T cell. In other embodiments, the cell is a cancerous or pre-cancerous cell. Additional methods provided include using an anti-CD39 antibody provided herein, for example, as an unconjugated antibody or conjugated antibody (ADC), with anti-tumor activity to mediate anti-tumor effects. In certain embodiments, the anti-CD39 antibodies provided herein have immunomodulatory effects. In certain embodiments, the anti-CD39 antibodies provided herein directly kill CD39-bearing tumor cells (e.g., via antibody-dependent cellular cytotoxicity (ADCC) and/or complement-dependent cytotoxicity (CDC). In certain embodiments, antibody drug conjugates (ADCs) comprising anti-CD39 antibodies provided herein directly kill CD39-bearing tumor cells (e.g., by binding to tumor cells expressing CD39 and allowing internalization of the cytotoxic drug).

The present disclosure provides herein are methods for detecting CD39 in a sample comprising contacting the sample with an anti-CD39 antibody provided herein, such as an antibody that comprises a detectible agent. In certain embodiments, the sample comprises a cell expressing CD39 on its surface.

The present disclosure also provides herein are methods of treating cancers comprising administering to a subject an anti-CD39 antibody or an antibody-drug conjugate (ADC) comprising an anti-CD39 (e.g., an ADC of the formula A-L-CTX, wherein A is the antibody, L is a linker, and CTX is a cytotoxic agent) in a therapeutically effective amount, including in an amount effective to kill a CD39-expressing tumor cell. In some embodiments the cancer is chronic lymphocytic leukemia (CLL).

The present disclosure also provides methods of killing tumor cells comprising contacting a CD39-expressing tumor cell with an amount of an anti-CD39 antibody or an antibody-drug conjugate (ADC) comprising an anti-CD39 (e.g., an ADC of the formula A-L-CTX, wherein A is the antibody, L is a linker, and CTX is a cytotoxic agent) effective to kill the tumor cell. In some embodiments, the tumor cell is a sarcoma cell. In another embodiment, the tumor cell is an CLL cell.

The present disclosure also provides kits comprising an anti-CD39 antibody that binds to a CD39 polypeptide, a CD39 polypeptide fragment, or a CD39 epitope provided herein. In some embodiments, the kits comprise an antibody-drug conjugate (ADC) wherein the antibody is an anti-CD39 antibody.

BRIEF DESCRIPTION OF THE DRAWINGS

FIG. 1A-1B shows a sequence alignment of heavy chain variable regions and light chain variable regions of exemplary anti-CD39 antibodies designated R21-5-13A, R21-9-8B, R21-5-71A, and R21-5-165C, including consensus sequences for VH CDR1, VH CDR2, VH CDR3, VL CDR1, VL CDR2, and VL CDR3. Boundaries of CDR's are indicated by Kabat, AbM, Chothia, Contact and IMGT numbering. SEQ ID NOs are depicted in bold within parenthesis.

FIG. 2A-2C show humanized sequences for an exemplary anti-CD39 antibody VH region (e.g., R21-5-13A). SEQ ID NOs are depicted in bold within parenthesis.

FIG. 3A-3C show humanized sequences for an exemplary anti-CD39 antibody VL region (e.g., R21-5-13A). SEQ ID NOs are depicted in bold within parenthesis.

FIG. 4A-4C show humanized sequences for an exemplary anti-CD39 antibody VH region (e.g., R21-5-165C). SEQ ID NOs are depicted in bold within parenthesis.

FIG. 5A-5C show humanized sequences for an exemplary anti-CD39 antibody VL region (e.g., R21-5-165C). SEQ ID NOs are depicted in bold within parenthesis.

FIG. 6A-6D show humanized sequences for an exemplary anti-CD39 antibody VH region (e.g., R21-9-8B). SEQ ID NOs are depicted in bold within parenthesis.

FIG. 7A-7C show humanized sequences for an exemplary anti-CD39 antibody VL region (e.g., R21-9-8B). SEQ ID NOs are depicted in bold within parenthesis.

TERMINOLOGY

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

The term "about" or "approximately" means within 20%, such as within 10%, or within 5% (or 1% or less) of a given value or range.

As used herein, "administer" or "administration" refers to the act of injecting or otherwise physically delivering a substance as it exists outside the body (e.g., an anti-CD39 antibody provided herein) into a patient, such as by mucosal, intradermal, intravenous, intramuscular delivery and/or any other method of physical delivery described herein or known in the art. When a disease, or a symptom thereof, is being treated, administration of the substance typically occurs after the onset of the disease or symptoms thereof. When a disease, or symptoms thereof, are being prevented, administration of the substance typically occurs before the onset of the disease or symptoms thereof.

As used herein, an "agonist" of CD39 refers to a molecule that is capable of activating or otherwise increasing one or more of the biological activities of CD39, such as in a cell expressing CD39 or in a cell expressing a CD39 ligand, such as a CD39 receptor. In some embodiments, an agonist of CD39 (e.g., an agonistic antibody provided herein) may, for example, act by activating or otherwise increasing the activation and/or cell signaling pathways of the cell expressing a CD39 or a CD39 receptor, thereby increasing a CD39-mediated biological activity of the cell the relative to the CD39-mediated biological activity in the absence of agonist. In certain embodiments the antibodies provided herein are agonistic anti-CD39 antibodies.

The term "alkyl," as used herein, means a straight, branched chain, or cyclic (in this case, it would also be known as "cycloalkyl") hydrocarbon containing from 1-10 carbon atoms. Examples of alkyl include, but are not limited to, methyl, ethyl, n-propyl, iso-propyl, n-butyl, sec-butyl, tert-butyl, n-pentyl, isopentyl, neopentyl, n-hexyl, 3-methylhexyl, 2,2-dimethylpentyl, 2,3-dimethylhexyl, n-heptyl, n-octyl, n-nonyl, and n-decyl. In certain embodiments, alkyl groups are optionally substituted.

The term "$C_{1-6}$alkyl," as used herein, means a straight, branched chain, or cyclic (in this case, it would also be known as "cycloalkyl") hydrocarbon containing from 1-6 carbon atoms.

The term "$C_{1-3}$alkyl," as used herein, means a straight or branched chain hydrocarbon containing from 1-3 carbon atoms.

The term "alkenyl," as used herein, means a straight, branched chain, or cyclic (in which case, it would also be known as a "cycloalkenyl") hydrocarbon containing from 2-10 carbons and containing at least one carbon-carbon double bond formed by the removal of two hydrogens. In some embodiments, depending on the structure, an alkenyl group is a monoradical or a diradical (e.g., an alkenylene group). In some embodiments, alkenyl groups are optionally substituted. Examples of alkenyl include, but are not limited to, ethenyl, 2-propenyl, 2-methyl-2-propenyl, 3-butenyl, 4-pentenyl, 5-hexenyl, 2-heptenyl, and 2-methyl-1-heptenyl. In certain embodiments, alkenyl groups are optionally substituted.

The term "$C_{2-6}$ alkenyl," as used herein, means a straight, branched chain, or cyclic (in this case, it would also be known as "cycloalkyl") hydrocarbon containing from 2-6 carbon atoms and at least one carbon-carbon double bond formed by the removal of two hydrogens.

The term "alkoxy," as used herein, means an alkyl group, as defined herein, appended to the parent molecular moiety through an oxygen atom. Examples of alkoxy include, but are not limited to, methoxy, ethoxy, propoxy, 2-propoxy, butoxy, tert-butoxy, pentyloxy, and hexyloxy.

An "amino acid" (or AA) or amino acid residue include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, homocysteine, homoserine, ornithine and methionine sulfone. The amino acid residue of the present application also include the corresponding N-methyl amino acids, such as —N(CH$_3$)CH$_2$C(O)O—, —NHC(O)CH$_2$CH$_2$CH(NHCH$_3$)C(O)O—, etc. The amino acids, dipeptides, tripeptides, oligomers and polypeptides designated as -(AA)$_r$- of the present application may include the corresponding non-N-alkylated amino acids and peptides (such as non-N-methylated amino acids in the peptides), as well as a mixture of the non-N-alkylated amino acids and the N-alkylated amino acids of the peptides.

An "antibody-drug conjugate" or "ADC" is an antibody that is conjugated to one or more cytotoxins, through one or more linkers. An antibody-drug conjugate (ADC) may be of the formula A-L-CTX, wherein A is an antibody, L is a linker, and CTX is a cytotoxin.

In the context of a polypeptide, the term "analog" as used herein refers to a polypeptide that possesses a similar or identical function as a CD39 polypeptide, a fragment of a CD39 polypeptide, or an anti-CD39 antibody but does not necessarily comprise a similar or identical amino acid sequence of a CD39 polypeptide, a fragment of a CD39 polypeptide, or an anti-CD39 antibody, or possess a similar or identical structure of a CD39 polypeptide, a fragment of a CD39 polypeptide, or an anti-CD39 antibody. A polypeptide that has a similar amino acid sequence refers to a polypeptide that satisfies at least one of the following: (a) a polypeptide having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of a CD39 polypeptide (e.g., SEQ ID NO:1), a fragment of a CD39 polypeptide, or an anti-CD39 antibody described herein; (b) a polypeptide encoded by a nucleotide sequence that hybridizes under stringent conditions to a nucleotide sequence encoding a CD39 polypeptide, a fragment of a CD39 polypeptide, or an anti-CD39 antibody (or VH or VL region thereof) described herein of at least 5 amino acid residues, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues (see, e.g., Sambrook et al. (2001) *Molecular Cloning: A Laboratory Manual*, Cold Spring Harbor Laboratory Press, Cold Spring Harbor, N.Y.; Maniatis et al. (1982) *Molecular Cloning: A Laboratory Manual*, Cold Spring Harbor Press, Cold Spring Harbor, N.Y.); and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the nucleotide sequence encoding a CD39 polypeptide, a fragment of a CD39 polypeptide, or an anti-CD39 antibody (or VH or VL region thereof) described herein. A polypeptide with similar structure to a CD39 polypeptide, a fragment of a CD39 polypeptide, or an anti-CD39 antibody described herein refers to a polypeptide that has a similar secondary, tertiary or quaternary structure of a CD39 polypeptide, a fragment of a CD39, or a CD39 antibody described herein. The structure of a polypeptide can determined by methods known to those skilled in the art, including but not limited to, X-ray crystallography, nuclear magnetic resonance, and crystallographic electron microscopy.

As used herein, an "antagonist" or "inhibitor" of CD39 refers to a molecule that is capable of inhibiting or otherwise decreasing one or more of the biological activities of CD39, such as in a cell expressing CD39 or in a cell expressing a CD39 ligand, such as a CD39 receptor. In some embodiments, an antagonist of CD39 (e.g., an antagonistic antibody provided herein) may, for example, act by inhibiting or otherwise decreasing the activation and/or cell signaling pathways of the cell expressing a CD39 or a CD39 receptor, thereby inhibiting a CD39-mediated biological activity of the cell the relative to the CD39-mediated biological activity in the absence of antagonist. In certain embodiments the antibodies provided herein are antagonistic anti-CD39 antibodies.

The terms "antibody" and "immunoglobulin" or "Ig" are used interchangeably herein, and are intended to include a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa) and each amino-terminal portion of each chain includes a variable region of about 100 to about 130 or more amino acids and each carboxy-terminal portion of each chain includes a constant region (See, Borrebaeck (ed.) (1995) *Antibody Engineering*, Second Ed., Oxford University Press.; Kuby (1997) *Immunology*, Third Ed., W.H. Freeman and Company, New York). In specific embodiments, the specific molecular antigen can be bound by an antibody provided herein includes the target CD39 polypeptide, fragment or epitope.

Antibodies also include, but are not limited to, synthetic antibodies, monoclonal antibodies, recombinantly produced antibodies, multispecific antibodies (including bi-specific antibodies), human antibodies, humanized antibodies, camelized antibodies, chimeric antibodies, intrabodies, anti-idiotypic (anti-Id) antibodies, and functional fragments of any of the above, which refers a portion of an antibody heavy or light chain polypeptide that retains some or all of the binding activity of the antibody from which the fragment was derived. Non-limiting examples of functional fragments include single-chain Fvs (scFv) (e.g., including monospecific, bispecific, etc.), Fab fragments, F(ab') fragments, F(ab)$_2$ fragments, F(ab')$_2$ fragments, disulfide-linked Fvs (sdFv), Fd fragments, Fv fragments, diabody, triabody, tetrabody and minibody. In particular, antibodies provided herein include immunoglobulin molecules and immunologically active portions of immunoglobulin molecules, e.g., antigen binding regions/domains or molecules that contain an antigen-binding site that binds to a CD39 antigen (e.g., one or more complementarity determining regions (CDRs) of an anti-CD39 antibody). Such antibody fragments can be found described in, for example, Harlow and Lane, *Antibodies: A Laboratory Manual*, Cold Spring Harbor Laboratory, New York (1989); Myers (ed.), *Molec. Biology and Biotechnology: A Comprehensive Desk Reference*, New York: VCH Publisher, Inc.; Huston et al., *Cell Biophysics*, 22:189-224 (1993); Pluckthun and Skerra, *Meth. Enzymol.*, 178:497-515 (1989) and in Day, E. D., *Advanced Immunochemistry*, Second Ed., Wiley-Liss, Inc., New York, N.Y. (1990). The antibodies provided herein can be of any type (e.g., IgG, IgE, IgM, IgD, IgA and IgY), any class (e.g., IgG1, IgG2, IgG3, IgG4, IgA1 and IgA2), or any subclass (e.g., IgG2a and IgG2b) of immunoglobulin molecule. An anti-CD39 antibodies provided herein can be agonistic antibodies or antagonistic antibodies.

The terms "antibodies that specifically bind to CD39," "antibodies that specifically bind to a CD39 epitope," "anti-CD39 antibodies" and analogous terms are also used interchangeably herein and refer to antibodies that specifically bind to a CD39 polypeptide, such as a CD39 antigen or epitope. An antibody that specifically binds to a CD39 antigen may be cross-reactive with related antigens. In certain embodiments, an antibody that specifically binds to a CD39 antigen does not cross-react with other antigens. An antibody that specifically binds to a CD39 antigen can be identified, for example, by immunoassays, BIAcore, or other techniques known to those of skill in the art. An antibody binds specifically to a CD39 antigen when it binds to a CD39 antigen with higher affinity than to any cross-reactive antigen as determined using experimental techniques, such as radioimmunoassays (RIA) and enzyme-linked immunosorbent assays (ELISAs). Typically a specific or selective reaction will be at least twice background signal or noise and more typically more than 10 times background. See, e.g., Paul, ed., 1989, *Fundamental Immunology Second Edition*, Raven Press, New York at pages 332-336 for a discussion regarding antibody specificity. In certain embodiments, an antibody "which binds" an antigen of interest is one that binds the antigen with sufficient affinity such that the antibody is useful as a diagnostic and/or therapeutic agent in targeting a cell or tissue expressing the antigen, and does not significantly cross-react with other proteins. In such embodiments, the extent of binding of the antibody to a "non-target" protein will be less than about 10% of the binding of the antibody to its particular target protein as determined by fluorescence activated cell sorting (FACS) analysis or radioimmunoprecipitation (RIA). With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-6}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope. In certain embodiments, an antibody that binds to CD39 has a dissociation constant (Kd) of ≤1 μM, ≤100 nM, ≤10 nM, ≤1 nM, or ≤0.1 nM. In certain embodiments, anti-CD39 antibody binds to an epitope of CD39 that is conserved among CD39 from different species.

An "anti-CD39 antibody" or "an antibody that binds to CD39" refers to an antibody that is capable of binding CD39, including, for example, an antibody, with sufficient affinity such that the antibody is useful as a diagnostic and/or therapeutic agent in targeting CD39. Preferably, the extent of binding of an anti-CD39 antibody to an unrelated, non-CD39 protein is less than about 10% of the binding of the antibody to CD39 as measured, e.g., by fluorescence activated cell sorting (FACS) analysis or a radioimmunoassay (RIA). An antibody that "specifically binds to" or is "specific for" CD39 is defined as above. In certain embodiments, an antibody that binds to CD39 has a dissociation constant (Kd) of <1 μM, <100 nM, <10 nM, <1 nM, or <0.1 nM. In certain embodiments, anti-CD39 antibody binds to an epitope of CD39 that is conserved among CD39 from different species.

An "antigen" is a predetermined antigen to which an antibody can selectively bind. The target antigen may be a polypeptide, carbohydrate, nucleic acid, lipid, hapten or other naturally occurring or synthetic compound. In specific embodiments, the target antigen is a polypeptide.

The term "antigen binding fragment," "antigen binding domain," "antigen binding region," and similar terms refer to that portion of an antibody which comprises the amino acid residues that interact with an antigen and confer on the binding agent its specificity and affinity for the antigen (e.g., the complementarity determining regions (CDRs)).

The terms "binds" or "binding" as used herein refer to an interaction between molecules to form a complex. Interactions can be, for example, non-covalent interactions including hydrogen bonds, ionic bonds, hydrophobic interactions, and/or van der Waals interactions. A complex can also include the binding of two or more molecules held together by covalent or non-covalent bonds, interactions or forces. The strength of the total non-covalent interactions between a single antigen-binding site on an antibody and a single epitope of a target molecule, such as CD39, is the affinity of the antibody or functional fragment for that epitope. The ratio of association ($k_1$) to dissociation ($k_{-1}$) of an antibody to a monovalent antigen (($k_1/k_{-1}$) is the association constant K, which is a measure of affinity. The value of K varies for different complexes of antibody and antigen and depends on both $k_1$ and $k_{-1}$. The association constant K for an antibody provided herein can be determined using any method provided herein or any other method well known to those skilled in the art. The affinity at one binding site does not always reflect the true strength of the interaction between an antibody and an antigen. When complex antigens containing multiple, repeating antigenic determinants, such as a polyvalent CD39, come in contact with antibodies containing multiple binding sites, the interaction of antibody with antigen at one site will increase the probability of a reaction at a second site. The strength of such multiple interactions between a multivalent antibody and antigen is called the avidity. The avidity of an antibody can be a better measure of its binding capacity than is the affinity of its individual binding sites. For example, high avidity can compensate for low affinity as is sometimes found for pentameric IgM antibodies, which can have a lower affinity than IgG, but the high avidity of IgM, resulting from its multivalence, enables it to bind antigen effectively.

The term "CD39" or "CD39 polypeptide" and similar terms refers to the polypeptide ("polypeptide," "peptide" and "protein" are used interchangeably herein) known as ectonucleoside triphosphate diphosphohydrolase 1 (EN-TPD1) referred to herein as CD39, which is also known in the art as ATPDase or NTPDase or ecto-apyrase or lymphoid cell activation antigen, comprising, for example, the amino acid sequence of:

```
                                                          (SEQ ID NO. 1)
         10         20         30         40         50         60
   MEDTKESNVK TFCSKNILAI LGFSSIIAVI ALLAVGLTQN KALPENVKYG IVLDAGSSHT 70         80         90        100        110        120
   SLYIYKWPAE KENDTGVVHQ VEECRVKGPG ISKFVQKVNE IGIYLTDCME RAREVIPRSQ 130        140        150        160        170        180
   HQETPVYLGA TAGMRLLRME SEELADRVLD VVERSLSNYP FDFQGARIIT GQEEGAYGWI 190        200        210        220        230        240
   TINYLLGKFS QKTRWFSIVP YETNNQETFG ALDLGGASTQ VTFVPQNQTI ESPDNALQFR 250        260        270        280        290        300
   LYGKDYNVYT HSFLCYGKDQ ALWQKLAKDI QVASNEILRD PCFHPGYKKV VNVSDLYKTP 310        320        330        340        350        360
   CTKRFEMTLP FQQFEIQGIG NYQQCHQSIL ELFNTSYCPY SQCAFNGIFL PPLQGDFGAF 370        380        390        400        410        420
   SAFYFVMKFL NLTSEKVSQE KVTEMMKKFC AQPWEEIKTS YAGVKEKYLS EYCFSGTYIL 430        440        450        460        470        480
   SLLLQGYHFT ADSWEHIHFI GKIQGSDAGW TLGYMLNLTN MIPAEQPLST PLSHSTYVFL 490        500        510
   MVLFSLVLFT VAIIGLLIFH KPSYFWKDMV
``` and related polypeptides, including SNP variants thereof. The CD39 polypeptide has been shown to or is predicted to comprise several distinct regions within the amino acid sequence including: a topological domain (e.g., cytoplasmic) (residues 1-16; transmembrane region (e.g., helical) (residues 17-37); a topological domain (e.g., extracellular) (residues 38-478); a transmembrane domain (e.g., helical) (residues 479-499), and a topological domain (e.g., cytoplasmic (residues 500-510). Related polypeptides include allelic variants (e.g., SNP variants); splice variants; fragments; derivatives; substitution, deletion, and insertion variants; fusion polypeptides; and interspecies homologs, preferably, which retain CD39 activity and/or are sufficient to generate an anti-CD39 immune response. As those skilled in the art will appreciate, an anti-CD39 antibody provided herein can bind to a CD39 polypeptide, polypeptide fragment, antigen, and/or epitope, as an epitope is part of the larger antigen, which is part of the larger polypeptide fragment, which, in turn, is part of the larger polypeptide. CD39 can exist in a native or denatured form. The CD39 polypeptides described herein may be isolated from a variety of sources, such as from human tissue types or from another source, or prepared by recombinant or synthetic methods. A "native sequence CD39 polypeptide" comprises a polypeptide having the same amino acid sequence as the corresponding CD39 polypeptide derived from nature. Such native sequence CD39 polypeptides can be isolated from nature or can be produced by recombinant or synthetic means. The term "native sequence CD39 polypeptide" specifically encompasses naturally-occurring truncated or secreted forms of the specific CD39 polypeptide (e.g., an extracellular or topological domain sequence), naturally-occurring variant forms (e.g., alternatively spliced forms) and naturally-occurring allelic variants of the polypeptide.

A "CD39-expressing cell," "a cell having expression of CD39" or a grammatical equivalent thereof refers to a cell that expresses endogenous or transfected CD39 on the cell surface. A cell expressing CD39 produces sufficient levels of CD39 on its surface, such that an anti-CD39 antibody can bind thereto. In some aspect, such binding may have a therapeutic effect with respect to the cancer. A cell that "overexpresses" CD39 is one that has significantly higher levels of CD39 at the cell surface thereof, compared to a cell of the same tissue type that is known to express CD39. Such overexpression may be caused by gene amplification or by increased transcription or translation. CD39 overexpression may be determined in a diagnostic or prognostic assay by evaluating increased levels of the CD39 protein present on the surface of a cell (e.g. via an immunohistochemistry assay; FACS analysis). Alternatively, or additionally, one may measure levels of CD39-encoding nucleic acid or mRNA in the cell, e.g. via fluorescent in situ hybridization; (FISH; see WO98/45479 published October, 1998), Southern blotting, Northern blotting, or polymerase chain reaction (PCR) techniques, such as real time quantitative PCR (RT-PCR). Aside from the above assays, various in vivo assays are available to the skilled practitioner. For example, one may expose cells within the body of the patient to an antibody which is optionally labeled with a detectable agent, and binding of the antibody to cells in the patient can be evaluated, e.g. by external scanning for radioactivity or by analyzing a biopsy taken from a patient previously exposed to the antibody. A CD39-expressing tumor cell includes, but is not limited to, chronic lymphocytic leukemia (CLC) tumor cells.

A "CD39-mediated disease" and "CD39-mediated disorder" are used interchangeably and refer to any disease that is completely or partially caused by or is the result of CD39. In certain embodiments, CD39 is aberrantly (e.g., highly) expressed on the surface of a cell. In some embodiments, CD39 may be aberrantly upregulated on a particular cell type. In other embodiments, normal, aberrant or excessive cell signaling is caused by binding of CD39 to a CD39 ligand, which can bind or otherwise interact with CD39.

The terms "cell proliferative disorder" and "proliferative disorder" refer to disorders that are associated with some degree of abnormal cell proliferation. In one embodiment, the cell proliferative disorder is a tumor or cancer. "Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein. The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, oral cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain cancer, as well as head and neck cancer, and associated metastases.

The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a exemplary carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in *Remington's Pharmaceutical Sciences* (1990) Mack Publishing Co., Easton, Pa. Such compositions will contain a prophylactically or therapeutically effective amount of the antibody, e.g., in isolated or purified form, together with a suitable amount of carrier so as to provide the form for proper administration to the patient. The formulation should suit the mode of administration.

The term "chemical group," as used herein, refers to two or more atoms bound together as a single unit and forming part of a molecule.

A "chemotherapeutic agent" is a chemical agent (e.g., compound or drug) useful in the treatment of cancer, regardless of mechanism of action. Chemotherapeutic agents include compounds used in targeted therapy and conventional chemotherapy. Examples of chemotherapeutic agents include, but are not limited to, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, AR1NOL®)); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammal I and calicheamicin omega II (see, e.g., *Agnew, Chem Intl. Ed. Engl.* 33:183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN®, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin. Additional chemotherapeutic agents include cytotoxic agents useful as antibody drug conjugates, such as maytansinoids (DM1 and DM4, for example) and auristatins (MMAE and MMAF, for example).

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY 117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RI VISor® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as ME inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAX1DC); PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

"Chemotherapeutic agents" may also include agents used in the treatment of leukemias, including alkylating agents such as chlorambucil, bendamustine hydrochloride or cyclophosphamide (CYTOXANC)); purine analogs such as fludurabine (FLUDARAO), pentostatin (NIPENT®), cladribine or nelarabine; pyrimidine analogs such as cytarabine;

corticosteroids such as prednisone, prednisolone or methylprednisolone, immunomodulatory agents such as lenalidomide or thalidomide, synthetic flavons such as flavopiridol, Bcl2 antagonists such as oblimersen or ABT-263, antibiotics such as doxorubicin (ADRIAMYCIN®), daunorubicin, idarubicin, or mitoxentrone; anti-metabolites such as methotrexate and clofarabine; tyrosine kinase inhibitors such as imatinib mesylate (GLEEVEC®), bosutinib, dasatinib, and nilotinib; a hypomethylating agents such as azacytidine or decitabine, an FLT3 inhibitor such as midostaurin, sorafenib, or AC220; arsenic trioxide; all-trans retinoic acid; vincristine sulfate; and monoclonal antibodies such as rituximab (RITUXAN®), ofatumumab, obinutuzumab, veltuzumab, ocrelizumab, lumiliximab or alemtuzumab (CAMPATH®); pharmaceutically acceptable salts, acids or derivatives of any of the above; as well as combinations of two or more of the above; as well as combinations of two or more of the above such as fludarabine plus cyclophosphamide (FC), cladribine plus cyclophosphamide (CC), fludarabine plus rituximab, fludarabine plus cyclophosphamide plus rituximab (FCR), and FCR plus alemtuzumab (CFAR). Chemotherapeutic agents may also include agents used in the treatment of multiple myeloma, including thalidomide, lenalidomide, bortezomib, dexamethesone, prednisone, and melphalan, as well as combinations of two or more of the above, such as thalidomide or lenalidomide plus dexamethasone, or bortezomib or lenalidomide plus melphalan and prednisone.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

The antibodies provided herein can include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Nat!. Acad. Sci. USA, 81:6851-6855 (1984)).

As used herein, the term "composition" is intended to encompass a product containing the specified ingredients (e.g., an antibody provided herein) in, optionally, the specified amounts, as well as any product which results, directly or indirectly, from combination of the specified ingredients in, optionally, the specified amounts.

A "CDR" or "complementary determining region" refers to one of three hypervariable regions (H1, H2 or H3) within the non-framework region of the immunoglobulin (Ig or antibody) VH β-sheet framework (e.g., VH CDR1, VH CDR2, VH CDR3), or one of three hypervariable regions (L1, L2 or L3) within the non-framework region of the antibody VL β-sheet framework (e.g., VL CDR1, VL CDR2, VL CDR3). Accordingly, CDRs are variable region sequences interspersed within the framework region sequences (see, e.g., Tables 1-4 for exemplary CDRs of anti-CD39 antibodies, including humanized antibodies). CDR regions are well known to those skilled in the art and have been defined by, for example, Kabat as the regions of most hypervariability within the antibody variable (V) regions or domains (Kabat et al., J. Biol. Chem. 252:6609-6616 (1977); Kabat, Adv. Prot. Chem. 32:1-75 (1978)). CDR region sequences also have been defined structurally by Chothia as those residues that are not part of the conserved β-sheet framework, and thus are able to adapt different conformations (Chothia and Lesk, J. Mol. Biol. 196:901-917 (1987)). Both terminologies are well recognized in the art. The positions of CDRs within a canonical antibody variable domain have been determined by comparison of numerous structures (Al-Lazikani et al., J. Mol. Biol. 273:927-948 (1997); Morea et al., Methods 20:267-279 (2000)). Because the number of residues within a hypervariable region varies in different antibodies, additional residues relative to the canonical positions are conventionally numbered with a, b, c and so forth next to the residue number in the canonical variable domain numbering scheme (Al-Lazikani et al., supra (1997)). Such nomenclature is similarly well known to those skilled in the art.

The term "hypervariable region", "HVR", or "HV", when used herein refers to the regions of an antibody variable domain or region that are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

Recently, a universal numbering system has been developed and widely adopted, ImMunoGeneTics (IMGT) Information System® (Lafranc et al., Dev. Comp. Immunol. 27(1):55-77 (2003)). IMGT is an integrated information system specializing in immunoglobulins (IG), T cell receptors (TR) and major histocompatibility complex (MHC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues and are readily identified. This information can be used in grafting and replacement of CDR residues from immunoglobulins of one species into an acceptor framework from, typically, a human antibody. Correspondence between the Kabat numbering and the IMGT unique numbering system is also well known to one skilled in the art (e.g. Lefranc et al., supra).

|  | Kabat + Chothia | IMGT | Kabat | AbM | Chothia | Contact |
|---|---|---|---|---|---|---|
| $V_H$ CDR1 | 26-35 | 27-38 | 31-35 | 26-35 | 26-32 | 30-35 |
| $V_H$ CDR2 | 50-65 | 56-65 | 50-65 | 50-58 | 53-55 | 47-58 |
| $V_H$ CDR3 | 95-102 | 105-117 | 95-102 | 95-102 | 96-101 | 93-101 |
| $V_L$ CDR1 | 24-34 | 27-38 | 24-34 | 24-34 | 26-32 | 30-36 |
| $V_L$ CDR2 | 50-56 | 56-65 | 50-56 | 50-56 | 50-52 | 46-55 |
| $V_L$ CDR3 | 89-97 | 105-117 | 89-97 | 89-97 | 91-96 | 89-96 |

Hypervariable regions may comprise "extended hypervariable regions" as follows: 24-36 or 24-34 (L1), 46-56 or 50-56 (L2) and 89-97 or 89-96 (L3) in the VL and 26-35 or 26-35A (H1), 50-65 or 49-65 (H2) and 93-102, 94-102, or 95-102 (H3) in the VH. The variable domain residues are numbered according to Kabat et al., supra, for each of these definitions. As used herein, the terms "HVR" and "CDR" are used interchangeably.

The term "constant region" or "constant domain" refers to a carboxy terminal portion of the light and heavy chain which is not directly involved in binding of the antibody to antigen but exhibits various effector function, such as interaction with the Fc receptor. The terms refer to the portion of an immunoglobulin molecule having a more conserved amino acid sequence relative to the other portion of the immunoglobulin, the variable domain, which contains the antigen binding site. The constant domain contains the CH1, CH2 and CH3 domains of the heavy chain and the CL domain of the light chain.

Exemplary human heavy chain constant region sequences, including an exemplary CH1, CH2 and CH3 sequence, are provided below:

```
                                           (SEQ ID NO: 178)
ASTKGPSVFPLAPSSKSTSGGTAALGCLVKDYFPEPVTVSWNSGALT

SGVHTFPAVLQSSGLYSLSSVVTVPSSSLGTQTYICNVNHKPSNTKVD

KKVEPKSCDKTHTCPPCPAPELLGGPSVFLFPPKPKDTLMISRTPEVT

CVVVDVSHEDPEVKFNWYVDGVEVHNAKTKPREEQYNSTYRVVSVL
```

```
TVLHQDWLNGKEYKCKVSNKALPAPIEKTISKAKGQPREPQVYTLPPS

REEMTKNQVSLTCLVKGFYPSDIAVEWESNGQPENNYKTTPPVLDSD

GSFFLYSKLTVDKSRWQQGNVFSCSVMHEALHNHYTQKSLSLSPGK.
```

An Exemplary human light chain constant region sequence is provided below:

```
                                           (SEQ ID NO: 179)
RTVAAPSVFIFPPSDEQLKSGTASVVCLLNNFYPREAKVQWKVDNAL

QSGNSQESVTEQDSKDSTYSLSSTLTLSKADYEKHKVYACEVTHQGL

SSPVTKSFNRGEC
```

Such human heavy chain and light chain constant regions may be used in chimeric and humanized heavy chain and light chain constructs. For example, mouse variable region sequences may be placed in frame with a human IgG1 (pFUSE-CHIg-hG1, InvivoGen, San Diego, Calif.) or a human kappa (pFUSE2-CLIg-hk, InvivoGen, San Diego, Calif. constant region. Exemplary chimeric construct comprises murine VH sequence (e.g., FIG. 1A, 2A-2B, 4A-4B, or 6A-6C) and human heavy chain constant region (e.g., SEQ ID:178). Exemplary chimeric construct comprises murine VL sequence (e.g., 1B, 3A-3B, 5A-5B, or 7A-7B) and human light chain constant region (e.g., SEQ ID: 179). Exemplary chimeric construct comprises humanized VH sequence (e.g., FIG. 2A-2B, 4A-4B, or 6A-6C) and human heavy chain constant region (e.g., SEQ ID:178). Exemplary chimeric construct comprises humanized VL sequence (e.g., FIG. 3A-3B, 5A-5B, or 7A-7B) and human light chain constant region (e.g., SEQ ID: 179).

The term "framework" or "FR" residues are those variable domain residues flanking the CDRs (e.g., for the heavy chain variable region (VH) VH FR1, VH FR2, VH FR3, VH FR4) and for the light chain variable regions (VL) VL FR1, VL FR2, VL FR3 and VL FR4). FR residues are present, e.g., in chimeric, humanized, human, domain antibodies, diabodies, linear antibodies, and bispecific antibodies. FR residues are those variable domain residues other than the hypervariable region residues herein defined (see, e.g., Tables 1-4 or Figures for exemplary CDRs of anti-CD39 antibodies, including humanized antibodies).

The term "variable domain residue numbering as in Kabat" or "amino acid position numbering as in Kabat", and variations thereof, refers to the numbering system used for heavy chain variable domains or light chain variable domains of the compilation of antibodies in Kabat et al., *Sequences of Proteins of Immunological Interest*, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g., residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., *Sequences of Immunological Interest,* 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody.

The term "cycloalkyl," as used herein, means a monocyclic or polycyclic radical that contains only carbon and hydrogen, and includes those that are saturated, partially unsaturated, or fully unsaturated. Cycloalkyl groups include groups having from 3 to 10 ring atoms.

In the context of a polypeptide, the term "derivative" as used herein refers to a polypeptide that comprises an amino acid sequence of a CD39 polypeptide, a fragment of a CD39 polypeptide, or an antibody that binds to a CD39 polypeptide which has been altered by the introduction of amino acid residue substitutions, deletions or additions. The term "derivative" as used herein also refers to a CD39 polypeptide, a fragment of a CD39 polypeptide, or an antibody that binds to a CD39 polypeptide which has been chemically modified, e.g., by the covalent attachment of any type of molecule to the polypeptide. For example, but not by way of limitation, a CD39 polypeptide, a fragment of a CD39 polypeptide, or a CD39 antibody may be chemically modified, e.g., by glycosylation, acetylation, pegylation, phosphorylation, amidation, derivatization by known protecting/blocking groups, proteolytic cleavage, linkage to a cellular ligand or other protein, etc. The derivatives are modified in a manner that is different from naturally occurring or starting peptide or polypeptides, either in the type or location of the molecules attached. Derivatives further include deletion of one or more chemical groups which are naturally present on the peptide or polypeptide. A derivative of a CD39 polypeptide, a fragment of a CD39 polypeptide, or a CD39 antibody may be chemically modified by chemical modifications using techniques known to those of skill in the art, including, but not limited to specific chemical cleavage, acetylation, formulation, metabolic synthesis of tunicamycin, etc. Further, a derivative of a CD39 polypeptide, a fragment of a CD39 polypeptide, or a CD39 antibody may contain one or more non-classical amino acids. A polypeptide derivative possesses a similar or identical function as a CD39 polypeptide, a fragment of a CD39 polypeptide, or a CD39 antibody described herein.

The term "cytotoxic agent" or "cytotoxin" or "CTX" as used herein refers to a substance that inhibits or prevents the function of cells and/or has a cytotoxic effect on cells (e.g., causes destruction of cells). The term is intended to include alkylating agents, an anthracyclines, a cytoskeletal disruptors (taxanes), an epothilones, an histone deacetylase Inhibitor (HDAC), an inhibitor of Topoisomerase I, an Inhibitor of Topoisomerase II, a kinase inhibitor, a monoclonal antibodies, a nucleotide analog, a peptide antibiotic, a platinum-based agent, a retinoids, a Vinca alkaloid or a derivative thereof, and radioisotope. The term is also intended to include Actinomycin, all-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, and Vinorelbine. The term is also intended to include a tubulin stabilizer, a tubulin destabilizer, a DNA alkylator, a DNA minor groove binder, a DNA intercalator, a topoisomerase I inhibitor, a topoisomerase II inhibitor, a gyrase inhibitor, a protein synthesis inhibitor, a proteosome inhibitor, and an anti-metabolite. The term is also intended to include Actinomycin D, Amonafide, an auristatin, benzophenone, benzothiazole, a calicheamicin, Camptothecin, CC-1065 (NSC 298223), Cemadotin, Colchicine, Combretastatin A4, Dolastatin, Doxorubicin, Elinafide, Emtansine (DM1), Etoposide, KF-12347 (Leinamycin), a maytansinoid, Methotrexate, Mitoxantrone, Nocodazole, Proteosome Inhibitor 1 (PSI 1), Roridin A, T-2 Toxin (trichothecene analog), Taxol, a tubulysin, Velcade®, and Vincristine. Preferred cytotoxins include an auristatin, a calicheamicin, a maytansinoid, a pyrrolobenzodiazepine (PBD) (monomeric or dimeric), and a tubulysin. Other preferred cytotoxins include monomethylauristatin E (MMAE), monomethylauristatin F (MMAF), calicheamicin γ, mertansine, tubulysin T3 (T3), and tubulysin T4 (T4).

The structures for T3 and T4 are provided below:

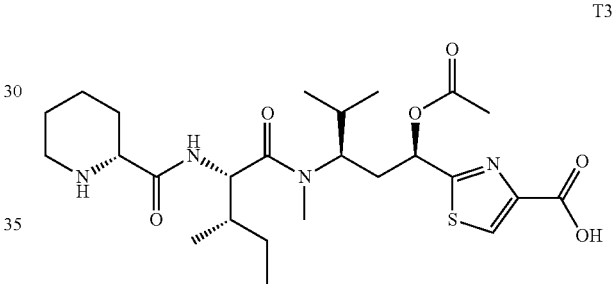

T3

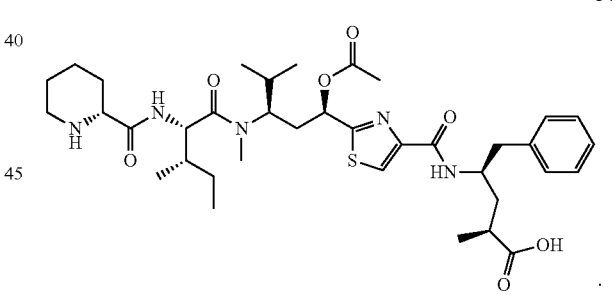

T4

The structures for MMAE and MMAF are provided below:

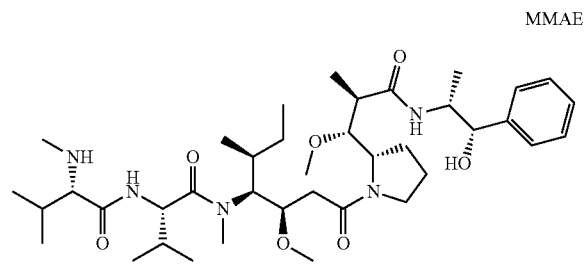

MMAE

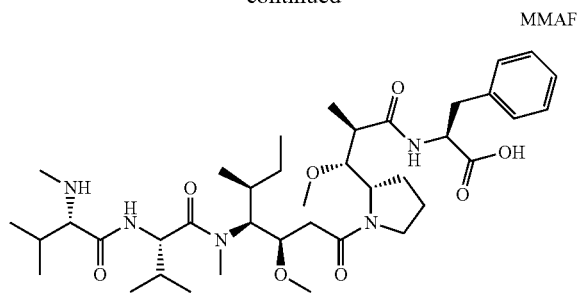

MMAF

Other cytotoxic agents including various antitumor or anticancer agents are known in the art. The term is also intended to include radioactive isotopes (e.g., At211, I131, I125, Y90, Re186, Re188, Sm153, Bi212, P32 and radioactive isotopes of Lu), chemotherapeutic agents e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells. A "toxin" is any substance capable of having a detrimental effect on the growth or proliferation of a cell.

The term "detectable probe," as used herein, refers to a composition that provides a detectable signal. The term includes, without limitation, any fluorophore, chromophore, radiolabel, enzyme, antibody or antibody fragment, and the like, that provide a detectable signal via its activity.

The term "diagnostic agent" refers to a substance administered to a subject that aids in the diagnosis of a disease. Such substances can be used to reveal, pinpoint, and/or define the localization of a disease causing process. In certain embodiments, a diagnostic agent includes a substance that is conjugated to an antibody provided herein, that when administered to a subject or contacted to a sample from a subject aids in the diagnosis of cancer, tumor formation, or any other CD39-mediated disease.

The term "detectable agent" refers to a substance that can be used to ascertain the existence or presence of a desired molecule, such as an antibody provided herein, in a sample or subject. A detectable agent can be a substance that is capable of being visualized or a substance that is otherwise able to be determined and/or measured (e.g., by quantitation).

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the agent, the route of administration, etc. In some embodiments, effective amount also refers to the amount of an antibody provided herein to achieve a specified result (e.g., inhibition of a CD39 biological activity of a cell, such as modulating T cell activation and/or proliferation). In some embodiments, this term refers to the amount of a therapy (e.g., an antibody or pharmaceutical composition provided herein) which is sufficient to reduce and/or ameliorate the severity and/or duration of a given disease and/or a symptom related thereto. This term also encompasses an amount necessary for the reduction or amelioration of the advancement or progression of a given disease, reduction or amelioration of the recurrence, development or onset of a given disease, and/or to improve or enhance the prophylactic or therapeutic effect(s) of another therapy (e.g., a therapy other than anti-CD39 antibody provided herein). In some embodiments, the effective amount of an antibody is from about 0.1 mg/kg (mg of antibody per kg weight of the subject) to about 100 mg/kg. In certain embodiments, an effective amount of an antibody provided therein is about 0.1 mg/kg, about 0.5 mg/kg, about 1 mg/kg, 3 mg/kg, 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg about 90 mg/kg or about 100 mg/kg (or a range therein).

The term "electrophilic leaving group," as used herein, refers to a leaving group that accepts an electron pair to make a covalent bond. In general, electrophiles are susceptible to attack by complementary nucleophiles, including the reduced thiols from the disulfide bond of an antibody.

The term "electrophilic leaving group that reacts selectively with thiols," as used herein, refers to electrophilic leaving group that reacts selectively with thiols, over other nucleophiles. In certain embodiments, an electrophilic leaving group that reacts selectively with thiols reacts selectively with the reduced thiols from the disulfide bond of an antibody.

The term "encode" or grammatical equivalents thereof as it is used in reference to nucleic acid molecule refers to a nucleic acid molecule in its native state or when manipulated by methods well known to those skilled in the art that can be transcribed to produce mRNA, which is then translated into a polypeptide and/or a fragment thereof. The antisense strand is the complement of such a nucleic acid molecule, and the encoding sequence can be deduced therefrom.

The term "epitope" as used herein refers to a localized region on the surface of an antigen, such as CD39 polypeptide or CD39 polypeptide fragment, that is capable of being bound to one or more antigen binding regions of an antibody, and that has antigenic or immunogenic activity in an animal, such as a mammal (e.g., a human), that is capable of eliciting an immune response. An epitope having immunogenic activity is a portion of a polypeptide that elicits an antibody response in an animal. An epitope having antigenic activity is a portion of a polypeptide to which an antibody binds as determined by any method well known in the art, for example, by an immunoassay. Antigenic epitopes need not necessarily be immunogenic. Epitopes usually consist of chemically active surface groupings of molecules such as amino acids or sugar side chains and have specific three dimensional structural characteristics as well as specific charge characteristics. A region of a polypeptide contributing to an epitope may be contiguous amino acids of the polypeptide or the epitope may come together from two or more non-contiguous regions of the polypeptide. The epitope may or may not be a three-dimensional surface feature of the antigen. In certain embodiments, a CD39 epitope is a three-dimensional surface feature of a CD39 polypeptide. In other embodiments, a CD39 epitope is linear feature of a CD39 polypeptide. Generally an antigen has several or many different epitopes and reacts with many different antibodies.

The term "excipient" as used herein refers to an inert substance which is commonly used as a diluent, vehicle, preservative, binder, or stabilizing agent, and includes, but not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.). See, also, Remington's Pharmaceutical Sciences (1990) Mack Publishing Co., Easton, Pa., which is hereby incorporated by reference in its entirety.

In the context of a peptide or polypeptide, the term "fragment" as used herein refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may, for example, result from alternative RNA splicing or from in vivo protease activity. In certain embodiments, CD39 fragments include polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a CD39 polypeptide or an antibody that binds to a CD39 polypeptide. In a specific embodiment, a fragment of a CD39 polypeptide or an antibody that binds to a CD39 antigen retains at least 1, at least 2, or at least 3 functions of the polypeptide or antibody.

The term "framework" or "FR" residues are those variable region residues flanking the CDRs. FR residues are present, e.g., in chimeric, humanized, human, domain antibodies, diabodies, linear antibodies, and bispecific antibodies. FR residues are those variable region residues other than the hypervariable region residues herein defined.

A "functional fragment" of an antibody will exhibit at least one if not some or all of the biological functions attributed to the intact antibody, the function comprising at least specific binding to the target antigen.

The term "fusion protein" as used herein refers to a polypeptide that comprises an amino acid sequence of an antibody and an amino acid sequence of a heterologous polypeptide or protein (e.g., a polypeptide or protein not normally a part of the antibody (e.g., a non-anti-CD39 antigen antibody)). The term "fusion" when used in relation to CD39 or to an anti-CD39 antibody refers to the joining of a peptide or polypeptide, or fragment, variant and/or derivative thereof, with a heterologous peptide or polypeptide. In certain embodiments, the fusion protein retains the biological activity of the CD39 or anti-CD39 antibody. In certain embodiments, the fusion protein comprises a CD39 antibody VH region, VL region, VH CDR (one, two or three VH CDRs), and/or VL CDR (one, two or three VL CDRs), wherein the fusion protein binds to a CD39 epitope.

The term "heavy chain" when used in reference to an antibody refers to a polypeptide chain of about 50-70 kDa, wherein the amino-terminal portion includes a variable region of about 120 to 130 or more amino acids and a carboxy-terminal portion that includes a constant region. The constant region can be one of five distinct types, referred to as alpha (α), delta (δ), epsilon (ε), gamma (γ) and mu (μ), based on the amino acid sequence of the heavy chain constant region. The distinct heavy chains differ in size: α, δ and γ contain approximately 450 amino acids, while μ and ε contain approximately 550 amino acids. When combined with a light chain, these distinct types of heavy chains give rise to five well known classes of antibodies, IgA, IgD, IgE, IgG and IgM, respectively, including four subclasses of IgG, namely IgG1, IgG2, IgG3 and IgG4. A heavy chain can be a human heavy chain.

The term "host" as used herein refers to an animal, such as a mammal (e.g., a human).

The term "host cell" as used herein refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

"Humanized" forms of nonhuman (e.g., murine) antibodies are chimeric antibodies that include human immunoglobulins (recipient antibody) in which the native CDR residues are replaced by residues from the corresponding CDR of a nonhuman species (donor antibody) such as mouse, rat, rabbit or nonhuman primate having the desired specificity, affinity, and capacity. In some instances, one or more FR region residues of the human immunoglobulin are replaced by corresponding nonhuman residues. Furthermore, humanized antibodies can comprise residues that are not found in the recipient antibody or in the donor antibody. These modifications are made to further refine antibody performance. A humanized antibody heavy or light chain can comprise substantially all of at least one or more variable domains, in which all or substantially all of the CDRs correspond to those of a nonhuman immunoglobulin and all or substantially all of the FRs are those of a human immunoglobulin sequence. In certain embodiments, the humanized antibody will comprise at least a portion of an immunoglobulin constant region (Fc), typically that of a human immunoglobulin. For further details, see, Jones et al., Nature, 321:522-525 (1986); Riechmann et al., Nature, 332:323-329 (1988); and Presta, Curr. Op. Struct. Biol., 2:593-596 (1992); Carter et al., Proc. Natl. Acd. Sci. USA 89:4285-4289 (1992); and U.S. Pat. No. 6,800,738 (issued Oct. 5, 2004), U.S. Pat. No. 6,719,971 (issued Sep. 27, 2005), U.S. Pat. No. 6,639,055 (issued Oct. 28, 2003), U.S. Pat. No. 6,407,213 (issued Jun. 18, 2002), and U.S. Pat. No. 6,054,297 (issued Apr. 25, 2000).

An "immunoconjugate" as used herein refers to an antibody that is conjugated to one or more cytotoxic agents (e.g., a chemotherapeutic agent, a drug, a growth inhibitory agent, a toxin, or a radioisotype) or diagnostic agents (e.g., a radioisotope, a metal chelator, an enzyme, a fluorescent compound, a bioluminescent compound, or a chemiluminescent compound). In some embodiments the antibody is covalently bound by a synthetic linker to the one or more cytotoxic or diagnostic agents. Immunoconjugates comprising antibodies conjugated to cytotoxic agents are also referred to herein as "antibody drug conjugates," or "ADCs". An "antibody-drug conjugate" or "ADC" is an antibody that is conjugated to one or more cytotoxic agents, for example, through one or more linkers. An ADC may be of the formula A-L-CTX, wherein A is an antibody, L is a linker, and CTX is a cytotoxic agent.

An antibody that "inhibits the growth of cells expressing a CD39 polypeptide" or a "growth inhibitory" antibody is one which results in measurable growth inhibition of cells expressing or overexpressing the appropriate CD39 polypeptide. In a specific embodiment, antibodies inhibit the growth of a cancer cell, a pre-cancerous cell, or a cell comprising a tumor. Certain growth inhibitory anti-CD39 antibodies inhibit growth of CD39-expressing cells by greater than 20%, such as from about 20% to about 50%, or by greater than 50% (e.g., from about 50% to about 100%) as compared to the appropriate control, the control typically being cells not treated with the antibody being tested. In one embodiment, growth inhibition can be measured at an antibody concentration of about 0.1 to 30 g/ml or about 0.5 nM to 200 nM in cell culture, where the growth inhibition is determined 1-10 days after exposure of the tumor cells to the antibody. Growth inhibition of cells in vivo can be determined in various ways such as is described below. In the context of inhibiting a cancer cell or a cell comprising a tumor, the antibody is growth inhibitory in vivo if administration of the anti-CD39 antibody at about 1 g/kg to about 100 mg/kg body weight results in reduction in tumor size or tumor cell proliferation within about 5 days to 3 months from the first administration of the antibody, such as within about 5 to 30 days.

As used herein, the term "in combination" in the context of the administration of other therapies refers to the use of more than one therapy. The use of the term "in combination" does not restrict the order in which therapies are administered to a subject with an infection. A first therapy can be administered before (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks), concurrently, or after (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks) the administration of a second therapy to a subject which had, has, or is susceptible to a CD39-mediated disease. Any additional therapy can be administered in any order with the other additional therapies. In certain embodiments, the antibodies can be administered in combination with one or more therapies (e.g., therapies that are not the antibodies that are currently administered to prevent, treat, manage, and/or ameliorate a CD39-mediated disease. Non-limiting examples of therapies that can be administered in combination with an antibody include analgesic agents, anesthetic agents, antibiotics, or immunomodulatory agents or any other agent listed in the U.S. Pharmacopoeia and/or Physician's Desk Reference.

An antibody that "induces cell death" is one that causes a viable cell to become nonviable. The cell is of a cell type that specifically expresses or overexpresses a CD39 polypeptide. The cell may be cancerous or a normal cell of the particular cell type, such as a regulatory T cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (e.g., in the absence of complement) and in the absence of immune effector cells. To determine whether the antibody is able to induce cell death, loss of membrane integrity as evaluated by uptake of propidium iodide (PI), trypan blue (see Moore et al. Cytotechnology 17:1-11 (1995)). In some embodiments, cell death-inducing antibodies are those which induce PI uptake in the PI uptake assay in CD39 expressing cells.

An "isolated" antibody is substantially free of cellular material or other contaminating proteins from the cell or tissue source and/or other contaminant components from which the antibody is derived, or substantially free of chemical precursors or other chemicals when chemically synthesized. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, or 5% (by dry weight) of heterologous protein (also referred to herein as a "contaminating protein"). In certain embodiments, when the antibody is recombinantly produced, it is substantially free of culture medium, e.g., culture medium represents less than about 20%, 10%, or 5% of the volume of the protein preparation. In certain embodiments, when the antibody is produced by chemical synthesis, it is substantially free of chemical precursors or other chemicals, e.g., it is separated from chemical precursors or other chemicals which are involved in the synthesis of the protein. Accordingly such preparations of the antibody have less than about 30%, 20%, 10%, 5% (by dry weight) of chemical precursors or compounds other than the antibody of interest. Contaminant components can also include, but are not limited to, materials that would interfere with therapeutic uses for the antibody, and may include enzymes, hormones, and other proteinaceous or nonproteinaceous solutes. In certain embodiments, the antibody will be purified (1) to greater than 95% by weight of antibody as determined by the Lowry method (Lowry et al. J. Bio. Chem. 193: 265-275, 1951), such as 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step. In a specific embodiment, antibodies provided herein are isolated An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, a nucleic acid molecule(s) encoding an antibody provided herein is isolated or purified.

The term "leaving group," as used herein, refers to any group that leaves in the course of a chemical reaction involving the group as described herein and includes but is not limited to halogen, sulfonates (brosylate, mesylate, tosylate triflate etc . . . ), p-nitrobenzoate and phosphonate groups, for example.

The term "light chain" when used in reference to an antibody refers to a polypeptide chain of about 25 kDa, wherein the amino-terminal portion includes a variable region of about 100 to about 110 or more amino acids and a carboxy-terminal portion that includes a constant region. The approximate length of a light chain is 211 to 217 amino acids. There are two distinct types, referred to as kappa (κ) of lambda (λ) based on the amino acid sequence of the constant domains. Light chain amino acid sequences are well known in the art. A light chain can be a human light chain.

A "linker" (noted as L or L1, L2 and L3) is a molecule with two reactive termini, one for conjugation to an antibody or to another linker and the other for conjugation to a cytotoxin. The antibody conjugation reactive terminus of the linker is typically a site that is capable of conjugation to the antibody through a cysteine thiol or lysine amine group on the antibody, and so is typically a thiol-reactive group such as a double bond (as in maleimide) or a leaving group such as a chloro, bromo or iodo or an R-sulfanyl group or sulfonyl group, or an amine-reactive group such as a carboxyl group or as defined herein; while the antibody conjugation reactive terminus of the linker is typically a site that is capable of conjugation to the cytotoxin through formation of an amide bond with a basic amine or carboxyl group on the cytotoxin, and so is typically a carboxyl or basic amine group. In one embodiment, when the term "linker" is used in describing the linker in conjugated form, one or both of the reactive termini will be absent (such as the leaving group of the thiol-reactive group) or incomplete (such as the being only the carbonyl of the carboxylic acid) because of the formation of the bonds between the linker and/or the cytotoxin or cytotoxic agent.

The linker may be a "cleavable linker" facilitating release of the cytotoxic drug in the cell, but non-cleavable linkers are also contemplated herein. Linkers for use in the immunoconjugates of the invention include without limitation acid labile linkers (e.g., hydrazone linkers), disulfide-containing linkers, peptidase-sensitive linkers (e.g., peptide linkers comprising amino acids, for example, valine and/or citrulline such as citrulline-valine or phenylalanine-lysine), photolabile linkers, dimethyl linkers (Chari et al., Cancer Research 52:127-131 (1992); U.S. Pat. No. 5,208,020), thioether linkers, or hydrophilic linkers designed to evade multidrug transporter-mediated resistance (Kovtun et al., Cancer Res. 70: 2528-2537, 2010).

As used herein, the terms "manage," "managing," and "management" refer to the beneficial effects that a subject derives from a therapy (e.g., a prophylactic or therapeutic agent), which does not result in a cure of the disease. In certain embodiments, a subject is administered one or more therapies (e.g., prophylactic or therapeutic agents, such as an antibody provided herein) to "manage" a CD39-mediated disease, one or more symptoms thereof, so as to prevent the progression or worsening of the disease.

The term "monoclonal antibody" refers to an antibody obtained from a population of homogenous or substantially homogeneous antibodies, and each monoclonal antibody will typically recognize a single epitope on the antigen. In specific embodiments, a "monoclonal antibody," as used herein, is an antibody produced by a single hybridoma or other cell, wherein the antibody binds to only a CD39 epitope as determined, e.g., by ELISA or other antigen-binding or competitive binding assay known in the art. The term "monoclonal" is not limited to any particular method for making the antibody. For example, monoclonal antibodies provided herein may be made by the hybridoma method as described in Kohler et al.; Nature, 256:495 (1975) or may be isolated from phage libraries using the techniques. Other methods for the preparation of clonal cell lines and of monoclonal antibodies expressed thereby are well known in the art (see, for example, Chapter 11 in: Short Protocols in Molecular Biology, (2002) 5th Ed., Ausubel et al., eds., John Wiley and Sons, New York). Other exemplary methods of producing other monoclonal antibodies are provided in the Examples herein.

The term "native" when used in connection with biological materials such as nucleic acid molecules, polypeptides, host cells, and the like, refers to those which are found in nature and not manipulated by a human being.

The term "pharmaceutically acceptable" as used herein means being approved by a regulatory agency of the Federal or a state government, or listed in the U.S. Pharmacopeia, European Pharmacopeia or other generally recognized Pharmacopeia for use in animals, and more particularly in humans.

"Polyclonal antibodies" as used herein refers to an antibody population generated in an immunogenic response to a protein having many epitopes and thus includes a variety of different antibodies directed to the same and to different epitopes within the protein. Methods for producing polyclonal antibodies are known in the art (See, e.g., see, for example, Chapter 11 in: Short Protocols in Molecular Biology, (2002) 5th Ed., Ausubel et al., eds., John Wiley and Sons, New York).

As used herein, the term "polynucleotide," "nucleotide," nucleic acid" "nucleic acid molecule" and other similar terms are used interchangeable and include DNA, RNA, mRNA and the like.

A "pre-cancerous cell" refers to a cell that has an abnormal appearance such as a difference in size or shape in comparison to cells of the surrounding tissue or normal cells of its cell type, but are not invasive. The appearance of pre-cancerous cells can be suggestive of an increased cancer risk. Pre-cancerous cells expressing CD39 can be identified using methods disclosed herein, which can include analyzing a sample of cells from a patient.

As used herein, the terms "prevent," "preventing," and "prevention" refer to the total or partial inhibition of the development, recurrence, onset or spread of a CD39-mediated disease and/or symptom related thereto, resulting from the administration of a therapy or combination of therapies provided herein (e.g., a combination of prophylactic or therapeutic agents, such as an antibody provided herein).

As used herein, the term "prophylactic agent" refers to any agent that can totally or partially inhibit the development, recurrence, onset or spread of a CD39-mediated disease and/or symptom related thereto in a subject. In certain embodiments, the term "prophylactic agent" refers to an anti-CD39 antibody provided herein. In certain other embodiments, the term "prophylactic agent" refers to an agent other than an anti-CD39 antibody provided herein. In certain embodiments, a prophylactic agent is an agent which is known to be useful to or has been or is currently being used to prevent a CD39-mediated disease and/or a symptom related thereto or impede the onset, development, progression and/or severity of a CD39-mediated disease and/or a symptom related thereto. In specific embodiments, the prophylactic agent is a humanized anti-CD39 antibody, such as a humanized anti-CD39 monoclonal antibody.

In certain embodiments, a "prophylactically effective serum titer" is the serum titer in a subject, preferably a human, that totally or partially inhibits the development, recurrence, onset or spread of a CD39-mediated disease and/or symptom related thereto in the subject.

The term "recombinant antibody" refers to an antibody that is prepared, expressed, created or isolated by recombinant means. Recombinant antibodies can be antibodies expressed using a recombinant expression vector transfected into a host cell, antibodies isolated from a recombinant, combinatorial antibody library, antibodies isolated from an animal (e.g., a mouse or cow) that is transgenic and/or transchromosomal for human immunoglobulin genes (see e.g., Taylor, L. D. et al. (1992) Nucl. Acids Res. 20:6287-6295) or antibodies prepared, expressed, created or isolated by any other means that involves splicing of immunoglobulin gene sequences to other DNA sequences. Such recombinant antibodies can have variable and constant regions derived from human germline immunoglobulin sequences (See Kabat, E. A. et al. (1991) Sequences of Proteins of Immunological Interest, Fifth Edition, U.S. Department of Health and Human Services, NIH Publication No. 91-3242). In certain embodiments, however, such recombinant antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "serum titer" as used herein refers to an average serum titer in a population of least 10, such as at least 20, or at least 40 subjects, up to about 100, 1000 or more.

As used herein, the term "side effects" encompasses unwanted and adverse effects of a therapy (e.g., a prophylactic or therapeutic agent). Unwanted effects are not necessarily adverse. An adverse effect from a therapy (e.g., a prophylactic or therapeutic agent) might be harmful or uncomfortable or risky. Examples of side effects include, diarrhea, cough, gastroenteritis, wheezing, nausea, vomiting, anorexia, abdominal cramping, fever, pain, loss of body weight, dehydration, alopecia, dyspenea, insomnia, dizziness, mucositis, nerve and muscle effects, fatigue, dry mouth, and loss of appetite, rashes or swellings at the site of administration, flu-like symptoms such as fever, chills and fatigue, digestive tract problems and allergic reactions. Additional undesired effects experienced by patients are numerous and known in the art. Many are described in the Physician's Desk Reference (67th ed., 2013).

As used herein, the terms "subject" and "patient" are used interchangeably. As used herein, in certain embodiments, a subject is a mammal, such as a non-primate (e.g., cows, pigs, horses, cats, dogs, rats, etc.) or a primate (e.g., monkey and human). In specific embodiments, the subject is a human. In one embodiment, the subject is a mammal (e.g., a human) having a CD39-mediated disease. In another embodiment, the subject is a mammal (e.g., a human) at risk of developing a CD39-mediated disease.

As used herein "substantially all" refers to refers to at least about 60%, at least about 70%, at least about 75%, at least about 80%, at least about 85%, at least about 90%, at least about 95%, at least about 98%, at least about 99%, or about 100%.

As used herein, the term "therapeutic agent" refers to any agent that can be used in treating, preventing or alleviating a disease, disorder or condition, including in the treatment, prevention or alleviation of one or more symptoms of a CD39-mediated disease, disorder, or condition and/or a symptom related thereto. In certain embodiments, a therapeutic agent refers to an antibody provided herein. In certain other embodiments, a therapeutic agent refers to an agent other than an antibody provided herein. In certain embodiments, a therapeutic agent is an agent which is known to be useful for, or has been or is currently being used for the treatment, prevention or alleviation of one or more symptoms of a CD39-mediated disease, disorder, condition, or a symptom related thereto.

The combination of therapies (e.g., use of therapeutic agents) can be more effective than the additive effects of any two or more single therapy. For example, a synergistic effect of a combination of therapeutic agents permits the use of lower dosages of one or more of the agents and/or less frequent administration of the agents to a subject with a CD39-mediated disease. The ability to utilize lower dosages of therapeutic therapies and/or to administer the therapies less frequently reduces the toxicity associated with the administration of the therapies to a subject without reducing the efficacy of the therapies in the prevention, treatment or alleviation of one or more symptom of a CD39-mediated disease. In addition, a synergistic effect can result in improved efficacy of therapies in the prevention, treatment or alleviation of one or more symptom of a CD39-mediated disease. Finally, synergistic effect of a combination of therapies (e.g., therapeutic agents) may avoid or reduce adverse or unwanted side effects associated with the use of any single therapy.

The term "therapeutically effective amount" as used herein refers to the amount of a therapeutic agent (e.g., an antibody provided herein or any other therapeutic agent provided herein) that is sufficient to reduce and/or ameliorate the severity and/or duration of a given disease and/or a symptom related thereto. A therapeutically effective amount of a therapeutic agent can be an amount necessary for the reduction or amelioration of the advancement or progression of a given disease, reduction or amelioration of the recurrence, development or onset of a given disease, and/or to improve or enhance the prophylactic or therapeutic effect of another therapy (e.g., a therapy other than the administration of an antibody provided herein).

In certain embodiments, a "therapeutically effective serum titer" is the serum titer in a subject, preferably a human, that reduces the severity, the duration and/or the symptoms associated with a CD39-mediated disease in the subject.

As used herein, the term "therapy" refers to any protocol, method and/or agent that can be used in the prevention, management, treatment and/or amelioration of a CD39-mediated disease. In certain embodiments, the terms "therapies" and "therapy" refer to a biological therapy, supportive therapy, and/or other therapies useful in the prevention, management, treatment and/or amelioration of a CD39-mediated disease known to one of skill in the art such as medical personnel.

The term "thiol," as used herein, refers to the radical —SH.

As used herein, the terms "treat," "treatment" and "treating" refer to the reduction or amelioration of the progression, severity, and/or duration of a CD39-mediated disease resulting from the administration of one or more therapies (including, but not limited to, the administration of one or more therapeutic agents, such as an antibody provided herein). In specific embodiments, such terms refer to the reduction or inhibition of cancer or tumor formation. In yet other specific embodiments, such terms refer to the reduction or amelioration of the progression, severity, and/or duration of a disease that is responsive to immune modulation, such modulation resulting from increasing T cell activation, increasing T cell proliferation or increasing cytokine production.

"Tubulysin" includes both the natural products described as tubulysins, such as by Sasse et al. and other authors mentioned in the Description of the related art, and also the tubulysin analogs described in US Patent Application Publication No. US 2011/0021568 A1. Tubulysins disclosed in the present application are noted herein and may include the tubulysins of the formulae T3 and T4, and other tubulysins where the terminal N-methylpiperidine has been replaced by an unsubstituted piperidine, allowing amide bond formation with a linker.

The term "variable domain" or "variable region" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable domains differ extensively in sequence between different antibodies. The variability in sequence is concentrated in the CDRs while the less variable portions in the variable domain are referred to as framework regions (FR). The CDRs of the light and heavy chains are primarily responsible for the interaction of the antibody with antigen. In specific embodiments, the variable region is a human variable region.

The term "variable domain residue numbering as in Kabat" or "amino acid position numbering as in Kabat", and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc, according to Kabat) after heavy chain FR residue 82. The Kabat numbering of residues may be determined for a given antibody by alignment at regions of homology of the sequence of the antibody with a "standard" Kabat numbered sequence. The Kabat numbering system is generally used when referring to a residue in the variable domain (approximately residues 1-107 of the light chain and residues 1-113 of the heavy chain) (e.g, Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG 1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system. As used herein, the terms "variable region" and "variable domain" are used interchangeably.

The term "variant" when used in relation to CD39 or to an anti-CD39 antibody refers to a peptide or polypeptide comprising one or more (such as, for example, about 1 to about 25, about 1 to about 20, about 1 to about 15, about 1 to about 10, or about 1 to about 5) amino acid sequence substitutions, deletions, and/or additions as compared to a native or unmodified sequence. For example, a CD39 variant may result from one or more (such as, for example, about 1 to about 25, about 1 to about 20, about 1 to about 15, about 1 to about 10, or about 1 to about 5) changes to an amino acid sequence of native CD39. Also by way of example, a variant of an anti-CD39 antibody may result from one or more (such as, for example, about 1 to about 25, about 1 to about 20, about 1 to about 15, about 1 to about 10, or about 1 to about 5) changes to an amino acid sequence of a native or previously unmodified anti-CD39 antibody. Variants may be naturally occurring, such as allelic or splice variants, or may be artificially constructed. Polypeptide variants may be prepared from the corresponding nucleic acid molecules encoding the variants. In specific embodiments, the CD39 variant or anti-CD39 antibody variant at least retains CD39 or anti-CD39 antibody functional activity, respectively. In specific embodiments, an anti-CD39 antibody variant binds CD39 and/or is antagonistic to CD39 activity. In specific embodiments, an anti-CD39 antibody variant binds CD39 and/or is agonistic to CD39 activity. In certain embodiments, the variant is encoded by a single nucleotide polymorphism (SNP) variant of a nucleic acid molecule that encodes CD39 or anti-CD39 antibody VH or VL regions or subregions.

The term "vector" refers to a substance that is used to introduce a nucleic acid molecule into a host cell. Vectors applicable for use include, for example, expression vectors, plasmids, phage vectors, viral vectors, episomes and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more nucleic acid molecules are to be co-expressed (e.g. both an antibody heavy and light chain), both nucleic acid molecules can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The introduction of nucleic acid molecules into a host cell can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the nucleic acid molecule is expressed in a sufficient amount to produce the desired product (e.g. an anti-CD39 antibody provided herein), and it is further understood that expression levels can be optimized to obtain sufficient expression using methods well known in the art.

DETAILED DESCRIPTION

Provided herein are antibodies that bind to CD39 (e.g., a cell surface-expressed or soluble CD39), including a CD39 polypeptide, a CD39 polypeptide fragment, or a CD39 epitope. Also provided are antibodies that competitively block an anti-CD39 antibody provided herein from binding to CD39 (e.g., a cell surface-expressed or soluble CD39), including a CD39 polypeptide, a CD39 polypeptide fragment, or a CD39 epitope. The anti-CD39 antibodies provided herein can also be conjugated or recombinantly fused to a diagnostic agent, detectable agent or therapeutic agent (e.g., for use as an antibody-drug conjugate). For example, a detectable agent may be a detectable probe. For example, a therapeutic agent may be a drug or cytotoxin conjugated to the anti-CD39 antibody. Further provided are compositions comprising an anti-CD39 antibody.

Also provided herein are isolated nucleic acid molecules encoding a heavy chain, light chain, VH region, VL region, VH CDR1, VH CDR2, VH CDR3, VL CDR1, VL CDR2, and/or VL CDR3 of anti-CD39 antibodies that bind to CD39 (e.g., a cell surface-expressed or soluble CD39), including a CD39 polypeptide, a CD39 polypeptide fragment, or a CD39 epitope. Further provided are vectors and host cells comprising nucleic acid molecules encoding anti-CD39 antibodies that bind to CD39 (e.g., a cell surface-expressed or soluble CD39), including a CD39 polypeptide, a CD39 polypeptide fragment, or a CD39 epitope. Also provided are methods of making antibodies that bind to CD39 (e.g., a cell surface-expressed or soluble CD39), including a CD39 polypeptide, a CD39 polypeptide fragment, or a CD39 epitope.

Methods of using the anti-CD39 antibodies are provided. The methods include treating, preventing or alleviating a disease, disorder or condition, including treating, preventing or alleviating one or more symptoms of a disease, disorder or condition in a subject or inhibiting the growth of a cell having cell surface expression of a CD39 polypeptide. Additional methods provided include using an anti-CD39 antibody provided herein, for example, as an unconjugated antibody or conjugated antibody (ADC), with anti-tumor activity to mediate anti-tumor effects. In certain embodiments, the anti-CD39 antibodies provided herein inhibit CD39-mediated suppressor activity on T cells (e.g., to allow an effective anti-tumor immune response). In certain embodiments, the anti-CD39 antibodies provided herein directly kill CD39-bearing tumor cells (e.g., via antibody-dependent cellular cytotoxicity (ADCC) and/or complement-dependent cytotoxicity (CDC). In certain embodiments, antibody drug conjugates (ADCs) comprising anti-CD39 antibodies provided herein directly kill CD39-bearing tumor cells (e.g., by binding to tumor cells expressing CD39 and allowing internalization of the cytotoxic drug). Additional methods provided include using an anti-CD39 antibody to modulate an immune response in a subject or detecting CD39 in a sample.

Anti-CD39 Antibodies

In one embodiment, the present disclosure provides anti-CD39 antibodies, including humanized anti-CD39 antibodies, or functional fragments thereof that may find use as antibodies or as antibody drug conjugates (ADCs) herein as therapeutic agents. Exemplary antibodies include polyclonal, monoclonal, humanized, human, bispecific, and heteroconjugate antibodies, as well as variants thereof having improved affinity or other properties.

In some embodiments, provided herein are antibodies that bind to CD39, including a CD39 polypeptide, a CD39 polypeptide fragment, a CD39 peptide or a CD39 epitope. In some embodiments the anti-CD39 antibodies are humanized antibodies (e.g., comprising human constant regions) that bind CD39, including CD39 polypeptide, a CD39 polypeptide fragment, a CD39 peptide or a CD39 epitope.

In certain embodiments, the anti-CD39 antibody, including a humanized anti-CD39 antibody, or functional fragment thereof comprises a VH region, VL region, VH CDR1, VH CDR2, VH CDR3, VL CDR1, VL CDR2, and/or VL CDR3 of any one of the anti-CD39 antibodies described herein, such as an amino acid sequence depicted in Tables 1-4. Accordingly, in some embodiments, the antibody or functional fragment thereof (e.g., CD39 binding) provided herein comprises one, two, or three heavy chain CDRs and/or one, two, or three light chain CDRs from: (a) the antibody designated R29-5-13A; (b) the antibody designated R29-5-71A; (c) the antibody designated R29-5-165C; or (d) the antibody designated R29-9-8B.

TABLE 1

Antibody R21-5-13A CDR Sequences

| | | IMGT | Kabat | Chothia | Contact | AbM |
|---|---|---|---|---|---|---|
| VH CDR Seq. | VH CDR1 | GYTFTGYY (SEQ ID NO: 87) | GYYVH (SEQ ID NO: 88) | GYTFTGY (SEQ ID NO: 89) | TGYYVH (SEQ ID NO: 90) | GYTFTGYYVH (SEQ ID NO: 87) |
| | VH CDR2 | IYPGNVNT (SEQ ID NO: 91) | WIYPGNVNT KYNEKFKA (SEQ ID NO: 92) | PGNV (SEQ ID NO: 93) | WIGWIYPGNVN TK (SEQ ID NO: 94) | WIYPGNVNTK (SEQ ID NO: 95) |
| | VH CDR3 | ARSPYYGTTYY YTMDY (SEQ ID NO: 96) | SPYYGTTYY YTMDY (SEQ ID NO: 97) | PYYGTTYYYT MD (SEQ ID NO: 98) | ARSPYYGTTYY YTMD (SEQ ID NO: 99) | SPYYGTTYY YTMDY (SEQ ID NO: 97) |
| VL CDR Seq. | VL CDR1 | LIISSRN (SEQ ID NO: 100) | SVSLIISSRNLH (SEQ ID NO: 101) | SLIISSRN (SEQ ID NO: 102) | SSRNLHWY (SEQ ID NO: 103) | SVSLIISSRN LH (SEQ ID NO: 101) |
| | VL CDR2 | GTS (SEQ ID NO: 103) | GTSNLAS (SEQ ID NO: 104) | GTS (SEQ ID NO: 103) | PWIYGTSNLA (SEQ ID NO: 105) | GTSNLAS (SEQ ID NO: 104) |
| | VL CDR3 | QQWSDYPLT (SEQ ID NO: 106) | QQWSDYPLT (SEQ ID NO: 106) | WSDYPL (SEQ ID NO: 107) | QQWSDYPL (SEQ ID NO: 108) | QQWSDYPLT (SEQ ID NO: 106) |

VH Sequence with Leader Sequence:

(SEQ ID NO: 16)

MGWSRIFLFLLSIIAGVHCQVQLQQSGPELVKPGASVRISCKASGYTFTGYYVHWVKQRPGQGLEWIGWIYPG

NVNTKYNEKFKAKATLTADKSSTGYMQLSRLTSEDSAVYFCARSPYYGTTYYYTMDYWGQGTSVTVSS

TABLE 1-continued

Antibody R21-5-13A CDR Sequences

VL Sequence with Leader Sequence:
(SEQ ID NO: 17)

<u>MDFHVQIFSFMLISVTVILSSG</u>EIVLTQSPAFMAASPGEKVTITCSVSLIISSRNLHWYQQKSETSPKPWIYGTSN

LASGVPVRFSGSGSGTSYSLTISSMEAEDAATYYCQQWSDYPLTFGSGTKLEIK

Underlined amino acids represent leader sequence.

TABLE 2

Antibody R21-5-71A CDR Sequences

|  |  | IMGT | Kabat | Chothia | Contact | AbM |
|---|---|---|---|---|---|---|
| VH CDR Seq. | VH CDR1 | GFTFSSFG (SEQ ID NO: 109) | SFGMH (SEQ ID NO: 110) | GFTFSSF (SEQ ID NO: 111) | SSFGMH (SEQ ID NO: 112) | GFTFSSFGMH (SEQ ID NO: 113) |
|  | VH CDR2 | ISSGSTIR (SEQ ID NO: 114) | YISSGSTIRYYSDTVKG (SEQ ID NO: 115) | SGST (SEQ ID NO: 116) | LVAYISSGSTIRY (SEQ ID NO: 117) | YISSGSTIRY (SEQ ID NO: 118) |
|  | VH CDR3 | ARFLYEGFRYGMDY (SEQ ID NO: 119) | FLYEGFRYGMDY (SEQ ID NO: 120) | LYEGFRYGMD (SEQ ID NO: 121) | ARFLYEGFRYGMD (SEQ ID NO: 122) | FLYEGFRYGMDY (SEQ ID NO: 120) |
| VL CDR Seq. | VL CDR1 | QSIVHSNGNTY (SEQ ID NO: 123) | RSSQSIVHSNGNTYLE (SEQ ID NO: 124) | SQSIVHSNGNTY (SEQ ID NO: 125) | VHSNGNTYLEWY (SEQ ID NO: 126) | RSSQSIVHSNGNTYLE (SEQ ID NO: 124) |
|  | VL CDR2 | KVS (SEQ ID NO: 127) | KVSNRFS (SEQ ID NO: 128) | KVS (SEQ ID NO: 127) | LLIYKVSNRF (SEQ ID NO: 129) | KVSNRFS (SEQ ID NO: 128) |
|  | VL CDR3 | FQGSHVPNT (SEQ ID NO: 130) | FQGSHVPNT (SEQ ID NO: 130) | GSHVPN (SEQ ID NO: 131) | FQGSHVPN (SEQ ID NO: 132) | FQGSHVPNT (SEQ ID NO: 130) |

VH Sequence with Leader Sequence:
(SEQ ID NO: 18)

<u>MDSRLNLVFLVLILKGVQC</u>DVQLVESGGGLVQPGGSRKLSCAASGFTFSSFGMHWVRQAPEKGLELVAY

ISSGSTIRYYSDTVKGRFTISRDNPKNTLFLQMTSLRSEDTAMYYCARFLYEGFRYGMDYWGQGTSV

TVSS

VL Sequence with Leader Sequence:
(SEQ ID NO: 19)

<u>MKLPVRLLVLMFWIPASSS</u>DVLMTQTPLSLPVSLGDQASISCRSSQSIVHSNGNTYLEWYLQKPGQSPKL

LIYKVSNRFSGVPDRFSGSGSGTDFTLKISRVEAEDLGIYYCFQGSHVPNTFGGGTKLEIK

Underlined amino acids represent leader sequence.

TABLE 3

Antibody R21-5-165C CDR Sequences

|  |  | IMGT | Kabat | Chothia | Contact | AbM |
|---|---|---|---|---|---|---|
| VH CDR Seq. | VH CDR1 | GFTFSRYG (SEQ ID NO: 133) | RYGMS (SEQ ID NO: 134) | GFTFSRY (SEQ ID NO: 135) | SRYGMS (SEQ ID NO: 136) | GFTFSRYGMS (SEQ ID NO: 137) |
|  | VH CDR2 | ITSGGIYT (SEQ ID NO: 138) | TITSGGIYTYYPDSVKG (SEQ ID NO: 139) | SGGI (SEQ ID NO: 140) | WVATITSGGIYT (SEQ ID NO: 141) | TITSGGIYTY (SEQ ID NO: 142) |
|  | VH CDR3 | ARHGQFGDYYGMDY (SEQ ID NO: 143) | HGQFGDYYGMDY (SEQ ID NO: 144) | GQFGDYYGMD (SEQ ID NO: 145) | ARHGQFGDYYGMD (SEQ ID NO: 146) | HGQFGDYYGMDY (SEQ ID NO: 144) |

TABLE 3-continued

Antibody R21-5-165C CDR Sequences

| | | | | | | |
|---|---|---|---|---|---|---|
| VL CDR Seq. | VL CDR1 | QSLLHSNGNTY GNTYLH (SEQ ID NO: 147) | RSSQSLLHSN (SEQ ID NO: 148) | SQSLLHSNG NTY (SEQ ID NO: 149) | LHSNGNTYLHWY (SEQ ID NO: 150) | RSSQSLLHS NGNTYLH (SEQ ID NO: 148) |
| | VL CDR2 | KVS (SEQ ID NO: 127) | KVSNRFS (SEQ ID NO: 128) | KVS (SEQ ID NO: 127) | LLIYKVSNRF (SEQ ID NO: 129) | KVSNRFS (SEQ ID NO: 128) |
| | VL CDR3 | SQSTHVPYT (SEQ ID NO: 151) | SQSTHVPYT (SEQ ID NO: 151) | STHVPY (SEQ ID NO: 152) | SQSTHVPY (SEQ ID NO: 153) | SQSTHVPYT (SEQ ID NO: 151) |

VH Sequence with Leader Sequence:
(SEQ ID NO: 20)
<u>MHFGLSLIFLALILKGVQC</u>EVQLVESGGDLVKPGGSLKLSCAAFGFTFSRYGMSWVRQTPDKRLEWVAT

ITSGGIYTYYPDSVKGRFTISRDNAKNTLYLQMSSLKSEETAMYYCARHGQFGDYYGMDYWGQGTSVT

VSS

VL Sequence with Leader Sequence:
(SEQ ID NO: 21)
<u>MKLPVRLLVLMFWIPASSS</u>DVVMTQTPLSLPVSLGDQASISCRSSQSLLHSNGNTYLHWYLQKPGQSP

KLLIYKVSNRFSGVPDRFSGSGSGTDFTLKISRVEAEDLGVYFCSQSTHVPYTFGGGTKLEIK

Underlined amino acids represent leader sequence.

TABLE 4

Antibody R21-9-8B CDR Sequences

| | | IMGT | Kabat | Chothia | Contact | AbM |
|---|---|---|---|---|---|---|
| VH CDR Seq. | VH CDR1 | GYTFTHYG (SEQ ID NO: 154) | HYGMN (SEQ ID NO: 155) | GYTFTHY (SEQ ID NO: 156) | THYGMN (SEQ ID NO: 157) | GYTFTHYGMN (SEQ ID NO: 158) |
| | VH CDR2 | INTYTGEL (SEQ ID NO: 159) | WINTYTGELTY ADDFKG (SEQ ID NO: 160) | TYTG (SEQ ID NO: 161) | WMGWINTYTG ELT (SEQ ID NO: 162) | WINTYTGELT (SEQ ID NO: 163) |
| | VH CDR3 | ARRAYYRYD YVMDY (SEQ ID NO: 164) | RAYYRYDYVM DY (SEQ ID NO: 165) | AYYRYDYVMD (SEQ ID NO: 166) | ARRAYYRYDYV MD (SEQ ID NO: 167) | RAYYRYDYV MDY (SEQ ID NO: 165) |
| VL CDR Seq. | VL CDR1 | HNVGTN (SEQ ID NO: 168) | KASHNVGTNVA (SEQ ID NO: 169) | SHNVGTN (SEQ ID NO: 170) | GTNVAWY (SEQ ID NO: 171) | KASHNVGTN VA (SEQ ID NO: 169) |
| | VL CDR2 | SAS (SEQ ID NO: 172) | SASYRYS (SEQ ID NO: 173) | SAS (SEQ ID NO: 172) | ALIYSASYRY (SEQ ID NO: 174) | SASYRYS (SEQ ID NO: 173) |
| | VL CDR3 | HQYNNYPYT (SEQ ID NO: 175) | HQYNNYPYT (SEQ ID NO: 175) | YNNYPY (SEQ ID NO: 176) | HQYNNYPY (SEQ ID NO: 177) | HQYNNYPYT (SEQ ID NO: 175) |

VH Sequence with Leader Sequence:
(SEQ ID NO: 22)
<u>MAWVWTLLFLMAAAQSAQA</u>QIQLVQSGPELKKPGETVKISCKASGYTFTHYGMNWVKQAPGKGLKWM

GWINTYTGELTYADDFKGRFAFSLETSASTAYLQINNLKNEDTATYFCARRAYYRYDYVMDYWGQGT

SVTVSS

VL Sequence with Leader Sequence:
(SEQ ID NO: 23)
<u>MGIKMESQTQVFVYMLLWLSGVDG</u>DIVMTQSQKFMSTSVGDRVSVTCKASHNVGTNVAWYQQKPGQS

PKALIYSASYRYSGVPGRFTGSGSGTDFTLTISNVQSEDLAEYFCHQYNNYPYTFGGGTKLEIK

Underlined amino acids represent leader sequence.

In some embodiments, the anti-CD39 antibodies, including humanized antibodies, or functional fragments thereof provided herein comprise a VH region having an amino acid sequence identified in FIG. 1A, 2A-2B, 4A-4B, or 6A-6C and/or a VL region having an amino acid sequence identified in FIG. 1B, 3A-3B, 5A-5B, or 7A-7B.

In some embodiments, the anti-CD39 antibodies, including humanized antibodies, or functional fragments thereof provided herein comprise a VH region that comprises or consists of a VH domain. In other embodiments, the anti-CD39 antibodies, including humanized antibodies, or functional fragments thereof provided herein comprise a VH region that comprises or consists of a VH chain. In some embodiments, the anti-CD39 antibodies, including humanized antibodies, or functional fragments thereof provided herein comprise a VL region that comprises or consists of a VL domain. In other embodiments, the anti-CD39 antibodies, including humanized antibodies, or functional fragments thereof provided herein comprise a VL region that comprises or consists of a VL chain. In some embodiments, the anti-CD39 antibodies, including humanized antibodies, or functional fragments thereof provided herein comprise a combination of (i) a VH domain or VH chain; and/or (ii) a VL domain or VL chain.

In some embodiments, the anti-CD39 antibodies, including humanized antibodies, or functional fragments thereof provided herein comprise or consist of six CDRs, for example, VH CDR1, VH CDR2, VH CDR3, VL CDR1, VL CDR2, and/or VL CDR3 identified in Tables 1-4 or FIG. 1A-1B, 2A-2B, 3A-3B, 4A-4B, 5A-5B, 6A-6C, or 7A-7B. In certain embodiments, the anti-CD39 antibodies, including humanized antibodies, or functional fragments thereof provided herein comprise less than six CDRs. In some embodiments, the anti-CD39 antibodies, including humanized antibodies, or functional fragments thereof provided herein comprise or consist of one, two, three, four, or five CDRs selected from the group consisting of VH CDR1, VH CDR2, VH CDR3, VL CDR1, VL CDR2, and/or VL CDR3. In specific embodiments, the anti-CD39 antibody, including a humanized antibody, comprises or consists of one, two, three, four, or five CDRs selected from the group consisting of VH CDR1, VH CDR2, VH CDR3, VL CDR1, VL CDR2, and/or VL CDR3 of an anti-CD39 antibody selected from the group consisting of: (a) the antibody designated R29-5-13A; (b) the antibody designated R29-5-71A; (c) the antibody designated R29-5-165C; or (d) the antibody designated R29-9-8B described herein. Accordingly, in some embodiments, the anti-CD39 antibody, including a humanized antibody, or functional fragment thereof comprises or consists of one, two, three, four or five CDRs of anyone of the VH CDR1, VH CDR2, VH CDR3, VL CDR1, VL CDR2, and/or VL CDR3 identified in Tables 1-4 or FIG. 1A-1B, 2A-2B, 3A-3B, 4A-4B, 5A-5B or 6A-6C.

In some embodiments, the anti-CD39 antibodies, including humanized antibodies, or functional fragments thereof provided herein comprise one or more (e.g., one, two or three) VH CDRs listed in Tables 1-4 or FIG. 1A, 2A-2B, 4A-4B, or 6A-6C. In other embodiments, the anti-CD39 antibodies, including humanized antibodies, or functional fragments thereof provided herein comprise one or more (e.g., one, two or three) VL CDRs listed in Tables 1-4 or FIG. 1B, 3A-3B, 5A-5B, or 7A-7B. In yet other embodiments, the anti-CD39 antibodies, including humanized antibodies, or functional fragments thereof provided herein comprise one or more (e.g., one, two or three) VH CDRs listed in Tables 1-4 or FIG. 1A, 2A-2B, 4A-4B, or 6A-6C, and one or more VL CDRs listed in Tables 1-4 or FIG. 1B, 3A-3B, 5A-5B, or 7A-7B. Accordingly, in certain embodiments, the antibodies comprise a VH CDR1 having the amino acid sequence of any one of the SEQ ID NOS depicted in Tables 1-4 or FIG. 1A, 2A-2B, 4A-4B, or 6A-6C. In another embodiment, the antibodies comprise a VH CDR2 having the amino acid sequence of any one of the SEQ ID NOS depicted in Tables 1-4 or FIG. 1A, 2A-2B, 4A-4B, or 6A-6C. In another embodiment, the antibodies comprise a VH CDR3 having the amino acid sequence of any one of the SEQ ID NOS depicted in Tables 1-4 or FIG. 1A, 2A-2B, 4A-4B, or 6A-6C. In certain embodiments, the antibodies comprise a VH CDR1 and/or a VH CDR2 and/or a VH CDR3 independently selected from a VH CDR1, VH CDR2, VH CDR3 as depicted in any one of the amino acid sequences depicted in Tables 1-4 or FIG. 1A, 2A-2B, 4A-4B, or 6A-6C. In certain embodiments, the antibodies comprise a VL CDR1 having the amino acid sequence of any one of the SEQ ID NOS depicted in Tables 1-4 or FIG. 1B, 3A-3B, 5A-5B, or 7A-7B. In another embodiment, the antibodies comprise a VL CDR2 having the amino acid sequence of any one of the SEQ ID NOS depicted in Tables 1-4 or FIG. 1B, 3A-3B, 5A-5B, or 7A-7B. In another embodiment, the antibodies comprise a VL CDR3 having the amino acid sequence of any one of the SEQ ID NOS depicted in Tables 1-4 or FIG. 1B, 3A-3B, 5A-5B, or 7A-7B. In certain embodiments, the antibodies comprise a VL CDR1 and/or a VL CDR2 and/or a VL CDR3 independently selected from a VL CDR1, VL CDR2, VL CDR3 as depicted in any one of the amino acid sequences depicted in Tables 1-4 or FIG. 1B, 3A-3B, 5A-5B, or 7A-7B.

Also provided herein are antibodies comprising one or more VH CDRs (e.g., one, two or three) and one or more (e.g., one, two or three) VL CDRs listed in Tables 1-4 or FIG. 1A-1B, 2A-2B, 3A-3B, 4A-4B, 5A-5B or 6A-6C. Also provided herein are antibodies comprising any combination of the VH CDRs and VL CDRs listed in Tables 1-4 or FIG. 1A-1B, 2A-2B, 3A-3B, 4A-4B, 5A-5B or 6A-6C.

In some embodiments, the anti-CD39 antibodies, including humanized antibody, or functional fragment thereof provided herein comprise a VH FR1, VH FR2, VH FR3, VH FR4, VL FR1, VL FR2, VL FR3, and/or VL FR4 of a human germline immunoglobulin amino acid sequence or a variant thereof. For example, in some embodiments, the humanized anti-CD39 antibody comprises a VH FR1, VH FR2, VH FR3, and/or VH FR4 depicted in a human germline sequence identified in FIG. 1A, 2A-2B, 4A-4B, or 6A-6C. Accordingly, in some embodiments, the humanized anti-CD39 antibody comprises a VH FR1, VH FR2, VH FR3, and/or VH FR4 of the human germline IGHV1-2 and IGHJ4. In some embodiments, the humanized anti-CD39 antibody comprises a VH FR1, VH FR2, VH FR3, and/or VH FR4 of the human germline IGHV3-48 and IGHJ4. In some embodiments, the humanized anti-CD39 antibody comprises a VH FR1, VH FR2, VH FR3, and/or VH FR4 of the human germline IGHV3-21 and IGHJ4. In some embodiments, the humanized anti-CD39 antibody comprises a VH FR1, VH FR2, VH FR3, and/or VH FR4 of the human germline IGHV7-4-1 and IGHJ4. In some embodiments, the humanized anti-CD39 antibody comprises a VH FR1, VH FR2, VH FR3, and/or VH FR4 of the human germline IGHV1-18 and IGHJ4. As another example, in some embodiments, the humanized anti-CD39 antibody comprises a VL FR1, VL FR2, VL FR3, and/or VL FR4 depicted in a human germline sequence identified in FIG. 1B, 3A-3B, 5A-5B, or 7A-7B. Accordingly, in some embodiments, the humanized the humanized anti-CD39 antibody comprises a VL FR1, VL FR2, VL FR3, and/or VL FR4 of the human germline IGKV3-15 and IGKJ2. In some embodiments, the humanized the humanized anti-CD39 antibody comprises a VL FR1, VL FR2, VL FR3, and/or VL FR4 of the human germline IGKV1-39 and IGKJ2. In some embodiments, the humanized the humanized anti-CD39 antibody comprises a VL FR1, VL FR2, VL FR3, and/or VL FR4 of the human germline IGKV2D-29 and IGKJ2. In some embodiments, the humanized the humanized anti-CD39 antibody comprises a VL FR1, VL FR2, VL FR3, and/or VL FR4 of the human germline IGKV1-16 and IGKJ2.

In some embodiments, the anti-CD39 antibodies, including humanized antibodies, or functional fragments thereof provided herein comprise a VH region that comprises: (1) a VH FR1 having the amino acid sequence of any one of the SEQ ID NOS depicted in FIG. 1A, 2A-2B, 4A-4B, or 6A-6C; (2) a VH FR2 having the amino acid sequence of any one of the SEQ ID NOS depicted in FIG. 1A, 2A-2B, 4A-4B, or 6A-6C; (3) a VH FR3 having the amino acid sequence of any one of the SEQ ID NOS depicted in FIG. 1A, 2A-2B, 4A-4B, or 6A-6C; and/or (4) a VH FR4 having the amino acid sequence of any one of the SEQ ID NOS depicted in FIG. 1A, 2A-2B, 4A-4B, or 6A-6C. Accordingly, in some aspects, the humanized antibody comprises a VH region that includes a VH FR1 having the amino acid sequence of any one of the SEQ ID NOS depicted in FIG. 1A, 2A-2B, 4A-4B, or 6A-6C. In some aspects, the humanized antibody comprises a VH region that includes a VH FR2 having the amino acid sequence of any one of the SEQ ID NOS depicted in FIG. 1A, 2A-2B, 4A-4B, or 6A-6C. In some aspects, the humanized antibody comprises a VH region that includes a VH FR3 having the amino acid sequence of any one of the SEQ ID NOS depicted in FIG. 1A, 2A-2B, 4A-4B, or 6A-6C. In some aspects, the humanized antibody comprises a VH region that includes a VH FR4 having the amino acid sequence of any one of the SEQ ID NOS depicted in FIG. 1A, 2A-2B, 4A-4B, or 6A-6C.

In certain embodiments, an antibody or fragment thereof described herein comprises a VL region that comprises: (1) a VL FR1 having the amino acid sequence of any one of the SEQ ID NOS depicted in FIG. 1B, 3A-3B, 5A-5B, or 7A-7B; (2) a VL FR2 having the amino acid sequence of any one of the SEQ ID NOS depicted in FIG. 1B, 3A-3B, 5A-5B, or 7A-7B; (3) a VL FR3 having the amino acid sequence of any one of the SEQ ID NOS depicted in FIG. 1B, 3A-3B, 5A-5B, or 7A-7B; and/or (4) a VL FR4 having the amino acid sequence of any one of the SEQ ID NOS depicted in FIG. 1B, 3A-3B, 5A-5B, or 7A-7B. Accordingly, in some aspects, the humanized antibody comprises a VL region that includes a VL FR1 having the amino acid sequence of any one of the SEQ ID NOS depicted in FIG. 1B, 3A-3B, 5A-5B, or 7A-7B. In some aspects, the humanized antibody comprises a VL region that includes a VL FR2 having the amino acid sequence of any one of the SEQ ID NOS depicted in FIG. 1B, 3A-3B, 5A-5B, or 7A-7B. In some aspects, the humanized antibody comprises a VL region that includes a VL FR3 having the amino acid sequence of any one of the SEQ ID NOS depicted in FIG. 1B, 3A-3B, 5A-5B, or 7A-7B. In some aspects, the humanized antibody comprises a VL region that includes a VL FR4 having the amino acid sequence of any one of the SEQ ID NOS depicted in FIG. 1B, 3A-3B, 5A-5B, or 7A-7B.

In certain embodiments, an antibody or fragment thereof described herein comprises a VH region and a VL region, wherein the VH region further comprises: (1) a VH FR1 having the amino acid sequence of any one of the SEQ ID NOS depicted in FIG. 1A, 2A-2B, 4A-4B, or 6A-6C; (2) a VH FR2 having the amino acid sequence of any one of the SEQ ID NOS depicted in FIG. 1A, 2A-2B, 4A-4B, or 6A-6C; (3) a VH FR3 having the amino acid sequence of any one of the SEQ ID NOS depicted in FIG. 1A, 2A-2B, 4A-4B, or 6A-6C; and/or (4) a VH FR4 having the amino acid sequence of any one of the SEQ ID NOS depicted in FIG. 1A, 2A-2B, 4A-4B, or 6A-6C; and wherein the VL region further comprises: (1) a VL FR1 having the amino acid sequence of any one of the SEQ ID NOS depicted in FIG. 1B, 3A-3B, 5A-5B, or 7A-7B; (2) a VL FR2 having the amino acid sequence of any one of the SEQ ID NOS depicted in FIG. 1B, 3A-3B, 5A-5B, or 7A-7B; (3) a VL FR3 having the amino acid sequence of any one of the SEQ ID NOS depicted in FIG. 1B, 3A-3B, 5A-5B, or 7A-7B; and/or (4) a VL FR4 having the amino acid sequence of any one of the SEQ ID NOS depicted in FIG. 1B, 3A-3B, 5A-5B, or 7A-7B.

Also provided herein are antibodies comprising one or more (e.g., one, two, three or four) VH FRs and one or more (e.g., one, two, three or four) VL FRs listed in FIG. 1A-1B, 2A-2B, 3A-3B, 4A-4B, 5A-5B or 6A-6C. Also provided herein are antibodies comprising any combination of the VH FRs and VL FRs listed in FIG. 1A-1B, 2A-2B, 3A-3B, 4A-4B, 5A-5B or 6A-6C.

Antibodies

In some embodiments, antibodies provided herein are antibodies that bind to a CD39 epitope, and include antibodies comprising derivatives of the VH domains, VH CDRs, VL domains, and VL CDRs described herein that bind to a CD39 epitope. Standard techniques known to those of skill in the art can be used to introduce mutations in the nucleotide sequence encoding an antibody, or fragment thereof, provided herein, including, for example, site-directed mutagenesis and PCR-mediated mutagenesis which results in amino acid substitutions. In certain embodiments, the derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In a specific embodiment, the derivatives have conservative amino acid substitutions are made at one or more predicted non-essential amino acid residues. A "conservative amino acid substitution" is one in which an amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined.

In one embodiment, an antibody that binds to a CD39 epitope comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of an anti-CD39 antibody, or an antigen-binding fragment thereof, such as a VH domain or VL domain.

In certain embodiments, the antibodies used in accordance with the methods provided herein have a high affinity for a CD39 polypeptide, or polypeptide fragment or epitope thereof. In one embodiment, the antibodies used in accordance with the methods provided herein have a higher affinity for a CD39 antibody than known antibodies (e.g., commercially available monoclonal antibodies discussed elsewhere herein). In a specific embodiment, the antibodies used in accordance with the methods provided herein have a 2- to 10-fold (or more) higher affinity for a CD39 antigen than a known anti-CD39 antibody as assessed by techniques described herein or known to one of skill in the art (e.g., a BIAcore assay). In accordance with these embodiments, the affinity of the antibodies are, in one embodiment, assessed by a BIAcore assay.

In a specific embodiment, an antibody that binds a CD39 epitope comprises an amino acid sequence of a VH domain and/or an amino acid sequence a VL domain encoded by a nucleotide sequence that hybridizes to (1) the complement of a nucleotide sequence encoding a VH and/or VL domain under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art (see, for example, Ausubel, F. M. et al., eds., 1989, Current Protocols in Molecular Biology, Vol. I, Green Publishing Associates, Inc. and John Wiley & Sons, Inc., New York at pages 6.3.1-6.3.6 and 2.10.3).

In some embodiments, antibodies provided herein are chemically modified, e.g., by the covalent attachment of any type of molecule to the antibody. For example, but not by way of limitation, the antibody derivatives include antibodies that have been chemically modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formulation, metabolic synthesis of tunicamycin, etc. Additionally, the antibody may contain one or more non-classical amino acids.

Also provided herein are antibodies that bind to a CD39 epitope which comprises a framework region known to those of skill in the art (e.g., a human or non-human fragment). The framework region may, for example, be naturally occurring or consensus framework regions. In specific embodiments, the framework region of an antibody provided herein is human (see, e.g., Chothia et al., 1998, J. Mol. Biol. 278:457-479 for a listing of human framework regions, which is incorporated by reference herein in its entirety). See also Kabat et al. (1991) Sequences of Proteins of Immunological Interest (U.S. Department of Health and Human Services, Washington, D.C.) 5th ed.

Also provided herein are antibodies that bind to a CD39 epitope, the antibodies comprising the amino acid sequence of one or more of the CDRs of an anti-CD39 antibody, and human framework regions with one or more amino acid substitutions at one, two, three or more of the following residues: (a) rare framework residues that differ between the murine antibody framework (e.g., donor antibody framework) and the human antibody framework (e.g., acceptor antibody framework); (b) Venier zone residues when differing between donor antibody framework and acceptor antibody framework; (c) interchain packing residues at the VH/VL interface that differ between the donor antibody framework and the acceptor antibody framework; (d) canonical residues which differ between the donor antibody framework and the acceptor antibody framework sequences, particularly the framework regions crucial for the definition of the canonical class of the murine antibody CDR loops; (e) residues that are adjacent to a CDR; (g) residues capable of interacting with the antigen; (h) residues capable of interacting with the CDR; and (i) contact residues between the VH domain and the VL domain. In certain embodiments, antibodies that bind to a CD39 antigen comprising the human framework regions with one or more amino acid substitutions at one, two, three or more of the above-identified residues are antagonistic CD39 antibodies. In certain embodiments, antibodies that bind to a CD39 antigen comprising the human framework regions with one or more amino acid substitutions at one, two, three or more of the above-identified residues are agonistic CD39 antibodies.

Antibodies provided herein include, but are not limited to, synthetic antibodies, monoclonal antibodies, recombinantly produced antibodies, multispecific antibodies (including bi-specific antibodies), human antibodies, humanized antibodies, camelized antibodies, chimeric antibodies, intrabodies, anti-idiotypic (anti-Id) antibodies, and functional fragments of any of the above. Non-limiting examples of functional fragments include single-chain Fvs (scFv) (e.g., including monospecific, bispecific, etc.), Fab fragments, F(ab') fragments, F(ab)2 fragments, F(ab')2 fragments, disulfide-linked Fvs (sdFv), Fd fragments, Fv fragments, diabody, triabody, tetrabody and minibody.

In particular, antibodies provided herein include immunoglobulin molecules and immunologically active portions of immunoglobulin molecules, e.g., molecules that contain an antigen binding site that bind to a CD39 epitope. The immunoglobulin molecules provided herein can be of any type (e.g., IgG, IgE, IgM, IgD, IgA and IgY), class (e.g., IgG1, IgG2, IgG3, IgG4, IgA1 and IgA2) or subclass of immunoglobulin molecule.

Variants and derivatives of antibodies include antibody functional fragments that retain the ability to bind to a CD39 epitope. Exemplary functional fragments include Fab fragments (an antibody fragment that contains the antigen-binding domain and comprises a light chain and part of a heavy chain bridged by a disulfide bond); Fab' (an antibody fragment containing a single anti-binding domain comprising an Fab and an additional portion of the heavy chain through the hinge region); F(ab')2 (two Fab' molecules joined by interchain disulfide bonds in the hinge regions of the heavy chains; the Fab' molecules may be directed toward the same or different epitopes); a bispecific Fab (a Fab molecule having two antigen binding domains, each of which may be directed to a different epitope); a single chain Fab chain comprising a variable region, also known as, a sFv (the variable, antigen-binding determinative region of a single light and heavy chain of an antibody linked together by a chain of 10-25 amino acids); a disulfide-linked Fv, or dsFv (the variable, antigen-binding determinative region of a single light and heavy chain of an antibody linked together by a disulfide bond); a camelized VH (the variable, antigen-binding determinative region of a single heavy chain of an antibody in which some amino acids at the VH interface are those found in the heavy chain of naturally occurring camel antibodies); a bispecific sFv (a sFv or a dsFv molecule having two antigen-binding domains, each of which may be directed to a different epitope); a diabody (a dimerized sFv formed when the VH domain of a first sFv assembles with the VL domain of a second sFv and the VL domain of the first sFv assembles with the VH domain of the second sFv; the two antigen-binding regions of the diabody may be directed towards the same or different epitopes); and a triabody (a trimerized sFv, formed in a manner similar to a diabody, but in which three antigen-binding domains are created in a single complex; the three antigen binding domains may be directed towards the same or different epitopes). Derivatives of antibodies also include one or more CDR sequences of an antibody combining site. The CDR sequences may be linked together on a scaffold when two or more CDR sequences are present. In certain embodiments, the antibody comprises a single-chain Fv ("scFv"). scFvs are antibody fragments comprising the VH and VL domains of an antibody, wherein these domains are present in a single polypeptide chain. Generally, the scFv polypeptide further comprises a polypeptide linker between the VH and VL domains which enables the scFv to form the desired structure for antigen binding. For a review of scFvs see Pluckthun in The Pharmacology of Monoclonal Antibodies, vol. 113, Rosenburg and Moore eds. Springer-Verlag, New York, pp. 269-315 (1994).

The antibodies provided herein may be monospecific, bispecific, trispecific or of greater multispecificity. Multispecific antibodies may be specific for different epitopes of a CD39 polypeptide or may be specific for both a CD39 polypeptide as well as for a heterologous epitope, such as a heterologous polypeptide or solid support material. In specific embodiments, the antibodies provided herein are monospecific for a given epitope of a CD39 polypeptide and do not bind to other epitopes.

Also provided herein are fusion proteins comprising an antibody provided herein that binds to a CD39 antigen and a heterologous polypeptide. In some embodiments, the heterologous polypeptide to which the antibody is fused is useful for targeting the antibody to cells having cell surface-expressed CD39.

Also provided herein are panels of antibodies that bind to a CD39 antigen. In specific embodiments, panels of antibodies have different association rate constants different dissociation rate constants, different affinities for CD39 antigen, and/or different specificities for a CD39 antigen. In some embodiments, the panels comprise or consist of about 10, about 25, about 50, about 75, about 100, about 125, about 150, about 175, about 200, about 250, about 300, about 350, about 400, about 450, about 500, about 550, about 600, about 650, about 700, about 750, about 800, about 850, about 900, about 950, or about 1000 antibodies or more. Panels of antibodies can be used, for example, in 96 well or 384 well plates, such as for assays such as ELISAs.

Antibody Conjugates and Fusion Proteins

In some embodiments, antibodies provided herein are conjugated or recombinantly fused to a diagnostic, detectable or therapeutic agent or any other molecule. The conjugated or recombinantly fused antibodies can be useful, e.g., for monitoring or prognosing the onset, development, progression and/or severity of a CD39-mediated disease as part of a clinical testing procedure, such as determining the efficacy of a particular therapy.

Such diagnosis and detection can accomplished, for example, by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; chemiluminescent material, such as but not limited to, an acridinium based compound or a HALOTAG; radioactive materials, such as, but not limited to, iodine (131I, 125I, 123I, and 121I,), carbon (14C), sulfur (35S), tritium (3H), indium (115In, 113In, 112In, and 111In,), technetium (99Tc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142Pr, 105Rh, 97Ru, 68Ge, 57Co, 65Zn, 85Sr, 32P, 153Gd, 169Yb, 51Cr, 54Mn, 75Se, 113Sn, and 117Sn; and positron emitting metals using various positron emission tomographies, and non-radioactive paramagnetic metal ions.

Also provided herein are antibodies that are conjugated or recombinantly fused to a therapeutic moiety (or one or more therapeutic moieties), as well as uses thereof. The antibody may be conjugated or recombinantly fused to a therapeutic moiety, such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Therapeutic moieties include, but are not limited to, antimetabolites (e.g., methotrexate, 6-mercaptopurine, 6-thioguanine, cytarabine, 5-fluorouracil decarbazine); alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP), and cisplatin); anthracyclines (e.g., daunorubicin (formerly daunomycin) and doxorubicin); antibiotics (e.g., d actinomycin (formerly actinomycin), bleomycin, mithramycin, and anthramycin (AMC)); Auristatin molecules (e.g., auristatin PHE, auristatin F, monomethyl auristatin E, bryostatin 1, and solastatin 10; see Woyke et al., Antimicrob. Agents Chemother. 46:3802-8 (2002), Woyke et al., Antimicrob. Agents Chemother. 45:3580-4 (2001), Mohammad et al., Anticancer Drugs 12:735-40 (2001), Wall et al., Biochem. Biophys. Res. Commun. 266:76-80 (1999), Mohammad et al., Int. J. Oncol. 15:367-72 (1999), all of which are incorporated herein by reference); hormones (e.g., glucocorticoids, progestins, androgens, and estrogens), DNA-repair enzyme inhibitors (e.g., etoposide or topotecan), kinase inhibitors (e.g., compound ST1571, imatinib mesylate (Kantarjian et al., Clin Cancer Res. 8(7):2167-76 (2002)); cytotoxic agents (e.g., paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucorticoids, procaine, tetracaine, lidocaine, propranolol, and puromycin and analogs or homologs thereof and those compounds disclosed in U.S. Pat. Nos. 6,245,759, 6,399,633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459); farnesyl transferase inhibitors (e.g., R115777, BMS-214662, and those disclosed by, for example, U.S. Pat. Nos. 6,458,935, 6,451,812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040, 305); topoisomerase inhibitors (e.g., camptothecin; irinotecan; SN-38; topotecan; 9-aminocamptothecin; GG-211 (GI 147211); DX-8951f; IST-622; rubitecan; pyrazoloacridine; XR-5000; saintopin; UCE6; UCE1022; TAN-1518A; TAN 1518B; KT6006; KT6528; ED-110; NB-506; ED-110; NB-506; and rebeccamycin); bulgarein; DNA minor groove binders such as Hoescht dye 33342 and Hoechst dye 33258; nitidine; fagaronine; epiberberine; coralyne; beta-lapachone; BC-4-1; bisphosphonates (e.g., alendronate, cimadronte, clodronate, tiludronate, etidronate, ibandronate, neridronate, olpandronate, risedronate, piridronate, pamidronate, zolendronate) HMG-CoA reductase inhibitors, (e.g., lovastatin, simvastatin, atorvastatin, pravastatin, fluvastatin, statin, cerivastatin, lescol, lupitor, rosuvastatin and atorvastatin); antisense oligonucleotides (e.g., those disclosed in the U.S. Pat. Nos. 6,277,832, 5,998,596, 5,885, 834, 5,734,033, and 5,618,709); adenosine deaminase inhibitors (e.g., Fludarabine phosphate and 2-Chlorodeoxyadenosine); ibritumomab tiuxetan (Zevalin®); tositumomab (Bexxar®)) and pharmaceutically acceptable salts, solvates, clathrates, and prodrugs thereof.

Further, an antibody provided herein may be conjugated or recombinantly fused to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, pseudomonas exotoxin, cholera toxin, or diphtheria toxin; a protein such as tumor necrosis factor, γ-interferon, α-interferon, nerve growth factor, platelet derived growth factor, tissue plasminogen activator, an apoptotic agent, e.g., TNF-γ, TNF-γ, AIM I (see, International Publication No. WO 97/33899), AIM II (see, International Publication No. WO 97/34911), Fas Ligand (Takahashi et al., 1994, J. Immunol., 6:1567-1574), and VEGF (see, International Publication No. WO 99/23105), an anti-angiogenic agent, e.g., angiostatin, endostatin or a component of the coagulation pathway (e.g., tissue factor); or, a biological response modifier such as, for example, a lymphokine (e.g., interferon gamma, interleukin-1 ("IL-1"), interleukin-2 ("IL-2"), interleukin-5 ("IL-5"), interleukin-6 ("IL-6"), interleukin-7 ("IL-7"), interleukin 9 ("IL-9"), interleukin-10 ("IL-10"), interleukin-12 ("IL-12"), interleukin-15 ("IL-15"), interleukin-23 ("IL-23"), granulocyte macrophage colony stimulating factor ("GM-CSF"), and granulocyte colony stimulating factor ("G-CSF")), or a growth factor (e.g., growth hormone ("GH")), or a coagulation agent (e.g., calcium, vitamin K, tissue factors, such as but not limited to, Hageman factor (factor XII), high-molecular-weight kininogen (HMWK), prekallikrein (PK), coagulation proteins-factors II (prothrombin), factor V, XIIa, VIII, XIIIa, XI, XIa, IX, IXa, X, phospholipid, and fibrin monomer).

Also provided herein are antibodies that are recombinantly fused or chemically conjugated (covalent or non-covalent conjugations) to a heterologous protein or polypeptide (or fragment thereof, for example, to a polypeptide of about 10, about 20, about 30, about 40, about 50, about 60, about 70, about 80, about 90 or about 100 amino acids) to generate fusion proteins, as well as uses thereof. In particular, provided herein are fusion proteins comprising an antigen-binding fragment of an antibody provided herein (e.g., a Fab fragment, Fd fragment, Fv fragment, F(ab)2 fragment, a VH domain, a VH CDR, a VL domain or a VL CDR) and a heterologous protein, polypeptide, or peptide. In one embodiment, the heterologous protein, polypeptide, or peptide that the antibody is fused to is useful for targeting the antibody to a particular cell type, such as a cell that expresses CD39 or an CD39 receptor. For example, an antibody that binds to a cell surface receptor expressed by a particular cell type (e.g., an immune cell) may be fused or conjugated to a modified antibody provided herein.

A conjugated or fusion protein can comprise any antibody provided herein described herein and a heterologous polypeptide. In one embodiment, a conjugated or fusion protein provided herein comprises the VH or VL domain of an anti-CD39 antibody, including any one of the antibodies R2I-5-13A, R21-9-8B, R21-5-71A or R21-5-165C, as depicted in Tables 1-4 or FIG. 1A or 1B, and a heterologous polypeptide. In another embodiment, a conjugated or fusion protein provided herein comprises a VH domain having the amino acid sequence of an anti-CD39 VH domain, including any one of the VH domains depicted in Tables 1-4 or FIG. 1A, 2A-2B, 4A-4B, or 6A-6C, and/or a VL domain having the amino acid sequence of an anti-CD39 VL domain, including any one of the VL domains depicted Tables 1-4 or FIG. 1B, 3A-3B, 5A-5B, or 7A-7B, and a heterologous polypeptide. In another embodiment, a conjugated or fusion protein provided herein comprises one or more VH CDRs, including having the amino acid sequence of any one of the VH CDRs depicted in Tables 1-4 or FIG. 1A, 2A-2B, 4A-4B, or 6A-6C, and a heterologous polypeptide. In another embodiment, a conjugated or fusion protein comprises one or more VL CDRs, including having the amino acid sequence of any one of the VL CDRs depicted in Tables 1-4 or FIG. 1B, 3A-3B, 5A-5B, or 7A-7B, and a heterologous polypeptide. In another embodiment, a conjugated or fusion protein provided herein comprises at least one VH domain and at least one VL domain, including as depicted in Tables 1-4 or FIGS. 1A-1B, 3A-3B, 2A-2B, 4A-4B, 5A-5B, 6A-6C, 7A-7B, and a heterologous polypeptide. In yet another embodiment, a conjugated or fusion protein provided herein comprises at least one VH CDR and at least one VL CDR, including depicted in Tables 1-4 or FIGS. 1A-1B, 3A-3B, 2A-2B, 4A-4B, 5A-5B, 6A-6C, 7A-7B, and a heterologous polypeptide.

In addition, an antibody provided herein can be conjugated to therapeutic moieties such as a radioactive metal ion, such as alpha-emitters such as 213Bi or macrocyclic chelators useful for conjugating radiometal ions, including but not limited to, 131 In, 131LU, 131Y, 131Ho, 131Sm, to polypeptides. In certain embodiments, the macrocyclic chelator is 1,4,7,10-tetraazacyclododecane-N,N',N",N'''-tetraacetic acid (DOTA) which can be attached to the antibody via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

Moreover, antibodies provided herein can be fused to marker sequences, such as a peptide to facilitate purification. In specific embodiments, the marker amino acid sequence is a hexa-histidine peptide, such as the tag provided in a pQE vector (QIAGEN, Inc.), among others, many of which are commercially available. As described in Gentz et al., 1989, Proc. Natl. Acad. Sci. USA 86:821-824, for instance, hexahistidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "FLAG" tag.

Methods for fusing or conjugating therapeutic moieties (including polypeptides) to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), Thorpe et al., 1982, Immunol. Rev. 62:119-58; U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367, 166; EP 394,827; PCT publications WO 91/06570, WO 96/04388, WO 96/22024, WO 97/34631, and WO 99/04813; Ashkenazi et al., Proc. Natl. Acad. Sci. USA, 88: 10535-10539, 1991; Traunecker et al., Nature, 331:84-86, 1988; Zheng et al., J. Immunol., 154:5590-5600, 1995; Vil et al., Proc. Natl. Acad. Sci. USA, 89:11337-11341, 1992, which are incorporated herein by reference in their entireties.

Fusion proteins may be generated, for example, through the techniques of gene-shuffling, motif-shuffling, exon-shuffling, and/or codon-shuffling (collectively referred to as "DNA shuffling"). DNA shuffling may be employed to alter the activities of antibodies provided herein (e.g., antibodies with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson et al., 1999, J. Mol. Biol. 287:265-76; and Lorenzo and Blasco, 1998, Biotechniques 24(2):308-313 (each of these patents and publications are hereby incorporated by reference in its entirety). Antibodies, or the encoded antibodies, may be altered by being subjected to random mutagenesis by error-prone PCR, random nucleotide insertion or other methods prior to recombination. A polynucleotide encoding an antibody provided herein may be recombined with one or more components, motifs, sections, parts, domains, fragments, etc. of one or more heterologous molecules.

An antibody provided herein can also be conjugated to a second antibody to form an antibody heteroconjugate as described in U.S. Pat. No. 4,676,980, which is incorporated herein by reference in its entirety.

The therapeutic moiety or drug conjugated or recombinantly fused to an antibody provided herein that binds to a CD39 antigen should be chosen to achieve the desired prophylactic or therapeutic effect(s). In certain embodiments, the antibody is a modified antibody. A clinician or other medical personnel should consider the following when deciding on which therapeutic moiety or drug to conjugate or recombinantly fuse to an antibody provided herein: the nature of the disease, the severity of the disease, and the condition of the subject.

Antibodies provided herein may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene. Conjugates of the antibody and cytotoxic agent may be made using a variety of bifunctional protein coupling agents such as BMPS, EMCS, GMBS, HBVS, LC-SMCC, MBS, MPBH, SBAP, SIA, STAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate)). For example, a ricin immunotoxin can be prepared as described in Vitetta et al., Science 238:1098 (1987). The invention further contemplates that conjugates of antibodies and cytotoxic agents may be prepared using any suitable methods as disclosed in the art, e.g., in Bioconjugate Techniques, 2nd Ed., G. T. Hermanson, ed., Elsevier, San Francisco, 2008.

Conventional antibody-drug conjugation strategies have been based on random conjugation chemistries involving the ε-amino group of Lys residues or the thiol group of Cys residues, which results in heterogenous conjugates. Recently developed techniques allow site-specific conjugation to antibodies, resulting in homogeneous drug loading and avoiding ADC subpopulations with altered antigen-binding or pharmacokinetics. These include engineering of "thiomabs" comprising cysteine substitutions at positions on the heavy and light chains that provide reactive thiol groups and do not disrupt immunoglobulin folding and assembly or alter antigen binding (Junutula et al., J. Immunol. Meth. 332: 41-52 (2008); Junutula et al., Nat. Biotechnol. 26: 925-932, 2008). In another method, selenocysteine is cotranslationally inserted into an antibody sequence by recoding the stop codon UGA from termination to selenocysteine insertion, allowing site specific covalent conjugation at the nucleophilic selenol group of selenocysteine in the presence of the other natural amino acids (Hofer et al., Proc. Natl. Acad. Sci. USA 105: 12451-12456 (2008); Hofer et al., Biochemistry 48(50): 12047-12057, 2009).

Immunoconjugates

The invention also provides immunoconjugates (interchangably referred to as "antibody drug conjugates," or "ADCs") comprising any one of the anti-CD39 antibodies of the invention covalently bound by a synthetic linker to one or more cytotoxic agents. ADCs combine the high specificity of monoclonal antibodies with the pharmacological potency of cytotoxic molecules, allowing specific targeting of cytotoxic agents to tumor cells and avoiding the nonspecific toxicity of most anticancer drugs. For review, see, e.g., Carter and Senter, Cancer J. 14: 154-169 (2008); Ducry and Stump, Bioconjugate Chem. 21:5-13 (2010); Beck et al., Discov. Med. 10: 329-339 (2010).

Cytotoxic agents for use in the immunoconjugates of the invention may include chemotherapeutic agents, drugs or growth inhibitory agents as described above, toxins (e.g., an enzymatically active toxin of bacterial, fungal, plant or animal origin, or fragments thereof) or radioisotopes. In some embodiments, the immunoconjugate comprises a DNA binder (e.g., calicheamycin) or a tubulin depolymerization agent (e.g., a maytansinoid or an auristatin). The present invention further contemplates an immunoconjugate formed between an antibody and a compound with nucleolytic activity (e.g., a ribonuclease or a DNA endonuclease such as a deoxyribonuclease; DNase).

Enzymatically active toxins and fragments thereof that can be used in the immunoconjugates of the invention include diphtheria A chain, nonbinding active fragments of diphtheria toxin, exotoxin A chain (from Pseudomonas aeruginosa), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. See, e.g., WO 93/21232.

A variety of radioactive isotopes are available for the production of radioconjugated antibodies. Examples include At211, 14, 14, Y4, Re4, Re4, Sm4, Bi4, P4, Pb4 and radioactive isotopes of Lu. When the conjugate is used for detection, it may comprise a radioactive atom for scintigraphic studies, for example tc4 or I4, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron. The radioisotopes may be incorporated in the conjugate in known ways as described, e.g., in Reilly, "The radiochemistry of monoclonal antibodies and peptides," in Monoclonal Antibody and Peptide-Targeted Radiotherapy of Cancer, R. M. Reilly, ed., Wiley, Hoboken N.J., 2010.

Antibody-Drug Conjugates (ADCs)

In some embodiments, provided herein are antibody-drug conjugates, including an antibody-drug conjugate of the following formulas (Ia) and (Ib):

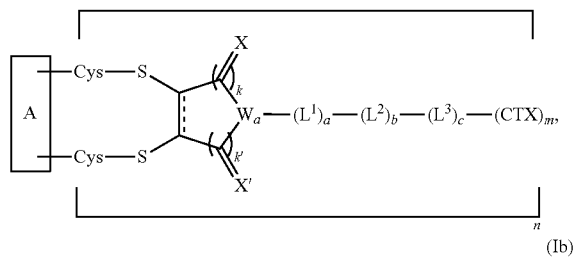

(Ia)

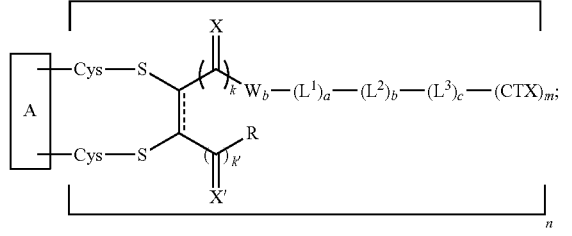

(Ib)

or a pharmaceutically acceptable salt thereof;
wherein:

A is an antibody or antibody fragment;

the two depicted cysteine residues are from an opened cysteine-cysteine disulfide and in A;

each X and X' is independently O, S, NH, or NR$^1$ wherein R$^1$ is C$_{1-6}$ alkyl;

$W_a$ is =N—, =CH—, =CHCH$_2$—, =C(R$^2$)—, or =CHCH(R$^2$)—; $W_b$ is —NH—, —N(R$^1$)—, —CH$_2$—, —CH$_2$—NH—, —CH$_2$—N(R$^1$)—, —CH$_2$CH$_2$—, —CH(R$^2$)—, or —CH$_2$CH(R$^2$)—; wherein R$^1$ and R$^2$ are independently C$_{1-6}$ alkyl;

CTX is a cytotoxin;

R is any chemical group; or R is absent;

each L$^1$, L$^2$ and L$^3$ is independently a linker selected from the group consisting of —O—, —C(O)—, —S—, —S(O)—, —S(O)$_2$—, —NH—, —NCH$_3$—, —(CH$_2$)$_q$—, —NH(CH$_2$)$_2$NH—, —OC(O)—, —CO$_2$—, —NHCH$_2$CH$_2$C(O)—, —C(O)NHCH$_2$CH$_2$NH—, —NHCH$_2$C(O)—, —NHC(O)—, —C(O)NH—, —NCH$_3$C(O)—, —C(O)NCH$_3$—, —(CH$_2$CH$_2$O)p, —(CH$_2$CH$_2$O)$_p$CH$_2$CH$_2$—, —CH$_2$CH$_2$—(CH$_2$CH$_2$O)$_p$—, —OCH(CH$_2$O—)$_2$, -(AA)$_r$-, cyclopentanyl, cyclohexanyl, unsubstituted phenylenyl, and phenylenyl substituted by 1 or 2 substituents selected from the group consisting of halo, CF$_3$—, CF$_3$O—, CH$_3$O—, —C(O)OH, —C(O)OC$_{1-3}$ alkyl, —(O)CH$_3$, —CN, —NH$_2$, —OH, —NHCH$_3$, —N(CH$_3$)$_2$, and C$_{1-3}$ alkyl;

a, b and c are each independently an integer of 0, 1, 2 or 3, provided that at least one of a, b or c is 1;

each k and k' is independently an integer of 0 or 1;

each p is independently an integer of 1 to 14;

each q is independently an integer from 1 to 12;

each AA is independently an amino acid;

each r is 1 to 12;

m is an integer of 1 to 4;

n is an integer of 1 to 4; and the ===== bond represents a single or a double bond.

In certain embodiments of the antibody-drug conjugate of formula (Ia) or (Ib), A is an antibody to CD39, optionally, a humanized antibody to CD39.

In certain embodiments of the antibody-drug conjugate of formula (Ib), R is selected from the group consisting of W, (L$^1$)$_a$, (L$^2$)$_b$, (L$^3$)$_c$, Z, W-(L$^1$)$_a$-(L$^2$)$_b$-(L$^3$)$_c$, (L$^1$)$_a$-(L$^2$)$_b$-(L$^3$)$_c$-Z, and W-(L$^1$)$_a$-(L$^2$)$_b$-(L$^3$)$_c$-Z, as defined herein. In certain embodiments, R is selected from the group consisting of W, (L$^1$)$_a$, (L$^2$)$_b$, (L$^3$)$_c$, and W-(L$^1$)$_a$-(L$^2$)$_b$-(L$^3$)$_c$. In certain embodiments, R is selected from the group consisting of Z, (L$^1$)$_a$-(L$^2$)$_b$-(L$^3$)$_c$-Z, and W-(L$^1$)$_a$-(L$^2$)$_b$-(L$^3$)$_c$-Z.

In certain embodiments of the antibody-drug conjugate of formula (Ib), R is a detectable probe. In certain embodiments, R is a fluorophore, chromophore, radiolabel, enzyme, antibody or antibody fragment. In certain embodiments, R is an antibody fragment.

In certain embodiments of the antibody-drug conjugate of formula (Ib), R is bonded to the rest of the linker molecule via an amide, an N—(C$_{1-6}$alkyl)amide, a carbamate, an N—(C$_{1-6}$alkyl)carbamate, an amine, an N—(C$_{1-6}$alkyl)amine, an ether, a thioether, an urea, an N—(C$_{1-6}$alkyl)urea, or an N,N-di(C$_{1-6}$alkyl)urea bond.

In certain embodiments of the antibody-drug conjugate of formula (Ia) or (Ib), CTX is bonded to (L$^1$)$_a$-(L$^2$)$_b$-(L$^3$)$_c$ via a group selected from —NHC(O)—, —NHC(O)O—, —N(C$_{1-3}$alkyl)C(O)O—, —NH—, —N(C$_{1-3}$alkyl)-, —N(C$_{1-3}$alkyl)C(O)NH— and —N(C$_{1-3}$alkyl)C(O)N(C$_{1-3}$alkyl)-.

Also provided herein are antibody-drug conjugates of the following formula (Ic):

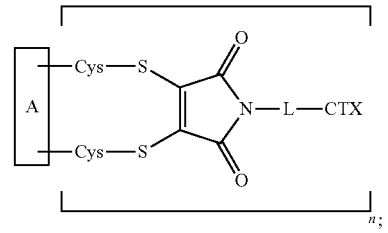

(Ic)

or a pharmaceutically acceptable salt thereof, wherein:

A is an antibody or antibody fragment;

the two depicted cysteine residues are from an opened cysteine-cysteine disulfide bond in A;

L is a cleavable or a noncleavable linker;

CTX is cytotoxin;

and n is an integer of 1 to 4.

In certain embodiments of the antibody-drug conjugate of formula (Ic), A is an antibody to CD39, optionally, a humanized antibody to CD39.

In certain embodiments of the antibody-drug conjugate of formula (Ia), or (Ib), or (Ic), CTX is selected from the group consisting of a tubulin stabilizer, a tubulin destabilizer, a DNA alkylator, a DNA minor groove binder, a DNA intercalator, a topoisomerase I inhibitor, a topoisomerase II inhibitor, a gyrase inhibitor, a protein synthesis inhibitor, a proteosome inhibitor, and an anti-metabolite.

In certain embodiments of the antibody-drug conjugate of formula (Ia), or (Ib), or (Ic), CTX is selected from MMAF and MMAE. In certain embodiments, CTX is selected from MMAF and MMAE, and each $L^1$, $L^2$ and $L^3$ is independently $-(AA)_r-$, for example, valine and/or citrulline such as citrulline-valine.

In certain embodiments of the antibody-drug conjugate of formula (Ia), or (Ib), or (Ic), CTX is a chemotherapeutic agent. Those of ordinary skill in the art will be aware of appropriate chemotherapeutic agents as disclosed, for example, in Chu, E., DeVite, V. T., 2012, Physicians' Cancer Chemotherapy Drug Manual 2012 (Jones & Bartlett Learning Oncology), and similar documents.

In certain embodiments of the antibody-drug conjugate of formula (Ia), or (Ib), or (Ic), CTX may be any FDA-approved chemotherapeutic agent. In certain embodiments, CTX may be any FDA-approved chemotherapeutic agent available for cancer treatment.

In certain embodiments of the antibody-drug conjugate of formula (Ia), or (Ib), or (Ic), CTX is selected from the group consisting of an alkylating agents, an anthracyclines, a cytoskeletal disruptors (taxanes), an epothilones, an histone deacetylase Inhibitor (HDAC), an inhibitor of Topoisomerase I, an Inhibitor of Topoisomerase II, a kinase inhibitor, a monoclonal antibodies, a nucleotide analog, a peptide antibiotic, a platinum-based agent, a retinoids, a Vinca alkaloid or a derivative thereof, and radioisotope.

In certain embodiments of the antibody-drug conjugate of formula (Ia), or (Ib), or (Ic), CTX is selected from the group consisting of Actinomycin, all-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, and Vinorelbine.

In certain embodiments of the antibody-drug conjugate of formula (Ia), or (Ib), or (Ic), CTX is selected from the group consisting of a tubulin stabilizer, a tubulin destabilizer, a DNA alkylator, a DNA minor groove binder, a DNA intercalator, a topoisomerase I inhibitor, a topoisomerase II inhibitor, a gyrase inhibitor, a protein synthesis inhibitor, a proteosome inhibitor, and an anti-metabolite.

In certain embodiments of the antibody-drug conjugate of formula (Ia), or (Ib), or (Ic), CTX is selected from the group consisting of Actinomycin D, Amonafide, an auristatin, benzophenone, benzothiazole, a calicheamicin, Camptothecin, CC-1065 (NSC 298223), Cemadotin, Colchicine, Combretastatin A4, Dolastatin, Doxorubicin, Elinafide, Emtansine (DM1), Etoposide, KF-12347 (Leinamycin), a maytansinoid, Methotrexate, Mitoxantrone, Nocodazole, Proteosome Inhibitor 1 (PSI 1), Roridin A, T-2 Toxin (trichothecene analog), Taxol, a tubulysin, Velcade®, and Vincristine. In certain embodiments, CTX is an auristatin, a calicheamicin, a maytansinoid, a pyrrolobenzodiazepine (PBD) (monomeric or dimeric), or a tubulysin. In certain embodiments, CTX is monomethylauristatin E (MMAE), monomethylauristatin F (MMAF), calicheamicin γ, mertansine, tubulysin T3 (T3), or tubulysin T4 (T4).

The structures for T3 and T4 are provided below:

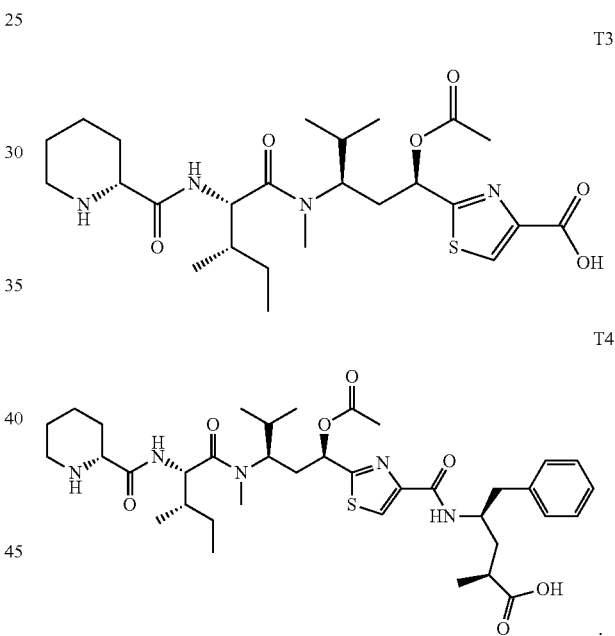

The structures for MMAE and MMAF are provided below:

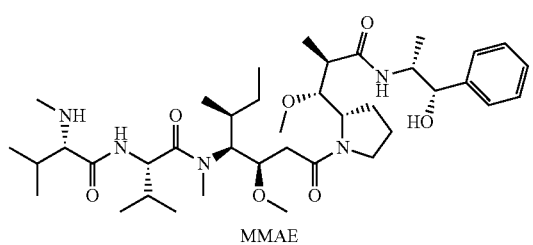

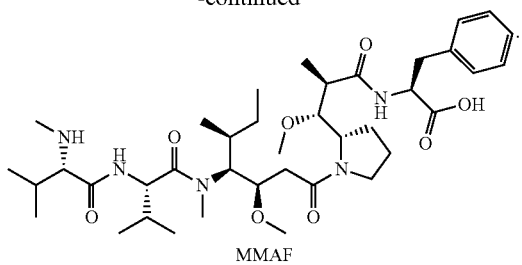

MMAF

In certain embodiments of the antibody-drug conjugate of formula (Ic), CTX is bonded to L by an amide bond, a carbamate bond, a disulfide bond, an ether bond, a thioether bond, or an ester bond.

In certain embodiments of the antibody-drug conjugate of formula (Ic), CTX is bonded to L by an amide bond or a carbamate bond.

In certain embodiments of the antibody-drug conjugate of formula (Ic), CTX is an auristatin bonded to L by an amide bond or a carbamate bond. In certain embodiments, CTX is MMAF bonded to L by an amide bond. In certain embodiments, CTX is MMAE bonded to L by a carbamate bond.

In certain embodiments of the antibody-drug conjugate of formula (Ic), CTX is a PBD bonded to L by an amide bond or a carbamate bond.

In certain embodiments of the antibody-drug conjugate of formula (Ic), CTX is a calicheamicin, doxorubicin, camptothecin, duocarmycin, DM1, DM4, a maytansinoid, or a tubulysin, wherein CTX is bonded to L by an amide bond, a carbamate bond, a disulfide bond, an ether bond, a thioether bond, or an ester bond;

In certain embodiments of the antibody-drug conjugate of formula (Ic), n is an integer of 2. In certain embodiments, n is an integer of 3. In certain embodiments, n is an integer of 4.

In certain embodiments of the antibody-drug conjugate of formula (Ic), where CTX is MMAF, and L is a noncleavable linker.

In certain embodiments of the antibody-drug conjugate of formula (Ic), where CTX is MMAF, and L is —$(CH_2)_mC(O)$—, wherein m is an integer of 5 to 11.

In certain embodiments of the antibody-drug conjugate of formula (Ic), where CTX is MMAF, and L is a cleavable linker.

In certain embodiments of the antibody-drug conjugate of formula (Ic), where CTX is MMAF, and L is —$(CH_2)_mC(O)$-Val-Ala-PAB-O—C(O)—, or —$(CH_2)_mC(O)$-Val-Cit-PAB-O—C(O)—, wherein m is an integer of 5 to 11.

In certain embodiments of the antibody-drug conjugate of formula (Ic), where CTX is MMAF, L is —$(CH_2)_5C(O)$—, and n is 4.

In certain embodiments of the antibody-drug conjugate of formula (Ic), the antibody-drug conjugate is of the following formula:

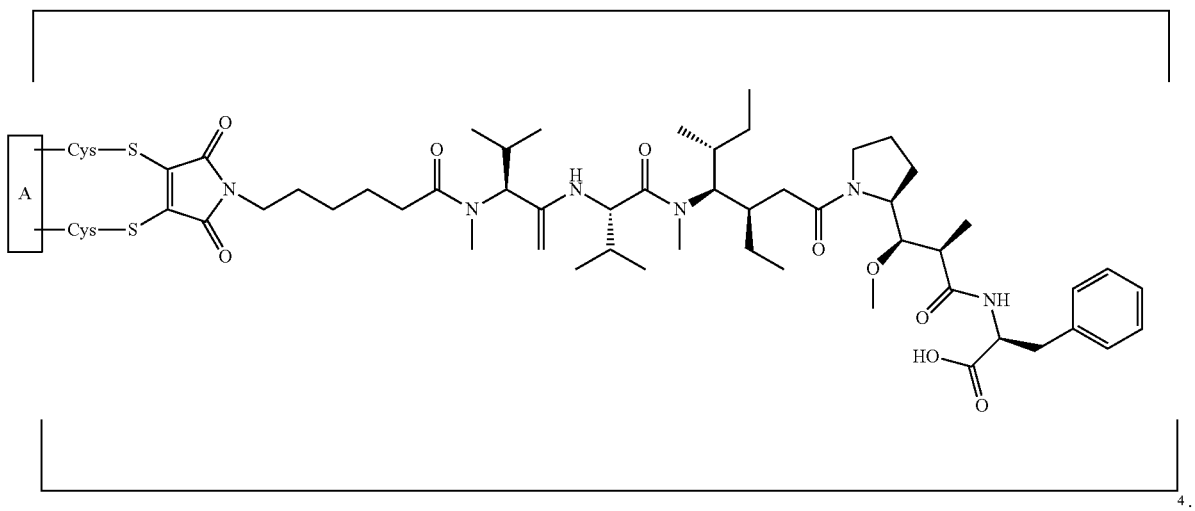

In certain embodiments of the antibody-drug conjugate of formula (Ic), where CTX is MMAE, and L is a cleavable linker.

In certain embodiments of the antibody-drug conjugate of formula (Ic), where CTX is MMAE, and L is —$(CH_2)_mC(O)$-Val-Ala-PAB-O—C(O)—, or —$(CH_2)_mC(O)$-Val-Cit-PAB-O—C(O)—, wherein m is an integer of 5 to 11.

In certain embodiments of the antibody-drug conjugate of formula (Ic), where CTX is MMAE, and L is —$(CH_2)_5C(O)$-Val-Ala-PAB-O—C(O)—, or —$(CH_2)_5C(O)$-Val-Cit-PAB-O—C(O)—, an n is 4.

In certain embodiments of the antibody-drug conjugate of formula (Ic), the antibody-drug conjugate is of the following formula:

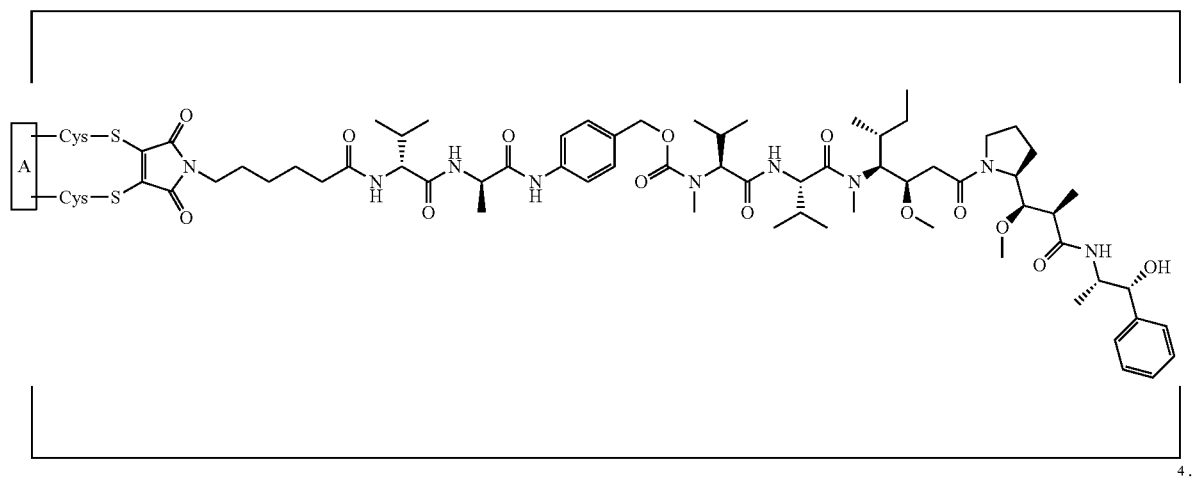

In certain embodiments of the antibody-drug conjugate of formula (Ic), where CTX is a PBD, and L is a cleavable linker.

In certain embodiments of the antibody-drug conjugate of formula (Ic), where CTX is a PBD, L is —(CH$_2$)$_m$C(O)-Val-Ala-PAB-O—C(O)—, or —(CH$_2$)$_m$C(O)-Val-Cit-PAB-O—C(O)—, wherein m is an integer of 5 to 11.

In certain embodiments of the antibody-drug conjugate of formula (Ic), where CTX is a PBD, L is —(CH$_2$)$_5$C(O)-Val-Ala-PAB-O—C(O)—, or —(CH$_2$)$_5$C(O)-Val-Cit-PAB-O—C(O)—, an n is 4.

In certain embodiments of the antibody-drug conjugate of formula (Ic), the antibody-drug conjugate is of one of the following formulas:

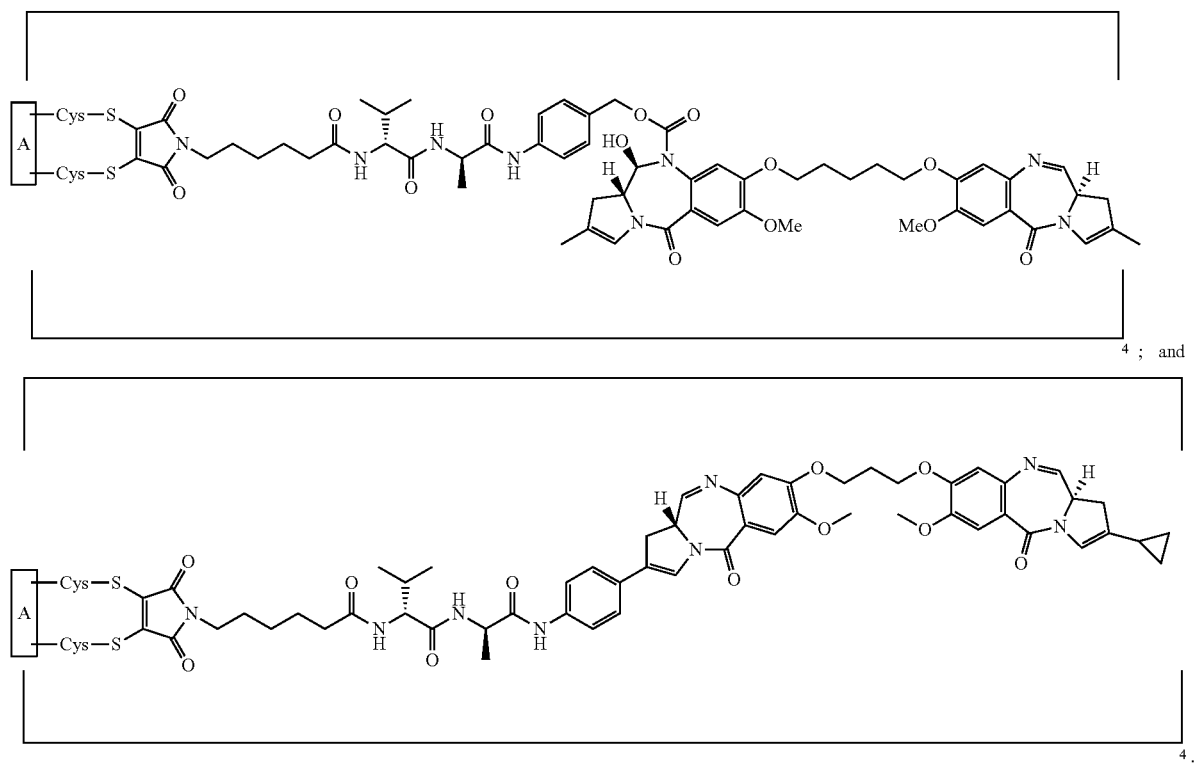

In certain embodiments of the antibody-drug conjugate of formula (Ic), n is 4.

In certain embodiments of the antibody-drug conjugate of formula (Ic), the opened cysteine-cysteine disulfide bond in A is an interchain disulfide bond. In certain embodiments, where the opened cysteine-cysteine disulfide bond in A is an interchain disulfide bond n is 4 (e.g., two heavy chain-light chain interchain disulfide bonds and two hinge heavy chain-heavy chain interchain disulfide bonds). In certain embodiments, where the opened cysteine-cysteine disulfide bond in A is an interchain disulfide bond n is 3 (e.g., two heavy chain-light chain interchain disulfide bonds and one hinge heavy chain-heavy chain interchain disulfide bond). In certain embodiments, where the opened cysteine-cysteine disulfide bond in A is an interchain disulfide bond n is 2 (e.g., two heavy chain-light chain interchain disulfide bonds).

Also provided herein are antibody-drug conjugates of the following formula (Id):

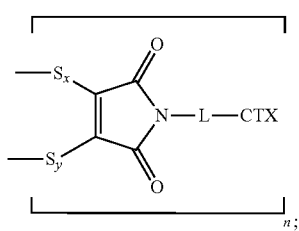

(Id)

wherein:

L is a cleavable or a noncleavable linker;

CTX is cytotoxic agent;

$S_x$ is a sulfur atom from a first cysteine residue, and $S_y$ is a sulfur atom from a second cysteine residue, wherein the first cysteine residue and the second cysteine residue are from different chains and/or from the same chain of a multi-chain antibody; and n is an integer of 1 to 4.

In certain embodiments of the antibody-drug conjugate of formula (Id), the multi-chain antibody is an antibody to CD39, optionally a humanized antibody to CD39.

In certain embodiments of the antibody-drug conjugate of formula (Id), CTX is selected from the group consisting of a tubulin stabilizer, a tubulin destabilizer, a DNA alkylator, a DNA minor groove binder, a DNA intercalator, a topoisomerase I inhibitor, a topoisomerase II inhibitor, a gyrase inhibitor, a protein synthesis inhibitor, a proteosome inhibitor, and an anti-metabolite.

In certain embodiments of the antibody-drug conjugate of formula (Id), CTX is a chemotherapeutic agent. Those of ordinary skill in the art will be aware of appropriate chemotherapeutic agents as disclosed, for example, in Chu, E., DeVite, V. T., 2012, Physicians' Cancer Chemotherapy Drug Manual 2012 (Jones & Bartlett Learning Oncology), and similar documents.

In certain embodiments of the antibody-drug conjugate of formula (Id), CTX may be any FDA-approved chemotherapeutic agent. In certain embodiments, CTX may be any FDA-approved chemotherapeutic agent available for cancer treatment.

In certain embodiments of the antibody-drug conjugate of formula (Id), CTX is selected from the group consisting of an alkylating agents, an anthracyclines, a cytoskeletal disruptors (taxanes), an epothilones, an histone deacetylase Inhibitor (HDAC), an inhibitor of Topoisomerase I, an Inhibitor of Topoisomerase II, a kinase inhibitor, a monoclonal antibodies, a nucleotide analog, a peptide antibiotic, a platinum-based agent, a retinoids, a Vinca alkaloid or a derivative thereof, and radioisotope.

In certain embodiments of the antibody-drug conjugate of formula (Id), CTX is selected from the group consisting of Actinomycin, all-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, and Vinorelbine.

In certain embodiments of the antibody-drug conjugate of formula (Id), CTX is selected from the group consisting of a tubulin stabilizer, a tubulin destabilizer, a DNA alkylator, a DNA minor groove binder, a DNA intercalator, a topoisomerase I inhibitor, a topoisomerase II inhibitor, a gyrase inhibitor, a protein synthesis inhibitor, a proteosome inhibitor, and an anti-metabolite.

In certain embodiments of the antibody-drug conjugate of formula (Id), CTX is selected from the group consisting of Actinomycin D, Amonafide, an auristatin, benzophenone, benzothiazole, a calicheamicin, Camptothecin, CC-1065 (NSC 298223), Cemadotin, Colchicine, Combretastatin A4, Dolastatin, Doxorubicin, Elinafide, Emtansine (DM1), Etoposide, KF-12347 (Leinamycin), a maytansinoid, Methotrexate, Mitoxantrone, Nocodazole, Proteosome Inhibitor 1 (PSI 1), Roridin A, T-2 Toxin (trichothecene analog), Taxol, a tubulysin, Velcade®, and Vincristine. In certain embodiments, CTX is an auristatin, a calicheamicin, a maytansinoid, a PBD (monomeric or dimeric), or a tubulysin. In certain embodiments, CTX is a calicheamicin, doxorubicin, camptothecin, duocarmycin, DM1, DM4, a maytansinoid, or a tubulysin. In certain embodiments, CTX is MMAE, MMAF, calicheamicin γ, mertansine, T3, or T4.

In certain embodiments of the antibody-drug conjugate of formula (Id), CTX is bonded to L by an amide bond, a carbamate bond, a disulfide bond, an ether bond, a thioether bond, or an ester bond.

In certain embodiments of the antibody-drug conjugate of formula (Id), CTX is an auristatin bonded to L by an amide bond or a carbamate bond. In certain embodiments, CTX is MMAF bonded to L by an amide bond. In certain embodiments, CTX is MMAE bonded to L by a carbamate bond.

In certain embodiments of the antibody-drug conjugate of formula (Id), CTX is a PBD bonded to L by an amide bond or a carbamate bond.

In certain embodiments of the antibody-drug conjugate of formula (Id), CTX is a calicheamicin, doxorubicin, camptothecin, duocarmycin, DM1, DM4, a maytansinoid, or a tubulysin, wherein CTX is bonded to L by an amide bond, a carbamate bond, a disulfide bond, an ether bond, a thioether bond, or an ester bond.

In certain embodiments of the antibody-drug conjugate of formula (Id), the multi-chain antibody comprises two heavy chains and two light chains.

In certain embodiments of the antibody-drug conjugate of formula (Id), the first cysteine residue is from a first heavy chain and the second cysteine residue is from a second heavy chain of the multi-chain antibody.

In certain embodiments of the antibody-drug conjugate of formula (Id), the first cysteine residue is from a heavy chain and the second cysteine residue is from a light chain of the multi-chain antibody.

In certain embodiments of the antibody-drug conjugate of formula (Id), the first and second cysteine residues are from the same heavy chain of the multi-chain antibody.

In certain embodiments of the antibody-drug conjugate of formula (Id), the antibody-drug conjugate is of the following formula:

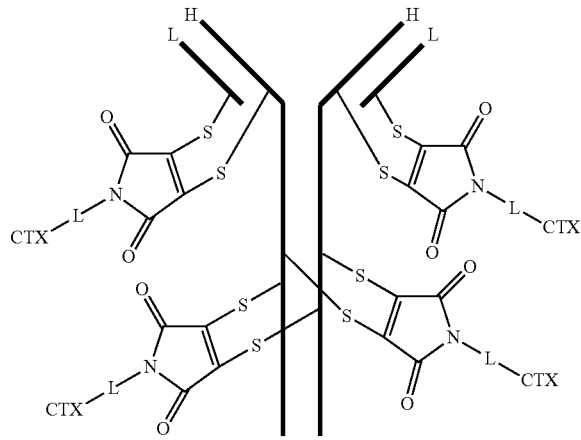

where each heavy chain of the multi-chain antibody is denoted by the letter H, and each light chain of the multi-chain antibody is denoted by the letter L.

In certain embodiments of the antibody-drug conjugate of formula (Id), the antibody-drug conjugate is of the following formula:

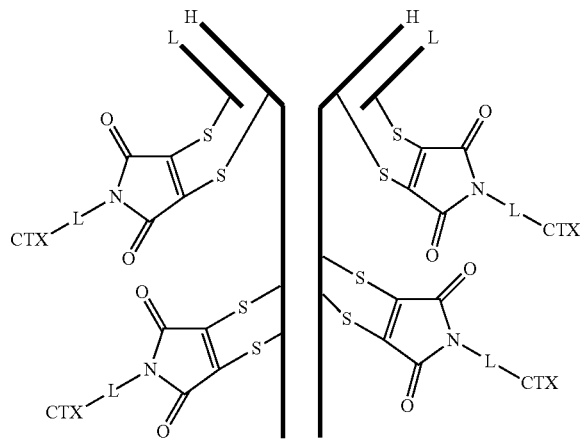

where each heavy chain of the multi-chain antibody is denoted by the letter H, and each light chain of the multi-chain antibody is denoted by the letter L.

In certain embodiments of the antibody-drug conjugate of formula (Id), the antibody-drug conjugate is of the following formula:

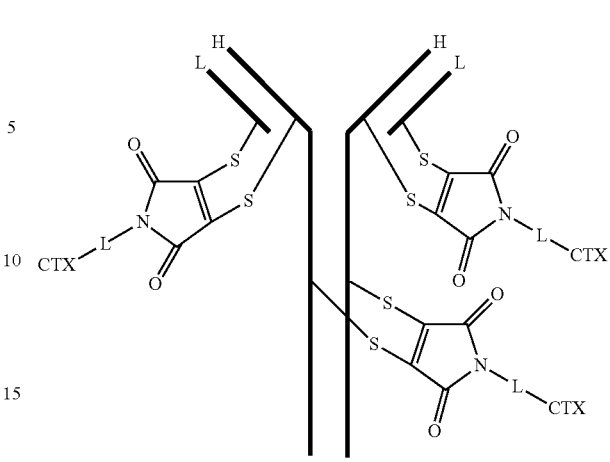

where each heavy chain of the multi-chain antibody is denoted by the letter H, and each light chain of the multi-chain antibody is denoted by the letter L.

In certain embodiments of the antibody-drug conjugate of formula (Id), the antibody-drug conjugate is of the following formula:

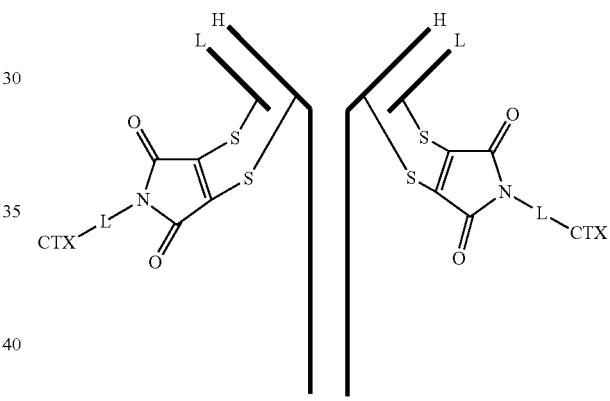

where each heavy chain of the multi-chain antibody is denoted by the letter H, and each light chain of the multi-chain antibody is denoted by the letter L.

In certain embodiments of the antibody-drug conjugate of formula (Id), L is a noncleavable linker.

In certain embodiments of the antibody-drug conjugate of formula (Id), L is —$(CH_2)_m C(O)$—, wherein m is an integer of 5 to 11.

In certain embodiments of the antibody-drug conjugate of formula (Id), L is a cleavable linker.

In certain embodiments of the antibody-drug conjugate of formula (Id), L is —$(CH_2)_m C(O)$-Val-Ala-PAB-O—C(O)—, or —$(CH_2)_m C(O)$-Val-Cit-PAB-O—C(O)—, wherein m is an integer of 5 to 11.

In certain embodiments of the antibody-drug conjugate of formula (Id), n is 4. In certain embodiments, CTX is MMAF, L is —$(CH_2)_5 C(O)$—, and n is 4. In certain embodiments, CTX is MMAE, L is —$(CH_2)_5 C(O)$-Val-Ala-PAB-O—C(O)—, and n is 4.

The present disclosure also provides a composition comprising an antibody-drug conjugate of the following formula:

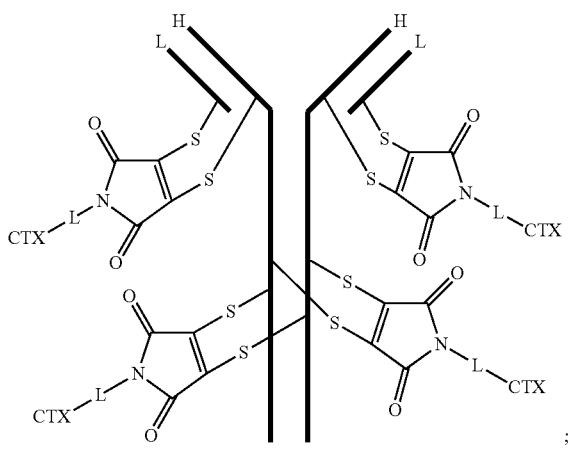

and/or
an antibody-drug conjugate of the following formula:

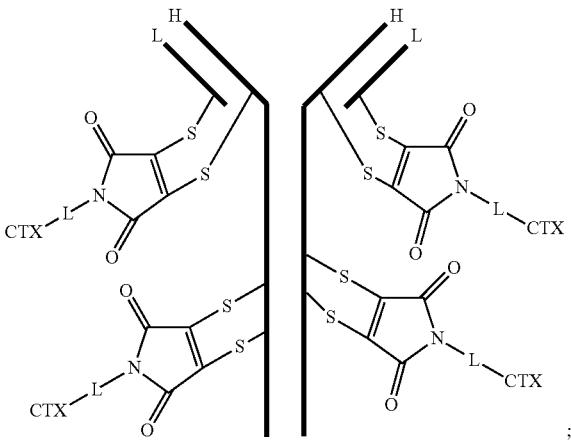

where each heavy chain of the multi-chain antibody is denoted by the letter H, and each light chain of the multi-chain antibody is denoted by the letter L. In certain embodiments, the multi-chain antibody is an anti-CD39 antibody, optionally a humanized anti-CD39 antibody.

Pharmaceutical Compositions

Therapeutic formulations containing one or more of the antibodies provided herein can be prepared for storage by mixing the antibody having the desired degree of purity with optional physiologically acceptable carriers, excipients or stabilizers (Remington's Pharmaceutical Sciences (1990) Mack Publishing Co., Easton, Pa.), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The antibodies provided herein can also, for example, be formulated in liposomes. Liposomes containing the molecule of interest are prepared by methods known in the art, such as described in Epstein et al. (1985) Proc. Natl. Acad. Sci. USA 82:3688; Hwang et al. (1980) Proc. Natl. Acad. Sci. USA 77:4030; and U.S. Pat. Nos. 4,485,045 and 4,544,545. Liposomes with enhanced circulation time are disclosed in U.S. Pat. No. 5,013,556.

Particularly useful immunoliposomes can be generated by the reverse phase evaporation method with a lipid composition containing phosphatidylcholine, cholesterol and PEG-derivatized phosphatidylethanolamine (PEG-PE). Liposomes are extruded through filters of defined pore size to yield liposomes with the desired diameter. Fab' fragments of an antibody provided herein can be conjugated to the liposomes as described in Martin et al. (1982) J. Biol. Chem. 257:286-288 via a disulfide interchange reaction. A chemotherapeutic agent (such as Doxorubicin) is optionally contained within the liposome; See Gabizon et al., (1989) J. National Cancer Inst. 81(19):1484.

Formulations, such as those described herein, can also contain more than one active compound as necessary for the particular indication being treated. In certain embodiments, formulations comprise an antibody provided herein and one or more active compounds with complementary activities that do not adversely affect each other. Such molecules are suitably present in combination in amounts that are effective for the purpose intended. For example, an antibody provided herein can be combined with one or more other therapeutic agents. Such combined therapy can be administered to the patient serially or simultaneously or in sequence.

An antibody provided herein can also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (1990) Mack Publishing Co., Easton, Pa.

The formulations to be used for in vivo administration can be sterile. This is readily accomplished by filtration through, e.g., sterile filtration membranes.

Sustained-release preparations can also be prepared. Suitable examples of sustained-release preparations include semipermeable matrices of solid hydrophobic polymers containing the polypeptide, which matrices are in the form of shaped articles, e.g., films, or microcapsule. Examples of sustained-release matrices include polyesters, hydrogels (for example, poly(2-hydroxyethyl-methacrylate), or poly(vinyl-alcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

In some embodiments, the pharmaceutical compositions provided herein contain therapeutically effective amounts of one or more of the antibodies provided herein, and optionally one or more additional prophylactic of therapeutic agents, in a pharmaceutically acceptable carrier. Such pharmaceutical compositions are useful in the prevention, treatment, or alleviation of one or more symptom of a CD39-mediated disease.

Pharmaceutical carriers suitable for administration of the compounds provided herein include any such carriers known to those skilled in the art to be suitable for the particular mode of administration.

In addition, the antibodies provided herein may be formulated as the sole pharmaceutically active ingredient in the composition or may be combined with other active ingredients (such as one or more other prophylactic or therapeutic agents).

The compositions can contain one or more antibodies provided herein. In one embodiment, the antibodies are formulated into suitable pharmaceutical preparations, such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the antibodies described above are formulated into pharmaceutical compositions using techniques and procedures well known in the art (see, e.g., Ansel (1985) Introduction to Pharmaceutical Dosage Forms, 4th Ed., p. 126).

In certain embodiments of the compositions, effective concentrations of one or more antibodies or derivatives thereof is (are) mixed with a suitable pharmaceutical carrier. In specific embodiments, concentrations of the compounds in the compositions are effective for delivery of an amount, upon administration, that treats, prevents, or ameliorates a CD39-mediated disease or symptom thereof.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

In some embodiments, the antibody provided herein is included in the pharmaceutically acceptable carrier in an effective amount sufficient to exert a therapeutically useful effect in the absence of undesirable side effects on the patient treated. The therapeutically effective concentration can be determined empirically by testing the compounds in in vitro and in vivo systems using routine methods and then extrapolated therefrom for dosages for humans.

The concentration of antibody in the pharmaceutical composition will depend on, e.g., the physicochemical characteristics of the antibody, the dosage schedule, and amount administered as well as other factors known to those of skill in the art.

In one embodiment, a therapeutically effective dosage produces a serum concentration of antibody of from about 0.1 ng/ml to about 50-100 µg/ml. The pharmaceutical compositions, in another embodiment, provide a dosage of from about 0.001 mg to about 2000 mg of antibody per kilogram of body weight per day. Pharmaceutical dosage unit forms can be prepared to provide from about 0.01 mg, 0.1 mg or 1 mg to about 500 mg, 1000 mg or 2000 mg, and in one embodiment from about 10 mg to about 500 mg of the antibody and/or a combination of other optional essential ingredients per dosage unit form.

The antibody can be administered at once, or may be divided into a number of smaller doses to be administered at intervals of time. It is understood that the precise dosage and duration of treatment is a function of the disease being treated and can be determined empirically using known testing protocols or by extrapolation from in vivo or in vitro test data. It is to be noted that concentrations and dosage values can also vary with the severity of the condition to be alleviated. It is to be further understood that for any particular subject, specific dosage regimens can be adjusted over time according to the individual need and the professional judgment of the person administering or supervising the administration of the compositions, and that the concentration ranges set forth herein are exemplary only and are not intended to limit the scope or practice of the claimed compositions.

Upon mixing or addition of the antibody, the resulting mixture can be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

In some embodiments, the pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The antibody is, in one embodiment, formulated and administered in unit-dosage forms or multiple-dosage forms. "Unit-dose" forms as used herein refers to physically discrete units suitable for human and animal subjects and packaged individually as is known in the art. Each unit-dose contains a predetermined quantity of the antibody sufficient to produce the desired therapeutic effect, in association with the required pharmaceutical carrier, vehicle or diluent. Examples of unit-dose forms include ampoules and syringes and individually packaged tablets or capsules. Unit-dose forms can be administered in fractions or multiples thereof. A "multiple-dose" form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

In specific embodiments, one or more anti-CD39 antibodies provided herein are in a liquid pharmaceutical formulation. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered can also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences (1990) Mack Publishing Co., Easton, Pa.

Dosage forms or compositions containing antibody in the range of 0.005% to 100% with the balance made up from non-toxic carrier can be prepared. Methods for preparation of these compositions are known to those skilled in the art.

Oral pharmaceutical dosage forms are either solid, gel or liquid. The solid dosage forms include tablets, capsules, granules, and bulk powders. Types of oral tablets include compressed, chewable lozenges and tablets which may be enteric-coated, sugar-coated or film-coated. Capsules can be hard or soft gelatin capsules, while granules and powders can be provided in non-effervescent or effervescent form with the combination of other ingredients known to those skilled in the art.

In certain embodiments, the formulations are solid dosage forms. In certain embodiments, the formulations are capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polyvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The antibodies provided herein can be provided in a composition that protects it from the acidic environment of the stomach. For example, the composition can be formulated in an enteric coating that maintains its integrity in the stomach and releases the active compound in the intestine. The composition can also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The antibody can also be mixed with other active materials which do not impair the desired action, or with materials that supplement the desired action, such as antacids, H2 blockers, and diuretics. The active ingredient is an antibody or pharmaceutically acceptable derivative thereof as described herein. Higher concentrations, up to about 98% by weight of the active ingredient may be included.

In all embodiments, tablets and capsules formulations can be coated as known by those of skill in the art in order to modify or sustain dissolution of the active ingredient. Thus, for example, they may be coated with a conventional enterically digestible coating, such as phenylsalicylate, waxes and cellulose acetate phthalate.

In specific embodiments, the formulations are liquid dosage forms. Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is, in one embodiment, encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, can be diluted with a sufficient quantity of a pharmaceutically acceptable liquid carrier, e.g., water, to be easily measured for administration.

Alternatively, liquid or semi-solid oral formulations can be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Parenteral administration, in one embodiment, is characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The antibody diffuses through the outer polymeric membrane in a release rate controlling step. The amount of antibody contained in such parenteral compositions is highly dependent on the specific nature thereof, as well as the activity of the compound and the needs of the subject.

Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations can be packaged in an ampoule, a vial or a syringe with a needle. All preparations for parenteral administration can be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The antibody can be suspended in micronized or other suitable form. The form of the resulting mixture depends upon a number of factors, including the intended mode of administration and the solubility of the compound in the selected carrier or vehicle. The effective concentration is sufficient for ameliorating the symptoms of the condition and may be empirically determined.

In other embodiments, the pharmaceutical formulations are lyophilized powders, which can be reconstituted for administration as solutions, emulsions and other mixtures. They may also be reconstituted and formulated as solids or gels.

The lyophilized powder is prepared by dissolving an antibody provided herein, or a pharmaceutically acceptable derivative thereof, in a suitable solvent. In some embodiments, the lyophilized powder is sterile. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical mixtures are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The antibodies provided herein can be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than 10 microns.

The compounds can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

Other routes of administration, such as transdermal patches, including iontophoretic and electrophoretic devices, and rectal administration, are also contemplated herein.

Transdermal patches, including iontophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration can be manufactured using the same pharmaceutically acceptable substance and by the same methods as for formulations for oral administration.

The antibodies and other compositions provided herein may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These can be prepared according to methods known to those skilled in the art. For example, liposome formulations can be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Methods of Administration and Dosing

Also provided herein are compositions comprising one or more antibodies provided herein for use in the prevention, treatment and/or alleviation of one or more symptom of a disease, such as a CD39-mediated disease.

In certain embodiments, provided herein are compositions comprising one or more antibodies provided herein for use in the management, prevention, or treatment of a CD39-mediated disease and/or the alleviation of one or more symptom of a CD39-mediated disease. Exemplary CD39-mediated diseases include a cell proliferative disorder, cancer, tumor, or a symptom thereof.

In certain embodiments, provided herein are compositions comprising one or more antibodies provided herein for use in the prevention, treatment and/or alleviation of one or more symptom of an CD39-mediated disease, such as a cell proliferative disorder. A cell proliferative disorder can include cancer or tumor formation, or a symptom thereof. In certain embodiments, the cell proliferative disorder is associated with increased expression and/or activity of CD39. For example, in certain embodiments, the cell proliferative disorder is associated with increased expression of CD39 on the surface of a cancer cell. Examples of cell proliferative disorders to be treated, prevented, or symptoms of which can be alleviated by the antibodies provided herein include, but are not limited to, bladder, breast, colon, connective tissue, rectal, gastric, esophageal, lung, laryx, kidney, oral, ovarian, or prostate cancers, or sarcomas, melanomas, gliomas, lymphomas or leukemias, or metastases of any of these cancers. Exemplary cell proliferative disorders include, but are not limited to, a leukemia, either acute or chronic, a sarcoma, and a bladder cancer.

Leukemias are cancers of the blood-forming tissues characterized by distorted proliferation and development of leukocytes and their precursors in the blood and bone marrow. Leukemias are typically classified as either chronic (slowly progressing) or acute (rapidly progressing). Leukemias can be further classified based upon the type of blood cell affected. For example, leukemia of lymphoid cells include lymphoid leukemia, lymphocytic leukemia or lymphoblastic leukemia, and leukemia of myeloid cells include myeloid leukemia, myelogenous leukemia, myeloblastic leukemia or granulocytic leukemia. Various leukemias can be treated, prevented or symptoms thereof alleviated by the methods provided herein, for example, acute lymphoblastic leukemia (ALL), chronic lymphocytic leukemia (CLL), acute myelogenous leukemia (CLL) and chronic myeloblastic leukemia (CML).

In one aspect, provided herein are methods for preventing or treating a disease described herein by administering to a subject a therapeutically effective amount, respectively, of an anti-CD39 antibody described herein, or a composition thereof. In certain embodiments, a method for treating the disease comprises administering to subject a therapeutically effective amount of a pharmaceutical formulation comprising an anti-CD39 antibody and a pharmaceutically acceptable carrier or excipient. A method provided herein can also optionally include at least one additional therapeutic agent, such as those provided herein, either as a separate treatment or conjugated or recombinately fused to an anti-CD39 antibody provided herein.

In one embodiment, an anti-CD39 antibody provided herein can be used for targeting CD39 expressed by the cancer cells by contacting the antibody with CD39 to form an antibody-antigen complex such that a conjugated or recombinately fused agent described herein accesses the interior of the cell. In one embodiment, the bound antibody is internalized into the cancer cell expressing CD39.

In certain embodiments, provided herein are compositions comprising one or more antibodies provided herein for use in the prevention, treatment and/or alleviation of one or more symptom of an CD39-mediated disease.

In certain embodiments, an antibody provided herein may be used in, for example, in vitro, ex vivo, and in vivo therapeutic methods. In some embodiments, provided herein are methods for inhibiting cell growth or proliferation, either in vivo or in vitro, the method comprising contacting a cell with an effective amount of a composition or an anti-CD39 antibody provided herein. In some embodiments, an antibody provided herein may be used in a method for inducing cell death. The method can comprise contacting a cell with an effective amount of a composition or an anti-CD39 antibody provided herein. The methods can be performed under conditions permissive for binding of the antibody to a CD39 polypeptide, polypeptide fragment or epitope, such as, but not limited to when the CD39 polypeptide is expressed on the surface of a cell. For inhibiting the cell growth or proliferation of a cell, the inhibition can include decreasing a cell's growth or proliferation by at least 10%, 20%, 30%, 40%, 50%, 60%, 70%, 80%, 90%, 95%, or 100%, and can include cell death. In certain embodiments, the cell is a cancer cell or a pre-cancerous cell. In certain embodiments, the cell is a bladder, breast, colon, connective tissue, rectal, gastric, esophageal, lung, laryx, kidney, oral, ovarian, or prostate cancer cell, or a sarcoma, melanoma, glioma, lymphoma or leukemia cell. In certain embodiments, the cell is an immune cell expressing a CD39 polypeptide, such as, but not limited to, a regulatory T cell.

An anti-CD39 antibody can be administered to a human for therapeutic or prophylactic purposes. Moreover, an anti-CD39 antibody can be administered to a non-human mammal expressing CD39 with which the antibody cross-reacts (e.g., a primate, pig, rat, or mouse) for veterinary purposes or as an animal model of human disease. Regarding the latter, such animal models may be useful for evaluating the therapeutic or prophylactic efficacy of antibodies or immunoconjugates provided herein (e.g., testing of dosages and time courses of administration).

In certain embodiments, an antibody provided herein can be used in a method of modulating an immune response in a subject. Such methods can include administering an effective amount of the composition of comprising an antibody provided herein to a subject. In some aspects, the modulating can include (a) increasing T cell activation; (b) increasing T cell proliferation; and/or (c) increasing cytokine production. Methods for assaying the modulation of an immune response are well known to one of skill in the art, and it is understood that a skill artisan would be able to readily conduct such assays.

In a specific embodiment, a composition for use in the management, prevention, treatment and/or alleviation of one or more symptom of a CD39-mediated disease comprises an antibody as described herein. In another specific embodiment, a composition for use in the management, prevention, treatment and/or alleviation of one or more symptom of a CD39-mediated disease comprises an antigen-binding fragment, a fusion protein or an functional fragment of an antibody as described herein.

In another embodiment, a composition for use in the management, prevention, treatment and/or alleviation of one or more symptom of a CD39-mediated disease comprises one or more antibodies described herein.

As discussed in more detail elsewhere herein, a composition provided herein may be used either alone or in combination with other compounds or compositions. Moreover, the antibodies may further be recombinantly fused to a heterologous polypeptide at the N- or C-terminus or chemically conjugated (including covalently and non-covalently conjugations) to polypeptides or other compositions. For example, antibodies provided herein may be recombinantly fused or conjugated to molecules useful as labels in detection assays and effector molecules such as heterologous polypeptides, drugs, radionucleotides, or toxins. See, e.g., PCT publications WO 92/08495; WO 91/14438; WO 89/12624; U.S. Pat. No. 5,314,995; and EP 396,387.

Antibodies provided herein may be used, for example, to purify, detect, and target CD39 antigens, in both in vitro and in vivo diagnostic and therapeutic methods. For example, the modified antibodies have use in immunoassays for qualitatively and quantitatively measuring levels of CD39 in biological samples. See, e.g., Harlow et al., Antibodies: A Laboratory Manual, (Cold Spring Harbor Laboratory Press, 2nd ed. 1988) (incorporated by reference herein in its entirety).

Also provided herein are methods of managing, treating, preventing and/or ameliorating one or more symptom of a CD39-mediated disease by administrating to a subject of an effective amount of an antibody, or pharmaceutical composition comprising an antibody provided herein. In one aspect, an antibody is substantially purified (e.g., substantially free from substances that limit its effect or produce undesired side-effects). In specific embodiments, the antibody is a humanized monoclonal antibody. The subject administered a therapy can be a mammal such as non-primate (e.g., cows, pigs, horses, cats, dogs, rats etc.) or a primate (e.g., a monkey, such as a cynomolgous monkey, or a human). In a specific embodiment, the subject is a human. In another embodiment, the subject is a human with a CD39-mediated disease.

Various delivery systems are known and can be used to administer a prophylactic or therapeutic agent (e.g., an antibody provided herein), including, but not limited to, encapsulation in liposomes, microparticles, microcapsules, recombinant cells capable of expressing the antibody, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent (e.g., an antibody provided herein), or pharmaceutical composition include, but are not limited to, parenteral administration (e.g., intradermal, intramuscular, intraperitoneal, intravenous and subcutaneous), epidural, and mucosal (e.g., intranasal and oral routes). In a specific embodiment, a prophylactic or therapeutic agent (e.g., an antibody provided herein), or a pharmaceutical composition is administered intranasally, intramuscularly, intravenously, or subcutaneously. The prophylactic or therapeutic agents, or compositions may be administered by any convenient route, for example by infusion or bolus injection, by absorption through epithelial or mucocutaneous linings (e.g., oral mucosa, intranasal mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

In a specific embodiment, it may be desirable to administer a prophylactic or therapeutic agent, or a pharmaceutical composition provided herein locally to the area in need of treatment. This may be achieved by, for example, and not by way of limitation, local infusion, by topical administration (e.g., by intranasal spray), by injection, or by means of an implant, the implant being of a porous, non-porous, or gelatinous material, including membranes, such as sialastic membranes, or fibers. In certain embodiments, when administering an antibody provided herein, care must be taken to use materials to which the antibody does not absorb.

In another embodiment, a therapeutic agent or composition provided herein can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In another embodiment, a therapeutic agent or composition provided herein can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of a therapeutic agent (e.g., an antibody provided herein) or a composition provided herein (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-co-glycolides) (PLGA), and polyorthoesters. In a specific embodiment, the polymer used in a sustained release formulation is inert, free of leachable impurities, stable on storage, sterile, and biodegradable. In yet another embodiment, a controlled or sustained release system can be placed in proximity of the therapeutic target, e.g., the nasal passages or lungs, thus requiring only a fraction of the systemic dose (see, e.g., Goodson, in Medical Applications of Controlled Release, supra, vol. 2, pp. 115-138 (1984)). Controlled release systems are discussed in the review by Langer (1990, Science 249:1527-1533). Any technique known to one of skill in the art can be used to produce sustained release formulations comprising one or more antibodies provided herein. See, e.g., U.S. Pat. No. 4,526,938, PCT publication WO 91/05548, PCT publication WO 96/20698, Ning et al., 1996, "Intratumoral Radioimmunotherapy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Intl Symp. Control. Rel. Bioact. Mater. 24:853-854, and Lam et al., 1997, "Microencapsulation of Recombinant Humanized Monoclonal Antibody for Local Delivery," Proc. Intl Symp. Control Rel. Bioact. Mater. 24:759-760.

In a specific embodiment, where the composition provided herein is a nucleic acid encoding a prophylactic or therapeutic agent (e.g., an antibody provided herein), the nucleic acid can be administered in vivo to promote expression of its encoded therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell surface receptors or transfecting agents, or by administering it in linkage to a homeobox-like peptide which is known to enter the nucleus (see, e.g., Joliot et al., 1991, Proc. Natl. Acad. Sci. USA 88:1864-1868), etc. Alternatively, a nucleic acid can be introduced intracellularly and incorporated within host cell DNA for expression by homologous recombination.

In a specific embodiment, a composition comprises one, two or more antibodies provided herein. In another embodiment, a composition comprises one, two or more antibodies provided herein and a prophylactic or therapeutic agent other than an antibody provided herein. In certain embodiments, the agents are known to be useful for or have been or are currently used for the prevention, treatment and/or alleviation of one or more symptom of a CD39-mediated disease. In addition to prophylactic or therapeutic agents, the compositions provided herein may also comprise a carrier.

The compositions provided herein include bulk drug compositions useful in the manufacture of pharmaceutical compositions (e.g., compositions that are suitable for administration to a subject or patient) that can be used in the preparation of unit dosage forms. In a specific embodiment, a composition provided herein is a pharmaceutical composition. Such compositions comprise a prophylactically or therapeutically effective amount of one or more prophylactic or therapeutic agents (e.g., an antibody provided herein or other prophylactic or therapeutic agent), and a pharmaceutically acceptable carrier. In certain embodiments, the pharmaceutical compositions are formulated to be suitable for the route of administration to a subject.

In a specific embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocamne to ease pain at the site of the injection. Such compositions, however, may be administered by a route other than intravenous.

Generally, the ingredients of compositions provided herein are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In certain embodiments, an antibody provided herein is packaged in a hermetically sealed container such as an ampoule or sachette indicating the quantity of antibody. In one embodiment, the antibody is supplied as a dry sterilized lyophilized powder or water free concentrate in a hermetically sealed container and can be reconstituted, e.g., with water or saline to the appropriate concentration for administration to a subject. In certain embodiments, the antibody is supplied as a dry sterile lyophilized powder in a hermetically sealed container at a unit dosage of at least 0.1 mg, at least 0.5 mg, at least 1 mg, at least 2 mg, or at least 3 mg, such as at least 5 mg, at least 10 mg, at least 15 mg, at least 25 mg, at least 30 mg, at least 35 mg, at least 45 mg, at least 50 mg, at least 60 mg, at least 75 mg, at least 80 mg, at least 85 mg, at least 90 mg, at least 95 mg, or at least 100 mg. The lyophilized antibody can be stored at between 2 and 8° C. in its original container and the antibody can be administered within 12 hours, such as within 6 hours, within 5 hours, within 3 hours, or within 1 hour after being reconstituted. In an alternative embodiment, an antibody is supplied in liquid form in a hermetically sealed container indicating the quantity and concentration of the antibody. In certain embodiments, the liquid form of the antibody is supplied in a hermetically sealed container at least 0.1 mg/ml, at least 0.5 mg/ml, or at least 1 mg/ml, such as at least 5 mg/ml, at least 10 mg/ml, at least 15 mg/ml, at least 25 mg/ml, at least 30 mg/ml, at least 40 mg/ml, at least 50 mg/ml, at least 60 mg/ml, at least 70 mg/ml, at least 80 mg/ml, at least 90 mg/ml, or at least 100 mg/ml.

The compositions provided herein can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of a therapeutic agent (e.g., an antibody provided herein) or a composition provided herein that will be effective in the prevention, treatment and/or alleviation of one or more symptom of a CD39-mediated disease can be determined by standard clinical techniques.

Accordingly, a dosage of an antibody or a composition that results in a serum titer of from about 0.1 μg/ml to about 450 μg/ml, and in some embodiments at least 0.1 μg/ml, at least 0.2 μg/ml, at least 0.4 μg/ml, at least 0.5 μg/ml, at least 0.6 μg/ml, at least 0.8 μg/ml, at least 1 μg/ml, at least 1.5 μg/ml, such as at least 2 μg/ml, at least 5 μg/ml, at least 10 μg/ml, at least 15 μg/ml, at least 20 μg/ml, at least 25 μg/ml, at least 30 μg/ml, at least 35 μg/ml, at least 40 μg/ml, at least 50 μg/ml, at least 75 μg/ml, at least 100 μg/ml, at least 125 μg/ml, at least 150 μg/ml, at least 200 μg/ml, at least 250 μg/ml, at least 300 μg/ml, at least 350 μg/ml, at least 400 μg/ml, or at least 450 μg/ml can be administered to a human for the prevention, treatment and/or alleviation of one or more symptom of a CD39-mediated disease. In addition, in vitro assays may optionally be employed to help identify optimal dosage ranges. The precise dose to be employed in the formulation will also depend on the route of administration, and the seriousness of a CD39-mediated disease, and should be decided according to the judgment of the practitioner and each patient's circumstances.

Effective doses may be extrapolated from dose-response curves derived from in vitro or animal model test systems.

For the antibodies provided herein, the dosage administered to a patient can be, in certain embodiments, 0.1 mg/kg to 100 mg/kg of the patient's body weight. In some embodiments, the dosage administered to the patient is about 1 mg/kg to about 75 mg/kg of the patient's body weight. In certain embodiments, the dosage administered to a patient is between 1 mg/kg and 20 mg/kg of the patient's body weight, such as 1 mg/kg to 5 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of the antibodies provided herein may be reduced by enhancing uptake and tissue penetration of the antibodies by modifications such as, for example, lipidation.

In one embodiment, approximately 100 mg/kg or less, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, or approximately 0.1 mg/kg or less of an antibody provided herein is administered 5 times, 4 times, 3 times, 2 times or 1 time to prevent, treat or alleviate one or more symptom of a CD39-mediated disease. In some embodiments, an antibody provided herein is administered about 1-12 times, wherein the doses may be administered as necessary, e.g., weekly, biweekly, monthly, bimonthly, trimonthly, etc., as determined by a physician. In some embodiments, a lower dose (e.g., 1-15 mg/kg) can be administered more frequently (e.g., 3-6 times). In other embodiments, a higher dose (e.g., 25-100 mg/kg) can be administered less frequently (e.g., 1-3 times). However, as will be apparent to those in the art, other dosing amounts and schedules are easily determinable and within the scope of the invention.

In a specific embodiment, approximately 100 mg/kg, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, approximately 0.1 mg/kg or less of an antibody provided herein in a sustained release formulation is administered to a subject, such as a human, to prevent, treat and/or alleviate one or more symptom of a CD39-mediated disease. In another specific embodiment, an approximately 100 mg/kg, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, or approximately 0.1 mg/kg or less bolus of an antibody provided herein not in a sustained release formulation is administered to a subject, such as a human, to prevent, treat and/or alleviate one or more symptom of a CD39-mediated disease, and after a certain period of time, approximately 100 mg/kg, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, or approximately 5 mg/kg or less of an antibody provided herein in a sustained release is administered to the subject (e.g., intranasally or intramuscularly) one, two, three or four times. In accordance with this embodiment, a certain period of time can be 1 to 5 days, a week, two weeks, or a month.

In some embodiments, a single dose of an antibody provided herein is administered to a patient to prevent, treat and/or alleviate one or more symptom of a CD39-mediated disease two, three, four, five, six, seven, eight, nine, ten, eleven, twelve times, thirteen, fourteen, fifteen, sixteen, seventeen, eighteen, nineteen, twenty, twenty-one, twenty-two, twenty-three, twenty-four, twenty five, or twenty six at bi-weekly (e.g., about 14 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (e.g., each dose monthly dose may or may not be identical).

In another embodiment, a single dose of an antibody provided herein is administered to patient to prevent, treat and/or alleviate one or more symptom of a CD39-mediated disease two, three, four, five, six, seven, eight, nine, ten, eleven, or twelve times at about monthly (e.g., about 30 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (e.g., each dose monthly dose may or may not be identical).

In one embodiment, a single dose of an antibody provided herein is administered to a patient to treat, prevent and/or alleviate a symptom of a CD39-mediated disease two, three, four, five, or six times at about bi-monthly (e.g., about 60 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (e.g., each bi-monthly dose may or may not be identical).

In some embodiments, a single dose of an antibody provided herein is administered to a patient to treat, prevent and/or alleviate one or more symptom of a CD39-mediated disease two, three, or four times at about tri-monthly (e.g., about 120 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (e.g., each tri-monthly dose may or may not be identical).

In certain embodiments, the route of administration for a dose of an antibody provided herein to a patient is intranasal, intramuscular, intravenous, or a combination thereof, but other routes described herein are also acceptable. Each dose may or may not be administered by an identical route of administration. In some embodiments, an antibody provided herein may be administered via multiple routes of administration simultaneously or subsequently to other doses of the same or a different antibody provided herein.

In certain embodiments, antibodies provided herein are administered prophylactically or therapeutically to a subject. Antibodies can be prophylactically or therapeutically administered to a subject so as to prevent, lessen or alleviate a CD39-mediated disease or symptom thereof.

Diagnostic use of Antibodies

Labeled antibodies provided herein and derivatives and analogs thereof, which bind to a CD39 antigen can be used for diagnostic purposes to detect, diagnose, or monitor a CD39-mediated disease. Also provided herein are methods for the detection of a CD39-mediated disease comprising: (a) assaying the expression of a CD39 antigen in cells or a tissue sample of a subject using one or more antibodies provided herein that bind to the CD39 antigen; and (b) comparing the level of the CD39 antigen with a control level, e.g., levels in normal tissue samples (e.g., from a patient not having a CD39-mediated disease, or from the same patient before disease onset), whereby an increase in the assayed level of CD39 antigen compared to the control level of the CD39 antigen is indicative of a CD39-mediated disease.

Also provided herein is a diagnostic assay for diagnosing a CD39-mediated disease comprising: (a) assaying for the level of a CD39 antigen in cells or a tissue sample of an individual using one or more antibodies provided herein that bind to a CD39 antigen; and (b) comparing the level of the CD39 antigen with a control level, e.g., levels in normal tissue samples, whereby an increase in the assayed CD39 antigen level compared to the control level of the CD39 antigen is indicative of a CD39-mediated disease. A more definitive diagnosis of a CD39-mediated disease may allow health professionals to employ preventative measures or aggressive treatment earlier thereby preventing the development or further progression of the CD39-mediated disease.

Antibodies provided herein can be used to assay CD39 antigen levels in a biological sample using classical immunohistological methods as described herein or as known to those of skill in the art (e.g., see Jalkanen et al., 1985, J. Cell. Biol. 101:976-985; and Jalkanen et al., 1987, J. Cell. Biol. 105:3087-3096). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (121 In), and technetium (99Tc); luminescent labels, such as luminol; and fluorescent labels, such as fluorescein and rhodamine, and biotin.

One aspect provided herein is the detection and diagnosis of a CD39-mediated disease in a human. In one embodiment, diagnosis comprises: a) administering (for example, parenterally, subcutaneously, or intraperitoneally) to a subject an effective amount of a labeled antibody that binds to a CD39 antigen; b) waiting for a time interval following the administering for permitting the labeled antibody to preferentially concentrate at sites in the subject where the CD39 antigen is expressed (and for unbound labeled molecule to be cleared to background level); c) determining background level; and d) detecting the labeled antibody in the subject, such that detection of labeled antibody above the background level indicates that the subject has a CD39-mediated disease. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99Tc. The labeled antibody will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled antibody to preferentially concentrate at sites in the subject and for unbound labeled antibody to be cleared to background level is 6 to 48 hours or 6 to 24 hours or 6 to 12 hours. In another embodiment the time interval following administration is 5 to 20 days or 5 to 10 days.

In one embodiment, monitoring of a CD39-mediated disease is carried out by repeating the method for diagnosing the a CD39-mediated disease, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the diagnostic methods provided herein include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

Methods of Producing Antibodies

Antibodies provided herein that bind to an antigen can be produced by any method known in the art for the synthesis of antibodies, in particular, by chemical synthesis or by recombinant expression techniques. The practice of the invention employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al. (1982) Molecular Cloning: A Laboratory Manual, Cold Spring Harbor Laboratory Press; Sambrook et al. (1989), Molecular Cloning: A Laboratory Manual, Second Edition, Cold Spring Harbor Laboratory Press; Sambrook et al. (2001) Molecular Cloning: A Laboratory Manual, Cold Spring Harbor Laboratory Press, Cold Spring Harbor, N.Y.; Ausubel et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren et al. (eds.) (1999) Genome Analysis: A Laboratory Manual, Cold Spring Harbor Laboratory Press.

Polyclonal antibodies that bind to an antigen can be produced by various procedures well-known in the art. For example, a human antigen can be administered to various host animals including, but not limited to, rabbits, mice, rats, etc. to induce the production of sera containing polyclonal antibodies specific for the human antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling et al., in: Monoclonal Antibodies and T-Cell Hybridomas 563 681 (Elsevier, N.Y., 1981) (the references incorporated by reference in their entireties). The term "monoclonal antibody" as used herein is not limited to antibodies produced through hybridoma technology. Other exemplary methods of producing monoclonal antibodies are discussed elsewhere herein, such as e.g., use of the KM Mouser™. Additional exemplary methods of producing monoclonal antibodies are provided in the Examples herein.

Methods for producing and screening for specific antibodies using hybridoma technology are routine and well known in the art. Briefly, mice can be immunized with a CD39 antigen and once an immune response is detected, e.g., antibodies specific for CD39 antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution.

Additionally, a RIMMS (repetitive immunization multiple sites) technique can be used to immunize an animal (Kilptrack et al., 1997 Hybridoma 16:381-9, incorporated by reference in its entirety). The hybridoma clones are then assayed by methods known in the art for cells that secrete antibodies capable of binding a given polypeptide. Ascites fluid, which generally contains high levels of antibodies, can be generated by immunizing mice with positive hybridoma clones.

Accordingly, also provided herein are methods of generating antibodies by culturing a hybridoma cell secreting a modified antibody provided herein wherein, in certain embodiments, the hybridoma is generated by fusing splenocytes isolated from a mouse immunized with a CD39 antigen with myeloma cells and then screening the hybridomas resulting from the fusion for hybridoma clones that secrete an antibody able to bind to a CD39 antigen.

Antibody fragments which recognize specific CD39 antigens may be generated by any technique known to those of skill in the art. For example, Fab and F(ab')2 fragments provided herein may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies provided herein can also be generated using various phage display methods known in the art.

For example, antibodies can also be generated using various phage display methods. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies provided herein include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/O1 134; International Publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043 (the references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lambda constant regions. The VH and VL domains may also cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, human or chimeric antibodies can be used. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741; each of which is incorporated herein by reference in its entirety.

In specific embodiments, human antibodies are produced. Human antibodies and/or fully human antibodies can be produced using any method known in the art, including the Examples provided herein. For example, transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of the polypeptide. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., PCT publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. Other methods are detailed in the Examples herein. In addition, companies such as Abgenix, Inc. (Freemont, Calif.) and Genpharm (San Jose, Calif.) can be engaged to provide human antibodies directed against a selected antigen using technology similar to that described above.

A chimeric antibody is a molecule in which different portions of the antibody are derived from different immunoglobulin molecules. Methods for producing chimeric antibodies are known in the art. See, e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331,415, which are incorporated herein by reference in their entirety.

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains (Fab, Fab', F(ab')2, Fabc, Fv) in which all or substantially all of the CDR regions correspond to those of a non human immunoglobulin (e.g., donor antibody) and all or substantially all of the framework regions are those of a human immunoglobulin consensus sequence. In certain embodiments, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the humanized antibody exhibit cytotoxic activity, and the class is typically IgG1. Where such cytotoxic activity is not desirable, the constant domain may be of the IgG2 class. Examples of VL and VH constant domains that can be used in certain embodiments include, but are not limited to, C-kappa and C-gamma-1 (nG1m) described in Johnson et al. (1997) J. Infect. Dis. 176, 1215-1224 and those described in U.S. Pat. No. 5,824,307. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental FR and CDR sequences, more often 90%, or greater than 95%. Humanized antibodies can be produced using variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. Nos. 6,407,213, 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16):10678-84

(1997), Roguska et al., Protein Eng. 9(10):895 904 (1996), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), which is incorporated by reference herein in its entirety. Often, framework residues in the framework regions will be substituted with the corresponding residue from the CDR donor antibody to alter (e.g., improve) antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Reichmann et al., 1988, Nature 332:323, which are incorporated herein by reference in their entireties.)

Single domain antibodies, for example, antibodies lacking the light chains, can be produced by methods well-known in the art. See Riechmann et al., 1999, J. Immunol. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301, each of which is incorporated herein by reference in its entirety.

Further, the antibodies that bind to a CD39 antigen can, in turn, be utilized to generate anti-idiotype antibodies that "mimic" an antigen using techniques well known to those skilled in the art. (See, e.g., Greenspan & Bona, 1989, FASEB J. 7(5):437-444; and Nissinoff, 1991, J. Immunol. 147(8):2429-2438).

Polynucleotides Encoding an Antibody

Also provided herein are polynucleotides comprising a nucleotide sequence encoding an antibody provided herein that binds to a CD39 epitope. Also provided herein are polynucleotides that hybridize under high stringency, intermediate or lower stringency hybridization conditions, e.g., as defined supra, to polynucleotides that encode a antibody or modified antibody provided herein.

In certain embodiments, nucleic acid molecules provided herein comprise or consist of a nucleic acid sequence encoding a VH and/or VL amino acid sequence disclosed herein, or any combination thereof (e.g., as a nucleotide sequence encoding an antibody provided herein, such as a full-length antibody, heavy and/or light chain of an antibody, or a single chain antibody provided herein).

Recombinant Expression of an Antibody

Recombinant expression of an antibody provided herein (e.g., a full-length antibody, heavy and/or light chain of an antibody, or a single chain antibody provided herein) that binds to a CD39 antigen requires construction of an expression vector containing a polynucleotide that encodes the antibody. Once a polynucleotide encoding an antibody molecule, heavy or light chain of an antibody, or fragment thereof (such as that containing the heavy and/or light chain variable domain) has been obtained, the vector for the production of the antibody molecule may be produced by recombinant DNA technology using techniques well-known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. Thus, also provided herein are replicable vectors comprising a nucleotide sequence encoding an antibody molecule provided herein, a heavy or light chain of an antibody, a heavy or light chain variable domain of an antibody or a fragment thereof, or a heavy or light chain CDR, operably linked to a promoter. Such vectors may include the nucleotide sequence encoding the constant region of the antibody molecule (see, e.g., International Publication Nos. WO 86/05807 and WO 89/01036; and U.S. Pat. No. 5,122,464) and the variable domain of the antibody may be cloned into such a vector for expression of the entire heavy, the entire light chain, or both the entire heavy and light chains.

The expression vector is transferred to a host cell by conventional techniques and the transfected cells are then cultured by conventional techniques to produce an antibody provided herein. Thus, also provided herein are host cells containing a polynucleotide encoding an antibody provided herein or fragments thereof, or a heavy or light chain thereof, or fragment thereof, or a single chain antibody provided herein, operably linked to a heterologous promoter. In certain embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibodies provided herein (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express an antibody provided herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., Saccharomyces Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In certain embodiments, bacterial cells, such as *Escherichia coli*, or eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In specific embodiments, antibodies provided herein are produced in CHO cells. In a specific embodiment, the expression of nucleotide sequences encoding antibodies provided herein which bind to a CD39 antigen is regulated by a constitutive promoter, inducible promoter or tissue specific promoter.

In bacterial systems, a number of expression vectors may be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified may be desirable. Such vectors include, but are not limited to, the E. coli expression vector pUR278 (Ruther et al., 1983, EMBO 12:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in Spodoptera frugiperda cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region El or E3) will result in a recombinant virus that is viable and capable of expressing the antibody molecule in infected hosts (e.g., see Logan & Shenk, 1984, Proc. Natl. Acad. Sci. USA 8 1:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NSO (a murine myeloma cell line that does not endogenously produce any immunoglobulin chains), CRL7O3O and HsS78Bst cells. In specific embodiments, fully human, monoclonal anti-CD39 antibodies provided herein are produced in mammalian cells, such as CHO cells.

For long-term, high-yield production of recombinant proteins, stable expression is useful, but not mandatory. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIB TECH 11(5):155-2 15); and hygro, which confers resistance to hygromycin (Santerre et al., 1984, Gene 30:147). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds.), Current Protocols in Human Genetics, John Wiley & Sons, NY (1994); Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors provided herein, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2197-2199). The coding sequences for the heavy and light chains may comprise cDNA or genomic DNA.

Once an antibody has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies provided herein may be fused to heterologous polypeptide sequences described herein or otherwise known in the art to facilitate purification.

Kits

Also provided herein is a pharmaceutical pack or kit comprising one or more containers filled with one or more of the ingredients of the pharmaceutical compositions provided herein, such as one or more antibodies provided herein. Optionally associated with such container(s) can be a notice in the form prescribed by a governmental agency regulating the manufacture, use or sale of pharmaceuticals or biological products, which notice reflects approval by the agency of manufacture, use or sale for human administration. In some embodiments, the kit comprises a package insert. The term "package insert" is used to refer to instructions customarily included in commercial packages of therapeutic products, that contain information about the indications, usage, dosage, administration, contraindications and/or warnings concerning the use of such therapeutic products, as well as instructions for use.

Also provided herein are kits that can be used in the above methods. In one embodiment, a kit comprises an antibody provided herein, such as an isolated antibody, in one or more containers. In a specific embodiment, the kits provided herein contain a substantially isolated CD39 antigen as a control. In certain embodiments, the kits provided herein further comprise a control antibody which does not react with the CD39 antigen. In another specific embodiment, the kits provided herein contain a means for detecting the binding of a modified antibody to a CD39 antigen (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, the kit may include a recombinantly produced or chemically synthesized CD39 antigen. The CD39 antigen provided in the kit may also be attached to a solid support. In a more specific embodiment the detecting means of the above described kit includes a solid support to which CD39 antigen is attached. Such a kit may also include a non-attached reporter-labeled anti-human antibody. In this embodiment, binding of the antibody to the CD39 antigen can be detected by binding of the reporter-labeled antibody.

The following examples are offered by way of illustration, and not by way of limitation.

EXAMPLES

The following are examples of methods and compositions of the present disclosure. It is understood that various other embodiments may be practiced, given the general description provided above.

The following are examples of methods and compositions of the invention. It is understood that various other embodiments may be practiced, given the general description provided above.

Example 1—Identification of CD39 on the Surface of Tumor Cells

Tumor cells from patients were analyzed. For example, peripheral blood mononuclear cells (PBMCs) from patients with CLL were obtained. As a control, fresh PBMC samples from healthy donors were analyzed. To monitor the quality of individual CLL samples, hematoxylin and eosin staining of CLL blasts were performed or CLL marker expression was monitored using flow cytometry/FACS analysis. Sample handling was optimized so as to maximally maintain cell viability during sample isolation. Optimal labeling times for CLL samples were determined to allow for efficient labeling without compromise of cellular integrity.

Surface tagged antigen profiling (sTAg) was used to identify and quantitatively profile the repertoire of surface proteins on cells in the samples. The extracellular domains of proteins associated with the cell membranes of intact primary CLL tumor cells were chemically tagged and then chromatographically enriched for tagged proteins using a solid-phase affinity resin. Eluted proteins were stored at −80° C. prior to mass spectrometry analysis as described below.

Proteins enriched by the sTAg method were identified and quantified using high-resolution, shotgun liquid chromatography tandem mass spectrometry (MS). A hybrid Thermo-Fisher LTQ-ORBITRAP VELOS mass spectrometer, which combines the sensitivity of a linear ion trap with the high-resolution and mass accuracy afforded by the revolutionary orbitrap mass analyzer (Olsen et al., Mol. Cell Proteomics 8:2759-2769, 2009) coupled to a nanoflow liquid chromatography apparatus was employed for shotgun-based, bottoms-up proteomics to determine the identities and quantitative abundance measurements of proteins in the CLL cell surface enrichment fractions (Yates et al., Annu. Rev. Biomed. Eng. 11:49-79, 2009). Tryptic digests from enriched surface proteins were separated by hydrophobicity via online, nanoflow liquid chromatography as peptide masses and fragmentation patterns were recorded dynamically by the mass spectrometer. To determine peptide and protein identities, the raw MS data were processed using the SEQUEST algorithm executed on a fast-processing Sorcerer 2 platform (Lundgren et al., Curr. Protoc. Bioinformatics, Chapter 13: Unit 13.3, 2009), to determine best-fit matches between experimental fragmentation patterns and those determined in-silico from the human proteome. Resulting matches were statistically validated using the PEPTIDEPROPHET (Keller et al., Anal. Chem. 74:5383-5392, 2002) and PROTEINPROPHET (Nesvizhskii et al., Anal. Chem. 75: 4646-4658, 2003) algorithms as implemented in SCAFFOLD Software (Proteome Software) to ensure the lowest possible false discovery rates (FDR) and thus inclusion of only robustly identified proteins in the candidate pool.

The relative quantitative levels of identified proteins in the sTAg samples were determined using the spectral counting method (reviewed in Neilson et al., Proteomics 11:535-553, 2011). Spectral counting is based on the empirical demonstration that the number of assigned (positively identified) spectra associated with peptides from each protein correlates strongly with that protein's relative abundance in the original mixture (Liu et al., Anal. Chem. 76:4193-4201, 2004). Spectral counts of identified peptides were obtained from the SCAFFOLD Software program that displays, sorts and filters the results of SEQUEST-searched mass spectrometry data. Raw spectral counts were transformed to percent Normalized Spectral Abundance Factor (% NSAF) values (Zybailov et al., J. Proteome Res. 5:2339-2347, 2006) to account for differences in protein length and variability in total protein concentration. Selected monoclonal antibodies were used to validate the proteomic measurements using quantitative FACS analysis as an independent, external confirmatory measure of the sTAg mass spectrometry-based proteomic profiling of the primary tumor cell surface expression (see, e.g., Example 2).

Using sTAg analysis, CD39 was identified as being present on the surface of CLL tumor cells. The sTAg method identified CD39 in 38 of 40 primary CLL samples.

For another example, sarcoma specimens were obtained from the Cooperative Human Tissue Network (CHTN) and the National Disease Research Interchange, respectively. CHTN is funded by the National Cancer Institute. CD39 was identified as being present on the surface of sarcoma cells using sTAg analysis in 9 of 9 primary sarcoma samples.

The proteomic evaluation was subsequently corroborated by immunohistochemistry using an anti-CD39 antibody and soft tissue sarcoma tumor microarrays (TMA) as follows. Sarcoma TMAs comprising 141 readable tissue cores of liposarcoma, fibrosarcoma, dermatofibrosarcoma, leiomyosarcoma and non-malignant stroma were used to assess membranous staining intensity for CD39 (Table 5). Slides were deparaffinized, rehydrated and heat-induced antigen retrieval was performed (EDTA pH 9) prior to blocking and incubating with the rabbit anti-human CD39 polyclonal antibody (Sigma; # HPA014067; 1:750 dilution). CD39 expression was assessed by manually scoring intensity, location and cell types. The strength of CD39 staining was scored as negative (0), moderate (+1) or strong (+2-3). Only cores that showed a high percentage of tumor or normal stroma were analyzed. CD39 staining was moderate to strong (IHC score +2/3) in 25%, weakly positive (IHC score +1) in 30% and negative in 45% of all sarcomas combined. In contrast only 24% of non-malignant stroma was weakly positive for CD39 and 76% was negative.

TABLE 5

IHC score of CD39 in various soft tissue sarcomas and normal stroma

| Tissue | N | IHC Score [%] | | |
| --- | --- | --- | --- | --- |
| | | Negative | +1 | +2-3 |
| Normal stroma | 42 | 76 | 24 | 0 |
| Liposarcoma | 46 | 67 | 22 | 11 |
| Fibrosarcoma | 40 | 45 | 35 | 20 |
| Dermatofibrosarcoma | 40 | 35 | 37.5 | 27.5 |
| Leiomyosarcoma | 15 | 33 | 27 | 40 |
| | 141* | 45# | 30# | 25# |

*Total number of analyzed STS cores.
Mean IHC score % in analyzed STS cores.

Example 2—Preparation of Monoclonal Antibodies to CD39

Antibodies to CD39 were generated using the iTAb platform. In this system, a mouse tumor cell line is transduced to stably express the human protein and then implanted subcutaneously in syngeneic mice. The mice are treated with anti-CD8 antibody to remove the cell mediated rejection pathway while leaving the humoral immune response intact. Following this immunization, splenocytes are harvested, and are fused to an immortalized partner cell to generate hybridomas. Antibodies from these hybridomas are screened in multiple assays designed to identify a diverse panel of antibodies with good binding properties. The selected antibodies are then produced for in vivo testing as follows.

Murine sarcoma cell lines that express human CD39 (e.g., SEQ ID NO: 1) were prepared by virus infection of sarcoma cell lines. A PCR-amplified CD39 gene was cloned into a murine stem cell virus expression vector with a neomycin resistance gene and sequenced to confirm the identity. To prepare virus particles, HEK 293t cells with retroviral packaging proteins were transfected, in the presence of transfection reagent FUGENE HD (Roche), with the retroviral expression vector containing CD39. The virus particles collected from the supernatant of the culture media 48 hours after transfection were used to infect the sarcoma cells. After G418 selection, stable transfectants were pooled and then cloned by limiting dilution. Clones were then picked and expanded in the presence of antibiotics. Clones with the highest expression level of CD39 as measured by flow cytometry were expanded and banked. These cell lines were then used to immunize the syngeneic mice for antibody production and in the binding assays for antibody selection as follows.

For immunization, the mouse sarcoma cell line that expresses CD39 was implanted subcutaneously in 129s6/SvEv mice, which are syngeneic with the sarcoma line. Mice were boosted with the cell line three days prior to spleen harvest. Splenocytes were isolated as single cells and fused with SP2-MIL6 cells using PEG1500. Resulting hybridomas were plated in 384-well plates and allowed to grow for ten days in the presence of the selection agent azaserine-hypoxanthine (Sigma Aldrich). Four splenocyte preparations from four different mice were fused separately (Table 6).

Antibodies against CD39 were initially selected using a cell-based enzyme-linked immunosorbant assay (ELISA) to detect binding to CD39. For this assay, the CD39 expressing sarcoma cells were plated in 384-well plates one day prior to the binding assay. Cells were then treated with hybridoma supernatants. Following incubation and wash, the presence of bound antibody was detected using a peroxidase-conjugated goat anti-mouse IgG antibody (Jackson ImmunoResearch Laboratories) followed by a chemiluminescent substrate (ThermoScientific SuperSignal ELISA Pico Substrate). Hybridomas identified as positive in the initial screen were transferred to the wells of a 96-well plate. After growth, the supernatants were tested in a similar assay for confirmation. Specificity of the hybridoma supernatants to CD39 was established by using the untransfected sarcoma cell line as a control in the cell-based ELISA. In addition, binding of the hybridoma supernatants to two cancer cell lines that express CD39 (i.e. the B-prolymphocytic leukemia cell line JVM-13 [ATCC cat# CRL3003] and the multiple myeloma cell line IM-9 [ATCC cat#CCL-159]) was confirmed by flow cytometry.

The isotype of the antibodies was identified by ELISA by using isotype specific goat anti-mouse Fc antibodies. For this assay, CD39 expressing cells were plated in 384-well plates one day prior to assay. Cells were then treated with hybridoma supernatants. Following incubation and wash, cells were incubated with peroxidase-conjugated goat antibody specific for mouse IgG1 or IgG2a (Jackson Immun-Research Laboratories), followed by a chemiluminescent substrate (ThermoScientific SuperSignal ELISA Pico Substrate).

Concentration of antibody in supernatants found to be positive for binding to the CD39 expressing cells was measured by ELISA. Supernatants were tested at multiple dilutions. For each antibody, the dilution that generated a value within the linear range of the standard curve was used to calculate the concentration of the antibody in the supernatant. Thirty-five monoclonal antibodies (designated 1-21A, 2-187A, 5-3A, 5-8C, 5-9A, 5-13A, 5-16A, 5-18B, 5-19C, 5-43B, 5-50B, 5-66B, 5-71A, 5-76A, 5-85C, 5-92A, 5-126A, 5-133A, 5-143A, 5-165C, 5-168C, 5-193A, 5-208A, 5-220C, 5-222B, 9-8B, 9-11A, 9-31A, 9-33A, 9-40A, 9-68A, 9-73B, 9-78A, 9-84A, 9-105A) were selected for purification and further analyzed in vitro and in vivo as described herein.

The sequences for four monoclonal antibodies (5-13A, 5-71A, 5-165C, 9-8B) are shown below.

The nucleic acid and amino acid sequences for the heavy chain and light chain variable regions of the antibody 5-13A are shown below:

5-13A heavy chain variable region
(SEQ ID NO: 180)
ATGGGATGGAGCCGGATCTTTCTCTTCCTCCTGTCAATAATTGCAGGTGT

CCATTGCCAGGTCCAGCTGCAGCAGTCTGGACCTGAGCTGGTGAAGCCTG

GGGCTTCAGTGAGGATATCCTGCAAGGCTTCTGGCTACACCTTCACAGGC

TACTATGTACACTGGGTGAAGCAGAGGCCTGGACAGGGACTTGAGTGGAT

TGGATGGATTTATCCTGGAAATGTAAATACTAAGTACAATGAGAAGTTCA

AGGCCAAGGCCACACTGACTGCAGACAAATCCTCCAGCACAGGCTACATG

CAGCTCAGCAGACTGACCTCTGAGGACTCTGCGGTCTATTTCTGTGCAAG

ATCCCCTTACTACGGTACTACCTATTACTATACTATGGACTACTGGGGTC

AAGGAACCTCAGTCACCGTCTCCTCA

MGWSRIFLFLLSIIAGVHCQVQLQQSGPELVKPGASVRISCKAS<u>GYTFTG
YYVH</u>WVKQRPGQGLEWIG<u>WIYPGNVNTKYNEKFK</u>AKATLTADKSSSTGYM
QLSRLTSEDSAVYFCAR<u>SPYYGTTYYYTMDY</u>WGQGTSVTVSS (SEQ ID
NO: 16; exemplary CDRs areunderlined; see also, Table 1)

5-13A light chain variable region
(SEQ ID NO: 181)
ATGGATTTTCATGTGCAGATTTTCAGCTTCATGCTAATCAGTGTCACAGT

CATATTGTCCAGTGGAGAAATTGTGCTCACCCAGTCTCCAGCATTCATGG

CTGCATCTCCAGGGGAGAAGGTCACCATCACCTGCAGTGTCAGTTTAATT

ATAAGTTCCAGGAACTTGCACTGGTACCAGCAGAAGTCAGAAACCTCCCC

CAAACCCTGGATTTATGGCACATCCAACCTGGCTTCTGGAGTCCCTGTTC

GCTTCAGTGGCAGTGGATCTGGGACCTCTTATTCTCTCACAATCAGCAGC

ATGGAGGCTGAAGATGCTGCCACTTATTACTGTCAACAGTGGAGTGATTA

CCCACTTACGTTCGGCTCGGGGACAAAGTTGGAAATAAAA

MDFHVQIFSFMLISVTVILSSGEIVLTQSPAFMAASPGEKVTITC<u>SVSLI
ISSRNLH</u>WYQQKSETSPKPWIY<u>GTSNLAS</u>GVPVRFSGSGSGTSYSLTISS
MEAEDAATYYC<u>QQWSDYPLT</u>FGSGTKLEIK (SEQ ID NO: 17;

exemplary CDRs areunderlined; see also, Table 1)

The nucleic acid and amino acid sequences for the heavy chain and light chain variable regions of the antibody 5-71A are shown below:

5-71A heavy chain variable region
(SEQ ID NO: 182)
ATGGACTCCAGGCTCAATTTAGTTTTCCTTGTCCTTATTTTAAAAGGTGT

CCAGTGTGATGTGCAGCTGGTGGAGTCGGGGGGAGGCTTAGTGCAGCCTG

GAGGGTCCCGGAAACTCTCCTGTGCAGCCTCTGGATTCACTTTCAGTAGC

TTTGGAATGCACTGGGTTCGTCAGGCTCCAGAGAAGGGGCTGGAGTTGGT

CGCATACATTAGTAGTGGCAGTACTATCAGATACTATTCAGACACAGTGA

AGGGCCGATTCACCATCTCCAGAGACAATCCCAAGAACACCCTGTTCCTG

CAAATGACCAGTCTAAGGTCTGAGGACACGGCCATGTATTACTGTGCAAG

ATTTCTCTATGAAGGTTTCCGCTATGGTATGGACTACTGGGGTCAAGGAA

CCTCAGTCACCGTCTCCTCA

MDSRLNLVFLVLILKGVQCDVQLVESGGGLVQPGGSRKLSCAAS<u>GFTFSS
FGMH</u>WVRQAPEKGLELVA<u>YISSGSTIRYYSDTVK</u>GRFTISRDNPKNTLFL
QMTSLRSEDTAMYYCAR<u>FLYEGFRYGMDY</u>WGQGTSVTVSS (SEQ ID

NO: 18; exemplary CDRs are underlined; see also,

Table 2)

5-71A light chain variable region
(SEQ ID NO: 183)
ATGAAGTTGCCTGTTAGGCTGTTGGTGCTGATGTTCTGGATTCCTGCTTC

CAGCAGTGATGTTTTGATGACCCAGACTCCACTCTCCCTGCCTGTCAGTC

TTGGAGATCAAGCCTCCATCTCTTGCAGATCTAGTCAGAGCATTGTACAT

AGTAATGGAAACACCTATTTAGAATGGTACCTGCAGAAACCAGGCCAGTC

TCCAAAGCTCCTGATCTACAAAGTTTCCAACCGATTTTCTGGGGTCCCAG

ACAGGTTCAGTGGCAGTGGATCAGGGACAGATTTCACACTCAAGATCAGC

AGAGTGGAGGCTGAGGATCTGGGAATTTATTACTGCTTTCAAGGTTCACA

TGTTCCGAACACGTTCGGAGGGGGGACCAAGCTGGAAATAAAA

MKLPVRLLVLMFWIPASSSDVLMTQTPLSLPVSLGDQASISC<u>RSSQSIVH</u>

<u>SNGNTYLE</u>WYLQKPGQSPKLLIY<u>KVSNRFS</u>GVPDRFSGSGSGTDFTLKIS

RVEAEDLGIYYC<u>FQGSHVPNT</u>FGGGTKLEIK (SEQ ID NO: 19;

exemplary CDRs areunderlined; see also, Table 2)

The nucleic acid and amino acid sequences for the heavy chain and light chain variable regions of the antibody 5-165C are shown below:

5-165C heavy chain variable region
(SEQ ID NO: 184)
ATGCACTTCGGGCTCAGCTTGATTTTCCTTGCCCTCATTTTAAAAGGTGT

CCAGTGTGAGGTGCAGCTGGTGGAGTCGGGGGAGACTTAGTGAAGCCTG

GAGGGTCCCTGAAACTCTCCTGTGCAGCCTTTGGATTCACTTTCAGTAGG

TATGGCATGTCTTGGGTTCGCCAGACTCCAGACAAGAGGCTGGAGTGGGT

CGCAACCATTACTAGTGGTGGTATTTACACCTACTATCCAGACAGTGTGA

AGGGGCGATTCACCATTTCCAGAGACAATGCCAAGAACACCCTGTACCTG

CAAATGAGCAGTCTGAAGTCCGAGGAGACAGCCATGTATTACTGTGCAAG

ACATGGCCAGTTTGGGGATTACTATGGTATGGACTATTGGGGTCAAGGAA

CCTCAGTCACCGTCTCCTCA

MHFGLSLIFLALILKGVQCEVQLVESGGDLVKPGGSLKLSCAAF<u>GFTFSR</u>

<u>YGMS</u>WVRQTPDKRLEWVA<u>TITSGGIYTYYPDSVKG</u>RFTISRDNAKNTLYL

QMSSLKSEETAMYYCAR<u>HGQFGDYYGMDY</u>WGQGTSVTVSS (SEQ ID

NO: 20; exemplary CDRs are underlined; see also,

Table 3)

5-165C light chain variable region
(SEQ ID NO: 185)
ATGAAGTTGCCTGTTAGGCTGTTGGTGCTGATGTTCTGGATTCCTGCTTC

CAGCAGTGATGTTGTGATGACCCAAACTCCACTCTCCCTGCCTGTCAGTC

TTGGAGATCAAGCCTCCATCTCTTGCAGATCTAGTCAGAGCCTTTTACAC

AGTAATGGAAACACCTATTTACATTGGTACCTGCAGAAGCCAGGCCAGTC

TCCAAAGCTCCTGATCTACAAAGTTTCCAACCGATTTTCTGGGGTCCCAG

ACAGGTTCAGTGGCAGTGGATCAGGGACAGATTTCACACTCAAGATCAGC

AGAGTGGAGGCTGAGGATCTGGGAGTTTATTTCTGCTCTCAAAGTACACA

TGTTCCGTACACGTTCGGAGGGGGGACCAAGCTGGAAATAAAA

MKLPVRLLVLMFWIPASSSDVVMTQTPLSLPVSLGDQASISC<u>RSSQSLLH</u>

<u>SNGNTYLH</u>VVYLQKPGQSPKLLIY<u>KVSNRFS</u>GVPDRFSGSGSGTDFTLKI

SRVEAEDLGVYFC<u>SQSTHVPYT</u>FGGGTKLEIK (SEQ ID NO: 21;

exemplary CDRs are underlined; see also, Table 3)

The nucleic acid and amino acid sequences for the heavy chain and light chain variable regions of the antibody 9-8B are shown below:

9-8B heavy chain variable region
(SEQ ID NO: 186)
ATGGCTTGGGTGTGGACCTTGCTATTCCTGATGGCAGCTGCCCAAAGTGC

CCAAGCACAGATCCAGTTGGTGCAGTCTGGACCTGAGCTGAAGAAGCCTG

GAGAGACAGTCAAGATCTCCTGCAAGGCTTCTGGATATACCTTCACACAC

TATGGAATGAACTGGGTGAAGCAGGCTCCAGGAAAGGGTTTAAAGTGGAT

GGGCTGGATAAACACCTACACTGGAGAGTTAACATATGCTGATGACTTCA

AGGGACGGTTTGCCTTCTCTTTGGAGACCTCTGCCAGCACTGCCTATTTG

CAGATCAACAACCTCAAAAATGAGGACACGGCTACATATTTCTGTGCAAG

AAGAGCCTACTATAGGTACGACTATGTAATGGACTACTGGGGTCAAGGAA

CCTCAGTCACCGTCTCCTCA

MAWVWTLLFLMAAAQSAQAQIQLVQSGPELKKPGETVKISCKASGYTFT<u>H</u>

<u>YGMN</u>WVKQAPGKGLKWMG<u>WINTYTGELTYADDFKG</u>RFAFSLETSASTAYL

QINNLKNEDTATYFCAR<u>RAYYRYDYVMDY</u>WGQGTSVTVSS (SEQ ID

NO: 22; exemplary CDRs are underlined; see also,

Table 4)

9-8B light chain variable region
(SEQ ID NO: 187)
ATGGGCATCAAGATGGAGTCACAGACTCAGGTCTTTGTATACATGTTGCT

GTGGTTGTCTGGTGTTGATGGAGACATTGTGATGACCCAGTCTCAAAAAT

TCATGTCCACATCAGTAGGAGACAGGGTCAGCGTCACCTGCAAGGCCAGT

CACAATGTGGGTACTAATGTAGCCTGGTATCAACAGAAACCAGGGCAATC

TCCTAAAGCACTGATTTACTCGGCATCCTACCGGTACAGTGGAGTCCCTG

GTCGCTTCACAGGCAGTGGATCTGGGACAGATTTCACTCTCACCATCAGC

AATGTGCAGTCTGAAGACTTGGCAGAGTATTTCTGTCACCAATATAACAA

CTATCCGTACACGTTCGGAGGGGGGACCAAGCTGGAAATAAAA

MGIKMESQTQVFVYMLLWLSGVDGDIVMTQSQKFMSTSVGDRVSVTC<u>KAS</u>

<u>HNVGTNVA</u>WYQQKPGQSPKALIY<u>SASYRYS</u>GVPGRFTGSGSGTDFTLTIS

NVQSEDLAEYFC<u>HQYNNYPYT</u>FGGGTKLEIK (SEQ ID NO: 23;

exemplary CDRsare underlined; see also, Table 4)

Example 3—Isotyping and Binning of Anti-CD39 Antibodies

Individual hybridoma supernatants from Example 2 containing antibodies which recognize CD39 were assessed for isotype by ELISA detection using isotype—specific secondary antibodies, as described by Liao-Chan S, et al., (2014) *Journal of Immunological Methods* 405: 1-14. A competition ELISA was performed to establish competitive binding bins. Individual wells containing cells expressing CD39 were incubated with either buffer or each anti-CD39 isotyped (e.g., IgG1 or IgG2b) antibody containing hybridoma supernatant to be used in the competition ELISA. After 1 hour, the wells were washed. Next, these individual wells of the ELISA plate are incubated for 1 hour with each anti-CD39 isotyped (of a different isotype, e.g., IgG2a) antibody containing hybridoma supernatant. After washing, the wells were incubated with a specific secondary antibody (Jackson ImmunoResearch goat anti-mouse IgG2a HRP) and detected with SuperSignal ELISA Pico Chemiluminescent substrate (Thermo Scientific). For each anti-CD39 isotyped antibody (of a different isotype, e.g., IgG2a) containing hybridoma supernatant, the luminescence signals from the wells first incubated with each anti-CD39 isotyped (e.g., IgG1) antibody containing hybridoma supernatant are normalized against the luminescence signals from the wells first incubated with buffer only.

In the first round of competition ELISAs, out of a total of 276 hybridoma supernatants, 44 hybridoma supernatants of the IgG2a isotype were profiled against 41 hybridoma supernatants of the IgG1 or IgG2b isotype. Out of the set of 41 hybridoma supernatants of the IgG1 or IgG2b isotype, a smaller diverse set of 18 hybridoma supernatants of the IgG1 or IgG2b isotype was used in a second round of competition ELISAs. In the second round the complete set of 276 hybridoma supernatants of the IgG2a isotype was profiled against the diverse set of 18 hybridoma supernatants of the IgG1 or IgG2b isotype. To obtain a diverse antibody panel for in vivo testing, thirty-five out of 276 hybridomas of the IgG2a isotype (1-21A, 2-187A, 5-3A, 5-8C, 5-9A, 5-13A, 5-16A, 5-18B, 5-19C, 5-43B, 5-50B, 5-66B, 5-71A, 5-76A, 5-85C, 5-92A, 5-126A, 5-133A, 5-143A, 5-165C, 5-168C, 5-193A, 5-208A, 5-220C, 5-222B, 9-8B, 9-11A, 9-31A, 9-33A, 9-40A, 9-68A, 9-73B, 9-78A, 9-84A, 9-105A) were prioritized for purification. While 31 out of thirty-five antibodies were assigned to 1 of 7 epitope bins, 4 antibodies were not assigned to any epitope bin as shown in Table 6.

TABLE 6

| Purified antibody # | Hybridoma fusion # | Purified antibody identifier | Epitope bin |
|---|---|---|---|
| 1 | 1 | 1-21A | 5 |
| 2 | 2 | 2-187A | 5 |
| 3 | 3 | 5-3A | 6 |
| 4 | 3 | 5-8C | 1 |
| 5 | 3 | 5-9A | 5 |
| 6 | 3 | 5-13A | 6 |
| 7 | 3 | 5-16A | 3 |
| 8 | 3 | 5-18B | 5 |
| 9 | 3 | 5-19C | 6 |
| 10 | 3 | 5-43B | 2 |
| 11 | 3 | 5-50B | unassigned |
| 12 | 3 | 5-66B | 6 |
| 13 | 3 | 5-71A | 5 |
| 14 | 3 | 5-76A | 6 |
| 15 | 3 | 5-85C | 5 |
| 16 | 3 | 5-92A | 6 |
| 17 | 3 | 5-126A | 6 |
| 18 | 3 | 5-133A | unassigned |
| 19 | 3 | 5-143A | 5 |
| 20 | 3 | 5-165C | 2 |
| 21 | 3 | 5-168C | 5 |
| 22 | 3 | 5-193A | 4 |
| 23 | 3 | 5-208A | 7 |
| 24 | 3 | 5-220C | 4 |
| 25 | 3 | 5-222B | 7 |
| 26 | 4 | 9-8B | 1 |
| 27 | 4 | 9-11A | 3 |
| 28 | 4 | 9-31A | 3 |
| 29 | 4 | 9-33A | 4 |
| 30 | 4 | 9-40A | 3 |
| 31 | 4 | 9-68A | 2 |
| 32 | 4 | 9-73B | unassigned |
| 33 | 4 | 9-78A | unassigned |
| 34 | 4 | 9-84A | 4 |
| 35 | 4 | 9-105A | 3 |

Example 4—Binding and Binding Affinity Assays

Additional binding assays were conducted. Affinity measurements of thirty-five purified anti-CD39 antibodies as described in Example 2 were carried out on the OctetQK384 sytem (ForteBio). After coating anti-mouse IgG Fc sensors with a purified anti-CD39 antibody, association and dissociation of recombinant human CD39 (R&D Systems) was monitored. Affinity (KD) and kinetic constants (ka and kd) were derived using ForteBio's software. The KD, ka and kd values for thirty-five anti-CD39 antibodies are shown in Table 7.

TABLE 7

| Purified antibody identifier | KD (nM) | ka (M−1s−1) | kd (s−1) |
|---|---|---|---|
| 1-21A | 2.08 | 2.66E−05 | 5.53E−04 |
| 2-187A | 4.34 | 8.15E+04 | 3.54E−04 |
| 5-3A | 1.90 | 1.70E+05 | 3.22E−04 |
| 5-8C | 0.23 | 1.56E+05 | 3.61E−05 |
| 5-9A | 0.23 | 9.90E+04 | 2.31E−05 |
| 5-13A | 1.52 | 1.05E+05 | 1.59E−04 |
| 5-16A | 2.64 | 1.24E+05 | 3.28E−04 |
| 5-18B | 7.62 | 7.01E+04 | 5.34E−04 |
| 5-19C | 2.53 | 1.04E+05 | 2.63E−04 |
| 5-43B | 0.44 | 1.41E−05 | 6.27E−05 |
| 5-50B | 0.50 | 7.58E+04 | 3.76E−05 |
| 5-66B | 4.30 | 1.04E+05 | 4.46E−04 |
| 5-71A | 0.73 | 7.11E+04 | 5.22E−05 |
| 5-76A | 1.63 | 1.23E−05 | 2.00E−04 |
| 5-85C | 0.31 | 1.49E+05 | 4.55E−05 |
| 5-92A | 1.20 | 1.35E+05 | 1.63E−04 |
| 5-126A | 6.89 | 5.37E−04 | 3.70E−04 |
| 5-133A | 3.63 | 7.58E−04 | 2.75E−04 |
| 5-143A | 7.88 | 5.38E+04 | 4.24E−04 |
| 5-165C | 2.53 | 7.74E−04 | 1.96E−04 |
| 5-168C | 8.34 | 7.18E+04 | 5.99E−04 |
| 5-193A | 230.40 | 1.31E+04 | 3.01E−03 |
| 5-208A | 2.03 | 1.04E+05 | 2.11E−04 |
| 5-220C | 2.15 | 1.57E+05 | 3.36E−04 |
| 5-222B | 2.58 | 9.59E+04 | 2.47E−04 |
| 9-8B | 3.10 | 2.73E−05 | 8.48E−04 |
| 9-11A | 4.79 | 4.87E+04 | 2.33E−04 |
| 9-31A | 14.25 | 1.74E+05 | 2.48E−03 |
| 9-33A | 10.51 | 1.88E+05 | 1.98E−03 |
| 9-40A | 20.43 | 1.03E+04 | 2.11E−04 |
| 9-68A | 0.95 | 7.42E+04 | 7.03E−05 |
| 9-73B | no binding | no binding | no binding |
| 9-78A | 2.52 | 2.27E+05 | 5.71E−04 |
| 9-84A | no binding | no binding | no binding |
| 9-105A | 27.55 | 3.19E+04 | 8.79E−04 |

Binding of antibody was also assessed in a cell line that expresses endogenous human CD39 (e.g. the B-prolymphocytic leukemia cell line JVM-13). Thirty-five anti-CD39 antibodies as described in Example 2 were tested for their binding to JVM-13 cells. JVM-13 cells were washed with PBS with 0.1% BSA, incubated with 100, 25, 6.25, 1.56, 0.39, 0.09, 0.02 and 0 nM of anti-CD39 antibody for 4 hours at 4° C., washed twice with PBS with 0.1% BSA, incubated with 20 µg/ml of R-Phycoerythrin-AffiniPure F(ab')2 fragment goat anti-mouse IgG, Fc fragment specific (Jackson ImmunoResearch) for 30 minutes at 4° C., washed twice with PBS with 0.1% BSA, 15 incubated with the viability dye TO-PRO-3 iodide (Life Technologies), and immediately analyzed on a MACSQuant Analyzer instrument (Miltenyi). Median fluorescence intensities for each primary antibody concentration were used to derive a flow EC50/Kd using the one site—specific binding with Hill slope model in Prism (GraphPad Prism Software). Results are shown as Flow EC50 in Table 8.

TABLE 8

| Purified antibody identifier | Flow EC50 (nM) on JVM-13 cells |
|---|---|
| 1-21A | 10.49 |
| 2-187A | 0.16 |
| 5-3A | 0.09 |
| 5-8C | 0.14 |
| 5-9A | 0.06 |
| 5-13A | 0.18 |
| 5-16A | 0.09 |
| 5-18B | 0.26 |
| 5-19C | 0.12 |
| 5-43B | 0.13 |
| 5-50B | 0.44 |
| 5-66B | 0.17 |
| 5-71A | 0.09 |
| 5-76A | 0.16 |
| 5-85C | 0.12 |
| 5-92A | 0.14 |
| 5-126A | 0.35 |
| 5-133A | 0.40 |
| 5-143A | 0.21 |
| 5-165C | 0.11 |
| 5-168C | 0.07 |
| 5-193A | 0.51 |
| 5-208A | 0.10 |
| 5-220C | 0.15 |
| 5-222B | 0.12 |
| 9-8B | 0.26 |
| 9-11A | 0.20 |
| 9-31A | 0.10 |
| 9-33A | 0.15 |
| 9-40A | 1.29 |
| 9-68A | 0.39 |
| 9-73B | poor fit |
| 9-78A | 0.13 |
| 9-84A | poor fit |
| 9-105A | 0.17 |

Affinity measurements of four exemplary purified anti-CD39 antibodies (5-13A, 5-71A, 5-165C and 9-31A) were also carried on the ProteOn XPR36 (BioRad) using a GLM sensor chip. The running buffer contained 10 mM HEPES, 150 mM NaCl, 0.005% Tween-20 at pH 7.4. All data were collected at 25 degrees C. Anti-mouse capturing antibody was amine coupled at four densities on flow cells using standard s—NHS/EDC activation. A dilution series of 150, 16.6, 5.5 and 1.85 nM CD39 antigen (R&D Systems) was tested for binding to the anti-CD39 antibody surfaces. The data were processed by subtracting the response from the inter-reference surfaces as well as the buffer blank injection. The processed response data from four density surfaces were globally fit to a simple 1:1 interaction model using Scrubber 2 (Biologic Software Pty Ltd). The data are shown in Table 9.

TABLE 9

| Purified antibody identifier | KD (nM) | ka (M−1s−1) | kd (s−1) |
|---|---|---|---|
| 5-13A | 1.16 | 1.91E+05 | 2.21E−04 |
| 5-165C | 1.25 | 8.75E+05 | 1.09E−04 |
| 5-71A | 0.09 | 1.53E+05 | 1.40E−05 |
| 9-31A | 20.4 | 1.93E+05 | 3.92E−03 |

Example 5—Inhibition of ATPase Activity

Anti-CD39 antibodies were tested for their ability to modulate (e.g., inhibit) ATPase activity of CD39 expressed on different cell types, including, for example, the plasma cell leukemia ARH-77 line [ATCC Cat# CRL 1621], the multiple myeloma IM-9 line and primary HUVEC cells [Lonza Cat# CC-2519] (see, e.g., Tables 10, 11 and 12). Using a highly sensitive radioactive CD39-based assay, ATPase activity in cell suspension aliquots was measured by detecting 33Pi formed due to enzymatic cleavage of [γ-33P]-ATP. Uncleaved [γ-33P]-ATP was precipitated with charcoal suspension, and 33Pi was determined by liquid scintillation counting of supernatants. Antibodies were tested at either 1200 ng/mL (ARH-77 and IM-9 cells) or 900 ng/mL (HUVEC cells). Data are expressed as a concentration of formed 33Pi in 100 μL reaction volume per 1 minute incubation at 37° C. and normalized to control treated cells.

TABLE 10

Inhibition of ATPase Activity in ARH-77 cells

| Antibody clone | % Inhibition |
|---|---|
| 5-165C | −2.5 |
| 5-43B | −1.7 |
| 5-133A | 1.0 |
| 5-50B | 4.7 |
| 9-78A | 20.6 |
| 9-8B | 36.5 |
| 5-13A | −6.2 |
| 5-222B | −0.2 |
| 5-208A | −9.3 |
| 5-3A | −3.2 |
| 5-71A | 3.6 |
| 5-9A | 5.0 |
| 5-168C | −5.9 |
| 5-85C | 3.6 |
| 5-143A | 0.0 |
| 9-31 | 1.4 |
| 9-11A | −0.2 |
| 5-220C | 4.4 |
| 5-16A | 1.6 |
| 5-92A | −0.9 |
| BSA | −0.4 |

TABLE 11

Inhibition of ATPase Activity in IM-9 cells

| Antibody clone | % Inhibition |
|---|---|
| 5-165C | −0.1 |
| 9-78A | 21.2 |
| 9-8B | 29.8 |
| 5-13A | 0.8 |
| 5-3A | −5.3 |
| 5-85C | 0.5 |
| 5-168C | −0.9 |
| 5-220C | 0.4 |
| 5-16A | −0.4 |

TABLE 12

Inhibition of ATPase Activity in HUVEC cells

| Antibody clone | % Inhibition |
|---|---|
| 5-165C | −9.8 |
| 9-78A | 15.1 |
| 9-8B | 33.7 |
| 5-13A | −4.4 |
| 5-85C | 3.6 |
| 5-220C | 5.7 |
| 5-16A | −1.4 |

Anti-CD39 antibodies were also tested for their ability to modulate (e.g., inhibit) ATPase activity of CD39 with a flow-based platelet aggregation assay. Platelet aggregation was evaluated by flow cytometry (FC) in purified platelet (plts) samples as described previously (De Cuyper, et al., 2013, Blood 121(1): e70-80). Briefly, purified platelets incubated with either 0.3 µM carboxyfluorscein succinimidyl ester (CFSE; Molecular Probes, Eugene, Oreg.) or 2 µM PKH26 (Sigma-Aldrich, St. Louis, Mo.) were combined at a 1:1 ratio. Aliquots were pre-incubated with 2 µM recombinant human CD39 (SinoBiological) and 1 mM ATP (Tocris) at 37° C. while shaking at 1000 rpm. The pre-incubated aliquots received 4 µM 9-8B, 10 µM POM-1 or no treatment followed by a second incubation before analysis by FC. Human platelet samples were obtained from Allcells (Alameda, Calif.). Enzymatic inhibitory function of an exemplary anti-CD39 antibody (e.g., 9-8B) was determined with a flow-based platelet aggregation method. ADP-mediated platelet aggregation was induced by addition of ATP to enzymatically-active recombinant human CD39. ADP-induced platelet aggregation was increased 1.6 fold compared with untreated cells, but significantly inhibited by 67% in the presence of 4 µM 9-8B (p<0.001).

TABLE 13

Inhibition of ADP-induced Platelet Aggregation

| Anti-CD39 | % Inhibition |
| --- | --- |
| 9-8B | 67% |

Example 6—Anti-Tumor Activity of Anti-CD 39 Antibodies

Anti-CD39 antibodies were tested for their anti-tumor activity in animal tumor models.

For these studies, a plasma cell leukemia line ARH77 was obtained from ATCC and cultured according to the supplier's protocols. Animals were obtained from Taconic (Hudson, N.Y.).

In these experiments, 4-6 week-old immunodeficient CB17 female mice were used in an ARH77 tumor model. Mice were subcutaneously injected on the right flank with 4.6-5.2×10$^6$ viable ARH 77 cells in a mixture of PBS (without magnesium or calcium) and BD Matrigel (BD Biosciences) at a 1:1 ratio. The injected total volume per mouse was 200 µl with 50% being Matrigel (BD Biosciences). Once the tumor reached a specified size mice were randomized. Antibodies were administered weekly at 15 mg/kg for up to six weeks (ADCs weekly at 3 mg/kg for two weeks), bodyweights and tumors measured once and twice weekly, respectively. Tumor volume was calculated as described (van der Horst et al., 2009, Neoplasia 11(4):355-364). Experiments were performed on groups of at least 8 animals per experimental point.

Statistical significance between treatment and control groups was calculated using the Graphpad Prism software package and applying Student's two-tailed t-test. A p-value of less than 0.05 was considered significant. Cyclophosphamide and/or Rituxan were used as active controls. Results of exemplary experiments shown as tumor growth inhibition (TGI) are shown in Tables 14 and 15.

TABLE 14

Anti-CD39 mAbs in an ARH-77 Model*

| Treatments | Volume [mm$^3$] | Std Dev [mm$^3$] | TGI [%] | p-value |
| --- | --- | --- | --- | --- |
| Isotype CTRL | 2361 | 1346 | — | — |
| 5-13A | 301 | 37 | −93 | 0.00061 |
| 5-165C | 282 | 38 | −94 | 0.00056 |
| Cyclophosphamide | 527 | 396 | −83 | 0.00495 |

*Study# EVH-113; n = 8animals/group; measurements taken on Day 47 of study
5-165C antibody dosed at 15 mg/kg on days 9, 16, 23, 30, and 37
5-13A antibody dosed at 15 mg/kg on days 9 and 16
Cyclophosphamide dosed at 125 mg/kg

TABLE 15

Anti-CD39 mAbs in an ARH-77 Model*

| Treatments | Volume [mm$^3$] | Std Dev [mm$^3$] | TGI [%] | p-value |
| --- | --- | --- | --- | --- |
| Isotype CTRL | 4680 | 2312 | — | — |
| 9-8B | 431 | 448 | −96 | 0.000453 |
| 5-165C | 1213 | 882 | −78 | 0.003000 |
| Rituxan | 2105 | 1555 | −58 | 0.030903 |
| Cyclophosphamide | 828 | 124 | −96 | 0.000862 |

*Study# GH-13; n = 7 animals/group; measurements taken on Day 33 of study
Antibodies dosed at 15 mg/kg on days 15, 22, 29, and 36
Cyclophosphamide dosed at 125 mg/kg In additional experiments, anti-CD39 antibodies were tested for their in vivo anti-tumor effects against the cell line JVM-13. For these studies, a B-prolymphocytic leukemia cell line JVM-13 was obtained from ATCC and cultured according to the supplier's protocols.

In these experiments, 4-6 week-old immunodeficient NOD female mice were used for the JVM-13 tumor model. Mice were subcutaneously injected on the right flank with 1.1×10$^7$ viable JVM-13 cells in a mixture of PBS (without magnesium or calcium) and BD Matrigel (BD Biosciences) at a 1:1 ratio. The injected total volume per mouse was 200 µl with 50% being Matrigel (BD Biosciences). Once the tumor reached a 150 mm$^3$ in size, mice were randomized to treatment groups. Antibodies were administered weekly at 15 mg/kg for up to six weeks (ADCs weekly at 3 mg/kg for two weeks), bodyweights and tumors measured once and twice weekly, respectively. Tumor volume was calculated as described (van der Horst et al., 2009, Neoplasia 11(4):355-364). Experiments were performed on groups of at least 8 animals per experimental point.

Statistical significance between treatment and control groups was calculated using the Graphpad Prism software package and applying Student's two-tailed t-test. A p-value of less than 0.05 was considered significant. Cyclophosphamide dosed at 125 mg/kg was used as active control. Results of exemplary experiments shown as tumor growth inhibition (TGI) are shown in Table 16.

TABLE 16

Anti-CD39 mAbs in JVM-13 Model*

| Treatments | Volume [mm$^3$] | Std Dev [mm$^3$] | TGI [%] | p-value |
| --- | --- | --- | --- | --- |
| Isotype CTRL | 2554 | 891 | — | — |
| 5-13A | 2113 | 1112 | −18 | 0.414400 |

TABLE 16-continued

Anti-CD39 mAbs in JVM-13 Model*

| Treatments | Volume [mm³] | Std Dev [mm³] | TGI [%] | p-value |
|---|---|---|---|---|
| 5-165C | 1036 | 458 | −63 | 0.001420 |
| Cyclophosphamide | 1034 | 423 | −63 | 0.001250 |

*Study# EVH-107; n = 8 animals/group; measurements taken on Day 35 of study
5-165C and isotype control dosed at 15 mg/kg on days 7, 14, 21, 28 and 34
5-13A dosed at 8 mg/kg on day 14
Cyclophosphamide dosed at 125 mg/kg In additional experiments, anti-CD39 antibodies were tested for their in vivo anti-tumor effects against the cell line SW684. For these studies, a fibrosarcoma cell line SW684 was obtained from ATCC and cultured according to the supplier's protocols.

In these experiments, 4-6 week-old immunedeficient NOD female mice were used for the SW684 tumor model. Mice were subcutaneously injected on the right flank with $4.7 \times 10^6$ viable SW684 cells in a mixture of PBS (without magnesium or calcium) and BD Matrigel (BD Biosciences) at a 1:1 ratio. The injected total volume per mouse was 200 µl with 50% being Matrigel (BD Biosciences). Once the tumor reached a 150 mm³ in size, mice were randomized to treatment groups. Antibodies were administered weekly at 15 mg/kg for up to six weeks (ADCs weekly at 3 mg/kg for two weeks), bodyweights and tumors measured once and twice weekly, respectively. Tumor volume was calculated as described (van der Horst et al., 2009, Neoplasia 11(4):355-364). Experiments were performed on groups of at least 8 animals per experimental point.

Statistical significance between treatment and control groups was calculated using the Graphpad Prism software package and applying Student's two-tailed t-test. A p-value of less than 0.05 was considered significant. Abraxane dosed at 40 mg/kg was used as active control. Results of exemplary experiments shown as tumor growth inhibition (TGI) are shown in Table 17.

TABLE 17

Anti-CD39 mAbs in a SW684 Model*

| Treatments | Volume [mm³] | Std Dev [mm³] | TGI [%] | p-value |
|---|---|---|---|---|
| Isotype CTRL | 3849 | 898 | — | — |
| 5-13A | 2508 | 737 | −36 | 0.0125 |
| 5-165C | 1952 | 748 | −52 | 0.0010 |
| Abraxane | 188 | 135 | −99 | 3.8E-8 |

*Study# GH-7; n = 8 animals/group; measurements taken on Day 69 of study
Antibodies were dosed at 15 mg/kg on 49, 56, 63, and 69
Abraxane dosed at 40 mg/kg In additional experiments, anti-CD39 antibodies were tested for their in vivo anti-tumor effects in a patient-derived xenograft model (PDX) model named IGN-SRC-004.

Patient-derived tumor tissue was passaged in vivo as described previously (van der Horst et al., Neoplasia 2009). IGN-SRC-004 is a patient-derived sarcoma xenograft line that was established at Igenica Biotherapeutics. Studies were conducted with anti-CD39 antibodies in this aggressive tumor model (e.g., disseminated cells could be detected in lymph nodes as early as 21 days past implantation and after 30 days IGN-SRC-004 tumor cells had metastasized to the spleen, kidneys, liver and lungs). In these experiments, 4-6 week-old immunodeficient NOG female mice were used. NOG mice are T-, B-, and NK cell-deficient and have non-functional macrophages, so antibody-dependent cell-mediated cytotoxicity (ADCC) is not possible. Mice were subcutaneously injected on the right flank with $5-7.1 \times 10^6$ viable IGN-SRC-004 tumor cells in a mixture of PBS (without magnesium or calcium) and BD Matrigel™ (BD Biosciences). Once the tumor reached a size around 65-300 mm³ mice were randomized. Anti-CD39 antibodies were administered weekly, and bodyweights and tumors were measured once and twice weekly, respectively. Tumor volume was calculated as described (van der Horst et al., supra). Experiments were performed on groups of at least eight animals per experimental point.

Statistical significance between treatment and control groups was calculated using the Graphpad Prism® software package and applying Student's two-tailed t-test. A p-value of less than 0.05 was considered significant. Abraxane dosed at 40 mg/kg was used as active control. Results of exemplary experiments shown as tumor growth inhibition (TGI) are shown in Tables 18 and 19.

TABLE 18

Anti-CD39 mAbs in a IGN-SRC-004 Model*

| Treatments | Volume [mm³] | Std Dev [mm³] | TGI [%] | p-value |
|---|---|---|---|---|
| Isotype CTRL | 2643 | 617 | — | — |
| 5-13A | 1130 | 521 | −61 | 0.0007060 |
| 5-165C | 598 | 359 | −83 | 0.0000088 |
| Abraxane | 208 | 51 | −98 | 0.0000001 |

*Study# GH-08; n = 9 animals/group; measurements taken on Day 37 of study
Antibodies dosed at 15 mg/kg on days 13, 20, 27 and 34
Abraxane dosed at 40 mg/kg

TABLE 19

Anti-CD39 mAbs in a IGN-SRC-004 Model*

| Treatments | Volume [mm³] | Std Dev [mm³] | TGI [%] | p-value |
|---|---|---|---|---|
| Isotype CTRL | 2319 | 417 | — | — |
| 9-8B | 1542 | 459 | −37 | 0.001708 |
| 5-165C | 1205 | 411 | −53 | 0.000032 |
| Abraxane | 451 | 332 | −88 | 1.79589E-17 |

*Study# GH-14; n = 9 animals/group; measurements taken on Day 24 of study
Antibodies dosed at 15 mg/kg on days 13 and 21
Abraxane dosed at 40 mg/kg In additional experiments, anti-CD39 antibodies were tested for their in vivo anti-tumor effects (e.g., increasing survival) in a patient-derived xenograft (PDX) named IGN-SRC-004.

For these studies, mice were subcutaneously injected on the right flank with $5 \times 10^6$ viable IGN-SRC-004 tumor cells in a mixture of PBS (without magnesium or calcium) and BD Matrigel™ (BD Biosciences). Mice with established tumors of 122 mm³±21 mm³ were randomized and treated weekly at 15 mg/kg with an exemplary anti-CD39 antibody (e.g., 9-8B, 5-165C) or an isotype control antibody (n=38/treatment) and mice were euthanized when moribund. Tumors were measured twice weekly until day 27. Tumor volume was calculated as described (van der Horst et al., supra.)

Statistical significance between treatment and control group was calculated using the Graphpad Prism® software package and applying Mantel-Cox test. A p-value of less than 0.05 was considered significant.

The exemplary anti-CD39 antibodies 9-8B and 5-165C induced tumor growth inhibition of 49% and 47%, respectively (both p<0.001) as shown in Table 20. Moreover, 47% of 9-8B and 79% of 5-165C treated animals were alive on day 41, while 100% of the animals in the control group were moribund. The survival of the 9-8B and 5-165C treatment groups was increased by 21 and 17 days, respectively (62 days vs 41 days; p<0.0001, 58 days vs 41 days; p<0.0001) as shown in Table 21. Taken together, treatment with the anti-CD39 antibodies significantly improved survival in this metastatic patient-derived sarcoma model.

TABLE 20

Anti-CD39 mAbs in IGN-SRC-004 Model*

| Treatments | Volume [mm³] | Std Dev [mm³] | TGI [%] | p-value |
|---|---|---|---|---|
| Isotype CTRL | 1871 | 107 | — | — |
| 9-8B | 1010 | 91 | −49 | 4.6E−8 |
| 5-165C | 1056 | 94 | −47 | 2.3E−7 |

*Study# GH-15; n = 38 animals/group; TGI calculated with measurements taken on Day 27 of study
Antibodies dosed at 15 mg/kg on days 8, 15, 22, 29, 36, 43, 50 and 57

TABLE 21

Anti-CD39 mAbs in IGN-SRC-004 Model*

| Treatments | Increase survival [days] | 100% Animals moribund [Study day] | Mantel-Cox p-value |
|---|---|---|---|
| Isotype CTRL | — | 41 | — |
| 9-8B | 21 | 62 | <0.0001 |
| 5-165C | 17 | 58 | <0.0001 |

*Study# GH-15; n = 38 animals/group; log rank (Mantel Cox) calculated with data at end of study of study
Antibodies dosed at 15 mg/kg on days 8, 15, 22, 29, 36, 43, 50 and 57

Example 7—Preparation of Humanized Anti-CD39 Antibodies

Anti-CD39 antibodies prepared as described in Example 2 were selected for humanization. Exemplary anti-CD39 antibodies, including those designated 5-165C, 5-13A and 9-8B, were humanized by two methods. FIG. 1A and 1B show murine VH and VL sequences of exemplary anti-CD39 antibodies 5-13A, 9-8B, 5-71A and 5-165C (including consensus CDR sequences for 5-71A and 5-175C. Exemplary VH and VL sequences used for humanization and results of humanization, for example, for 5-165C, 5-13A and 9-8B anti-CD39 antibodies, are shown in FIGS. 2-7.

In a first humanization method, the sequence for each VH and for each VL was used as input to the IgBLAST program on the NCBI website (Ye, J. et al., Nucleic Acids Research 41: W34-W40 (2013)). IgBLAST is used to take a murine VH or VL sequence and compare it to a library of known human germline sequences; the databases used were IMGT human VH gene (F+ORF, 273 germline sequences) and IMGT human VL kappa gene (F+ORF, 74 germline sequences). IgBLAST returned the top 5 human germline sequences according to score.

In method 1, for 5-13A VH, human germline IGHV1-2-(allele 2) was chosen as the acceptor sequence; for 5-165C VH, human germline IGHV3-21 was chosen as acceptor sequence; and for 9-8B VH, human germline IGHV7-4 was chosen as acceptor sequence. The human heavy chain IGHJ4- (allele 1) joining region (J gene) was chosen from human joining region sequences compiled at IMGT® (the international ImMunoGeneTics information System® www.imgt.org). For 5-13A VL domain, human germline IGKV3-15 was chosen as acceptor sequences for 5-165C VL domain, human germline IGKV2D-29 was chosen as acceptor sequence; and for 9-8B VL domain, human germline IGKV1-16 was chosen as acceptor sequence. The human light chain IGKJ2-(allele 1) joining region (J gene) was chosen from human joining region sequences compiled at IMGT®

In a second humanization method (Carter et al., Proc Natl Acad Sci USA 89:4285-4289 (1992)), human VH subgroup III germline was used as acceptor for the exemplary murine VH sequences of 5-165C VH, 5-13A VH and 9-8B VH (e.g., IMGT IGHV3-48); human VL subgroup kappa I was used as acceptor for the exemplary 5-165C VL, 5-13A VL and 9-8B VH VL sequences (e.g., IMGT IGKV1-39).

Alteration of human germline framework (e.g., non-CDR residues in VH and VL) positions to corresponding parental murine 5-165C, 5-13A and 9-8B sequence was used to optimize binding of the humanized antibody. Potential changes for each humanized sequence were selected and are noted, for example, in FIGS. 2-7. Potential changes in the CDR sequences of the humanized antibodies in order to alleviate complications due to deamidation of solvent-exposed asparagines, oxidation of solvent-exposed methionines, and formation of isoaspartic acid, were selected and are also noted, for example, in FIGS. 2-7.

Computer-graphics models of murine 5-165C, 5-13A and 9-8B VH and VL domains were generated as a part of the selection of CDR and framework residues for alteration. The Swiss-PdB Viewer program was used (Guex, N and Peitsch, MC SWISS-MODEL and the Swiss-PdBViewer: An environment for comparative protein modeling. Electrophoresis 18:2714-2723 (1997) Expasy website. Crystal structures of antibodies were taken from the Protein Data Bank website (Berman, H M; Westbrook, J; Feng, Z; Gilliland, G; Bhat, T N; Weissig, H; Shindyalov, I N; Bourne P E, The Protein Data Bank Nucleic Acids Research 28:235-242 (2000). Exemplary sequences of humanized 5-13A, 5-165C, and 9-8B are shown, for example, in FIGS. 2-7.

Example 8—Preparation and Use of Antibody-Drug Conjugates

Antibody-drug conjugates (ADCs) are prepared and used in secondary ADC assays and direct ADC assays with antibodies to CD39, as illustrated in the following generic Scheme A, where a maleimido group is attached through a linker (L) to a cytotoxin (CTX):

Scheme A: ADCs with conventional maleimide linker-drug conjugates

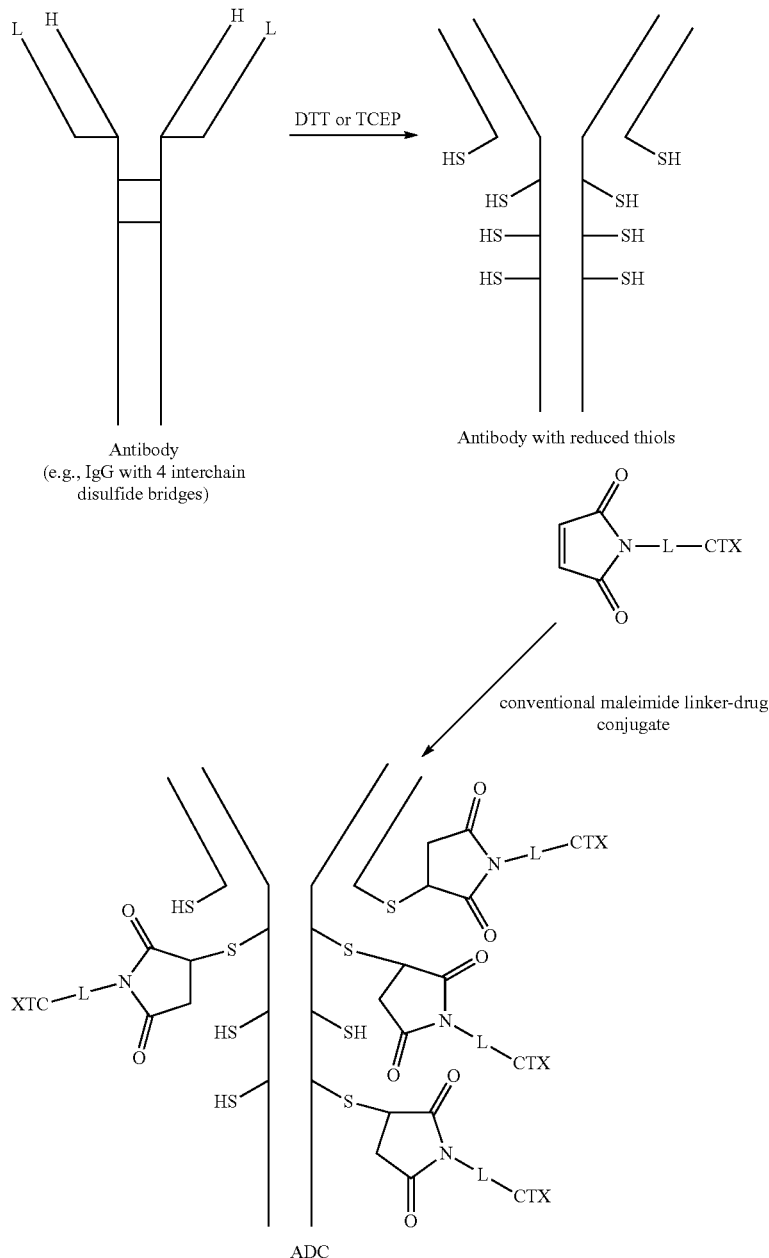

For example, according to Scheme A above, L may be one of the following: (i) —(CH$_2$)$_5$—C(O)—; (ii) —(CH$_2$)$_5$—C(O)-Valine-Citrulline-phenylenyl, where the phenylenyl is substituted by 2 substituents selected from the group consisting of —C(O)OH and —NH$_2$; or (iii) —(CH$_2$CH$_2$)—(CH$_2$CH$_2$O)$_4$—C(O)-Valine-Citrulline-phenylenyl, where the phenylenyl is substituted by 2 substituents selected from the group consisting of —C(O)OH and —NH$_2$.

For example, according to Scheme A above, L may be one of the following: (i) caproyl ("c"); (ii) caproyl-Valine-Citrulline-para aminobenzyl ("cValCit-PAB"); or (iii) (dPEG)$_4$-Valine-Citrulline-para aminobenzyl ("dPEG$_4$-ValCit-PAB").

For example, when the antibody-drug conjugate is prepared using a maleimido group ("m"), attached through the linker to a cytotoxin, CTX, as illustrated in Scheme A above, the antibody-drug conjugate may comprise one of the following: (i) maleimidocaproyl ("mc"); (ii) maleimidocaproyl-Valine-Citrulline-para aminobenzyl ("mcValCit-PAB"); or (iii) maleimidocaproyl-(dPEG)$_4$-Valine-Citrulline-para aminobenzyl ("m-dPEG4-ValCit-PAB").

As illustrated in the following Schemes B-E, the antibody-drug conjugate of Scheme A above may be prepared using maleimidocaproyl-monomethylauristatin F ("mc-MMAF"), maleimidocaproyl-Valine-Citrulline-para aminobenzyl-monomethylauristatin F ("mcValCit-PAB-MMAF"), maleimidocaproyl-Valine-Citrulline-para aminobenzyl-monomethylauristatin E ("mcValCit-PAB-MMAE"), or maleimidocaproyl-(dPEG)$_4$-Valine-Citrulline-para aminobenzyl-CC1065 ("m-dPEG$_4$-ValCit-PAB-CC1065").

Exemplary antibody-drug conjugates are prepared using maleimidocaproyl-monomethylauristatin F (mc-MMAF), as illustrated in the following Scheme B, where the maleimido group is attached through a linker (L=caproyl group) to a cytotoxin (CTX=MMAF):
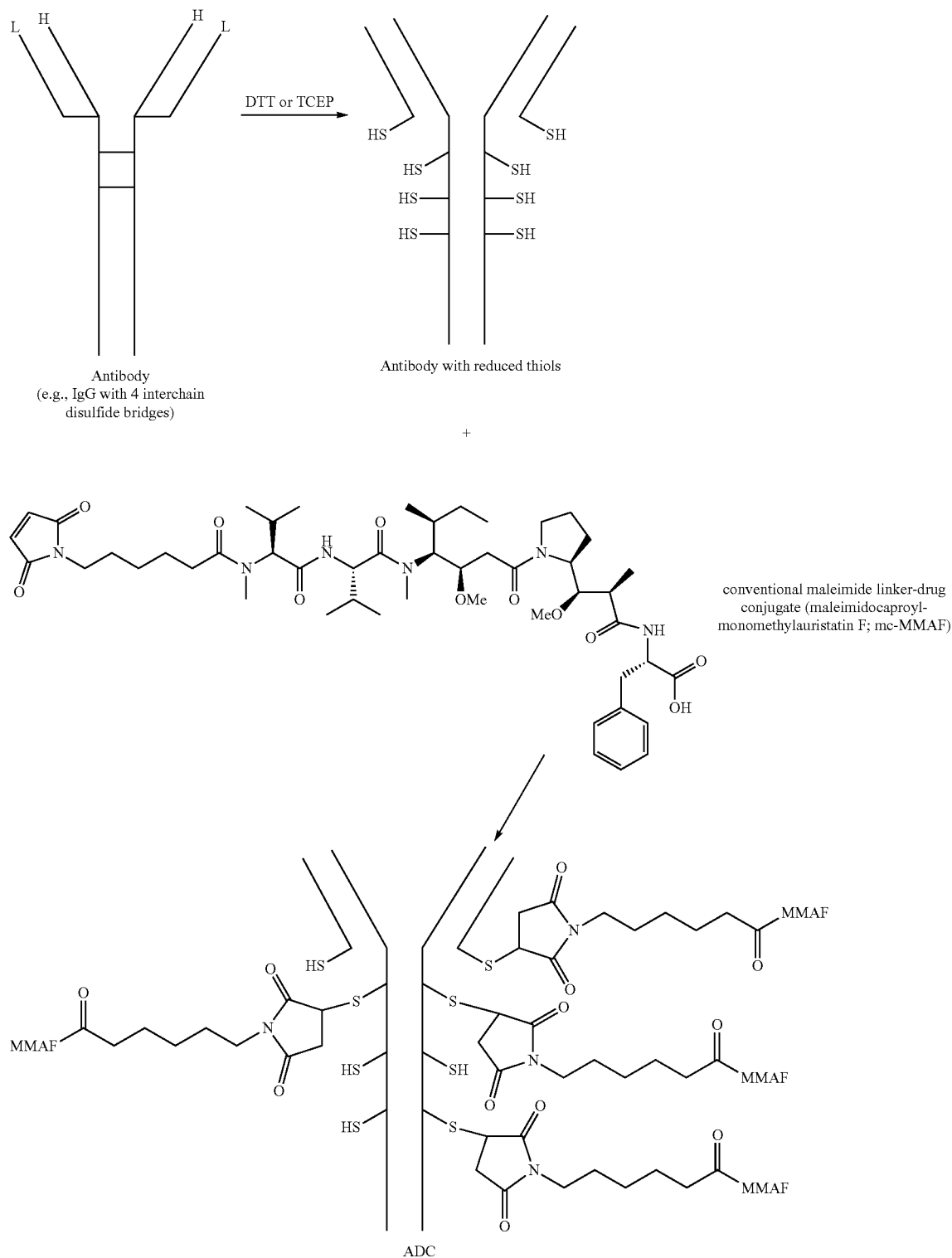

Exemplary antibody-drug conjugates are also prepared using maleimidocaproyl-Valine-Citrulline-para aminobenzyl-monomethylauristatin F (mcValCit-PAB-MMAF), as illustrated in the following Scheme C, where the maleimido group is attached through a linker (L=caproyl-Valine-Citrulline-para aminobenzyl) to a cytotoxin (CTX=MMAF):
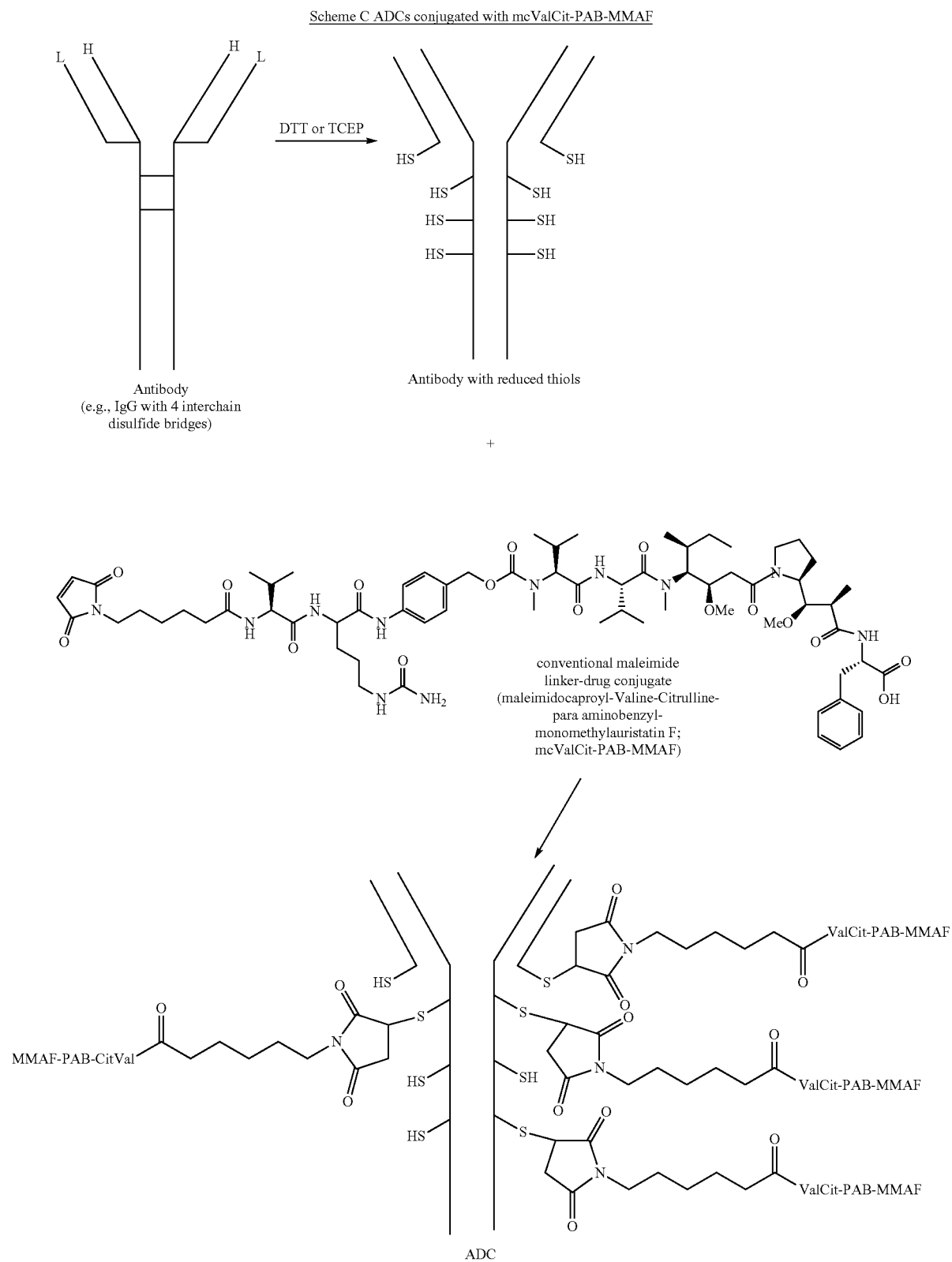

Exemplary antibody-drug conjugates are also prepared using maleimidocaproyl-Valine-Citrulline-para aminobenzyl-monomethylauristatin E (mcValCit-PAB-MMAE), as illustrated in the following Scheme D, where the maleimido group is attached through a linker (L=caproyl-Valine-Citrulline-para aminobenzyl) to a cytotoxin (CTX=MMAE):
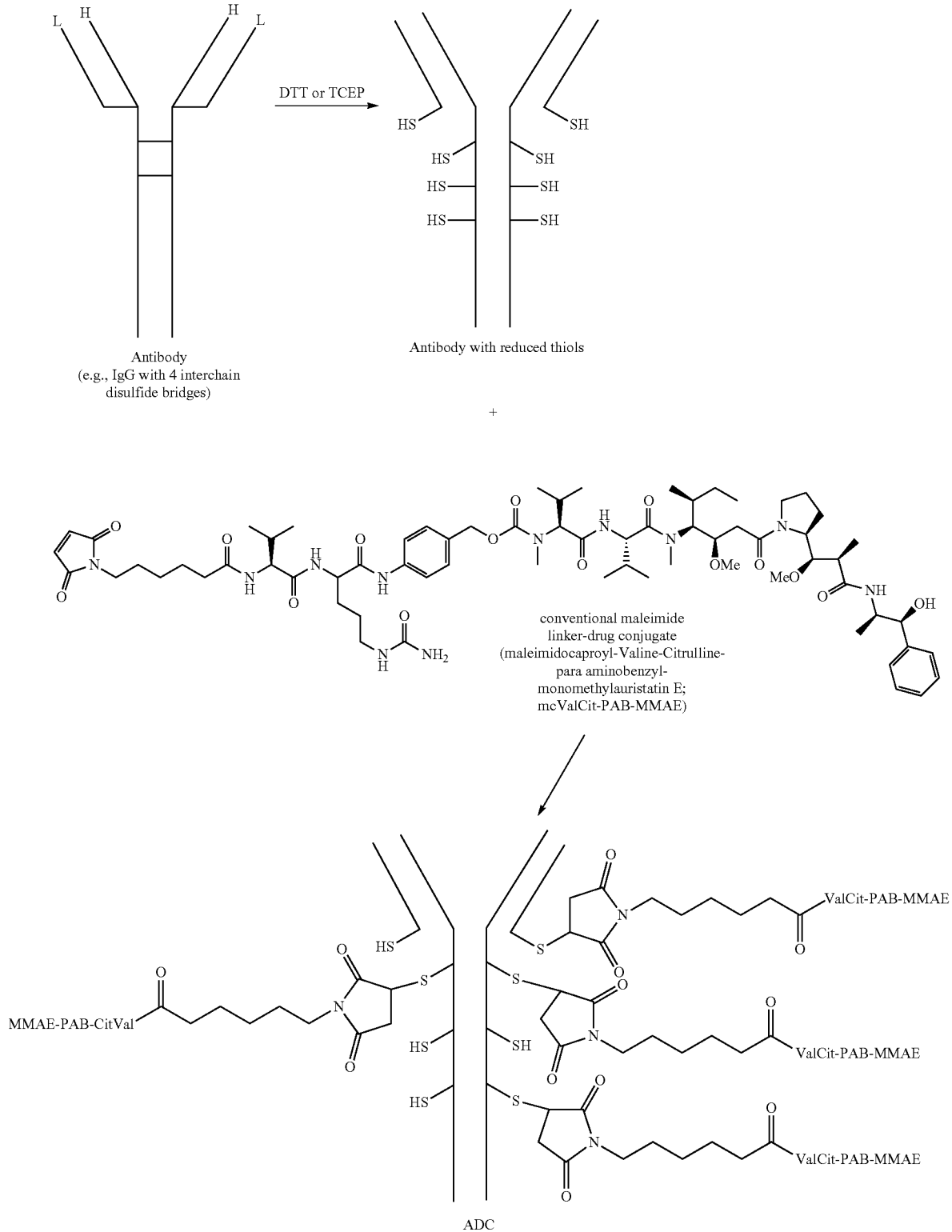

Exemplary antibody-drug conjugates are also prepared using maleimidocaproyl-(dPEG)$_4$-Valine-Citrulline-para aminobenzyl-CC1065 (m-dPEG$_4$-ValCit-PAB-CC1065), as illustrated in the following Scheme E, where the maleimido group is attached through a linker (L=(dPEG)$_4$-Valine-Citrulline-para aminobenzyl) to a cytotoxin (CTX=CC1065):
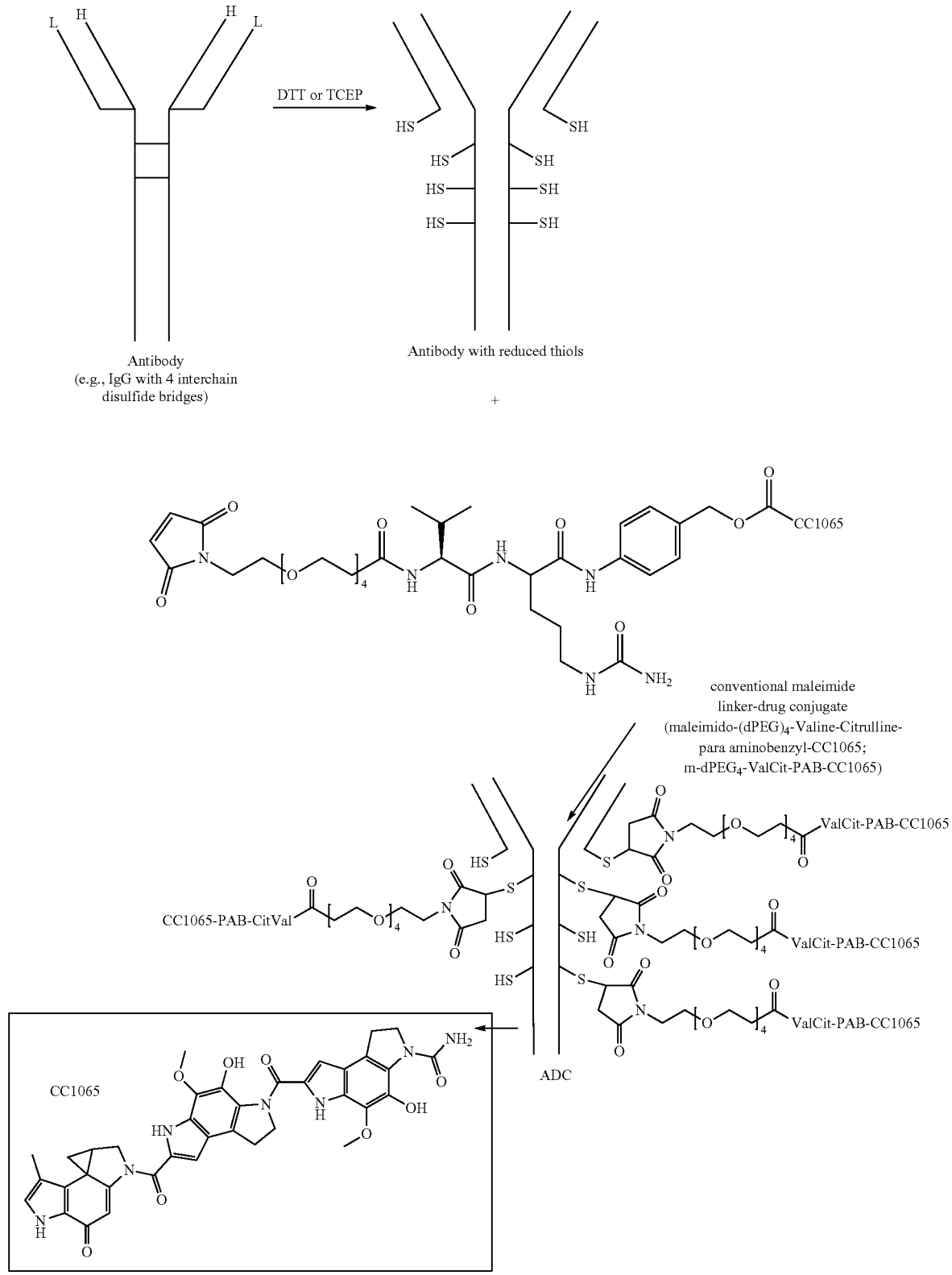

In Scheme E, the structure of the cyclophosphamide, CC1065, is depicted in the lower left-hand corner of the scheme, with an arrow indicating the point of attachment (e.g., via the free amino group on the CC1065 molecule) to the carbonyl group of the para aminobenzoate moiety of the linker.

The ADCs of exemplary Schemes B-E are made as follows. In a sterile 1.7 ml eppendorf tube, 20 mg of antibody at 20 mg/ml concentration in phosphate buffered saline (PBS) pH 7.4 (Gibco, Mg and Ca free) is reacted with 1 mM diethylene triamine pentaacetic acid (DTPA) as the chelator. Then 2.75 eq. of tris(2-carboxyethyl)phosphine hydrochloride solution (TCEP HCl) (Sigma ampule 0.5M concentration) or 50 μL of 100 mM dithiothreitol (DTT) is added for an average drug-antibody ratio (DAR) of 4 drugs per antibody and incubated at 37° C. for 1 hour, with the aim of having less than 10% of the total antibody being in the unlabeled or naked antibody.

Dithiobisnitro-benzoate (DTNB; Ellman's reagent) colorimetric assay is used to assess free thiols available for conjugation (Ellman et al., *Biochemical Pharmacology* 7:88-95 (1961)). The reduced antibody solution is cooled in an ice-bath at ~0° C. for 15 minutes. Then, linker-cytotoxin conjugate is added to the reduced antibody solution as follows: (i) for Scheme B, 60 μL of mc-MMAF from a 10 mM stock solution in DMSO (9.74 mg in 1.074 ml of DMSO for 10 mM) is added; (ii) for Scheme C, 60 μL of mcValCit-PAB-MMAF from a 10 mM stock solution in DMSO (9.4 mg in 707 μL of DMSO for 10 mM) is added; (iii) for Scheme D, 60 μL of mcValCit-PAB-MMAE from a 10 mM stock solution in DMSO (3.24 mg in 247 μL of DMSO for 10 mM) is added; and (iv) for Scheme E, 60 μL of mc-dPEG$_4$-ValCit-PAB-CC1065 from a 10 mM stock solution in DMSO (3.8 mg in 258 μL of DMSO for 10 mM) is added. Once the linker-cytotoxin conjugate is added to the reduced antibody solution, the solution is incubated on a roller-plate in a refrigerator at 4° C. overnight (or alternatively at 37° C. for 2 hours) to produce the ADC. The DTNB assay is repeated to demonstrate no free thiols remaining (clear means no free thiol and a yellow color indicates remaining free thiols and incomplete conjugation of payload). The concentration of the ADC is obtained via the NanoDrop spectrophotometer. The crude ADC is purified using either PD-10 SEC separation or SEC chromatography via a Superdex 200 column eluted with an appropriate working buffer or final formulation buffer. The purified ADC is stored at 4° C.

Hydrophobic Interaction Chromatography (HIC) HPLC method is used to determine average drug loads of the ADCs via HPLC. On an Agilent 1200 HPLC binary pump system attached to a Agilent 6130b Electrospray Mass Spectrometer, a Tosoh NPR Butyl-C4 column (2.1 mm×75 mm) is run with a binary gradient at 0.8 ml/min with diode-array UV-vis detection at 220 nm, 254 nm and 280 nm. Mobile phase A is 1.5M Sodium Sulfate in 1×PBS, Mobile phase B is 1×PBS with 25% isopropanol run on a O—100% linear gradient for 10-12 column volumes with a 5 minute initial equilibration and 5 minute 100% mobile phase B wash at the end of each HPLC run. Unlabeled or naked antibody elutes first in the linear gradient with peaks representing increasing average drug loads in order of hydrophobicity which correlates with increasing loading of antibody with payloads. Retention times of the naked antibody are confirmed via running a standard injection of 20 μL of a 1 mg/ml stock solution of the antibody. Co-elution of the naked antibody and ADC definitively confirms relative amounts of each.

In additional experiments, anti-CD39 antibodies and ADCs with anti-CD39 antibodies were tested for their in vivo anti-tumor effects against the cell line JVM-13, as described in Example 6. Results of exemplary experiments shown or tumor growth inhibition (TGI) are shown in Table 22.

TABLE 22

Anti-CD39 mAbs and ADCs in JVM-13 Model*

| Treatment | Volume [mm3] | Std Dev [mm3] | TGI (%) | p-value |
| --- | --- | --- | --- | --- |
| CTRL | 3160 | 996 | | |
| 9-31A | 2789 | 758 | −14 | 0.71025 |
| 5-13A | 2323 | 675 | −31 | 0.15632 |
| 5-165C | 2314 | 1112 | −31 | 0.25598 |
| 5-17A | 2211 | 519 | −35 | 0.06207 |
| Cyclophosphamide | 1802 | 467 | −50 | 0.00608 |
| CTRL mc-MMAF | 2814 | 833 | | |
| 5-13A dts-MMAF | 2559 | 758 | −16 | 0.67189 |
| 5-13A mc-MMAF | 2437 | 1308 | −11 | 0.37578 |
| 5-165C dts-MMAF | 2304 | 1389 | −21 | 0.41404 |
| 9-13A mc-MMAF | 1908 | 1066 | −38 | 0.10217 |
| 5-71A mc-MMAF | 1697 | 549 | −47 | 0.00833 |
| 5-165 mc-MMAF | 1682 | 1135 | −48 | 0.05485 |
| Cyclophosphamide | 1802 | 467 | −43 | 0.01117 |

*Study# GH-1 A&B; n = 8 animals/group; measurements taken on Day 59 of study
Antibodies dosed at 3 mg/kg on days 37 and 44; cyclophosphamide dosed at 125 mg/kg Example 9—Methods of Synthesizing Additional Anti-CD39 Antibody-Drug Conjugates Alternatively, antibody-drug conjugates of formula (Ia) or (Ib) of the present disclosure may be prepared as illustrated with formula (Ia) in the following Scheme F, and with formula (Ib) in the following Scheme G for:

Scheme F: ADCs of formula (Ia) of the present disclosure

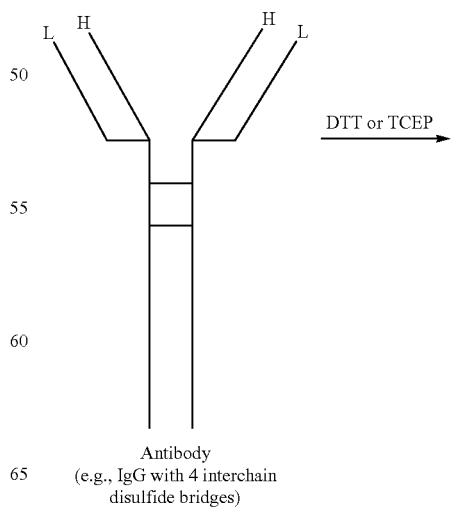

Antibody
(e.g., IgG with 4 interchain disulfide bridges)

121
-continued

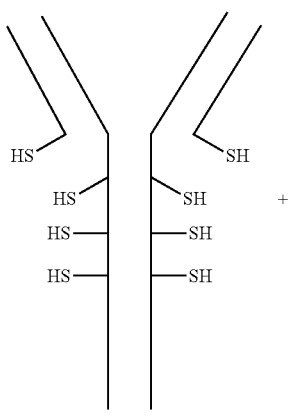

Antibody with reduced thiols

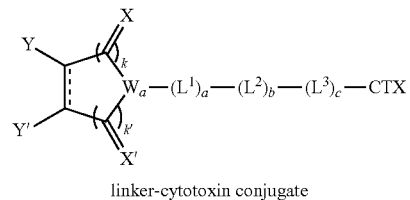

linker-cytotoxin conjugate

122
-continued

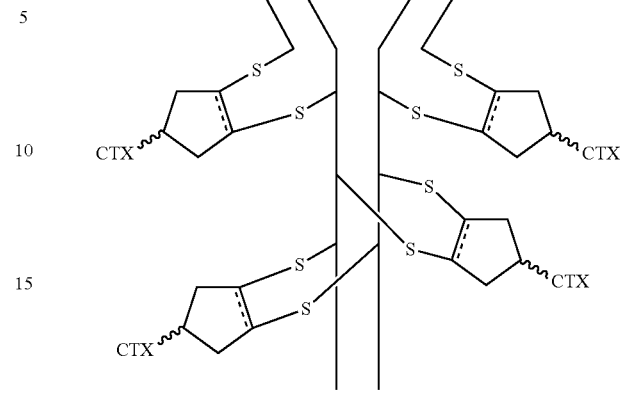

ADC

For ease of viewing, the linker-cytotoxin conjugate is represented by a cartoon, where the linker between $W_a$ and CTX is the squiggly line, k and k' are both 0, and Y and Y' are independently any electrophilic leaving group that reacts selectively with thiols.

Scheme G: ADCs of formula (Ib) of the present disclosure

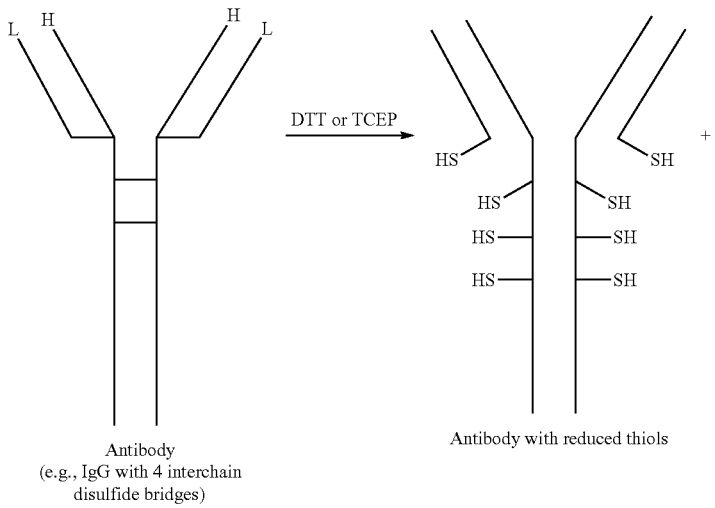

Antibody (e.g., IgG with 4 interchain disulfide bridges) → Antibody with reduced thiols

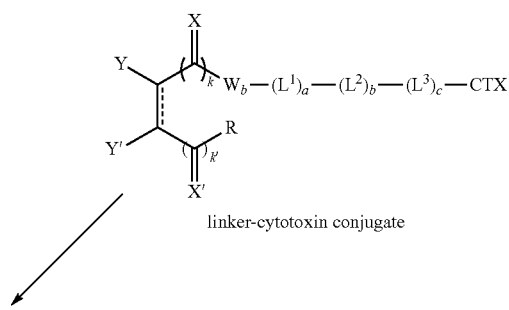

linker-cytotoxin conjugate

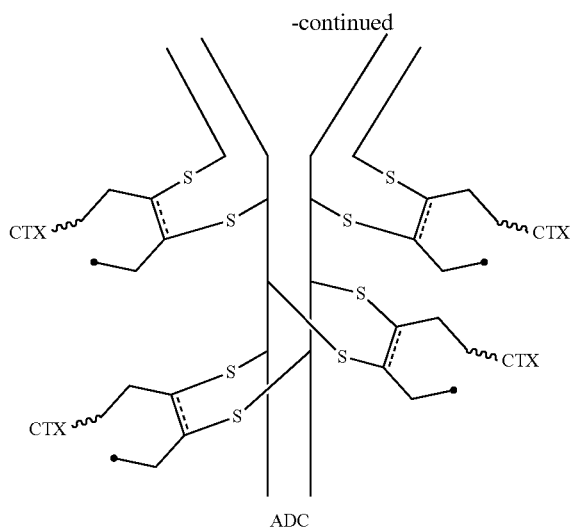

ADC

For ease of viewing, the linker-cytotoxin conjugate is represented by a cartoon, where the linker between $W_b$ and CTX is the squiggly line, k and k' are both 0, R is the black dot; and Y and Y' are independently any electrophilic leaving group that reacts selectively with thiols.

Additional antibody-drug conjugates of the present disclosure may be prepared, wherein the antibody-drug conjugates are according to formula (Ic):

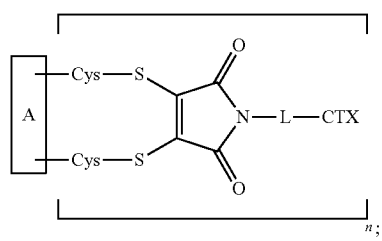

(Ic)

or a pharmaceutically acceptable salt thereof, wherein:

A is an anti-CD39 antibody, optionally a humanized anti-CD39 antibody;

the two depicted cysteine residues are from an opened cysteine-cysteine disulfide bond in A;

L is a cleavable or a noncleavable linker;

CTX is cytotoxin bonded to L by an amide bond or a carbamate bond; and n is an integer of 1 to 4.

For example, the antibody-drug conjugates of formula (Ic) are prepared where CTX is monomethylauristatin F (MMAF), L is —(CH$_2$)$_5$C(O)—, and n is 4.

For example, the antibody-drug conjugates of formula (Ic) are prepared where the antibody-drug conjugate has the following formula:

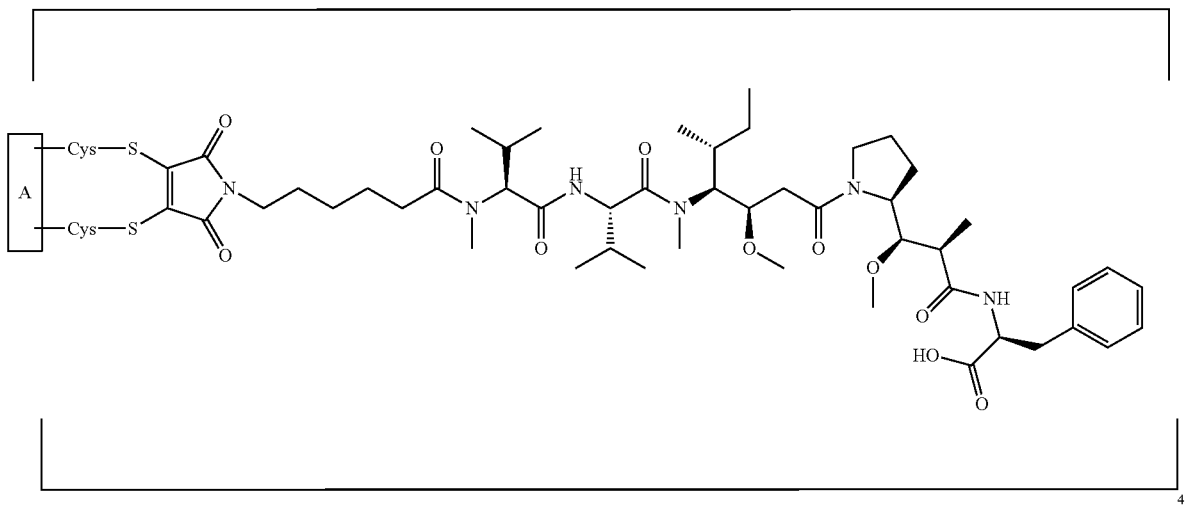

wherein A is an anti-CD39 antibody, optionally a humanized anti-CD39 antibody, and n is 4.

For example, the antibody-drug conjugates of formula (Ic) are those where CTX is monomethylauristatin E (MMAE), L is —(CH$_2$)$_5$C(O)-Val-Ala-PAB-O—C(O)—, or —(CH$_2$)$_5$C(O)-Val-Cit-PAB-O—C(O)—, and n is 4.

For example, the antibody-drug conjugates of formula (Ic) are those which have the following formula:

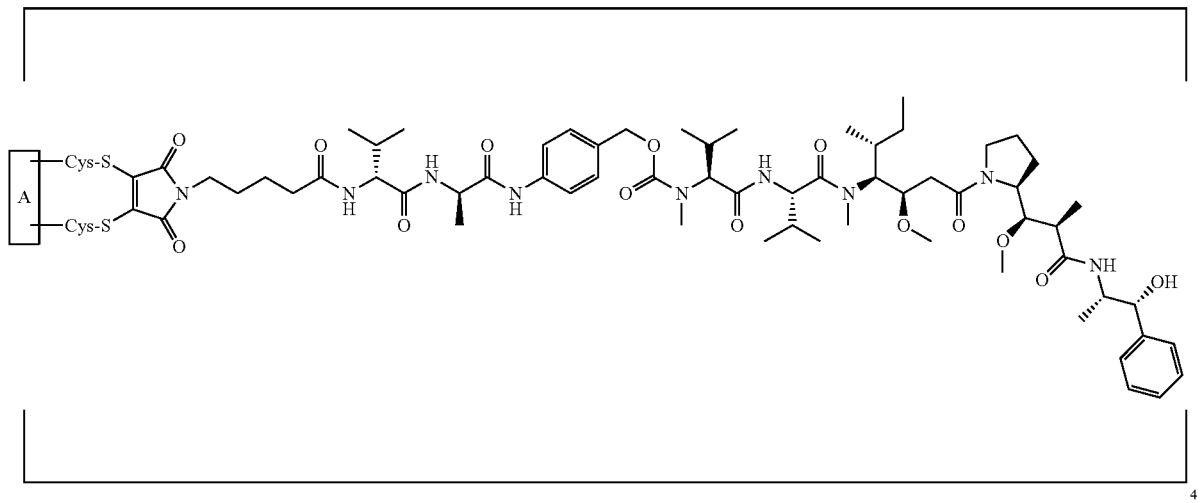

wherein A is an anti-CD39 antibody, optionally a humanized anti-CD39 antibody, and n is 4.

The antibody-drug conjugates of formula (Ic) are prepared using linker-cytotoxin conjugates of the following formula (IIc):

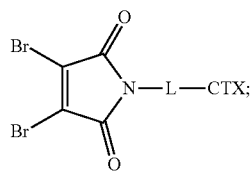

(IIc)

or an enantiomer, diasteriomer, or mixtures thereof;

wherein:

L is a cleavable or noncleavable linker; and

CTX is cytotoxin bonded to L by an amide bond or a carbamate bond.

For example, the antibody-drug conjugates of formula (Ic) were prepared with an anti-CD39 antibody, optionally a humanized anti-CD39 antibody, using the linker-cytotoxin conjugate of formula (IIc), where CTX is MMAF, and L is —(CH$_2$)$_5$C(O)—.

For example, the antibody-drug conjugates of formula (Ic) were prepared with an anti-CD39 antibody, optionally a humanized anti-CD39 antibody, using the linker-cytotoxin conjugate which has the following structure:

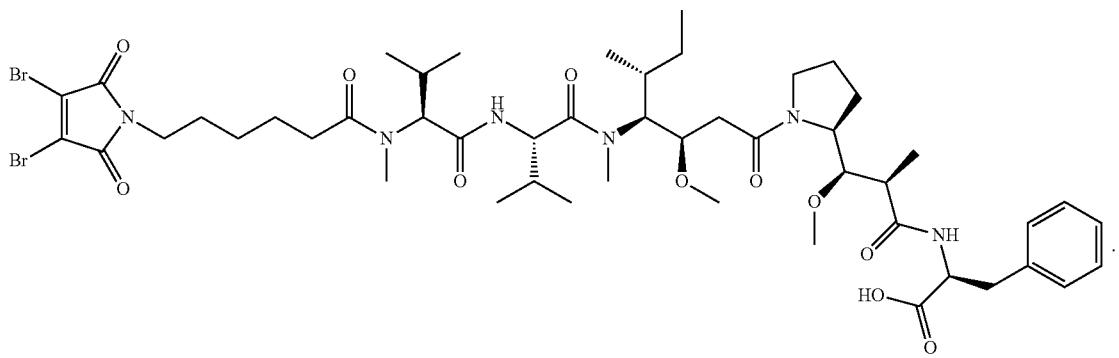 [SMILES: CC[C@@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C(=O)CCCCCN1C(=O)C(Br)=C(Br)C1=O)C(C)C]

For example, the antibody-drug conjugates of formula (Ic) are prepared with an anti-CD39 antibody, optionally a humanized anti-CD39 antibody, using the linker-cytotoxin conjugate of formula (IIc), where CTX is MMAE, and L is —(CH$_2$)$_5$C(O)—Val-Ala-PAB-O—C(O)—, or —(CH$_2$)$_5$C(O)-Val-Cit-PAB-O—C(O)—.

For example, the antibody-drug conjugates of formula (Ic) are prepared with an anti-CD39 antibody, optionally a humanized anti-CD39 antibody, using the linker-cytotoxin conjugate which has the following structure:

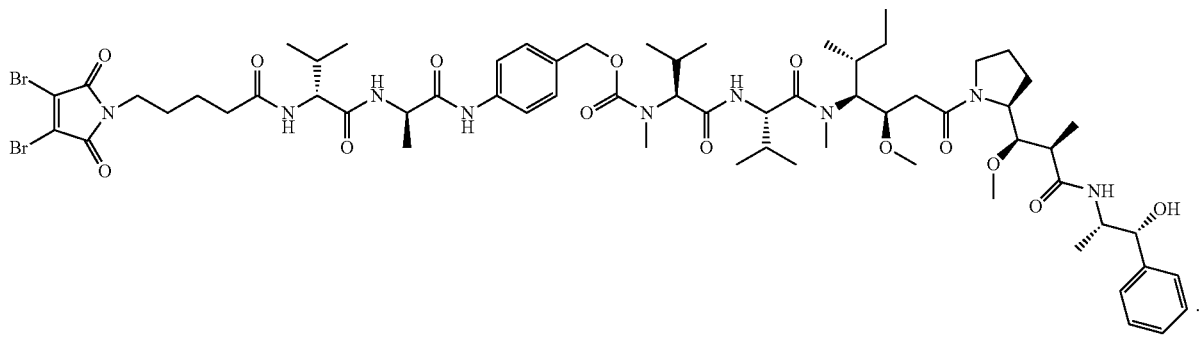 [SMILES: CC[C@@H](C)[C@@H]([C@@H](CC(=O)N1CCC[C@H]1[C@H](OC)[C@@H](C)C(=O)N[C@@H](C)[C@H](O)c1ccccc1)OC)N(C)C(=O)[C@@H](NC(=O)[C@H](C(C)C)N(C)C(=O)OCc1ccc(NC(=O)[C@@H](C)NC(=O)[C@H](NC(=O)CCCCN2C(=O)C(Br)=C(Br)C2=O)C(C)C)cc1)C(C)C]

Example 10—Preparation and Use of Additional Anti-CD39 Antibody-Drug Conjugates Alternatively, additional antibody-drug conjugates of the present disclosure may be prepared, wherein the antibody-drug conjugates are according to formula (Id):

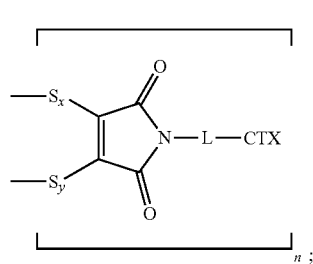

(Id)

or a pharmaceutically acceptable salt thereof,
wherein:
L is a cleavable or a noncleavable linker;
CTX is a cytotoxin bonded to L by an amide bond or a carbamate bond;
S$_x$ is a sulfur atom from a first cysteine residue, and S$_y$ is a sulfur atom from a second cysteine residue, wherein the first cysteine residue and the second cysteine residue are from different chains and/or from the same chain of a multi-chain antibody, wherein the multi-chain antibody is an anti-CD39 antibody, optionally a humanized anti-CD39 antibody; and
n is an integer of 1 to 4.

For example, the antibody-drug conjugates of formula (Id) are prepared where CTX is an auristatin bonded to L by an amide bond or a carbamate bond; wherein the auristatin is MMAF or MMAE.

For example, the antibody-drug conjugates of formula (Id) are prepared where CTX is MMAF, and L is —(CH$_2$)$_5$C(O)—.

For example, the antibody-drug conjugates of formula (Id) are prepared where CTX is MMAE, and L is —(CH$_2$)$_5$C(O)-Val-Ala-PAB-O—C(O)—, or —(CH$_2$)$_5$C(O)—Val-Cit-PAB-O—C(O)—.

For example, the antibody-drug conjugates of formula (Id) are prepared where the antibody-drug conjugate has the following formula:

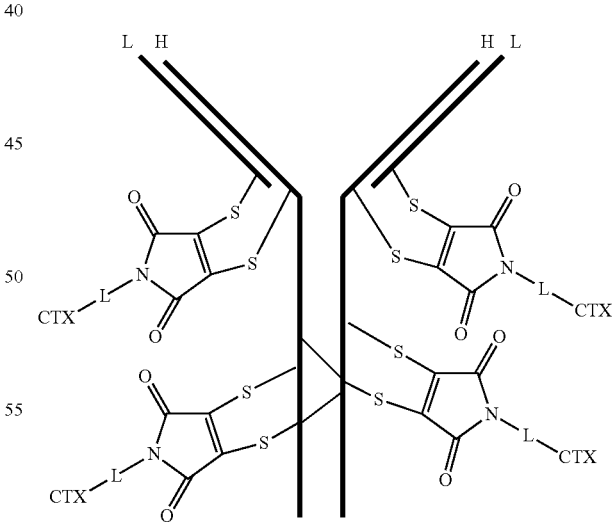

where each heavy chain of the multi-chain anti-CD39 antibody is denoted by the letter H, and each light chain of the multi-chain anti-CD39 antibody is denoted by the letter L.

For example, the antibody-drug conjugates of formula (Id) are prepared where the antibody-drug conjugate has the following formula:

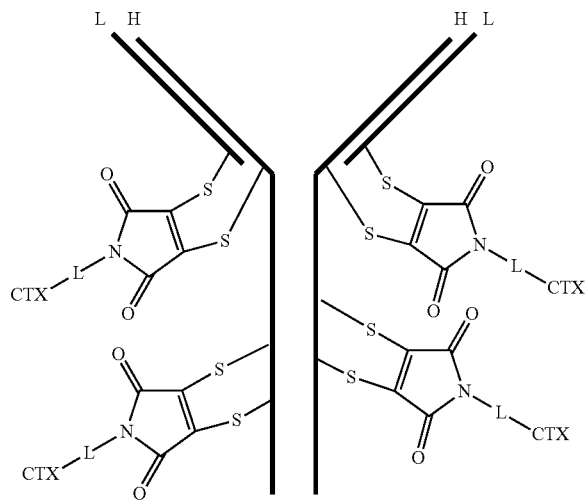

where each heavy chain of the multi-chain anti-CD39 antibody is denoted by the letter H, and each light chain of the multi-chain anti-CD39 antibody is denoted by the letter L.

For example, the antibody-drug conjugates of formula (Id) are prepared where the antibody-drug conjugate has the following formula:

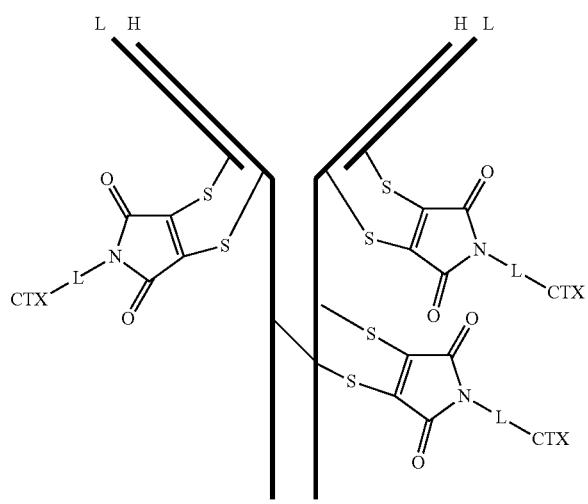

where each heavy chain of the multi-chain anti-CD39 antibody is denoted by the letter H, and each light chain of the multi-chain anti-CD39 antibody is denoted by the letter L.

For example, the antibody-drug conjugates of formula (Id) are prepared where the antibody-drug conjugate has the following formula:

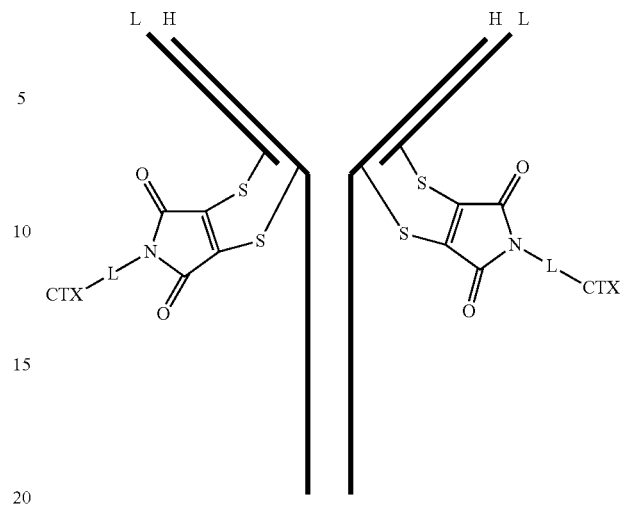

where each heavy chain of the multi-chain anti-CD39 antibody is denoted by the letter H, and each light chain of the multi-chain anti-CD39 antibody is denoted by the letter L.

For example, the antibody-drug conjugates of formula (Id) were prepared with an anti-CD39 antibody, optionally a humanized anti-CD39 antibody, using the linker-cytotoxin conjugate of formula (IIc), where CTX is MMAF, and L is —$(CH_2)_5C(O)$—.

For example, the antibody-drug conjugates of formula (Id) are prepared with an anti-CD39 antibody, optionally a humanized anti-CD39 antibody, using the linker-cytotoxin conjugate of formula (IIc), where CTX is MMAE, and L is —$(CH_2)_5C(O)$—Val-Ala-PAB-O—C(O)—, or —$(CH_2)_5C(O)$-Val-Cit-PAB-O—C(O)—.

The embodiments of the present invention described above are intended to be merely exemplary, and those skilled in the art will recognize, or be able to ascertain using no more than routine experimentation, numerous equivalents to the specific procedures described herein. All such equivalents are considered to be within the scope of the present invention and are covered by the following claims. Furthermore, as used in this specification and claims, the singular forms "a," "an" and "the" include plural forms unless the content clearly dictates otherwise. Thus, for example, reference to "an antibody" includes a mixture of two or more such antibodies, and the like. Additionally, ordinarily skilled artisans will recognize that operational sequences must be set forth in some specific order for the purpose of explanation and claiming, but the present invention contemplates various changes beyond such specific order.

The contents of all references described herein are hereby incorporated by reference.

Other embodiments are within the following claims.

What is claimed:

1. An isolated antibody that binds to CD39, wherein the antibody comprises:
   (a) a heavy chain variable (VH) region comprising a VH CDR1 having SEQ ID NO:155, a VH CDR2 having SEQ ID NO:160, and a VH CDR3 having SEQ ID NO:165; and/or
   (b) a light chain variable (VL) region comprising a VL CDR1 having SEQ ID NO:169, a VL CDR2 having SEQ ID NO:173, and a VL CDR3 having SEQ ID NO:175.

2. An isolated nucleic acid composition comprising a first nucleic acid encoding the VH region of claim 1 and a second nucleic acid encoding the VL region of claim 1.

3. An expression vector comprising the nucleic acid composition of claim 2.

4. A host cell comprising the nucleic acid composition of claim 2.

5. A method of producing an antibody comprising culturing the host cell of claim 4 under conditions that promote the production of the antibody.

* * * * *